US007842685B2

(12) United States Patent
Cee et al.

(10) Patent No.: US 7,842,685 B2
(45) Date of Patent: Nov. 30, 2010

(54) S1P1 RECEPTOR AGONISTS AND USE THEREOF

(75) Inventors: Victor J. Cee, Thousand Oaks, CA (US); Michael J. Frohn, Thousand Oaks, CA (US); Brian Alan Lanman, Oak Park, CA (US); Susana C. Neira, Naperville, IL (US); Anthony B. Reed, Thousand Oaks, CA (US); Kelvin K. C. Sham, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/456,687

(22) Filed: Jun. 18, 2009

(65) Prior Publication Data

US 2010/0029611 A1 Feb. 4, 2010

Related U.S. Application Data

(60) Provisional application No. 61/074,476, filed on Jun. 20, 2008.

(51) Int. Cl.
*A61K 31/397* (2006.01)
*A61K 31/4365* (2006.01)
*C07D 513/04* (2006.01)

(52) U.S. Cl. .................. 514/210.18; 514/301; 546/114

(58) Field of Classification Search ............ 514/210.18, 514/210.21, 301; 546/114
See application file for complete search history.

(56) References Cited

U.S. PATENT DOCUMENTS

2008/0015177 A1 1/2008 Saha et al.
2008/0027036 A1 1/2008 Burli et al.
2008/0064677 A9 3/2008 Saha et al.
2009/0082331 A1 3/2009 Neira et al.

FOREIGN PATENT DOCUMENTS

| | | | |
|---|---|---|---|
| JP | 2000038350 | A | 2/2000 |
| JP | 2008308448 | A | 12/2008 |
| WO | WO 02/28850 | A1 | 4/2002 |
| WO | WO 02/72549 | A1 | 9/2002 |
| WO | WO 03/045929 | A1 | 6/2003 |
| WO | WO 03/062252 | A1 | 7/2003 |
| WO | WO 2004/098494 | A2 | 11/2004 |
| WO | WO 2006/044503 | A2 | 4/2006 |
| WO | WO 2007/084857 | A2 | 7/2007 |
| WO | WO 2007/090550 | A1 | 8/2007 |
| WO | WO 2007/109334 | A2 | 9/2007 |
| WO | WO 2007/111864 | A2 | 10/2007 |
| WO | WO 2008/063202 | A2 | 5/2008 |
| WO | WO 2008/070447 | A2 | 6/2008 |
| WO | WO 2008/073865 | A2 | 6/2008 |

*Primary Examiner*—Kamal A Saeed
*Assistant Examiner*—Kristin Bianchi
(74) *Attorney, Agent, or Firm*—Rekha Bansal

(57) ABSTRACT

The present invention relates to compounds of Formula (I):

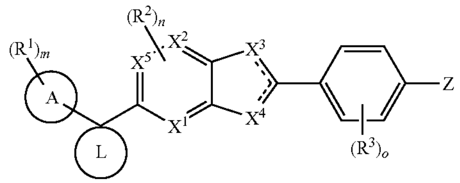

that are have activity as S1P receptor modulating agents, more specifically to specifically compounds that are S1P1 receptor agonists. The invention also related to the use of such compounds to treat diseases associated with inappropriate S1P1 receptor activity such as autoimmune diseases.

32 Claims, No Drawings

S1P1 RECEPTOR AGONISTS AND USE THEREOF

CROSS-REFERENCE

This application claims priority under 35 U.S.C. 119(e) to U.S. provisional application No. 61/074,476 filed on Jun. 20, 2008, the disclosures of which are incorporated herein by reference in its entirety.

FIELD OF THE INVENTION

The present invention relates to compounds that are have activity as S1P receptor modulating agents, more specifically to specifically compounds that are S1P1 receptor agonists. The invention also related to the use of such compounds to treat diseases associated with inappropriate S1P1 receptor activity such as autoimmune diseases.

BACKGROUND

Sphingosine-1-phosphate (S1P) has been demonstrated to induce many cellular effects, including those that result in platelet aggregation, cell proliferation, cell morphology changes, tumor cell invasion, endothelial cell chemotaxis and endothelial cell in vitro angiogenesis. S1P receptors are therefore good targets for therapeutic applications such as wound healing and tumor growth inhibition. S1P signals cells in part via a set of G protein-coupled receptors named S1P1, S1P2, S1P3, S1P4, and S1P5 (formerly called EDG-1, EDG-5, EDG-3, EDG-6, and EDG-8, respectively). These receptors share 50-55% amino acid and cluster identity with three other receptors (LPA1, LPA2, and LPA3 (formerly EDG-2, EDG-4 and EDG-7)) for the structurally-related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit, and each subunit can then associate with effector proteins, which activate second messengers leading to a cellular response. Eventually the GTP on the G-proteins is hydrolyzed to GDP, and the subunits of the G-proteins re-associate with each other and then with the receptor. Amplification plays a major role in the general GPCR pathway. The binding of one ligand to one receptor leads to the activation of many G-proteins, each capable of associating with many effector proteins, leading to an amplified cellular response.

S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other things.

For example, the S1P1 receptor subtype plays a key role in lymphocyte trafficking, and it is well established that synthetic small molecule S1P1 receptor agonists can suppress the peripheral immune response by inducing lymphocyte sequestration in secondary lymph organs (Cooke, N.; Zecri, F. Sphingosine 1-phosphate type 1 receptor modulators: recent advances and therapeutic potential. *Ann. Reports Med. Chem.* 2007; 42: 245-263).

Identification of the importance of this axis in modulating immune function was primarily accomplished via reverse pharmacology with the small molecule FTY720 (fingolimod). FTY720 is a prodrug that is phosphorylated in vivo to generate FTY720-P, an agonist of all known S1P receptors with the exception of $S1P_2$ (Mandala S, Hajdu R, Bergstrom J, et al. Alteration of lymphocyte trafficking by sphingosine-1-phosphate receptor agonists. *Science.* 2002; 296:346-349). Preclinical studies established that FTY720 administration resulted in peripheral lymphopenia that was associated with beneficial outcomes in animal models of transplantation (Brinkmann V and Lynch K. R. FTY720: targeting G-protein-coupled receptors for spingosine-1-phosphate in transplantation and autoimmunity. *Curr. Op. Immunol.* 2002; 14:569-575 and references therein) and autoimmune diseases (e.g. arthritis; Matsuura M, Imayoshi T and Okumoto T. Effect of FTY720, a novel immunosuppressant, on adjuvant- and collagen-induced arthritis in rats. *Int. J of Immunopharm.* 2000; 22:323-331), including experimental autoimmune encephalomyelitis (EAE), an animal model of multiple sclerosis (MS); (Kataoka H, Sugahara K, Shimano K, et al. FTY720, sphingosine 1-phosphate receptor modulator, ameliorates experimental autoimmune encephalomyelitis by inhibition of T cell infiltration. *Cell. and Mol. Immunol.* 2005; 2(6):439-448; MRL-lpr/lpr mice, an animal model of systemic lupus erythematosus (SLE) (Okazaki H, Hirata D, Kamimura T et al. Effects of FTY720 in MRL-lpr/lpr Mice: Therapeutic Potential in Systemic Lupus Erythematosus. *J. Rheumatol.* 2002; 29:707-716) and development of diabetes in NOD mice (Yang Z., Chen M. Fialkow L B et al. Immune modulator FTY720 prevents autoimmune diabetes in non obese diabetic mice. *Clin Immunol.* 2003; 107:30-35). In addition, results from a recently completed clinical trial of FTY720 (Phase 2) in MS patients highlight the potential of S1P receptor agonism as an effective therapeutic approach for treating human autoimmune diseases (Kappos L, Antel J, Comi G, et al. Oral fingolimod (FTY720) for relapsing multiple sclerosis. *N Engl. J. Med.* 2006; 355(11):1124-1140).

The current therapies for the treatment of immune diseases usually suppress the whole immune system of the patient and hence the bodys ability to react to infections is also severely compromised. Typical drugs in this class include azathioprine, chlorambucil, cyclophosphamide, cyclosporin, or methotrexate. Corticosteroids which reduce inflammation and suppress the immune response, cause side effects when used in long term treatment. Nonsteroidal anti-inflammatory drugs (NSAIDs) can reduce pain and inflammation, however, they exhibit considerable side effects such as gastrointestinal bleeding. Accordingly, there is a need for treatments that do not suffer from these side effects. The present invention fulfills this and related needs.

SUMMARY

In one aspect, provided are a compound of Formula (I):

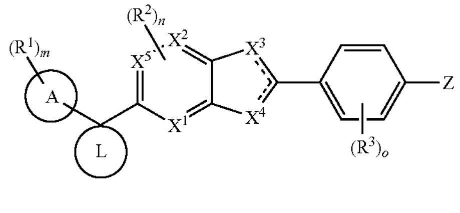

wherein:

m is 0, 1, 2 or 3;

n is 0, 1, 2 or 3;

o is 0, 1, 2 or 3;

A is a phenyl, heterocyclyl, three to six membered cycloalkyl, or a five or six membered heteroaryl ring;

L is a saturated 3, 4, 5, 6 or 7-member ring containing 0, 1 or 2 atoms selected from N, O and S and optionally containing a double bond, the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

$X^1$ is N or CH;

$X^2$ is N or CH;

$X^5$ is N or CH;

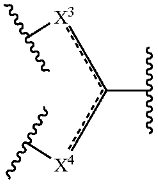

is selected from

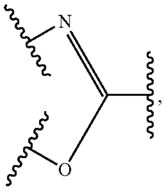,

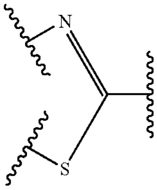,

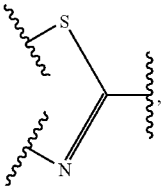,

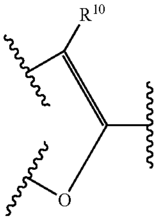,

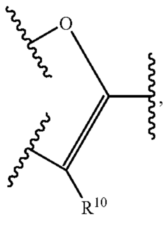,

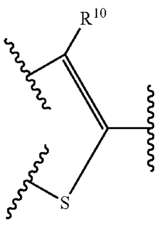

and

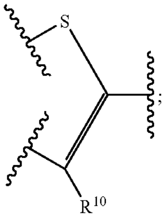;

$R^1$ is selected from F, Cl, $C_{1-4}$alkyl, $C_{1-4}$haloalkyl, OH, —$OC_{1-4}$alkyl, and —$OC_{1-4}$haloalkyl;

$R^2$ is selected from F, Cl, $C_{1-4}$alkyl, $C_{1-4}$haloalkyl, OH, —$OC_{1-4}$alkyl, and —$OC_{1-4}$haloalkyl;

$R^3$ is selected from F, Cl, $C_{1-4}$alkyl, $C_{1-4}$haloalkyl, OH, —$OC_{1-4}$alkyl, amino, and —$OC_{1-4}$haloalkyl;

Z is:

(i) a cycloalkyl substituted with amino, monoalkylamino or dialkylamino group; a cycloalkylalkyl substituted with one or two carboxy groups; a monosubstituted amino, disubstituted amino, carboxyalkylamino, hydroxyalkyl, substituted hydroxyalkyl, hydroxyalkoxy, substituted hydroxyalkoxy, aminoalkyl, aminoalkoxy, carboxyalkyl, substituted carboxyalkyl, carboxyalkyloxy, substituted carboxyalkyloxy, carboxyalkoxyalkyl, substituted carboxyalkoxyalkyl, aminocarbonyl, acylamino, aminosulfonyl, sulfonylamino, heterocycloamino, heterocycloaminoalkyl, heterocycloaminocarbonyl, heterocycloaminooxy, or heteroaralkyl group;

(ii) a group of formula (b):

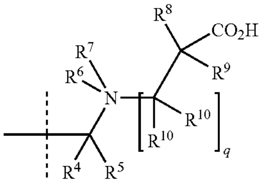

(b)

where:

q is 0, 1 or 2;

$R^4$ is selected from H, $C_{1-3}$haloalkyl, and $C_{1-6}$alkyl;

$R^5$ is selected from H, $C_{1-3}$haloalkyl, and $C_{1-4}$alkyl; or $R^4$ and $R^5$ together with the carbon atom to which they are attached form a 3, 4, 5, 6 or 7-member carbocyclic ring substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

$R^6$ is a lone pair of electrons or O;

$R^7$ is H or $C_{1-6}$alkyl;

$R^8$ is selected from H, F, Cl, $C_{1-4}$alkyl, $C_{1-4}$haloalkyl, OH, —$OC_{1-4}$alkyl, and —$OC_{1-4}$haloalkyl; or $R^7$ and $R^8$, when taken together, form a group that is selected from —$(CR^{10}R^{10})$—, —$(CR^{10}R^{10})O$—, —$O(CR^{10}R^{10})$—, —$(CR^{10}R^{10})(CR^{10}R^{10})$—, and —$(CR^{10}R^{10})_3$—;

$R^9$ is selected from H, F, $C_{1-3}$haloalkyl, $C_{1-4}$alkyl, OH and $OC_{1-4}$alkyl; or $R^8$ and $R^9$ together with the carbon atom to which they are attached from cycloalkyl; and each $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; or (iii) when $R^3$ is on a carbon atom of the phenyl ring that is adjacent to the carbon of the phenyl ring that is bonded to Z, then $R^3$ and Z can combine to form —CH═CH—$NR^{11}$—, —$(CH_2)_2NR^{11}$—, —$CH_2NR^{11}CH_2$—, —$CH_2)_2NR^{11}CH_2$—, —N═$CR^{11}$—NH—, or —N═CH—$NR^{11}$—, where $R^{11}$ is selected from hydrogen, hydroxyalkyl, aminoalkyl, carboxyalkyl, substituted hydroxyalkyl, substituted carboxyalkyl, or aminocarbonyl; or a pharmaceutically acceptable thereof; provided that when

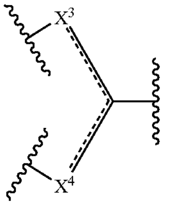

is selected from

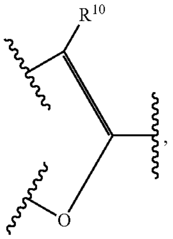

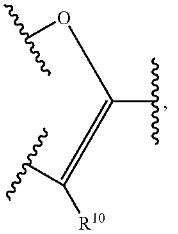

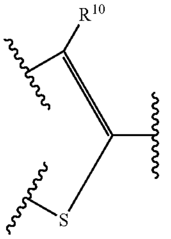

or

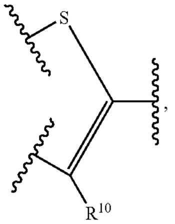

then at least one of $X^1$, $X^2$ and $X^5$ is N.

In one embodiment, the compound of Formula (I) has the Formula (Ia):

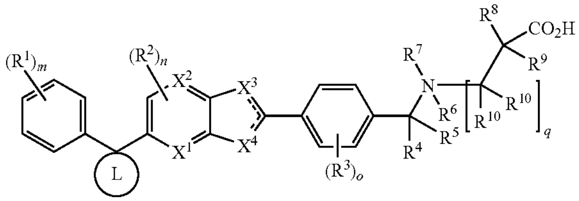

(Ia)

where:

$X^1$ is N or CH;

$X^2$ is N or CH;

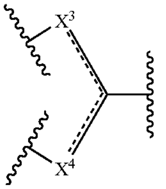

is selected from

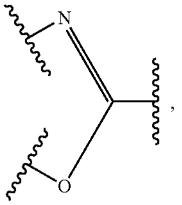

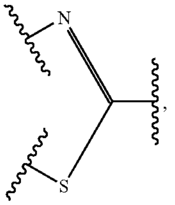

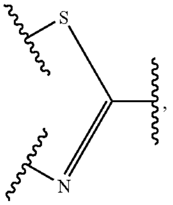

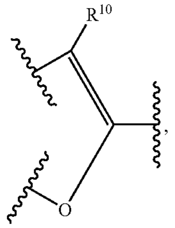

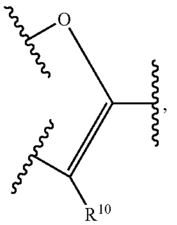

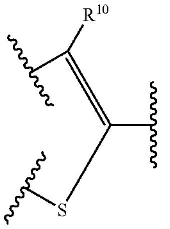

and

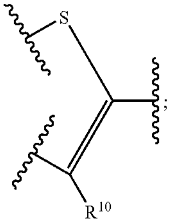

L is a saturated 3, 4, 5, 6 or 7-member ring containing 0, 1 or 2 atoms selected from N, O and S, the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

m is 0, 1, 2 or 3;

n is 0, 1, 2 or 3;

o is 0, 1, 2 or 3;

q is 1 or 2;

$R^1$ is selected from F, Cl, $C_{1-4}$alkyl, $C_{1-4}$haloalkyl, OH, $OC_{1-4}$alkyl, and —$OC_{1-4}$haloalkyl;

$R^2$ is selected from F, Cl, $C_{1-4}$alkyl, $C_{1-4}$haloalkyl, OH, —$OC_{1-4}$alkyl, and —$OC_{1-4}$haloalkyl;

$R^3$ is selected from F, Cl, $C_{1-4}$alkyl, $C_{1-4}$haloalkyl, OH, —$OC_{1-4}$alkyl, and —$OC_{1-4}$haloalkyl;

$R^4$ is selected from H, $C_{1-3}$haloalkyl, and $C_{1-6}$alkyl;

$R^5$ is selected from H, $C_{1-3}$haloalkyl, and $C_{1-4}$alkyl; or $R^4$ and $R^5$ together with the carbon atom to which they are attached form a 3, 4, 5, 6 or 7-member carbocyclic ring substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

$R^6$ is a lone pair of electrons or O;

$R^7$ is H or $C_{1-6}$alkyl;

$R^8$ is selected from H, F, Cl, $C_{1-4}$alkyl, $C_{1-4}$haloalkyl, OH, $OC_{1-4}$alkyl, and $OC_{1-4}$haloalkyl; or $R^7$ and $R^8$, when taken together, form a group that is selected from —$(CR^{10}R^{10})$—, —$(CR^{10}R^{10})O$—, —$O(CR^{10}R^{10})$— and —$(CR^{10}R^{10})(CR^{10}R^{10})$—;

$R^9$ is selected from H, F, $C_{1-3}$haloalkyl, $C_{1-4}$alkyl, OH and $OC_{1-4}$alkyl; and $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; and $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; or a pharmaceutically-acceptable salt thereof, provided that when

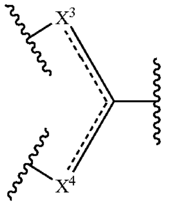

is selected from

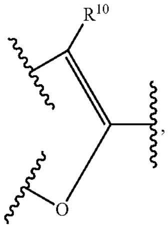
,
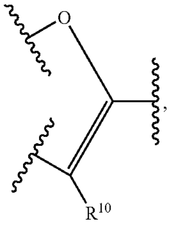
,
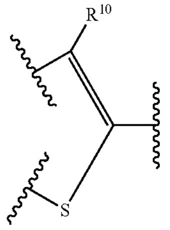
or
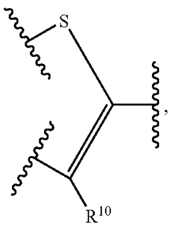
, then at least one of $X^1$ and $X^2$ is N.

In a second aspect, the present invention provides a method for treating an S1P1 receptor mediated condition in a patient. In such a method, an amount of a compound of Formula (I) or (Ia) effective to modulate an S1P1 receptor-mediated biological activity is administered to the patient. The S1P1 receptor mediated condition may be, e.g., transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

In a third aspect, the present invention provides methods for modulating S1P1 receptor mediated biological activity. The present invention also provides methods for using S1P1 modulators (i.e., agonists) of Formula (I) or (Ia) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostrate cancer; acute lung diseases, adult respiratory distress syndrome ("ARDS"), acute inflammatory exacerbation of chronic lung diseases such as asthma, surface epithelial cell injury such as transcorneal freezing or cutaneous burns, and cardiovascular diseases such as ischemia in a patient in need of such treatment or prevention.

In a fourth aspect, the invention provides methods for using S1P1 modulators of Formula (I) or (Ia) in treating disorders such as, but not limited to, vasoconstriction in cerebral arteries, autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma.

In a fifth aspect, the invention provides methods for using S1P1 modulators of Formula (I) or (Ia) to treat a disease or disorder in a patient, comprising administering to a subject in need of such treatment a therapeutically effective amount of an S1P-1 modulator, e.g., an agonist, of Formula (I) or (Ia) that stimulates the immune system. In certain embodiments, the patient is afflicted by an infectious agent. In other embodiments, the subject is immunocompromised.

In a sixth aspect, the invention provides a pharmaceutical composition comprising a compound of Formula (I) or (Ia) and a pharmaceutically acceptable salt thereof and a pharmaceutically acceptable excipient.

In a seventh aspect, this invention provides compounds of Formula (I) for use as medicament. In one embodiment, the use is multiple sclerosis.

In an eighth aspect, this invention is directed to the use of compounds of Formula (I) for the manufacture of medicament for use in the treatment of multiple sclerosis.

In a ninth aspect, this invention is directed to an intermediate of Formula (II):

(II)

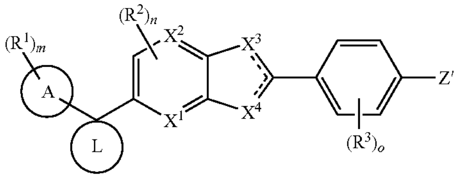

where Z' is hydroxy, amino, acyl, cyano, carboxy, 1,3-dioxan-2-yl, haloalkyl, or halo; and other groups are as defined for the compounds of Formula (I) above. In one embodiment, L is cyclopropyl, cyclopentyl or cyclohexyl. Within this group in one group of compounds, $X^1$ is —N—, $X^2$ is CH. Within this group in another group of compounds, $X^1$ is —N—, $X^2$ is CH, A is phenyl. Within this group in another group of compounds, $X^1$ is —N—, $X^2$ is CH, A is phenyl, m and n are 0, n is 1, and $R^3$ is halo or alkyl.

In a ninth aspect, this invention is directed to an intermediate of Formula (III):

(III)

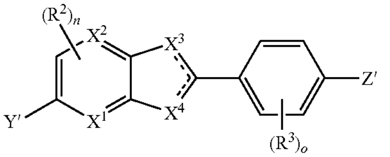

Where Y' is halo, preferably chloro, or trialkyltin and other groups are as defined for compounds of formula (I) above. Within this group in one group of compounds, $X^1$ is —N—, $X^2$ is CH. Within this group in another group of compounds, $X^1$ is —N—, $X^2$ is CH, A is phenyl. Within this group in another group of compounds, $X^1$ is —N—, $X^2$ is CH, A is phenyl, m and n are 0, n is 1, and $R^3$ is halo or alkyl.

DETAILED DESCRIPTION

Definitions

Unless otherwise stated, the following terms used in the specification and claims are defined for the purposes of this application and have the following meaning:

"$C_{\alpha\text{-}\beta}$alkyl" means an alkyl group comprising a minimum of α and a maximum of β carbon atoms in a branched, cyclical or linear relationship or any combination of the three, wherein α and β represent whole numbers. The alkyl groups described in this section may also contain one or two double or triple bonds. Examples of $C_{1\text{-}6}$alkyl include, but are not limited to the following:

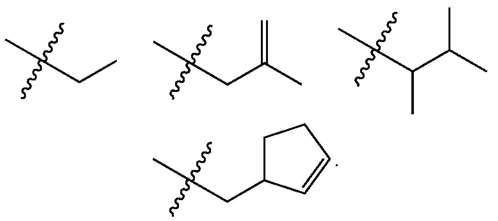

"—$OC_{\alpha\text{-}\beta}$alkyl" means a radical where $C_{\alpha\text{-}\beta}$alkyl is as defined above.

"Alkyl" means a linear saturated monovalent hydrocarbon radical of one to six carbon atoms or a branched saturated monovalent hydrocarbon radical of three to six carbon atoms, unless otherwise stated, e.g., methyl, ethyl, propyl, 2-propyl, butyl, and the like. Alkyl is independent of "$C_{\alpha\text{-}\beta}$alkyl" group defined above and is referred to when the alkyl group is not written in $C_{\alpha\text{-}\beta}$alkyl format.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Amino" means a —$NH_2$.

"Alkylcarbonyl" means a —COR radical where R is alkyl as defined above e.g., methylcarbonyl, and the like.

"Alkylsulfonyl" means a —$SO_2R$ radical where R is alkyl as defined above e.g., methylsulfonyl, and the like.

"Alkoxyalkyl" means a linear saturated hydrocarbon radical of one to six carbon atoms or a branched saturated monovalent hydrocarbon radical of three to six carbons substituted with one or two —OR groups where R is alkyl as defined above, e.g., 2-methoxyethyl, 1-, 2-, or 3-methoxypropyl, 2-ethoxyethyl, and the like.

"Aminoalkyl" means a linear saturated monovalent hydrocarbon radical of one to six carbon atoms or a branched saturated monovalent hydrocarbon radical of three to six carbons substituted with one or two, —NRR' where R is hydrogen or alkyl and R' is selected from hydrogen, alkyl, carboxyalkyl, substituted carboxyalkyl, hydroxyalkyl, substituted hydroxyalkyl, aralkyl, heterocycloaminoalkyl, alkylcarbonyl, alkylsulfonyl, or —C(O)COOH and/or one to three fluoro, each as defined herein, e.g., aminomethyl, methylaminoethyl, 2-ethylamino-2-methylethyl, 1,3-diaminopropyl, acetylaminopropyl, and the like; provided that when the Z group in section (i) of claim 1 is aminoalkyl then the aminoalkyl group is not —$CR^aR^b$—NRR' where each R, $R^a$ and $R^b$ is independently H or alkyl and R' is carboxyalkyl.

"Aminoalkoxy" means a —OR radical where R is a linear saturated monovalent hydrocarbon radical of one to six carbon atoms or a branched monovalent saturated hydrocarbon radical of three to six carbons substituted with one or two, —NRR' where R is hydrogen or alkyl and R' is selected from hydrogen, alkyl, carboxyalkyl, substituted carboxyalkyl, hydroxyalkyl, substituted hydroxyalkyl, alkylcarbonyl, aralkyl, heterocycloaminoalkyl, alkylsulfonyl, or —C(O)COOH, each as defined herein, e.g., 2-aminoethoxy, 2-dimethylaminopropoxy, and the like.

"Aminocarbonyl" means a —CONRR' radical where R is hydrogen or alkyl and R' is hydrogen, alkyl, hydroxyalkyl, carboxyalkyl, alkoxyalkyl or cycloalkyl, each as defined herein, e.g., —CONH-(3-hydroxypropyl), cyclopropylaminocarbonyl, and the like.

"Aminosulfonyl" means a —$SO_2NRR'$ radical where R is hydrogen or alkyl and R' is hydrogen, alkyl, hydroxyalkyl, carboxyalkyl, alkoxyalkyl or cycloalkyl, each as defined herein, e.g., —$SO_2NH$-(3-hydroxypropyl), cyclopropylaminosulfonyl, and the like.

"Acyl" means a —COR radical where R is alkyl or haloalkyl as defined herein.

"Acylamino" means a —NHCOR radical where R is haloalkyl, alkoxy, hydroxyalkyl, substituted hydroxyalkyl, carboxyalkyl, or substituted carboxyalkyl, each as defined herein, e.g., 2,2,2-trifluoroethylcarbonylamino, 3-carboxypropionylamino, —NHCO—$CH(NH_2)CH_2COOH$, and the like.

"Alkoxy" means a —OR radical where R is alkyl as defined above. Alkoxy is independent of "—$OC_{\alpha\text{-}\beta}$alkyl" group defined above and is referred to when the alkyl group is not written in $C_{\alpha\text{-}\beta}$alkyl format.

"Aralkyl" means a -(alkylene)-R radical where R is phenyl.

"Carbocyclic" means a cyclic ring that has only carbon ring atoms.

"Cycloalkyl" means a cyclic saturated monovalent hydrocarbon radical of three to ten carbon atoms, unless otherwise stated e.g., cyclopropyl, cyclobutyl, cyclopentyl, or cyclohexyl, and the like. The cycloalkyl group is optionally substituted with amino, alkylamino, dialkylamino or carboxy unless otherwise stated.

"Cycloalkylalkyl" means-(alkylene)-R radical where R is cycloalkyl as defined above.

"Carboxy" means —COOH.

"Carboxyalkyl" means a linear saturated monovalent hydrocarbon radical of one to six carbon atoms or a branched saturated monovalent hydrocarbon radical of three to six carbons substituted with a carboxy group e.g., 2-carboxyethyl, carboxymethyl, and the like.

"Substituted carboxyalkyl" means carboxyalkyl as defined above which is substituted with one or two amino.

"Carboxyalkyloxy" means —O—R radical where R is carboxyalkyl as defined above.

"Substituted carboxyalkyloxy" means —O—R radical where R is substituted carboxyalkyl as defined above.

"Carboxyalkoxyalkyl" means -(alkylene)-O—R radical where R is carboxyalkyl as defined above.

"Substituted carboxyalkoxyalkyl" means -(alkylene)-O—R radical where R is substituted carboxyalkyl as defined above.

"Carboxyalkylamino" means —NHR where R is carboxyalkyl group as defined above.

"Disubstituted amino" means a —NRR' radical where R and R' are independently alkyl or alkylsulfonyl, each as defined herein, e.g., dimethylamino, methylethylamino, and the like. When R and R' are alkyl, it is also referred to herein as dialkylamino.

"Halo" or "halogen" means a halogen atom selected from F, Cl, Br and I.

"$C_{V-W}$haloalkyl" means an alkyl group comprising a minimum of v and a maximum of w carbon atoms in a branched, cyclical or linear relationship or any combination of the three, wherein v and w represent whole numbers. The alkyl groups described in this section may also contain one or two double or triple bonds and wherein any number, at least one, of the hydrogen atoms attached to the alkyl chain is replaced by F, Cl, Br or I.

"—$OC_{V-W}$haloalkyl" means a radical where $C_{V-W}$haloalkyl is as defined above.

"Hydroxy" means —OH.

"Haloalkyl" means a linear saturated monovalent hydrocarbon radical of one to six carbon atoms or a branched saturated monovalent hydrocarbon radical of three to six carbon atoms, unless otherwise stated, that has one to three hydrogen atoms replaced by a halo group e.g., trifluoromethyl, and the like. Haloalkyl is independent of "$C_{V-W}$haloalkyl" group defined above and is referred to when the alkyl group is not written in $C_{V-W}$haloalkyl format.

"Hydroxyalkyl" means a linear saturated monovalent hydrocarbon radical of one to six carbon atoms or a branched saturated monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" or "hydroxyalkyloxy" means a —OR radical where R is hydroxyalkyl as defined above.

"Substituted hydroxyalkyl" means hydroxyalkyl as defined above that is substituted with one or two substituents independently selected from amino, mono or disubstituted amino, carboxyalkylamino, carboxy, or —$P(O)(OR)_3$ where R is hydrogen or alkyl; and/or one to three fluoro; provided that when the Z group in section (i) of Claim 1 is aminoalkyl then the aminoalkyl group is not —$CR^aR^b$—NRR' where each R, $R^a$ and $R^b$ is independently H or alkyl and R' is substituted hydroxyalkyl where the hydroxyalkyl is substituted with carboxy and/or fluoro.

"Substituted hydroxyalkyloxy" means —O—R where R is substituted hydroxyalkyl as defined above.

"Five or six membered heteroaryl" means a monovalent monocyclic aromatic radical of 5 or 6 ring atoms where one, two, or three, ring atoms are heteroatom(s) independently selected from N, O, or S, the remaining ring atoms being carbon. Representative examples include, but are not limited to, pyrrolyl, thienyl, thiazolyl, imidazolyl, furanyl, oxazolyl, isoxazolyl, pyridinyl, pyrimidinyl, pyrazinyl, pyridazinyl, triazolyl, and the like.

"Heteroaralkyl" means -(alkylene)-R where R is a heteroaryl ring which is a monovalent monocyclic aromatic radical of 5 or 6 ring atoms where one, two, or three, ring atoms are heteroatom independently selected from N, O, or S, the remaining ring atoms being carbon provided that at least one ring atom is N. The heteroaryl ring can be optionally substituted with carboxy.

"Heterocyclyl" means a saturated monovalent monocyclic group of 5 to 8 ring atoms in which one or two ring atoms are heteroatom(s) independently selected from N, O, or $S(O)_n$, where n is an integer from 0 to 2, the remaining ring atoms being C.

"Heterocycloamino" means a saturated monovalent monocyclic group of 5 to 8 ring atoms in which one or two ring atoms are heteroatom independently selected from N, O, $S(O)_n$, or C(O) where n is an integer from 0 to 2, the remaining ring atoms being C provided at least one ring atom is nitrogen e.g., pyrrolidinyl, piperidinyl, azetidinyl, aziridinyl, and the like. The heterocycloamino group can optionally be substituted with one to two substituents independently selected from hydroxyl, carboxy, fluoro, carboxyalkyl, or alkyl.

"Heterocycloaminocarbonyl" means a —C(O)—R radical where R is heterocycloamino group as defined above e.g., pyrrolidinylcarbonyl, azetidinylcarbonyl, and the like.

"Heterocycloaminooxy" means a —O—R radical where R is heterocycloamino group as defined above e.g., pyrrolidinyloxy, azetidinyloxy, and the like.

"Heterocycloaminoalkyl" means a -alkylene-R radical where R is heterocycloamino group as defined above e.g., pyrrolidinylethyl, azetidinylpropyl, and the like; provided that when the Z group in section (i) of Claim 1 is heterocycloaminoalkyl group where the heterocycloalkylamino group is substituted with a (one) carboxy group and optionally substituted with hydroxyl, carboxy, fluoro, or alkyl, then the alkylene chain is not —$CR^aR^b$ where $R^a$ and $R^b$ are independently H or alkyl.

"Monosubstituted amino" means a —NHR radical where R is alkyl or cycloalkyl substituted with carboxy, each as defined herein, e.g., methylamino, cyclopropylamino, 2-carboxycyclobutylamino, and the like. When R is alkyl, it is also referred to herein as monoalkylamino.

The terms "oxo" and "thioxo" represent the groups =O (as in carbonyl) and =S (as in thiocarbonyl), respectively.

"Halo" or "halogen" means a halogen atoms selected from F, Cl, Br and I.

"Sulfonylamino" means a —$NHSO_2R$ radical where R is alkyl or carboxalkyl, each as defined herein. When R is alkyl it is also referred to herein as alkylsulfonyl.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

"Treating" and "Treatment", includes any effect, e.g., lessening, reducing, modulating, or eliminating, that results in the improvement of the condition, disease, disorder, etc. and includes preventative and reactive treatment.

"Pharmaceutically-acceptable salt" means a salt prepared by conventional means, and are well known by those skilled in the art. The "pharmaceutically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., *J. Pharm. Sci.* 66:1 (1977).

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Alkenes can include either the E- or Z-geometry, where appropriate.

It should be noted that compounds of the invention may contain groups that may exist in tautomeric forms, such as heteroatom substituted heterocycloamino groups (Y'=O, S, NR), and the like, which are illustrated in the following examples:

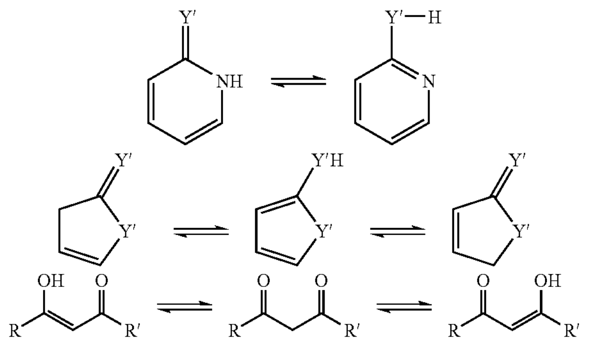

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyl-oxyalkyl (for example, pivaloyloxymethyl). Amines have been masked as arylcarbonyloxymethyl substituted derivatives, which are cleaved by esterases in vivo releasing the free drug and formaldehyde (Bungaard *J. Med. Chem.* 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

"$EC_{50}$ of an agent" included that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% activation is set at the amount of activity in the assay in the absence of added ligand/agonist.

"Purified" and like terms relate to the isolation of a molecule or compound in a form that is substantially free of contaminants normally associated with the molecule or compound in a native or natural environment.

"Immunomodulation" includes effects on the functioning of the immune system, and includes both the enhancement of an immune response as well as suppression of the immune response.

An "effective amount" includes an amount sufficient to produce a selected effect. For example, an effective amount of an S1P1 receptor agonist is an amount that decreases the cell signaling activity of the S1P1 receptor.

"Pharmaceutically acceptable" include molecular entities and compositions that do not produce an adverse, allergic or other untoward reaction when administered to an animal, or a human, as appropriate.

"Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The term "L is a saturated 3, 4, 5, 6 or 7-member ring containing 0, 1 or 2 atoms selected from N, O and S" means that L is saturated carbocyclic ring (ring with only carbon ring atoms) having 3, 4, 5, 6 or 7 carbon atoms wherein 0, 1, or 2 carbon ring atoms can be replaced by N, O, or S.

Embodiments (I) In one embodiment, the compounds of Formula (I) are those wherein:

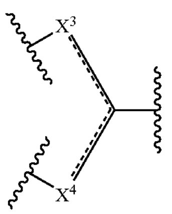 is 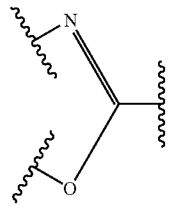 or

-continued

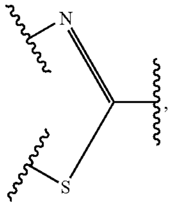

preferably

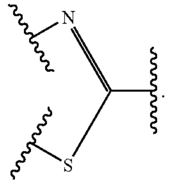

Within this group, in one group of compounds $X^1$ is N and $X^2$ and $X^5$ are CH. Within this group, another group of compounds is that $X^1$ and $X^2$ are CH and $X^5$ is N. Within group (I) and groups contained therein, in one group of compounds n is 0. Within group (I) and groups contained therein, in one group of compounds m is 0 and o is 1 or 2.

(a) Within the above embodiment (I) and groups contained therein, in one group of compounds L is a saturated 3, 4, 5, 6 or 7-member ring, preferably 3, 4, or 5-member ring, the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl. Within this group, in one group of compounds, L is cyclopropyl, cyclopentyl, cyclohexyl, preferably cyclopropyl. Within this group, in one group of compounds, $R^1$ is methyl, fluoro, hydroxyl, trifluoromethyl, methoxy or trifluoromethoxy.

(b) Within the above embodiment (I) and groups contained therein, in another group of compounds L is a saturated 3, 4, 5, 6 or 7-member ring containing 1 or 2 atoms selected from N, O, or S and the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl. Within this group, in one group of compounds, L is piperidinyl, tetrahydropyranyl or oxetanyl. Within this group, in one group of compounds, $R^1$ is methyl, fluoro, hydroxyl, trifluoromethyl, methoxy or trifluoromethoxy.

(II) In another embodiment, the compounds of Formula (I) are those wherein L is a saturated 3, 4, 5, 6 or 7-member ring the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl. Within this group, in one group of compounds, L is cyclopropyl, cyclopentyl, cyclohexyl, preferably cyclopropyl. Within this group, in one group of compounds, $R^1$ is methyl, fluoro, hydroxyl, trifluoromethyl, methoxy or trifluoromethoxy. Within this group, and groups contained therein, in one group of compounds, $R^3$ is F, Cl or $C_{1-4}$alkyl where alkyl is linear or branched and saturated. Within this group, and groups contained therein, in another group of compounds, $R^3$ is F, Cl, amino or $C_{1-4}$alkyl where alkyl is linear or branched and saturated, preferably $R^3$ is fluoro, amino, methyl.

(i) Within embodiments I, I(a), I(b), and II, and groups contained therein, in one embodiment, A is phenyl substituted with $R^1$ group as defined in the Summary. Within these groups, in another group of compounds $R^1$ is selected from F, Cl, $C_{1-4}$alkyl, $C_{1-4}$haloalkyl, OH, —$OC_{1-4}$alkyl, and —$OC_{1-4}$haloalkyl where the alkyl group is above listed groups is linear or branched and saturated. Preferably, $R^1$ is methyl, fluoro, hydroxyl, trifluoromethyl, methoxy or trifluoromethoxy. Preferably, A is phenyl or phenyl substituted at the 2 position with fluoro, or phenyl substituted at the 4-position with fluoro or hydroxyl, the carbon atom of the phenyl ring attached to L being the 1-position. Within this group, and groups contained therein, in one group of compounds, $R^3$ is F, Cl or $C_{1-4}$alkyl where alkyl is linear or branched and saturated. Within this group, and groups contained therein, in another group of compounds, $R^3$ is F, Cl, amino or $C_{1-4}$alkyl where alkyl is linear or branched and saturated, preferably $R^3$ is fluoro, amino, methyl.

(ii) Within embodiments I, I(a), I(b), and II, and groups contained therein, in another embodiment, the compounds of Formula (I) are those wherein A is cycloalkyl substituted with $R^1$ group as defined in the Summary. Within these groups, in one group of compounds, A is cyclopropyl, cyclobutyl, cyclopentyl or cyclohexyl and $R^1$ is selected from F, Cl, $C_{1-4}$alkyl, $C_{1-4}$haloalkyl, OH, —$OC_{1-4}$alkyl, and —$OC_{1-4}$haloalkyl where the alkyl group is above groups is linear or branched and saturated, preferably fluoro if $R^1$ is present. Preferably $R^1$ is methyl, fluoro, trifluoromethyl, hydroxyl, methoxy or trifluoromethoxy. Preferably, A is cyclopropyl, cyclohexyl disubstituted at the 4 position with two fluorine atoms, or cyclopentyl disubstituted at the 3-position with two fluorine atoms, the carbon atom attached to L being the 1-position. Within this group, and groups contained therein, in one group of compounds, $R^3$ is F, Cl or $C_{1-4}$ alkyl where alkyl is linear or branched and saturated. Within this group, and groups contained therein, in another group of compounds, $R^3$ is F, Cl, amino or $C_{1-4}$alkyl where alkyl is linear or branched and saturated, preferably $R^3$ is fluoro, amino, methyl.

(iii) Within embodiments I, I(a), I(b), and II, and groups contained therein, in another group of compounds, A is five or six membered heterocyclyl, preferably, A is tetrahydropyranyl, piperidinyl, tetrahydrofuranyl, substituted with $R^1$ group as defined in the Summary. Within this group in one group of compounds $R^1$ is selected from F, Cl, $C_{1-4}$alkyl, $C_{1-4}$haloalkyl, OH, —$OC_{1-4}$alkyl, and —$OC_{1-4}$haloalkyl where the alkyl group is above groups is linear or branched and saturated. Preferably $R^1$ is methyl, fluoro, trifluoromethyl, hydroxyl, methoxy or trifluoromethoxy. Preferably, A is tetrahydropyranyl, piperidinyl, tetrahydrofuranyl and m is 0. Within this group, and groups contained therein, in one group of compounds, $R^3$ is F, Cl or $C_{1-4}$alkyl where alkyl is linear or branched and saturated. Within this group, and groups contained therein, in another group of compounds, $R^3$ is F, Cl, amino or $C_{1-4}$alkyl where alkyl is linear or branched and saturated, preferably $R^3$ is fluoro, amino, methyl.

(iv) Within embodiments I, I(a), I(b), and II, and groups contained therein, in another group of compounds, A is five or six membered heteroaryl, preferably, A is pyridinyl, thienyl, pyrimidinyl, furanyl, or pyrrolyl, substituted with $R^1$ group as defined in the Summary. Within this group, in one group of compounds $R^1$ is selected from F, Cl, $C_{1-4}$alkyl, $C_{1-4}$haloalkyl, OH, —$OC_{1-4}$alkyl, and —$OC_{1-4}$haloalkyl where the alkyl group is above groups is linear or branched and saturated. Preferably $R^1$ is methyl, fluoro, trifluoromethyl, hydroxyl, methoxy or trifluoromethoxy. Preferably, A is pyridinyl, thienyl, pyrimidinyl, furanyl, or pyrrolyl, and m is 0. Within this group, and groups contained therein, in one group of compounds, $R^3$ is F, Cl or $C_{1-4}$alkyl where alkyl is linear or branched and saturated. Within this group, and groups contained therein, in another group of compounds, $R^3$ is F, Cl, amino or $C_{1-4}$alkyl where alkyl is linear or branched and saturated, preferably $R^3$ is fluoro, amino, methyl.

(A) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in one group of compounds, in group

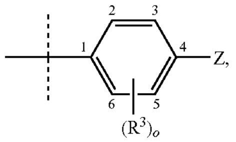

Z is cycloalkyl substituted with amino, monoalkylamino or dialkylamino; or cycloalkylalkyl substituted with one or two carboxy, preferably Z is 1-aminocycloprop-1-yl, 1-methylaminocycloprop-1-yl, 4-carboxycyclobutylmethyl, (cis)-3-carboxycyclobutylmethyl, (trans)-3-carboxycyclobutylmethyl, or 3,3-dicarboxycyclobutylmethyl. Within this group, in one group of compounds n is 0 and $R^3$ is fluoro, amino, or methyl and o is 1 or 2, preferably o is 1 and $R^3$ is fluoro and attached to the 2-position of the phenyl ring.

(B) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in another group of compounds, in group

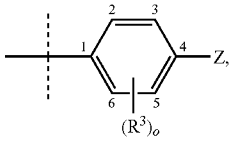

Z is monosubstituted amino, disubstituted amino, or sulfonylamino. Within this group, in one group of compounds n is 0 and $R^3$ is fluoro, amino, or methyl and o is 1 or 2, preferably o is 1 and $R^3$ is fluoro and attached to the 2-position of the phenyl ring.

(C) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in another group of compounds, in group

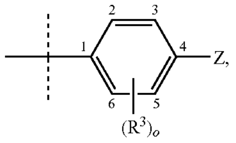

Z is heterocycloamino, heterocycloaminoalkyl, heterocycloaminocarbonyl, heterocycloaminooxy, or heteroaralkyl. Within this group in one group of compounds, the heterocycloamino ring in the above listed groups is pyrrolidinyl, piperidinyl, morpholinyl, or azetidinyl, each ring substituted as defined in the definition section. Preferably, Z is 1-(3-carboxyazetidin-1-yl)-ethyl, R-1-(3-carboxyazetidin-1-yl)ethyl, S-1-(3-carboxyazetidin-1-yl)-ethyl, (2S,4R)-2-carboxy-4-hydroxypyrrolidin-4-yl, (2R,4R)-2-carboxypyrrolidin-4-yl, (2S,4R)-2-carboxy-1-methylpyrrolidin-4-yl, (2S,4R)-2-carboxypyrrolidin-4-yl, 4-carboxylmidazol-1-ylmethyl, (2S,4R)-2-carboxypyrrolidin-4-yloxy, 3-hydroxyazetidin-1-ylmethyl, 3-carboxymethylazetidin-1-ylmethyl, 3-fluoroazetidin-1-ylmethyl, azetidin-1-ylmethyl, 2-oxopyrrolidin-1-yl, 3,3-difluoroazetidin-1-ylmethyl, 3-carboxypyrazol-1-ylmethyl, 4-carboxypyrazol-1-ylmethyl, 5-carboxypyrazol-1-yl-methyl, azetidin-1-ylcarbonyl, 3-carboxyazetidin-1-ylcarbonyl, morpholin-4-ylcarbonyl, (2S,4S)-2-hydroxymethylpyrrolidin-4-yl, 3R-carboxypyrrolidin-1-ylcarbonyl, 3R-carboxypiperidin-1-ylcarbonyl, or 5-carboxylmidazol-1-methyl. Within this group, and group contained therein, in one group of compounds, n is 0 and $R^3$ is fluoro, amino, or methyl and o is 1 or 2, preferably o is 1 and $R^3$ is fluoro and attached to the 2-position of the phenyl ring.

(D) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in another group of compounds, in group

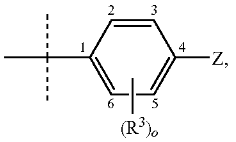

Z is carboxyalkylamino, hydroxyalkyl, substituted hydroxyalkyl, hydroxyalkoxy, substituted hydroxyalkoxy, aminoalkyl, aminoalkoxy, carboxyalkyl, substituted carboxyalkyl, carboxyalkoxyalkyl, substituted carboxyalkoxyalkyl, aminocarbonyl or acylamino. Within this group, in one group of compounds $R^3$ is fluoro, amino, methyl and o is 1 or 2. Within this group, and group contained therein, in one group of compounds, Z is carboxymethylNHCO-, 2-carboxyethyl-NHCO-, 3-carboxypropylNHCO-, 2-carboxyethylNHCH$_2$-, 1-(2-carboxyethylNH)ethyl, 1R-(2-carboxyethylNH)ethyl, 1S-(2-carboxyethylNH)ethyl, R-3-amino-3-carboxybutyl, 3-amino-3-$CH_2OP(O)(OH)_2$-4-hydroxybutyl, S-2-carboxy-2-hydroxyethylCONH-, R-1-amino-2-carboxyethylCONH-, S-1-amino-2-carboxyethylCONH-, R-2-hydroxy-2-carboxyethylCONH-, R-1-hydroxy-2-carboxyethylCONH-, 3-amino-3-carboxypropyl, R-2-amino-2-carboxyethyl-CONH-, S-2-amino-2-carboxyethylCONH-, 2-(carboxymethylamino)ethyl, S-1-hydroxy-2-carboxyethyl-CONH-, S-3-amino-3-carboxybutyl, 2-HOC(O)C(O)NH-ethyl, 3-carboxypropylamino, 2-carboxyethylamino, R-1-aminoethyl, 3-carboxypropyl, 3R-glyceryloxy, 3S-glyceryloxy, 2-amino-3-hydroxypropyl, 2-amino-2-hydroxymethyl-3-hydroxypropyl, 2-acetylaminoethyl, 2-hydroxyethyl, hydroxymethyl, 2-hydroxyethylNHCO-, S-1-hydroxy-2,2,2-trifluoroethyl, trifluoromethylCONH-, 2-hydroxymethyl-3-hydroxypropyl, 2-methoxyethylNHCO-, 2-aminoethyl, cyclopropylNHCO-, 1-hydroxy-2,2,2-trifluoroethyl, R-1-hydroxy-2,2,2-trifluoroethyl, 2-dimethylaminoethyl, 1-amino-1-methylethyl, 2-hydroxyethylN($CH_3$)CO-, 2-methylsulfonylaminoethyl, 2-methoxyethylN($CH_3$)CO-, 1-amino-2,2,2-trifluoroethyl, R-3-amino-3-carboxypropyl-, S-3-amino-3-carboxypropyl, 2-carboxyethyl, (S)-1-aminoethyl, 3-amino-3-hydroxymethyl-4-hydroxybutyl, 3-carboxypropylaminomethyl, 2-amino-2-carboxyethyl, 3-(azetidin-1-yl)propylaminomethyl, S-$CH_2NHCH(CH_3)CO_2H$, R—$CH_2NHCH(CH_3)CO_2H$, (1-carboxycyclopropyl)aminomethyl, —$CH_2NHC(CH_3)_2CO_2H$, carboxymethyloxymethyl, 1-hydroxyethyl, —$CH_2NHC(CH_3)_2$ $CH_2CO_2H$, —$CH_2NHCH(CH_3)$ $CH_2CO_2H$, —$CH(CH_3)NHCH(CH_3)CH_2CO_2H$, S-$CH_2NHCH(CH_3)$—$CH_2CO_2H$, R-$CH_2NHCH(CH_3)CH_2CO_2H$, (3S,1R)-$CH(CH_3)NHCH(CH_3)CH_2CO_2H$, (3R, 1S)—$CH(CH_3)NHCH(CH_3)CH_2CO_2H$, $CH_2CH(NH_2)CO_2H$, S-$CH_2CH(NH_2)CO_2H$, R—$CH_2CH(NH_2)CO_2H$, S-$(CH_2)_2CH(NH_2)CO_2H$, —$CONHC(CH_3)_2CH_2COOH$, —$CON(CH_3)$—$(CH_2)_2COOH$, —$CONHCH(CH_3)CH_2COOH$, —$NHCO(CH_2)_2COOH$, —$CH_2NHCH_2COOH$, or —$CONHCH(CH_3)CH_2COOH$. Within this group, and group contained therein, in one group of compounds, n is 0 and $R^3$ is fluoro, amino, or methyl and o is 1 or 2, preferably o is 1 and $R^3$ is fluoro and attached to the 2-position of the phenyl ring.

(E) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in another group of compounds, in group

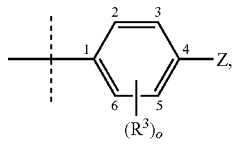

Z is a group of formula (b):

(b)

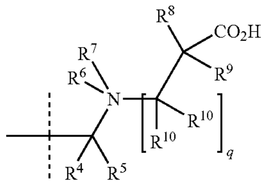

where:

q is 0, 1 or 2;

$R^4$ is selected from H, $C_{1-3}$haloalkyl, $C_{1-6}$alkyl; preferably H or linear or branched $C_{1-6}$alkyl; preferably $R^4$ is H or methyl;

$R^5$ is selected from H, $C_{1-3}$haloalkyl, $C_{1-4}$alkyl; preferably H or linear or branched $C_{1-6}$alkyl; preferably $R^5$ is H or methyl; or $R^4$ and $R^5$ together form a 3, 4, 5, 6 or 7-member carbocyclic ring substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl; preferably $R^4$ and $R^5$ together form cyclopropyl;

$R^6$ is a lone pair of electrons or O;

$R^7$ is H or $C_{1-6}$alkyl; preferably H or linear or branched $C_{1-6}$alkyl; preferably $R^7$ is H or methyl;

$R^8$ is selected from H, F, Cl, $C_{1-4}$alkyl, $C_{1-4}$haloalkyl, OH, —$OC_{1-4}$alkyl, and —$OC_{1-4}$haloalkyl; preferably H or linear or branched $C_{1-6}$alkyl; preferably $R^8$ is H or methyl; or $R^7$ and $R^8$ together is selected from —$(CR^{10}R^{10})$—, —$(CR^{10}R^{10})O$—, —$O(CR^{10}R^{10})$—, —$(CR^{10}R^{10})CR^{10}R^{10})$—, and —$(CR^{10}R^{10})_3$—; preferably $R^7$ and $R^8$ together is —$CH_2$—, —$(CH_2)_2$— or —$(CH_2)_3$—;

$R^9$ is selected from H, F, $C_{1-3}$haloalkyl, $C_{1-4}$alkyl, OH and $OC_{1-4}$alkyl; or $R^8$ and $R^9$ together with the carbon atom to which they are attached form cycloalkyl; preferably $R^9$ is H; and each $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; preferably H or linear or branched $C_{1-6}$alkyl; preferably $R^{10}$ is H or methyl.

Within this group of compounds, in one group of compounds:

q is 0, 1 or 2;

$R^4$ is selected from H, $C_{1-3}$haloalkyl, $C_{1-6}$alkyl; preferably or linear or branched $C_{1-6}$alkyl; preferably $R^4$ is H or methyl;

$R^5$ is selected from H, $C_{1-3}$haloalkyl, $C_{1-4}$alkyl; preferably or linear or branched $C_{1-6}$alkyl; preferably $R^5$ is H or methyl;

$R^6$ is a lone pair of electrons or O;

$R^7$ is H or $C_{1-6}$alkyl; preferably or linear or branched $C_{1-6}$alkyl; preferably $R^7$ is H or methyl;

$R^8$ is selected from H, F, Cl, $C_{1-4}$alkyl, $C_{1-4}$haloalkyl, OH, —$OC_{1-4}$alkyl, and —$OC_{1-4}$haloalkyl; preferably or linear or branched $C_{1-6}$alkyl; preferably $R^8$ is H or methyl;

$R^9$ is selected from H, F, $C_{1-3}$haloalkyl, $C_{1-4}$alkyl, OH and $OC_{1-4}$alkyl; preferably or linear or branched $C_{1-6}$alkyl; preferably $R^9$ is H or methyl; and each $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; preferably or linear or branched $C_{1-6}$alkyl; preferably $R^{10}$ is H or methyl.

Within this group of compounds, in another group of compounds:

q is 0, 1 or 2;

$R^4$ and $R^5$ together form a 3, 4, 5, 6 or 7-member carbocyclic ring substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl; preferably $R^4$ and $R^5$ together form cyclopropyl;

$R^6$ is a lone pair of electrons or O;

$R^7$ is H or $C_{1-6}$alkyl; preferably or linear or branched $C_{1-6}$alkyl; preferably $R^7$ is H or methyl;

$R^8$ is selected from H, F, Cl, $C_{1-4}$alkyl, $C_{1-4}$haloalkyl, OH, —$OC_{1-4}$alkyl, and —$OC_{1-4}$haloalkyl; preferably or linear or branched $C_{1-6}$alkyl; preferably $R^8$ is H or methyl;

$R^9$ is selected from H, F, $C_{1-3}$haloalkyl, $C_{1-4}$alkyl, OH and $OC_{1-4}$alkyl; preferably or linear or branched $C_{1-6}$alkyl; preferably $R^9$ is H or methyl; and each $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; preferably or linear or branched $C_{1-6}$alkyl; preferably $R^{10}$ is H or methyl.

Within this group of compounds, in yet another group of compounds:

q is 0, 1 or 2;

$R^4$ is selected from H, $C_{1-3}$haloalkyl, $C_{1-6}$alkyl; preferably or linear or branched $C_{1-6}$alkyl; preferably $R^4$ is H or methyl;

$R^5$ is selected from H, $C_{1-3}$haloalkyl, $C_{1-4}$alkyl; preferably or linear or branched $C_{1-6}$alkyl; preferably $R^5$ is H or methyl;

$R^6$ is a lone pair of electrons or O;

$R^7$ and $R^8$ together is selected from —$(CR^{10}R^{10})$—, —$(CR^{10}R^{10})O$—, —$O(CR^{10}R^{10})$—, —$(CR^{10}R^{10})(CR^{10}R^{10})$—, and —$(CR^{10}R^{10})_3$—; preferably $R^7$ and $R^8$ together is —$CH_2$—, —$(CH_2)_2$— or —$(CH_2)_3$—;

$R^9$ is selected from H, F, $C_{1-3}$haloalkyl, $C_{1-4}$alkyl, OH and $OC_{1-4}$alkyl; preferably or linear or branched $C_{1-6}$alkyl; preferably $R^9$ is H or methyl; and each $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; preferably or linear or branched $C_{1-6}$alkyl; preferably $R^{10}$ is H or methyl.

Within this group, and groups contained therein, in one group of compounds, n is 0 and $R^3$ is fluoro, amino, or methyl and o is 1 or 2 and Z is 3-carboxyazetidin-1-ylmethyl, 3-carboxy-3-hydroxyazetidin-1-ylmethyl, 3-carboxy-3-fluoroazetidin-1-ylmethyl, 3-carboxypyrrolidin-1-ylmethyl, R-3-carboxypyrrolidin-1-ylmethyl, S-3-carboxypyrrolidin-1- ylmethyl, 1R,3S-3-carboxy-N-oxoazetidin-1-ylmethyl, 1S,3R-3-carboxy-N-oxoazetidin-1-ylmethyl, R-1-(3-carboxyazetidin-1-yl)-ethyl, S-1-(3-carboxyazetidin-1-yl)-ethyl, 1-(2-carboxyethylamino)-1-methylethyl, (2S,4R)-2-carboxy-4-hydroxypyrrolidin-4-yl, R-2-carboxyazetidin-1-ylmethyl, S-2-carboxyazetidin-1-ylmethyl, R-2-carboxypyrrolidin-1-ylmethyl, or S-2-carboxypyrrolidin-1-ylmethyl. Within this group, and group contained therein, in one group of compounds, preferably o is 1 and $R^3$ is fluoro and attached to the 2-position of the phenyl ring and Z is 3-carboxyazetidin-1-ylmethyl, 3-carboxypyrrolidin-1-ylmethyl, R-3-carboxypyrrolidin-1-ylmethyl, or S-3-carboxypyrrolidin-1-ylmethyl.

(F) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in another group of compounds, in group

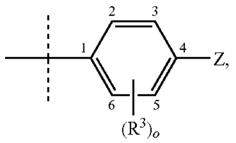

Z is where $R^3$ is on carbon atom on the phenyl ring that is adjacent to carbon carrying Z, and $R^3$ and Z can combine to form —CH═CH—$NR^{11}$—, —$(CH_2)_2NR^{11}$—, —$CH_2NR^{11}CH_2$—, —$(CH_2)_2NR^{11}CH_2$—, —N═$CR^{11}$—NH—, or —N═CH—$NR^{11}$—, where $R^{11}$ is selected from hydrogen, hydroxyalkyl, aminoalkyl, carboxyalkyl, substituted hydroxyalkyl or substituted carboxyalkyl; or aminocarbonyl. Within this group, in one group of compounds $R^3$ is fluoro, amino, methyl and o is 1 or 2. Within this group, and group contained therein, in one group of compounds,

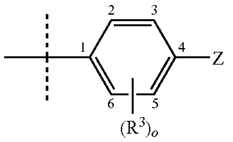

is 2-carboxyethylindol-5-yl, indol-5-yl, 3-carboxypropylindol-5-yl, 1,2,3,4-tetrahydroisoquinolin-6-yl, 1-carboxymethylindol-5-yl, 2-(2-carboxyethyl)-3,4-dihydro-2-(1H)-isoquinolin-6-yl, 2-(carboxymethyl)-3,4-dihydro-2-(1H)-isoquinolin-6-yl, 2-(2-carboxyethyl)-1,3-dihydro-2-(1H)-indol-5-yl, 2-(carboxymethyl)-1,3-dihydro-2-(1H)-indol-5-yl, 1-(2-carboxyethyl)-benzimidazol-6-yl, or 1-(2-carboxyethyl)-benzimidazol-5-yl. Within this group, and group contained therein, in one group of compounds, n is 0 and $R^3$ is fluoro, amino, or methyl and o is 1 or 2, preferably o is 1 and $R^3$ is fluoro and attached to the 2-position of the phenyl ring.

(G) Within embodiments I, I(a), I(b), I(a)(i), I(a)(ii), I(a)(iii), I(a)(iv), I(b)(i), I(b)(ii), I(b)(iii), I(b)(iv), II, I(i), I(ii), I(iii), I(iv), II(i), II(ii), II(iii), and II(iv), and groups contained therein, in another group of compounds, in group

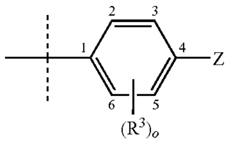

is 2-fluoro-4-(3-carboxyazetidin-1-ylmethyl)phenyl; 2-fluoro-4-(3-carboxy-3-hydroxyazetidin-1-ylmethyl)phenyl; 2-fluoro-4-(3-carboxy-3-fluoroazetidin-1-ylmethyl)phenyl; 2-fluoro-4-(3-carboxypyrrolidin-1-ylmethyl)phenyl; 2-fluoro-4-(R-3-carboxypyrrolidin-1-ylmethyl)phenyl; 2-fluoro-4-(carboxymethylNHCO-)phenyl; 2-fluoro-4-(2-carboxyethylNHCO-)phenyl; 2-fluoro-4-(3-carboxypropyl-NHCO-)phenyl; 2-fluoro-4-(S-3-carboxypyrrolidin-1-ylmethyl)phenyl; 2-fluoro-4-(2-carboxyethylNH$CH_2$-)phenyl; 2-fluoro-4-(1R,3S-3-carboxy-N-oxoazetidin-1-ylmethyl)phenyl; 2-fluoro-4-(1S,3R-3-carboxy-N-oxoazetidin-1-ylmethyl)phenyl; 2-fluoro-4-[R-1-(3-carboxyazetidin-1-yl)-ethyl)phenyl; 2-fluoro-4-[S-1-(3-carboxyazetidin-1-yl)-ethyl)phenyl; 2-fluoro-4-(R-2-amino-2-carboxyethylCONH-)phenyl; 2-fluoro-4-(S-2-amino-2-carboxyethylCONH-)phenyl; 2-fluoro-4-(2-(carboxymethylaminoethyl)phenyl; 2-fluoro-4-[(2R,4R)-2-carboxypyrrolidin-4-yl]phenyl; 2-fluoro-4-(S-1-hydroxy-2-carboxyethylCONH-)phenyl; 2-fluoro-4-[(2S,4R)-2-carboxy-1-methylpyrrolidin-4-yl]phenyl; 2-fluoro-4-(S-3-amino-3-carboxybutyl)phenyl; 2-fluoro-4-(R-3-amino-3-carboxybutyl)phenyl; 2-fluoro-4-(3-amino-3-$CH_2OP(O)(OH)_2$-4-hydroxybutyl)phenyl; 2-fluoro-4-(S-2-carboxy-2-hydroxyethylCONH-)phenyl, 2-fluoro-4-(S-1-amino-2-carboxyethylCONH-)phenyl, 2-fluoro-4-(R-1-amino-2-carboxyethylCONH-)phenyl, 2-fluoro-4-(R-2-hydroxy-2-carboxyethylCONH-)phenyl, 2-fluoro-4-(R-1-hydroxy-2-carboxyethylCONH-)phenyl, 2-fluoro-4-[(2S,4R)-2-carboxy-4-hydroxypyrrolidin-4-yl]phenyl, 2-fluoro-4-[(2S,4R)-2-carboxypyrrolidin-4-yl]phenyl; 1-(2-carboxyethyl-1,2,3,4-tetrahydroisoquinolin-6-yl; 2-fluoro-4-(4-carboxylmidazol-1-ylmethyl)phenyl; 2-fluoro-4-(cis-3-carboxycyclopropylamino]-phenyl; 4-(4-carboxyethylamino)-phenyl; 2-fluoro-4-(3-hydroxyazetidin-1-ylmethyl)phenyl; 2-fluoro-4-(trans-3-carboxycyclopropylamino]-phenyl; 2-fluoro-4-(2-HOC(O)C(O)NH-ethyl)-phenyl; 2-fluoro-4-(3-carboxypropyl-amino)-phenyl; 2-fluoro-4-(3-carboxymethylazetidin-1-ylmethyl)phenyl; 2-fluoro-4-(2-carboxyethylamino)-phenyl; 2-fluoro-4-(4-carboxypyrazol-1-ylmethyl)-phenyl; 2-fluoro-4-[(2S,4R)-2-carboxypyrrolidin-4-yloxy]phenyl; 2-fluoro-4-(R-2-carboxyazetidin-1-ylmethyl)phenyl; 2-fluoro-4-(S-2-carboxyazetidin-1-ylmethyl)phenyl; 2-fluoro-4-(R-1-aminoethyl)phenyl; 2-fluoro-4-(3-carboxypropyl)phenyl; 1-(2-carboxyethyl)indol-5-yl; 3,5-dimethyl-4-(3R-glyceryloxy)phenyl; 2-fluoro-4-(R-2-carboxypyrrolidin-1-ylmethyl)-phenyl; 2-fluoro-4-(2-dimethylaminoethyl)-phenyl; 2-fluoro-4-(3-fluoroazetidin-1-ylmethyl)phenyl; 2-fluoro-4-(S-2-carboxypyrrolidin-1-ylmethyl)phenyl; 3-carboxypropylindol-5-yl; 3,5-dimethyl-4-(3S-glyceryloxy)phenyl; 2-fluoro-4-(1-methylaminocycloprop-1-yl)phenyl; 3,5-dimethyl-4-(azetidin-1-ylmethyl)phenyl; 2-fluoro-4-(2-amino-3-hydroxypropyl)phenyl; 2-fluoro-4-(2-amino-2-hydroxymethyl-3-hydroxypropyl)phenyl; 2-fluoro-4-(2-acetylaminoethyl)phenyl; indol-5-yl; 3,5-dimethyl-4-[3-azetidin-1-ylpropyl)aminomethyl]-phenyl; 4-(hydroxymethyl)-3-methylphenyl; 2-fluoro-4-(2-hydroxyethyl)phenyl; 3,5-dimethyl-4-(hydroxymethyl)phenyl;

2-fluoro-4-(2-hydroxyethylNHCO-)-phenyl; 2-fluoro-4-(N,N-bis-methylsulfonylamino)phenyl; 2-fluoro-4-(2-oxopyrrolidin-1-yl)phenyl; 2-fluoro-4-(1-hydroxy-2,2,2-trifluoroethyl)-phenyl; 3-methyl-4-(3-carboxyazetidin-1-ylmethyl)phenyl, 3,5-dimethyl-4-(3-carboxyazetidin-1-ylmethyl)phenyl, 2-methyl-4-(3-carboxyazetidin-1-ylmethyl)phenyl, 2-fluoro-4-(azetidin-1-ylmethyl)phenyl, 2-fluoro-4-(1-amino-1-methylethyl)phenyl, 2-fluoro-4-[1-(2-carboxyethylamino)-1-methylethyl]-phenyl, 2-fluoro-4-[R-1-(3-carboxyazetidin-1-yl)propyl]phenyl, 2-fluoro-4-[S-1-(3-carboxyazetidin-1-yl)propyl]phenyl, 2-fluoro-4-(S-1-hydroxy-2,2,2-trifluoroethyl)-phenyl; 2-fluoro-4-(trifluoromethyl-CONH-)-phenyl; 2-fluoro-4-(2-hydroxymethyl-3-hydroxypropyl)phenyl; 2-fluoro-4-(2-methoxyethylNHCO-)phenyl; 4-hydroxymethyl-2-methylphenyl; 2-fluoro-4-(3,3-difluoroazetidin-1-ylmethyl)phenyl; 2-fluoro-4-(2-aminoethyl)phenyl; 2-fluoro-4-(3-carboxypyrazol-1-ylmethyl)phenyl; 4-hydroxymethyl-phenyl; 1,2,3,4-tetrahydroisoquinolin-6-yl; 2-fluoro-4-(4-carboxycyclobutylmethyl)-phenyl; 2-fluoro-4-(cyclopropylNHCO-)phenyl; 2-fluoro-4-(2-carboxyethyl$SO_2$NH)-phenyl; 2-fluoro-4-(5-carboxypyrazol-1-yl-methyl)phenyl; 2-fluoro-4-(cis)-3-carboxycyclobutylmethyl]phenyl; 2-fluoro-4-(R-1-hydroxy-2,2,2-trifluoroethyl)phenyl; 1-carboxymethylindol-5-yl; 2-fluoro-4-(2-hydroxyethylN($CH_3$)CO-)-phenyl; 2-fluoro-4-(trans)-3-carboxycyclobutylmethyl]phenyl]; 2-fluoro-4-(2-methylsulfonylaminoethyl)-phenyl; 2-fluoro-4-(3,3-dicarboxycyclobutyl-methyl)$_p$-ethylN($CH_3$)CO-)-phenyl; 2-fluoro-4-(morpholin-4-ylcarbonyl)phenyl; 2-fluoro-4-(1-amino-2,2,2-trifluoroethyl)phenyl; 2-fluoro-4-(R-3-amino-3-carboxypropyl-)-phenyl; 2-fluoro-4-(S-3-amino-3-carboxypropyl)-phenyl; 2-fluoro-4-hydroxymethylphenyl; 2-fluoro-4-(1R-(2-carboxyethylNH)ethyl)phenyl, 2-fluoro-4-(1S-(2-carboxyethylNH)ethyl)phenyl, 2-fluoro-4-(1-(2-carboxyethylNH)ethyl)-phenyl, 1S-(2-carboxyethylNH)ethyl, 2-fluoro-2-carboxyethyl-phenyl; 4-[(S)-1-aminoethyl]-2-fluorophenyl; 2-fluoro-4-(3-amino-3-hydroxymethyl-4-hydroxybutyl)phenyl; 2-fluoro-4-[(2S,4S)-2-hydroxymethylpyrrolidin-4-yl]-phenyl; 4-(3-carboxyazetidin-1-yl-methyl)phenyl; 2-fluoro-4-(S-$CH_2$NHCH($CH_3$)$CO_2$H)-phenyl; 2-fluoro-4-(R-$CH_2$NHCH($CH_3$)$CO_2$H)-phenyl; 2-fluoro-4-[(1-carboxycyclopropyl)-aminomethyl]-phenyl; 2-fluoro-4-(—$CH_2$NHC($CH_3$)$_2$ $CO_2$H))-phenyl; 2-(2-carboxyethyl)-3,4-dihydro-2-(1H)-isoquinolin-6-yl; 2-(carboxymethyl)-3,4-dihydro-2-(1H)-isoquinolin-6-yl; 2-fluoro-4-(carboxymethyloxymethyl)-phenyl; 2-fluoro-4-(1-hydroxyethyl)phenyl; 2-fluoro-4-(—$CH_2$NHC($CH_3$)$_2$ $CH_2CO_2$H)-phenyl; 2-fluoro-4-(—$CH_2$NHC($CH_2$)$_3$$CO_2$H)-phenyl; 2-fluoro-4-(—$CH_2$NHCH($CH_3$)$CH_2CO_2$H)-phenyl; 2-fluoro-4-(—CH($CH_3$)NHCH($CH_3$) $CH_2CO_2$H)-phenyl; 2-fluoro-4-(S-$CH_2$NHCH($CH_3$)$CH_2CO_2$H)-phenyl; 2-fluoro-4-(R—$CH_2$NHCH($CH_3$)$CH_2CO_2$H)-phenyl; 2-fluoro-4-[(3S,1R)-CH($CH_3$)NHCH($CH_3$)$CH_2CO_2$H]-phenyl; 2-fluoro-4-[(3R,1S)-CH($CH_3$)NHCH($CH_3$)$CH_2CO_2$H]-phenyl; 2-fluoro-4-[$CH_2$CH($NH_2$)$CO_2$H]-phenyl; 2-fluoro-4-[S-$CH_2$CH($NH_2$)$CO_2$H]-phenyl; 2-fluoro-4-[R—$CH_2$CH($NH_2$)$CO_2$H]-phenyl; 2-fluoro-4-[(S-($CH_2$)$_2$CH($NH_2$)$CO_2$H]-phenyl; 2-fluoro-4-(3R-carboxypyrrolidin-1-yl-carbonyl)phenyl; 2-fluoro-4-(3R-carboxypiperidin-1-ylcarbonyl)-phenyl; 2-fluoro-4-(3-carboxyazetidin-1-ylcarbonyl)phenyl; 2-fluoro-4-(—CONHC($CH_3$)$_2$$CH_2$—COOH)-phenyl; 2-fluoro-4-[—CON($CH_3$)($CH_2$)$_2$COOH]-phenyl; 2-fluoro-4-(—CONHCH($CH_3$)—$CH_2$COOH)-phenyl; 2-fluoro-4-(—NHCO($CH_2$)$_2$COOH)-phenyl; 2-fluoro-4-(—$CH_2$NH$CH_2$COOH)-phenyl; benzimidazol-5-yl; 2-(2-carboxyethyl)-1,3-dihydro-2-(1H)-isoindol-5-yl; 2-(carboxymethyl)-1,3-dihydro-2-(1H)-isoindol-5-yl; 1-(2-carboxyethyl)-benzimidazol-6-yl; 1-(2-carboxyethyl)-benzimidazol-5-yl; or 2-fluoro-4-(—CONHCH($CH_3$)—$CH_2$COOH)-phenyl. Preferably, 2-fluoro-4-(3-carboxyazetidin-1-ylmethyl)phenyl; 4-(3-carboxyazetidin-1-ylmethyl)phenyl, 3-methyl-4-(3-carboxyazetidin-1-ylmethyl)phenyl, 2-methyl-4-(3-carboxyazetidin-1-ylmethyl)phenyl, 2-amino-4-(3-carboxyazetidin-1-ylmethyl)phenyl, 2-fluoro-4-[R-1-(3-carboxyazetidin-1-yl)-ethyl)phenyl, 2-fluoro-4-[S-1-(3-carboxyazetidin-1-yl)-ethyl)phenyl, 2-fluoro-4-(R-3-carboxypyrrolidin-1-ylmethyl)phenyl, 2-fluoro-4-(S-3-carboxypyrrolidin-1-ylmethyl)phenyl, 2-fluoro-4-(2-carboxyethylNH$CH_2$)phenyl, 2-fluoro-4-[(2S,4R)-2-carboxy-1-methylpyrrolidin-4-yl]phenyl, 2-fluoro-4-[(2S,4R)-2-carboxypyrrolidin-4-yl]phenyl, 2-fluoro-4-(S-3-amino-3-carboxybutyl)-phenyl, 2-fluoro-4-(R-3-amino-3-carboxybutyl)-phenyl, 2-fluoro-4-[(S-($CH_2$)$_2$CH($NH_2$)$CO_2$H]-phenyl, 2-fluoro-4-[(R-($CH_2$)$_2$CH($NH_2$)$CO_2$H]-phenyl, 2-fluoro-4-[(1-carboxy)aminomethyl]-phenyl, 2-fluoro-4-(—NHCO($CH_2$)$_2$COOH)-phenyl, 2-fluoro-4-(S-2-carboxy-2-hydroxyethylCONH-)phenyl, or 2-fluoro-4-(S-1-amino-2-carboxyethylCONH-)phenyl.

Within this group, and group contained therein, in one group of compounds, n is 0 and $R^3$ is fluoro, amino, or methyl and o is 1 or 2.

(IV). Within compounds of Formula (Ia):

In one embodiment, in conjunction with any above or below embodiments,

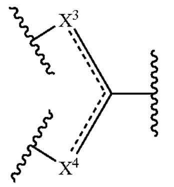

is selected from

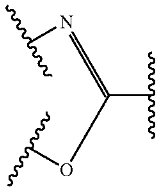

and

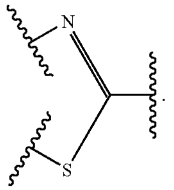

In another embodiment, in conjunction with any above or below embodiments,

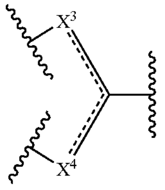

is

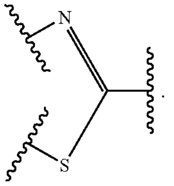

In another embodiment, in conjunction with any above or below embodiments,

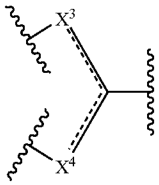

is selected from

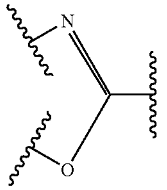
,
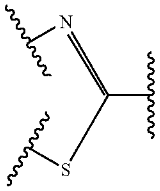
,
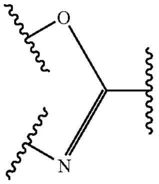
and
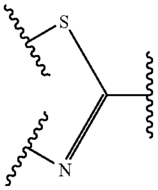
.

In another embodiment, in conjunction with any above or below embodiments, $X^1$ is N; and $X^2$ is CH.

In another embodiment, in conjunction with any above or below embodiments, $X^1$ is N; and $X^2$ is N.

In another embodiment, in conjunction with any above or below embodiments, $X^1$ is CH; and $X^2$ is N.

In another embodiment, in conjunction with any above or below embodiments, L is a saturated 3, 4 or 5-member ring substituted by 0, 1 or 2 groups selected from F, Cl, $C_{1-4}$alkyl, $C_{1-4}$haloalkyl, OH, $OC_{1-4}$alkyl, and $OC_{1-4}$haloalkyl.

In another embodiment, in conjunction with any above or below embodiments, L is an unsubstituted saturated 3, 4 or 5-member ring.

In another embodiment, in conjunction with any above or below embodiments, L is a saturated 3, 4 or 5-member ring substituted by 1 or 2 groups selected from F, Cl, $C_{1-4}$alkyl, $C_{1-4}$haloalkyl, OH, $OC_{1-4}$alkyl, and $OC_{1-4}$haloalkyl.

In another embodiment, in conjunction with any above or below embodiments, L is cyclopropyl substituted by 1 or 2 groups selected from F, Cl, $C_{1-4}$alkyl, $C_{1-4}$haloalkyl, OH, $OC_{1-4}$alkyl, and $OC_{1-4}$haloalkyl.

In another embodiment, in conjunction with any above or below embodiments, L is cyclopropyl.

In another embodiment, in conjunction with any above or below embodiments, m is 0 or 1; n is 0 or 1; and o is 1 or 2.

In another embodiment, in conjunction with any above or below embodiments, m is 0.

In another embodiment, in conjunction with any above or below embodiments, n is 0.

In another embodiment, in conjunction with any above or below embodiments, o is 1 or 2.

In another embodiment, in conjunction with any above or below embodiments, $R^7$ and $R^8$, when taken together, form a group that is selected from —$(CR^{10}R^{10})$—, —$(CR^{10}R^{10})$O—, —O$(CR^{10}R^{10})$— and —$(CR^{10}R^{10})(CR^{10}R^{10})$—.

In another embodiment, in conjunction with any above or below embodiments, $R^7$ and $R^8$, when taken together, form a group that is selected from —$(CR^{10}R^{10})$— and —$(CR^{10}R^{10})(CR^{10}R^{10})$—.

In another embodiment, in conjunction with any above or below embodiments, $R^7$ and $R^8$, when taken together, form a group that is —$(CR^{10}R^{10})$—.

In another embodiment, in conjunction with any above or below embodiments, $R^7$ and $R^8$, when taken together, form a group that is $CH_2$; q is 1; $R^9$ is H; and $R^{10}$ is H.

In another embodiment, in conjunction with any above or below embodiments, $R^1$ is F; $R^2$ is F; $R^3$ is F; $R^4$ is H; $R^5$ is H; and $R^6$ is a lone pair of electrons.

In another embodiment, in conjunction with any above or below embodiments, $R^1$ is F; and m is 1.

In another embodiment, in conjunction with any above or below embodiments, $R^2$ is F; and n is 1.

In another embodiment, in conjunction with any above or below embodiments, $R^3$ is F; and o is 1.

In another embodiment, in conjunction with any above or below embodiments, $R^4$ is selected from $C_{1-3}$haloalkyl and $C_{1-4}$alkyl; and $R^5$ is H.

In another embodiment, in conjunction with any above or below embodiments, $R^4$ and $R^5$ together form a 3, 4, 5, 6 or 7-member carbocyclic ring substituted by 0, 1 or 2 groups selected from F, Cl, $C_{1-4}$alkyl, $C_{1-4}$haloalkyl, OH, $OC_{1-4}$alkyl, and $OC_{1-4}$haloalkyl.

In another embodiment, in conjunction with any above or below embodiments, $R^4$ and $R^5$ together form a 3-member carbocyclic ring substituted by 0, 1 or 2 groups selected from F, Cl, $C_{1-4}$alkyl, $C_{1-4}$haloalkyl, OH, $OC_{1-4}$alkyl, and $OC_{1-4}$haloalkyl.

In another embodiment, in conjunction with any above or below embodiments, $R^4$ and $R^5$ together form cyclopropyl.

In another embodiment, in conjunction with any above or below embodiments, $R^6$ is a lone pair of electrons.

In another embodiment, in conjunction with any above or below embodiments, $R^6$ is O.

Representative compounds of the Invention where $R^1$ and $R^2$ are hydrogen and other groups are as shown in shown in Table 1 below are:

TABLE I

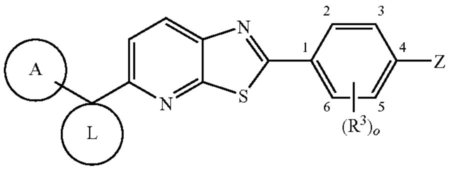

| Cpd # | A | 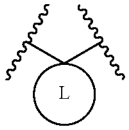 | 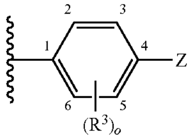 | Salt |
|---|---|---|---|---|
| 1 | phenyl | cyclopropyl | 2-fluoro-4-(3-carboxyazetidin-1-ylmethyl)phenyl | |
| 2 | phenyl | cyclopent-3-enyl | 2-fluoro-4-(3-carboxyazetidin-1-ylmethyl)phenyl | |
| 3 | phenyl | cyclopropyl | 2-fluoro-4-(3-carboxy-3-hydroxyazetidin-1-ylmethyl)phenyl | HCl |
| 4 | phenyl | cyclopropyl | 2-fluoro-4-(3-carboxy-3-fluoroazetidin-1-ylmethyl)phenyl | HCl |
| 5 | phenyl | cyclopentyl | 2-fluoro-4-(3-carboxyazetidin-1-ylmethyl)phenyl | |
| 6 | phenyl | cyclopropyl | 2-fluoro-4-[1-(2-carboxyethylNH)ethyl]phenyl | HCl |
| 7 | phenyl | cyclopropyl | 2-fluoro-4-(3-carboxypyrrolidin-1-ylmethyl)phenyl | HCl |
| 8 | phenyl | cyclopropyl | 2-fluoro-4-(carboxymethylNHCO—)phenyl | |
| 9 | phenyl | cyclopropyl | 2-fluoro-4-(2-carboxyethylNHCO—)phenyl | |
| 10 | phenyl | cyclopropyl | 2-fluoro-4-(3-carboxypropylNHCO—)phenyl | |
| 11 | phenyl | cyclopropyl | 2-fluoro-4-(S-3-carboxypyrrolidin-1-ylmethyl)phenyl | |
| 12 | phenyl | cyclopropyl | 2-fluoro-4-(2-carboxyethylNHCH$_2$—)phenyl | HCl |
| 13 | phenyl | cyclopropyl | 2-fluoro-4-[(1R,3S)-3-carboxy-N-oxoazetidin-1-ylmethyl]phenyl | |
| 14 | phenyl | cyclopropyl | 2-fluoro-4-[(1S,3R)-3-carboxy-N-oxoazetidin-1-ylmethyl)]henyl | |
| 15 | phenyl | cyclopropyl | 2-fluoro-4-[R-1-(3-carboxyazetidin-1-yl)-ethyl)phenyl | |
| 16 | phenyl | cyclopropyl | 2-fluoro-4-[S-1-(3-carboxyazetidin-1-yl)-ethyl)phenyl | |
| 17 | phenyl | cyclohexyl | 2-fluoro-4-(3-carboxyazetidin-1-ylmethyl)phenyl | |
| 18 | phenyl | cyclopropyl | 2-fluoro-4-[1-(2-carboxyethylNH)ethyl]phenyl | HCl |
| 19 | phenyl | oxetan-2-yl | 2-fluoro-4-(3-carboxyazetidin-1-ylmethyl)phenyl | |
| 20 | phenyl | cyclopropyl | 2-fluoro-4-(1-hydroxy-2,2,2-trifluoroethyl)phenyl | |
| 21 | phenyl | cyclopropyl | 3-methyl-4-(3-carboxyazetidin-1-ylmethyl)phenyl | |
| 22 | phenyl | cyclopropyl | 3,5-dimethyl-4-(3-carboxyazetidin-1-ylmethyl)phenyl | |
| 23 | phenyl | cyclopropyl | 2-methyl-4-(3-carboxyazetidin-1-ylmethyl)phenyl | |
| 24 | phenyl | cyclopropyl | 2-fluoro-4-(R-3-amino-3-carboxybutyl)phenyl | |
| 25 | phenyl | cyclopropyl | 2-fluoro-4-(3-amino-3-CH$_2$OP(O)(OH)$_2$-4-hydroxybutyl) phenyl | |
| 26 | phenyl | cyclopropyl | 2-fluoro-4-(S-2-carboxy-2-hydroxyethylCONH—)phenyl | |
| 27 | phenyl | cyclopropyl | 2-fluoro-4-(S-1-amino-2-carboxyethylCONH—)phenyl | TFA |
| 28 | phenyl | cyclopropyl | 2-fluoro-4-(R-1-amino-2-carboxyethylCONH—)phenyl | TFA |
| 29 | phenyl | cyclopropyl | 2-fluoro-4-(R-2-hydroxy-2-carboxyethylCONH—)phenyl | |
| 30 | phenyl | cyclopropyl | 2-fluoro-4-(R-1-hydroxy-2-carboxyethylCONH—)phenyl | |
| 31 | phenyl | cyclopropyl | 2-fluoro-4-[(2S,4R)-2-carboxy-4-hydroxypyrrolidin-4-yl]phenyl | TFA |
| 32 | phenyl | cyclopropyl | 2-fluoro-4-(R-3-amino-3-carboxypropyl)phenyl | HCl |
| 33 | phenyl | cyclopropyl | 2-fluoro-4-(R-2-amino-2-carboxyethylCONH—)phenyl | TFA |
| 34 | phenyl | cyclopropyl | 2-fluoro-4-(S-2-amino-2-carboxyethylCONH—)phenyl | TFA |
| 35 | phenyl | cyclopropyl | 2-fluoro-4-(2-(carboxymethylamino)ethyl)phenyl | |
| 36 | phenyl | cyclopropyl | 2-fluoro-4-[(2R,4R)-2-carboxypyrrolidin-4-yl]phenyl | |
| 37 | phenyl | cyclopropyl | 2-fluoro-4-(S-1-hydroxy-2-carboxyethylCONH—)phenyl | |
| 38 | phenyl | cyclopropyl | 2-fluoro-4-[(2S,4R)-2-carboxy-1-methylpyrrolidin-4-yl]phenyl | TFA |
| 39 | phenyl | cyclopropyl | 2-fluoro-4-(S-3-amino-3-carboxybutyl)phenyl | |
| 40 | phenyl | cyclopropyl | 2-fluoro-4-[(2S,4R)-2-carboxypyrrolidin-4-yl]phenyl | TFA |
| 41 | phenyl | cyclopropyl | 1-(2-carboxyethyl)-1,2,3,4-tetrahydroisoquinolin-6-yl | |
| 42 | phenyl | cyclopropyl | 2-fluoro-4-(4-carboxyimidazol-1-ylmethyl)phenyl | HCl |
| 43 | phenyl | cyclopropyl | 2-fluoro-4-(cis-3-carboxycyclobutylamino]phenyl | |
| 44 | phenyl | cyclopropyl | 4-(2-carboxyethylamino)-phenyl | TFA |
| 45 | phenyl | cyclopropyl | 2-fluoro-4-(3-hydroxyazetidin-1-ylmethyl)phenyl | TFA |
| 46 | phenyl | cyclopropyl | 2-fluoro-4-(trans-3-carboxycyclobutylamino]phenyl | |
| 47 | phenyl | cyclopropyl | 2-fluoro-4-(1-aminocycloprop-1-yl)phenyl | |
| 48 | phenyl | cyclopropyl | 2-fluoro-4-(azetidin-1-ylmethyl)phenyl | |
| 49 | phenyl | cyclopropyl | 2-fluoro-4-(2-HOC(O)C(O)NH-ethyl)-phenyl | |
| 50 | phenyl | cyclopropyl | 2-fluoro-4-(3-carboxypropylamino)-phenyl | |
| 51 | phenyl | cyclopropyl | 2-fluoro-4-(3-carboxymethylazetidin-1-ylmethyl)phenyl | TFA |
| 52 | phenyl | cyclopropyl | 2-fluoro-4-(2-carboxyethylamino)-phenyl | TFA |
| 53 | phenyl | cyclopropyl | 2-fluoro-4-(4-carboxypyrazol-1-ylmethyl)-phenyl | HCl |
| 54 | phenyl | cyclopropyl | 2-fluoro-4-[(2S,4R)-2-carboxypyrrolidin-4-yloxy]phenyl | TFA |
| 55 | phenyl | cyclopropyl | 2-fluoro-4-(R-2-carboxyazetidin-1-ylmethyl)phenyl | TFA |
| 56 | phenyl | cyclopropyl | 2-fluoro-4-(S-2-carboxyazetidin-1-ylmethyl)phenyl | TFA |
| 57 | phenyl | cyclopropyl | 2-fluoro-4-(R-1-aminoethyl)phenyl | |
| 58 | phenyl | cyclopropyl | 2-fluoro-4-(3-carboxypropyl)phenyl | |
| 59 | phenyl | cyclopropyl | 1-(2-carboxyethyl)indol-5-yl | |
| 60 | phenyl | cyclopropyl | 2-fluoro-4-(1-amino-1-methylethyl)phenyl | |
| 61 | phenyl | cyclopropyl | 3,5-dimethyl-4-(3R-glyceryloxy)phenyl | TFA |
| 62 | phenyl | cyclopropyl | 2-fluoro-4-(R-2-carboxypyrrolidin-1-ylmethyl)phenyl | TFA |

TABLE I-continued

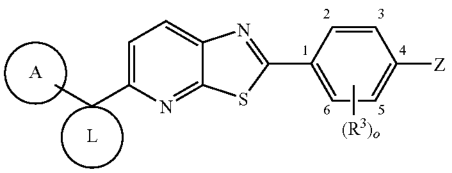

| Cpd # | A | 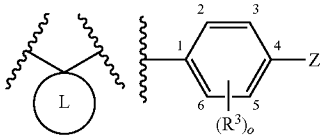 | | Salt |
|---|---|---|---|---|
| 63 | phenyl | cyclopropyl | 2-fluoro-4-(2-dimethylaminoethyl)-phenyl | |
| 64 | phenyl | cyclopropyl | 2-fluoro-4-(3-fluoroazetidin-1-ylmethyl)phenyl | |
| 65 | phenyl | cyclopropyl | 2-fluoro-4-(S-2-carboxypyrrolidin-1-ylmethyl)phenyl | TFA |
| 66 | phenyl | cyclopropyl | 3-carboxypropylindol-5-yl | |
| 67 | phenyl | cyclopropyl | 3,5-dimethyl-4-(3S-glyceryloxy)phenyl | TFA |
| 68 | phenyl | cyclopropyl | 2-fluoro-4-(1-methylaminocycloprop-1-yl)phenyl | |
| 69 | phenyl | cyclopropyl | 3,5-dimethyl-4-(azetidin-1-ylmethyl)phenyl | |
| 70 | phenyl | cyclopropyl | 2-fluoro-4-(2-amino-3-hydroxypropyl)phenyl | |
| 71 | phenyl | cyclopropyl | 2-fluoro-4-(2-amino-2-hydroxymethyl-3-hydroxypropyl)phenyl | |
| 72 | phenyl | cyclopropyl | 2-fluoro-4-(2-acetylaminoethyl)phenyl | |
| 73 | phenyl | cyclopropyl | indol-5-yl | |
| 74 | phenyl | cyclopropyl | 3,5-dimethyl-4-[(3-azetidin-1-ylpropyl)aminomethyl]-phenyl | TFA |
| 75 | phenyl | cyclopropyl | 4-(hydroxymethyl)-3-methylphenyl | TFA |
| 76 | phenyl | cyclopropyl | 2-fluoro-4-(2-hydroxyethyl)phenyl | |
| 77 | phenyl | cyclopropyl | 3,5-dimethyl-4-(hydroxymethyl)phenyl | |
| 78 | phenyl | cyclopropyl | 2-fluoro-4-(2-hydroxyethylNHCO—)phenyl | |
| 79 | phenyl | cyclopropyl | 2-fluoro-4-(N,N-bis-methylsulfonylamino)phenyl | |
| 80 | phenyl | cyclopropyl | 2-fluoro-4-(2-oxopyrrolidin-1-yl)phenyl | |
| 81 | phenyl | cyclopropyl | 2-fluoro-4-(aminocarbonyl)phenyl | |
| 82 | phenyl | cyclopropyl | 2-fluoro-4-(S-1-hydroxy-2,2,2-trifluoroethyl)phenyl | |
| 83 | phenyl | cyclopropyl | 2-fluoro-4-(trifluoromethylCONH—)-phenyl | |
| 84 | phenyl | cyclopropyl | 2-fluoro-4-(2-hydroxymethyl-3-hydroxypropyl)phenyl | |
| 85 | phenyl | cyclopropyl | 2-fluoro-4-(2-methoxyethylN($CH_3$)CO—)phenyl | |
| 86 | phenyl | cyclopropyl | 4-hydroxymethyl-2-methylphenyl | TFA |
| 87 | phenyl | cyclopropyl | 2-fluoro-4-(3,3-difluoroazetidin-1-ylmethyl)phenyl | |
| 88 | phenyl | cyclopropyl | 2-fluoro-4-(2-aminoethyl)phenyl | |
| 89 | phenyl | cyclopropyl | 2-fluoro-4-(3-carboxypyrazol-1-ylmethyl)phenyl | HCl |
| 90 | phenyl | cyclopropyl | 2-fluoro-4-[1-(2-carboxyethylamino)-1-methylethyl]-phenyl | |
| 91 | phenyl | cyclopropyl | 4-hydroxymethylphenyl | TFA |
| 92 | phenyl | cyclopropyl | 1,2,3,4-tetrahydroisoquinolin-6-yl | TFA |
| 93 | phenyl | cyclopropyl | 2-fluoro-4-(4-carboxycyclobutylmethyl)phenyl | |
| 94 | phenyl | cyclopropyl | 2-fluoro-4-(2-amino-2-hydroxymethyl-3-hydroxypropyl)phenyl | |
| 95 | phenyl | cyclopropyl | 2-fluoro-4-(cyclopropylNHCO—)phenyl | |
| 96 | phenyl | cyclopropyl | 2-fluoro-4-(methylamino)phenyl | |
| 97 | phenyl | cyclopropyl | 2-fluoro-4-(2-carboxyethyl$SO_2$NH)-phenyl | |
| 98 | phenyl | cyclopropyl | 2-fluoro-4-dimethylaminophenyl | |
| 99 | phenyl | cyclopropyl | 2-fluoro-4-(5-carboxypyrazol-1-yl-methyl)phenyl | HCl |
| 100 | phenyl | cyclopropyl | 2-fluoro-4-[(cis)-3-carboxycyclobutylmethyl]phenyl | |
| 101 | phenyl | cyclopropyl | 2-fluoro-4-(R-1-hydroxy-2,2,2-trifluoroethyl)phenyl | |
| 102 | phenyl | cyclopropyl | 1-carboxymethylindol-5-yl | |
| 103 | phenyl | cyclopropyl | 2-fluoro-4-(2-hydroxyethylN($CH_3$)CO—)-phenyl | |
| 104 | phenyl | cyclopropyl | 2-fluoro-4-[(trans)-3-carboxycyclobutylmethyl]phenyl | |
| 105 | phenyl | cyclopropyl | 2-fluoro-4-(2-methylsulfonylaminoethyl)phenyl | |
| 106 | phenyl | cyclopropyl | 2-fluoro-4-(3,3-dicarboxycyclobutylmethyl)phenyl | |
| 107 | phenyl | cyclopropyl | 2-fluoro-4-(azetidin-1-ylcarbonyl)phenyl | |
| 108 | phenyl | cyclopropyl | 2-fluoro-4-(2-methoxyethylNHCO—)-phenyl | |
| 109 | phenyl | cyclopropyl | 2-fluoro-4-(morpholin-4-ylcarbonyl)phenyl | |
| 110 | phenyl | cyclopropyl | 2-fluoro-4-(1-amino-2,2,2-trifluoroethyl)phenyl | TFA |
| 111 | phenyl | cyclopropyl | 2-fluoro-4-[1R-(2-carboxyethylNH)ethyl]phenyl | HCl |
| 112 | phenyl | cyclopropyl | 2-fluoro-4-(S-3-amino-3-carboxypropyl)-phenyl | |
| 113 | cyclopentyl | cyclopropyl | 2-fluoro-4-(3-carboxyazetidin-1-ylmethyl)phenyl | |
| 114 | cyclobutyl | cyclopropyl | 2-fluoro-4-(3-carboxyazetidin-1-ylmethyl)phenyl | |
| 115 | cyclohexyl | cyclopropyl | 2-fluoro-4-(3-carboxyazetidin-1-ylmethyl)phenyl | TFA |
| 116 | cyclopropyl | cyclopropyl | 2-fluoro-4-(3-carboxyazetidin-1-ylmethyl)phenyl | TFA |
| 117 | phenyl | cyclopropyl | 2-fluoro-4-hydroxymethylphenyl | |
| 118 | phenyl | cyclopropyl | 2-fluoro-2-carboxyethylphenyl | |
| 119 | 2-fluorophenyl | cyclopropyl | 2-fluoro-4-(3-carboxyazetidin-1-ylmethyl)phenyl | |
| 120 | phenyl | cyclopropyl | 4-[(S)-1-aminoethyl]-2-fluorophenyl | |
| 121 | 4-hydroxyphenyl | cyclopropyl | 2-fluoro-4-(3-carboxyazetidin-1-ylmethyl)phenyl | |
| 122 | 4-fluorophenyl | cyclopropyl | 2-fluoro-4-(3-carboxyazetidin-1-ylmethyl)phenyl | |
| 123 | phenyl | cyclobutyl | 2-fluoro-4-(3-carboxyazetidin-1-ylmethyl)phenyl | TFA |
| 124 | phenyl | cyclopropyl | 2-fluoro-4-(3-amino-3-hydroxymethyl-4-hydroxybutyl)phenyl | HCl |

TABLE I-continued

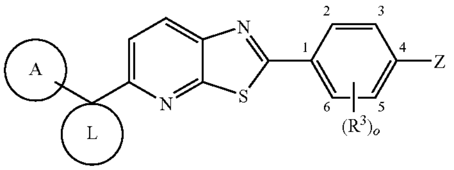

| Cpd # | A | 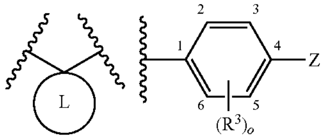 | | Salt |
|---|---|---|---|---|
| 125 | phenyl | cyclopropyl | 2-amino-4-(3-carboxyazetidin-1-ylmethyl)phenyl | |
| 126 | 4,4-difluorocyclohexyl | cyclopropyl | 2-fluoro-4-(3-carboxyazetidin-1-ylmethyl)phenyl | TFA |
| 127 | (1R)-3,3-difluorocyclopentyl | cyclopropyl | 2-fluoro-4-(3-carboxyazetidin-1-ylmethyl)phenyl | |
| 128 | (1S)-3,3-difluorocyclopentyl | cyclopropyl | 2-fluoro-4-(3-carboxyazetidin-1-ylmethyl)phenyl | |
| 129 | phenyl | cyclopropyl | 2-fluoro-4-[(2S,4S)-2-hydroxymethylpyrrolidin-4-yl]-phenyl | |
| 130 | tetrahydro-2H-pyran-4-yl | cyclopropyl | 2-fluoro-4-(3-carboxyazetidin-1-ylmethyl)phenyl | TFA |
| 131 | phenyl | cyclopropyl | 4-(3-carboxyazetidin-1-ylmethyl)phenyl | TFA |
| 132 | phenyl | cyclopropyl | 2-fluoro-4-(S—$CH_2NHCH(CH_3)CO_2H$)-phenyl | TFA |
| 133 | phenyl | cyclopropyl | 2-fluoro-4-(R—$CH_2NHCH(CH_3)CO_2H$)-phenyl | TFA |
| 134 | phenyl | cyclopropyl | 2-fluoro-4-[(1-carboxycyclopropyl)aminomethyl]-phenyl | TFA |
| 135 | phenyl | cyclopropyl | 2-fluoro-4-(—$CH_2NHC(CH_3)_2CO_2H$))-phenyl | TFA |
| 136 | phenyl | cyclopropyl | 2-(2-carboxyethyl)-3,4-dihydro-2-(1H)-isoquinolin-6-yl | TFA |
| 137 | phenyl | cyclopropyl | 2-(carboxymethyl)-3,4-dihydro-2-(1H)-isoquinolin-6-yl | TFA |
| 138 | 3,3-difluorocyclobutyl | cyclopropyl | 2-fluoro-4-(3-carboxyazetidin-1-ylmethyl)phenyl | |
| 139 | phenyl | cyclopropyl | 2-fluoro-4-(carboxymethyloxymethyl)-phenyl | |
| 140 | phenyl | cyclopropyl | 2-fluoro-4-(1-hydroxyethyl)phenyl | |
| 141 | phenyl | cyclopropyl | 2-fluoro-4-(—$CH_2NHC(CH_3)_2CH_2CO_2H$)-phenyl | HCl |
| 142 | phenyl | cyclopropyl | 2-fluoro-4-(—$CH_2NH(CH_2)_3CO_2H$)-phenyl | HCl |
| 143 | phenyl | cyclopropyl | 2-fluoro-4-(—$CH_2NHCH(CH_3)CH_2CO_2H$)-phenyl | HCl |
| 144 | phenyl | cyclopropyl | 2-fluoro-4-(—$CH(CH_3)NHCH(CH_3)CH_2CO_2H$)-phenyl | HCl |
| 145 | phenyl | cyclopropyl | 2-fluoro-4-(S—$CH_2NHCH(CH_3)CH_2CO_2H$)-phenyl | HCl |
| 146 | phenyl | cyclopropyl | 2-fluoro-4-(R—$CH_2NHCH(CH_3)CH_2CO_2H$)-phenyl | HCl |
| 147 | phenyl | cyclopropyl | 2-fluoro-4-[(3S,1R)-$CH(CH_3)NHCH(CH_3)CH_2CO_2H$]-phenyl | HCl |
| 148 | phenyl | cyclopropyl | 2-fluoro-4-[(3R,1S)-$CH(CH_3)NHCH(CH_3)CH_2CO_2H$]-phenyl | HCl |
| 149 | phenyl | cyclopropyl | 2-fluoro-4-[$CH_2CH(NH_2)CO_2H$]-phenyl | |
| 150 | phenyl | cyclopropyl | 2-fluoro-4-[S—$CH_2CH(NH_2)CO_2H$]-phenyl | TFA |
| 151 | phenyl | cyclopropyl | 2-fluoro-4-[R—$CH_2CH(NH_2)CO_2H$]-phenyl | TFA |
| 152 | phenyl | cyclopropyl | 2-fluoro-4-[(S—$(CH_2)_2CH(NH_2)CO_2H$)-phenyl | TFA |
| 153 | phenyl | cyclopropyl | 2-fluoro-4-(3R-carboxypyrrolidin-1-ylcarbonyl)phenyl | |
| 154 | phenyl | cyclopropyl | 2-fluoro-4-(3R-carboxypiperidin-1-ylcarbonyl)phenyl | |
| 155 | phenyl | cyclopropyl | 2-fluoro-4-(3-carboxyazetidin-1-ylcarbonyl)phenyl | |
| 156 | phenyl | cyclopropyl | 2-fluoro-4-(—$CONHC(CH_3)_2CH_2COOH$)-phenyl | |
| 157 | phenyl | cyclopropyl | 2-fluoro-4-[—$CON(CH_3)(CH_2)_2COOH$]-phenyl | |
| 158 | phenyl | cyclopropyl | 2-fluoro-4-(—$CONHCH(CH_3)CH_2COOH$)-phenyl | |
| 159 | phenyl | cyclopropyl | 2-fluoro-4-(—$NHCO(CH_2)_2COOH$)-phenyl | |
| 160 | phenyl | cyclopropyl | 2-fluoro-4-(—$CH_2NHCH_2COOH$)-phenyl | |
| 161 | phenyl | cyclopropyl | benzimidazol-5-yl | |
| 162 | phenyl | cyclopropyl | 2-(2-carboxyethyl)-1,3-dihydro-2-(1H)-isoindol-5-yl | |
| 163 | phenyl | cyclopropyl | 2-(carboxymethyl)-1,3-dihydro-2-(1H)-isoindol-5-yl | |
| 164 | phenyl | cyclopropyl | 1-(2-carboxyethyl)-benzimidazol-6-yl | |
| 165 | phenyl | cyclopropyl | 1-(2-carboxyethyl)-benzimidazol-5-yl | |
| 166 | phenyl | cyclopropyl | 2-fluoro-4-(—$CONHCH(CH_3)CH_2COOH$)-phenyl | |
| 167 | phenyl | cyclopropyl | 2-fluoro-4-[1-(2-carboxyethylamino)cycloprop-1-yl]phenyl | |
| 168 | phenyl | cyclopropyl | 2-fluoro-4-(5-carboxyimidazol-1-ylmethyl)phenyl | |
| 169 | phenyl | cyclopropyl | 2-fluoro-4-(R-3-carboxypyrrolidin-1-ylmethyl)phenyl | |
| 170 | phenyl | cyclopropyl | 2-fluoro-4-[1S-(2-carboxyethylNH)ethyl]phenyl | HCl |
| 171 | phenyl | cyclopropyl | 2-fluoro-4-(2-benzylaminoethyl)phenyl | |
| 172 | phenyl | cyclopropyl | 2-fluoro-4-[R-1-(3-carboxyazetidin-1-yl)propyl]phenyl | |
| 173 | phenyl | cyclopropyl | 2-fluoro-4-[S-1-(3-carboxyazetidin-1-yl)propyl]phenyl | |
| 173 | phenyl | cyclopropyl | 2-fluoro-4-[S—$CH_2CH(NH_2)CO_2H$]-phenyl | TFA |

TFA = trifluoroacetic acid;
HCl = hydrochloric acid.
Other compounds of Formula (I) are:
1-((3-fluoro-4-(6-(1-phenylcyclopropyl)benzo[d]thiazol-2-yl)phenyl)methyl)azetidine-3-carboxylic acid;
1-(3-fluoro-4-(5-(1-phenylcyclopropyl)[1,3]thiazolo[4,5-b]pyridine-2-yl)benzyl)-3-azetidinecarboxylic acid;
1-(3-fluoro-4-(6-(1-phenylcyclopropyl)[1,3]thiazolo[4,5-c]pyridine-2-yl)benzyl)-3-azetidinecarboxylic acid TFA salt;
1-((3-fluoro-4-(6-(1-(pyridine-2-yl)cyclopropyl)benzo[d]thiazol-2-yl)phenyl)methyl)azetidine-3-carboxylic acid; and
1-(3-fluoro-4-(5-(1-phenylcyclopropyl)thiazolo[4,5-b]pyridin-2-yl)-benzyl)azetidine-3-carboxylic acid trifluoroacetic acid salt.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 260° C., more preferably from about 0° C. to about 125° C. and most preferably at about room (or ambient) temperature, e.g., about 20° C.

Compounds of Formula (I) where A, L, $X^1$-$X^5$, $R^1$, $R^2$, $R^3$ are as defined in the Summary and Z is a group of formula (b) can be prepared as described in Scheme 1 below.

Scheme 1

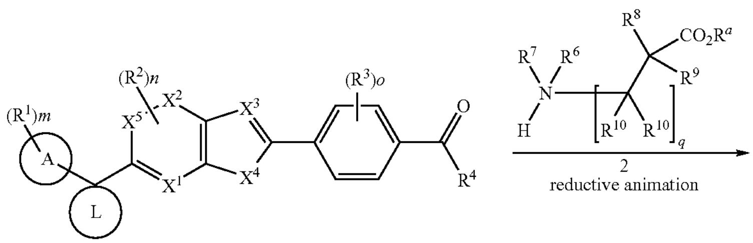

1

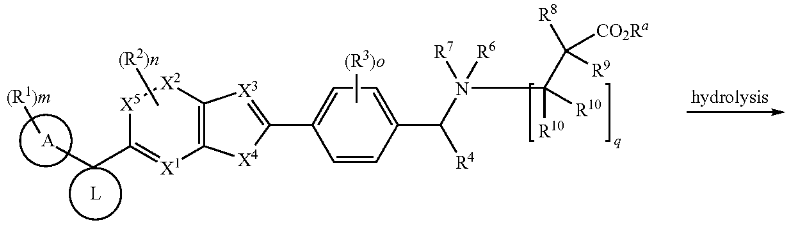

3

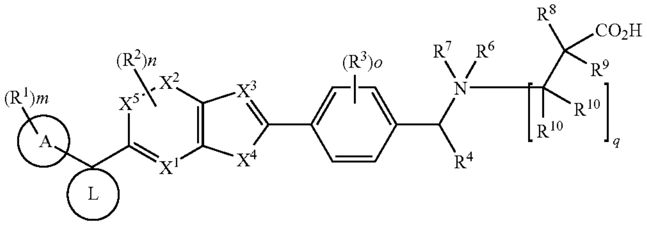

(I)

Reaction of a compound of formula 1 where $R^4$ is hydrogen or as defined in the Summary, with an amino compound of formula 2 where $R^a$ is alkyl under reductive amination reaction conditions provides a compound of formula 3. The reaction is typically carried out in in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like) or MeOH or mixtures thereof.

Hydrolysis of the ester group in 3 under basic hydrolysis reaction conditions, followed by acidic workup then provides a compound of Formula (I). Following the reductive amination procedure, compounds of Formula (I) where Z is aminoalkyl can also be prepared. Detailed syntheses of compounds of formula 1 and 2 and compounds of Formula (I) using the above procedure are provided in working examples below.

Alternatively, the above compounds can be prepared by reacting a halide of formula 1a with an amine of formula 2 as shown below.

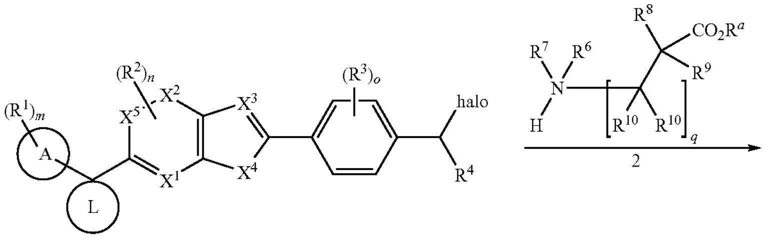

1a

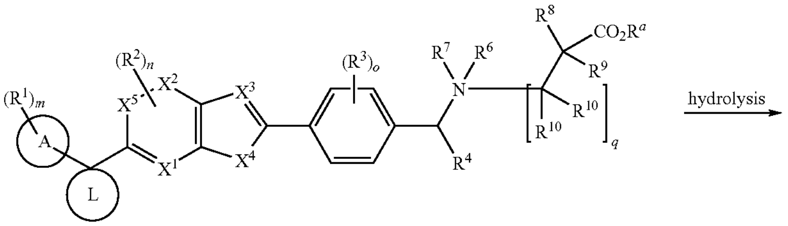

3

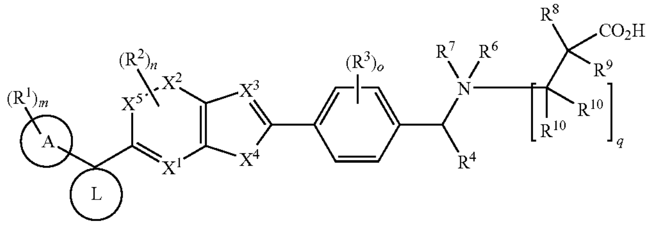

(I)

The reaction is carried out in the presence of a non-nucleophilic amine such as triethylamine, pyridine, DIPEA, and the like.

Compounds of Formula (I) where A, L, $X^1$-$X^5$, $R^1$, $R^2$, $R^3$ are as defined in the Summary and Z is an aminocarbonyl (—CONRR' where R and R' are as defined in the definition section) can be prepared as described in Scheme 2 below.

Scheme 2

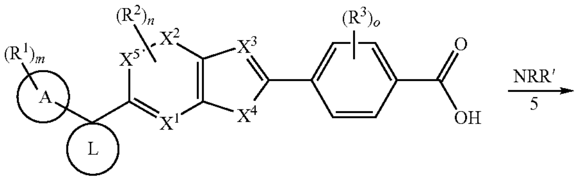

4

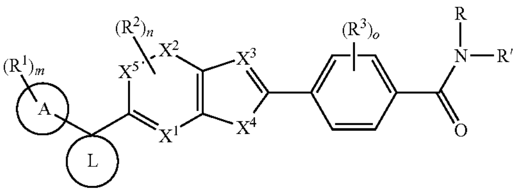

(I)

Compounds of Formula (I) where A, Y, $X^1$-$X^5$, $R^1$, $R^2$, $R^3$ are as defined in the Summary and Z is an aminocarbonyl (—CONRR' where R and R' are as defined in the definition of aminocarbonyl group) can be prepared by reacting a compound of formula 4 with an amine of formula 5. The reaction is carried out in the presence of coupling reagents known to one skilled in the art of organic synthesis such as EDCI/HOBT, O-(7-azabenzotriazole-1-yl)-N,N,N'N'-tetramethyluronium hexafluorophosphate (HATU) and chlorodipyrrolidinocarbenium hexafluorophosphate (PyCIU) (see for example, Han, S-Y.; Kim, Y-A. Tetrahedron 2005, 60 (11), 2447-67), in the presence of an amine such as diisopropylethylamine and in a suitable organic solvent such as dimethylformamide.

Alternatively, the acid 4 can be converted to an acid halide and then reacted with an amine of formula 5. The reaction is carried out in the presence of a non-nucleophilic amine such as triethylamine, pyridine, and the like. The acid chloride can be prepared in situ from the acid 4 using either oxalyl chloride or thionyl chloride.

Alternatively, compounds of Formula (I) where both $X^3$ and $X^4$ are N or one of $X^3$ and $X^4$ is N and the other is O or S and A, L, $X^1$, $X^2$, $X^5$, $R^1$, $R^2$, $R^3$ are as defined in the Summary and Z is a group of formula (b) can be prepared as described in Scheme 3 below.

Scheme 3

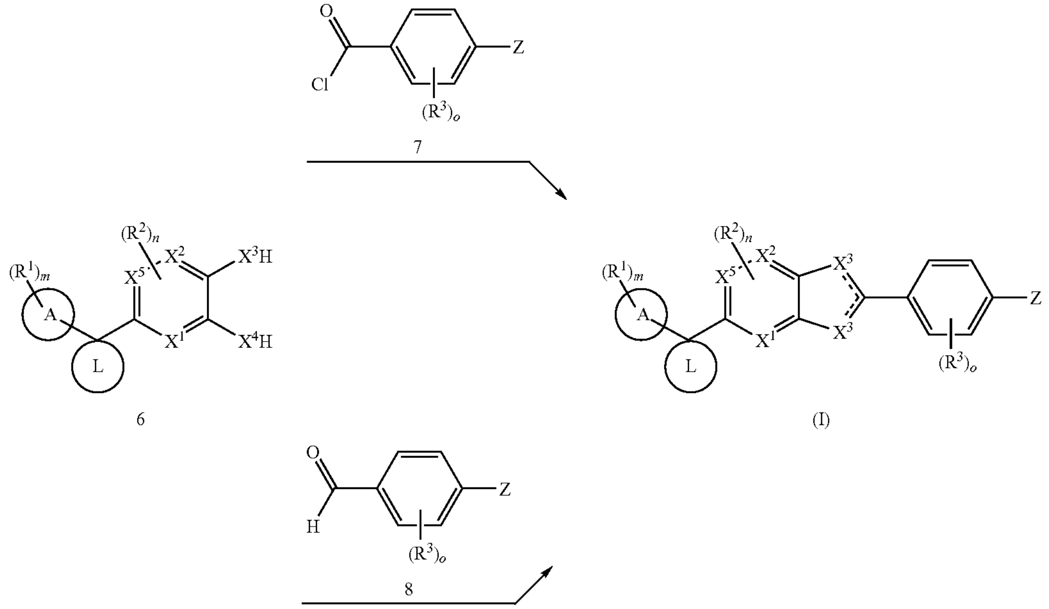

Reaction of a compound of formula 6 where both $X^3$ and $X^4$ are N or one of $X^3$ and $X^4$ is N and the other is O or S with an acid chloride of formula 7 provides a compound of Formula (I). The reaction is typically carried out in in the presence of an acid (e.g., camphorsulfonic acid, toluenesulfonic acid, and the like) and at elevated temperature. Suitable solvents for the reaction are nonpolar organic solvents (e.g., toluene, benzene, and the like). Alternatively, an aldehyde of formula 8 can be reacted with a compound of formula 6 in the presence of an oxidizing agent (e.g., DDQ, oxygen, and the like). Suitable solvents for the reaction are ethereal organic solvents (e.g., tetrahydrofuran, dioxane, and the like).

Alternatively, compounds of Formula (I) where one of $X^3$ or $X^4$ is N and other is O or S and A, L, $X^1$, $X^2$, $X^5$, $R^1$, $R^2$, $R^3$ are as defined in the Summary and Z is a group of formula (b) can be prepared as described in Scheme 4 below.

Scheme 4

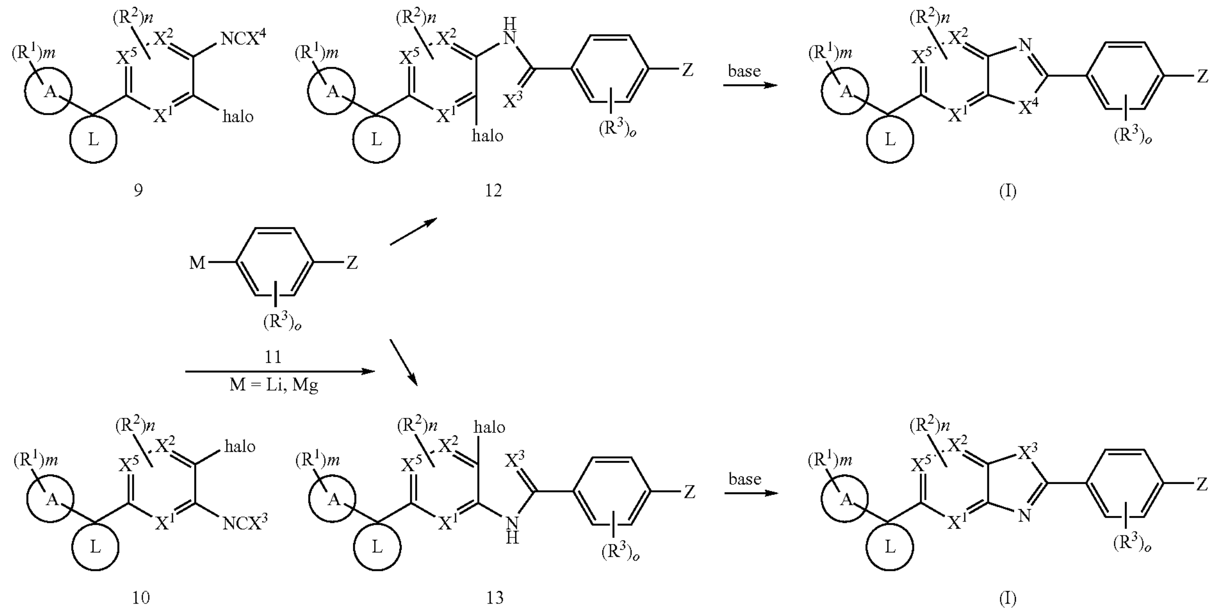

Reaction of a compound of formula 9 or 10 where ($X^3$ and $X^4$ are O or S) with a phenyl Grignard reagent or phenyl lithium reagent of formula 11 provides a compound of formula 12 or 13, respectfully. The phenyl Grignard reagent or phenyl lithium reagent is typically formed from the corresponding phenyl halide by treatment with an alkyllithium or alkyl Grignard at low temperature. Suitable solvents for the reaction are ethereal organic solvents (e.g., tetrahydrofuran, diethyl ether, and the like). The compound of formula 12 and 13 are cyclized upon treatment with a base (e.g., diisopropylethylamine, sodium carbonate, and the like) at elevated temperature to give compounds of Formula (I). Suitable solvents for the reaction are polar organic solvents (e.g., dimethylformamide, dimethylsulfoxide, and the like).

Compounds of Formula (I) where $X^3$ or $X^4$ is —CH— and A, L, $X^1$, $X^2$, $X^5$, $R^1$, $R^2$, $R^3$ are as defined in the Summary and Z is a group of formula (b) can be prepared as described in Scheme 5 below.

Scheme 5

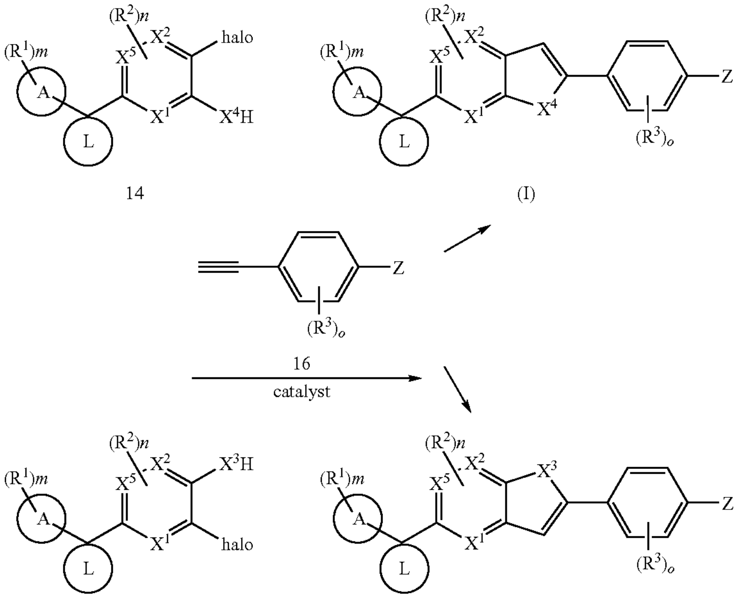

14 (I) 16 15 (I)

Reaction of a compound of formula 14 or 15 $X^3$ or $X^4$ is —CH— and A, Y, $X^1$, $X^2$, $X^5$, $R^1$, $R^2$, $R^3$ are as defined in the Summary and Z is a group of formula (b), with an alkyne of formula 16 provides a compound of Formula (I). The reaction is typically carried out in in the presence of transition metal catalysts (e.g., tetrakis(triphenylphosphine) palladium(0), copper (I) iodide, and the like) and at elevated temperature. Suitable solvents for the reaction are organic solvents (e.g., tetrahydrofuran, dimethylformamide, and the like).

Compounds of Formula (I) where L is cyclopropyl and A, $X^1$-$X^5$, $R^1$, $R^2$, $R^3$ are as defined in the Summary and Z is a group of formula (b) can be prepared as described in Scheme 6 below.

Scheme 6

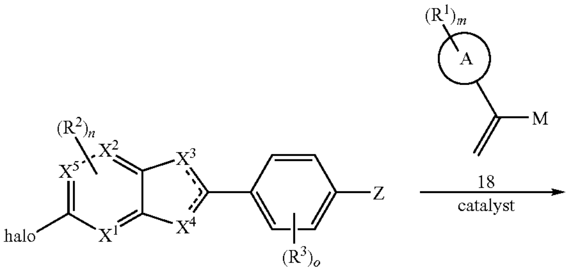

17

-continued

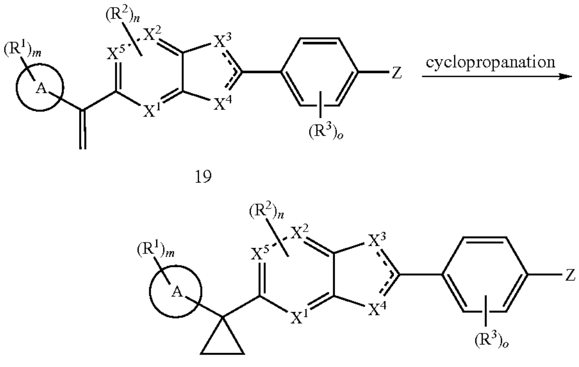

19

(I)

Reaction of halogenated compound 17 with a vinylmetal compound 18 (where M is typically $B(OH)_2$ or trialkylstannane) provides an intermediate compound 19. The reaction is typically carried out in the presence of a transition metal catalyst (e.g., tetrakis(triphenylphosphine) palladium(0), and the like) at elevated temperature in organic solvents (e.g., ethanol, methanol, toluene, tetrahydrofuran, dioxane, and the like). When $M{=}B(OH)_2$, the reaction typically also requires a base (e.g., sodium carbonate, sodium acetate, and the like), and water as a co-solvent. Compound 19 is then reacted with suitable cyclopropanating reagents (e.g., trimethylsulfoxonium iodide and potassium tert-butoxide, diethylzinc and diiodomethane, zinc amalgam and diiodomethane) to give a compound of Formula (I). Suitable solvents for the reaction are organic solvents (e.g., hexanes, tetrahydrofuran, dioxane, toluene, dimethylsulfoxide, and the like).

Compounds of Formula (I) where A, L, $X^1$-$X^5$, $R^1$, $R^2$, $R^3$ are as defined in the Summary and Z is an aminoalkyl (—NRR' where R and R' are as defined in the definition section) can be prepared as described in Scheme 7 below.

Scheme 7

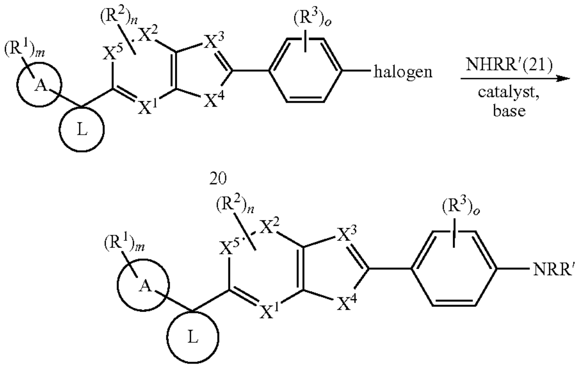

20

(I)

Compounds of Formula (I) can be prepared by reacting a compound of formula 20 with an amine of formula 21. The reaction is carried out in the presence of a transition metal catalyst (e.g., $Pd_2(dba)_3$, palladium (II) acetate, and the like), a suitable ligand (e.g., Xantphos, and the like), in the presence of a base such as sodium tert-butoxide and in a suitable organic solvent such as toluene.

Compounds of Formula (I) where A, L, $X^1$-$X^5$, $R^1$, $R^2$, $R^3$ are as defined in the Summary and Z is an acylamino (—NH-COR where R is as defined in the definition section) can be prepared as described in Scheme 8 below.

Scheme 8

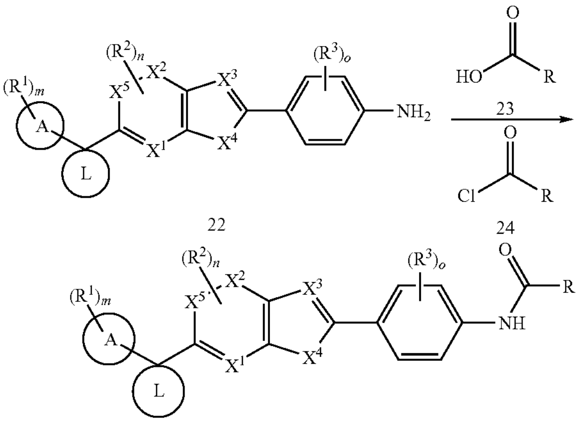

22

24

(I)

Compounds of Formula (I) where Z is acylamino can be prepared by reacting a compound of formula 22 with an acid of formula 23. The reaction is carried out in the presence of coupling reagents known to one skilled in the art of organic synthesis such as EDCI/HOBT, O-(7-azabenzotriazole-1-yl)-N,N,N'N'-tetramethyluronium hexafluorophosphate (HATU) and chlorodipyrrolidinocarbenium hexafluorophosphate (PyCIU) (see for example, Han, S-Y.; Kim, Y-A. *Tetrahedron* 2005, 60 (11), 2447-67), in the presence of an amine such as diisopropylethylamine and in a suitable organic solvent such as dimethylformamide. Alternatively, the acid 23 can be converted to an acid halide and then reacted with an amine of formula 22. The reaction is carried out in the presence of a non-nucleophilic amine such as triethylamine, pyridine, and the like. The acid chloride can be prepared in situ from the acid 23 using either oxalyl chloride or thionyl chloride.

Compounds of Formula ((I)) where A, L, $X^1$-$X^5$, $R^1$, $R^2$, $R^3$ are as defined in the Summary and Z is an carboxyalkyl or substituted carboxyalkyl can be prepared as described in Scheme 9 below.

Scheme 9

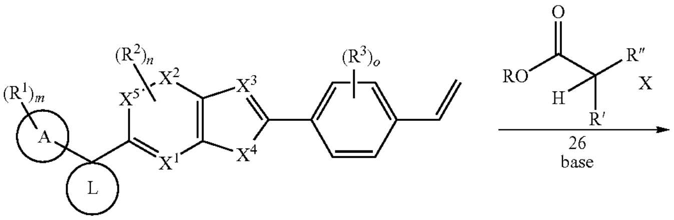

25

-continued

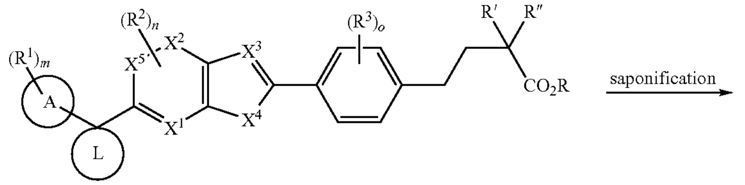

27

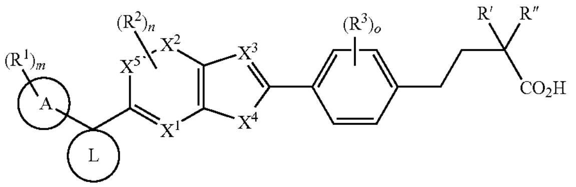

(I)

Compounds of Formula (I) where Z is carboxyalkyl or substituted carboxyalkyl can be prepared by reacting a compound of formula 25 with an ester of formula 26 in the presence of a base such as cesium carbonate in a suitable solvent such as dimethylformamide. Compound 27 is then saponified with a base such as sodium hydroxide in a solvent mixture such as tetrahydrofuran/water to give a compound of Formula (I).

Utility

The compounds of the invention are high affinity agonists (or antagonists) at various S1P receptors, in particular the compounds of this invention are S1P1 agonists, and hence are useful in the treatment of a variety of S1P, in particular S1P1, receptor-mediated clinical conditions. Such conditions include transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas where immunosuppression is central.

Specifically, S1P1 receptor agonists suppress the peripheral immune response by inducing lymphocyte sequestration in secondary lymph organs thereby resulting in lymphopenia. Thus the compounds of the invention can be used as immune modulators, and are useful in treating or preventing pathologies mediated by lymphocyte actions, including acute or chronic rejection of tissue grafts such as organ transplants, and autoimmune-diseases. Autoimmune diseases that may be treated with compounds of the invention include: systemic lupus erythematosus, multiple sclerosis, Behçet's disease, glomerulonephritis, rheumatoid arthritis, inflammatory bowel diseases such as Crohn's disease and ulcerative colitis, type I diabetes, uveitis, psoriasis, myasthenia gravis, Hashimoto's thyroiditis, autoimmune hemolytic anemia, autoimmune thrombocytopenic purpura, hepatitis and Wegner's granuloma. The compounds of the invention are useful also in treating inflammatory disorders, including atopic asthma, inflammatory glomerular injury and ischemia-reperfusion injury.

Lysophospholipids, S1P and lysophosphatidic acid (LPA), stimulate cellular proliferation and affect numerous cellular functions by signaling through G protein-coupled endothelial differentiation gene-encoded (S1P) receptors. Accordingly, the compounds of this invention are anticipated to have utility in immunomodulation, e.g., in anti-angiogenesis therapy, such as in neoplastic disease treatment.

It has also been reported that S1P inhibits fibrosis in various organs. Accordingly, the compounds of this invention can be used to prevent/treat diseases associated with organ fibrosis, such as pulmonary fibrosis, interstitial pneumonia, chronic hepatitis, hepatic cirrhosis, chronic renal insufficiency or kidney glomerular sclerosis. In addition, S1P compounds of the invention can inhibit exit of lymphocytes from secondary lymphoid tissues. Thus the present compounds can be used to reduce lymphocyte infiltration of transplanted organs, e.g., allografts, or healthy cells, e.g., pancreatic islets as in type I diabetes, myelin sheathing (multiple sclerosis), kidney, heart and lung transplantations or other tissues that may be subjected to an undesirable immunoresponse, and thus decrease damage to such tissues from the immune system.

In addition the compounds of this invention can be used to treat a disorder of abnormal cell growth and differentiation. These disorders include Alzheimer's disease, aberrant corpus luteum formation, osteoporosis, anovulation, Parkinson's disease, and cancer. S1P also acts as a survival factor in many cell types. Hence, the compounds of the invention are expected to be useful in protecting cells and tissues from hypoxic conditions, including injury sustained as a result of ischemia such as ischemia reperfusion type injury.

In particular, the compounds can be administered to patients as part of the treatment associated with organ transplantation, including pancreas, pancreatic islets, kidney, heart and lung transplantations.

Testing

The S1P1 agonistic activity of the compounds of the present invention can be tested using the in vitro and in vivo assays described in Biological Examples 1 and 2 below.

Administration and Pharmaceutical Composition

The compounds of the invention may be administered to patients in need of such treatment in dosages that will provide optimal pharmaceutical efficacy. An appropriate dosage level will generally be about 0.001 to 500 mg, preferably 0.001 to 50 mg per kg patient body weight per day, which may be administered in single or multiple doses. Preferably, the dosage level will be about 0.005 to about 250 mg/kg per day; more preferably about 0.005 to about 100 mg/kg per day, or about 0.005 to about 50 mg/kg per day; or 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

The compounds of the invention can be used in combination with other pharmacological agents (e.g., in combination with known immunosuppressants such as cyclosporine, tacrolimus, rapamycin, azathioprine, cyclophosphamide, methotrexate and corticosteroids such as cortisone, des-oxymetasone, betametasone, desametasone, flunisolide, prednisolone, prednisone, amcinomide, desonide, methylprednisolone, triamcinolone, and alclometasone). The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term “combination” further refers to the case where the compounds are provided in separate dosage forms and are administered sequentially.

“Combination therapy” (or “co-therapy”) includes the administration of a S1P receptor modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). “Combination therapy” may, but generally is not, intended to encompass the administration of two or more of these therapeutic agents as part of separate monotherapy regimens that incidentally and arbitrarily result in the combinations of the present invention.

“Combination therapy” is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

“Combination therapy” also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compositions and combination therapies of the invention may be administered in combination with a variety of pharmaceutical excipients, including stabilizing agents, carriers and/or encapsulation formulations as described herein.

The compositions and combination therapies of the invention can generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermolysis fluid or injected at the proposed site of infusion, (see for example, *Remington's Pharmaceutical Sciences* 15$^{th}$ Edition, pages 1035-1038 and 1570-1580).

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.005 to 500, preferably, 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

EXAMPLES

Synthetic Examples

Unless otherwise noted, all materials were obtained from commercial suppliers and used without further purification. All parts are by weight and temperatures are in degrees centigrade unless otherwise indicated. Microwave assisted reactions were conducted with a Discover™ model microwave reactor (CEM, Matthews, N.C.) or a Smith Synthesizer™ (Personal Chemistry, Uppsala, Sweden). All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography (HPLC).

The following abbreviations are used:

concd—concentrated
DAST—diethylamino sulfurtrifluoride
DMSO—dimethyl sulfoxide
DMF—N,N-dimethylformamide
THF—tetrahydrofuran
$Et_2O$—diethyl ether
EtOAc, EA—ethyl acetate
MeOH—methyl alcohol
EtOH—ethyl alcohol
MeCN—acetonitrile
MeI—iodomethane
NMP—1-methyl-2-pyrrolidinone
DCM—dichloromethane
TBAF—tetrabutylammonium fluoride
TBS—t-butyldimethylsilyl
TFA—trifluoroacetic acid
Amphos—4-(di-tert-butylphosphino)-N,N-dimethylbenzenamine
satd—saturated
h—hours
min—minutes The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified.

Reference A

Synthesis of 2-(4-(1,3-dioxan-2-yl)-2-fluorophenyl)-5-chlorothiazolo[5,4-b]pyridine

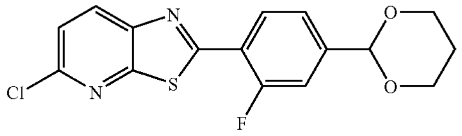

Step 1

4-Bromo-3-fluorobenzaldehyde (100.00 g, 492.6 mmol) was added to toluene (1 L). Propane-1,3-diol (42.72 mL, 591.1 mmol), and p-toluenesulfonic acid monohydrate (4.685 g, 24.63 mmol) were added to above and the reaction mixture was brought to reflux. The solvent (500 mL) was azeotroped off using a dean stark trap. The reaction mixture was cooled and extracted with sat. aqueous sodium bicarbonate (500 mL). The organics were dried over magnesium sulfate and concentrated in vacuo to give 2-(4-bromo-3-fluorophenyl)-1,3-dioxane as a white solid. MS (ESI) m/z: Calculated: 260.0/262.0; Observed: 260.9 ($M^+$+1).

Step 2

A slurry of sodium carbonate (15.2 g, 144 mmol), 2,6-dichloropyridin-3-amine (9.00 g, 55.2 mmol), and thiophosgene (5.50 mL, 71.8 mmol) in 100 mL anhydrous DCM was allowed to stir in a sealed vessel for 2 days. The reaction mixture was filtered through a glass frit, rinsing with DCM. The filtrate was concentrated in vacuo to give 2,6-dichloro-3-isothiocyanatopyridine as a peach-colored solid.

Step 3

To a solution of 2-(4-bromo-3-fluorophenyl)-1,3-dioxane (7.65 g, 29.3 mmol) in 75 mL THF under argon at −78° C. was added 1-butyllithium 2.5M in hexanes (12.9 mL, 32.2 mmol) in portions over ~20 min. The reaction mixture was allowed to stir 20 min, and was yellow. A solution of 2,6-dichloro-3-isothiocyanatopyridine (6.01 g, 29.3 mmol) in 20 mL THF was added dropwise via cannula. The resulting dark brown solution was allowed to stir 15 min, then was quenched by addition of sat'd aq. $NH_4Cl$. The reaction mixture was partitioned between sat'd aq. $NH_4Cl$ and $Et_2O$. The organic layer was washed with brine, dried over sodium sulfate, filtered, and concentrated to give an orange solid. The solid was treated with sodium carbonate (4.66 g, 44.0 mmol) and approximately 15 mL DMF, and stirred under nitrogen at 90° C. The reaction was heated overnight, and in the morning was a solid mass. The reaction was diluted with water, stirred rapidly for several hours, and filtered, rinsing with water and MeOH. The resulting solid was dried in vacuo to give 2-(4-(1,3-dioxan-2-yl)-2-fluorophenyl)-5-chlorothiazolo[5,4-b]pyridine. MS (ESI) m/z: Calculated: 350.0; Observed: 350.9 ($M^+$+1).

Reference B

Synthesis of 3-fluoro-4-(5-(1-phenylcyclopropylthiazolo[5,4-b]pyridine-2-yl-benzaldehyde

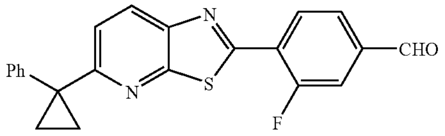

Step 1

A mixture of bis(4-(di-tert-butylphosphino)-N,N-dimethylbenzenamine) palladium dichloride (0.252 g, 0.356 mmol), potassium carbonate (6.70 g, 48.5 mmol), 1-phenylvinylboronic acid (4.64 g, 31.4 mmol), and 2-(4-(1,3-dioxan-2-yl)-2-fluorophenyl)-5-chlorothiazolo[5,4-b]pyridine (5.00 g, 14.3 mmol) in 50 mL dioxane and 15 mL water was sealed and heated to 80° C. overnight. The reaction was cooled, diluted with DCM, water, and the aq. Layer was extracted with DCM. The combined organic layers were dried over sodium sulfate, filtered, and concentrated in vacuo to give a brown semi-solid. The solid was suspended in 100 mL EA, heated to 75° C., and filtered, rinsing with a small volume of hot EA. The filtrate was allowed to stand overnight, resulting in crystals, and was placed in the freezer overnight. The resulting crystals were collected by filtration, rinsing with a small volume of cold EA to give 2-(4-(1,3-dioxan-2-yl)-2-fluorophenyl)-5-(1-phenylvinyl)-thiazolo[5,4-b]pyridine as light brown crystals. MS (ESI) m/z: Calculated: 418.1; Observed: 419.0 ($M^+$+1).

Step 2

To a solution of potassium tert-butoxide (4.02 g, 35.8 mmol) in 100 mL DMSO under nitrogen was added trimethyl sulfoxonium iodide (7.89 g, 35.8 mmol) in 4 portions over about 20 minutes. 2-(4-(1,3-Dioxan-2-yl)-2-fluorophenyl)-5-(1-phenylvinyl)thiazolo[5,4-b]pyridine (10.0 g, 23.9 mmol) was suspended in 150 mL THF and filtered through a glass frit, rinsing with 25 mL THF. The filtrate was added to the reaction dropwise very slowly from an addition funnel over 1.5-2 h. The resulting orange reaction was allowed to stir 30 min, at which point the THF was removed in vacuo, resulting in a precipitate. Water and ice was added slowly with stirring (approximately 400 mL total). The solid was isolated by filtration rinsing with water and MeOH. The solid was dried in vacuo to give 2-(4-(1,3-dioxan-2-yl)-2-fluorophenyl)-5-(1-phenylcyclopropyl)thiazolo[5,4-b]pyridine as a light orange solid. MS (ESI) m/z: Calculated: 432.1; Observed: 433.1 ($M^+$+1).

Step 3

To a slurry of 2-(4-(1,3-dioxan-2-yl)-2-fluorophenyl)-5-(1-phenylcyclopropyl)-thiazolo[5,4-b]pyridine (22.3 g, 51.6 mmol) in 200 mL THF was added 200 mL 5N HCl. The reaction mixture became warm, was fitted with a water-cooled reflux condenser, and was heated to 65° C. in an oil bath under argon. After 3 h, the reaction was nearly homogeneous. The bath was turned off and the reaction allowed to stir overnight. In the morning a nice yellow precipitate was evident. The THF was removed in vacuo, and the resulting slurry was filtered, rinsing with water, and dried under nitrogen, then dried in vacuo overnight to give 3-fluoro-4-(5-(1-phenylcyclopropyl)thiazolo[5,4-b]pyridine-2-yl)benzaldehyde as a light orange solid. MS (ESI) m/z: Calculated: 374.1; Observed: 375.1 ($M^+$+1).

Reference C

Synthesis of 1-(3-fluoro-4-(5-(1-phenylcyclopropylthiazolo[5,4-b]pyridine-2-ylphenyl-ethanone

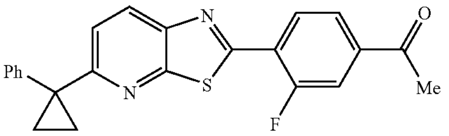

Step 1

Methylmagnesium chloride (1.8 mL, 5.3 mmol) was added dropwise to a solution of 3-fluoro-4-(5-(1-phenylcyclopropyl)thiazolo[5,4-b]pyridine-2-yl)benzaldehyde (1.00 g, 2.7 mmol) in THF (15.00 mL) at 0° C. The reaction mixture was allowed to stir 20 min at 0° C., at which time the reaction was quenched with saturated aqueous $NH_4Cl$. The solid was collected by filtration and purified by silica gel chromatography to afford the racemic mixture of 1-(3-fluoro-4-(5-(1-phenylcyclopropyl)thiazolo[5,4-b]pyridine-2-yl)phenyl)ethanol. MS (ESI) m/z: Calculated: 390.1; Observed: 391.0 ($M^+$+1).

Step 2

Dess-Martin periodinane (0.266 g, 0.627 mmol) was added to a solution of 1-(3-fluoro-4-(5-(1-phenylcyclopropyl)thiazolo[5,4-b]pyridine-2-yl)phenyl)ethanol (0.204 g, 0.522 mmol) in dichloromethane (15.00 mL, 0.522 mmol), and the reaction mixture was stirred at ambient temperature for 65 min. Saturated aqueous $NaHCO_3$ was added and the reaction stirred for 5 min. The organic layer was dried and concentrated in vacuo, and purified by silica gel chromatography:

ISCO 40 g column, 20-40% (3% $Et_3N$ in EtOAc)/hexanes to give 1-(3-fluoro-4-(5-(1-phenylcyclopropyl)thiazolo[5,4-b]pyridine-2-yl)phenyl)ethanone. MS (ESI) m/z: Calculated: 388.1; Observed: 389.0 ($M^+$+1).

Reference D

Synthesis of 3-fluoro-4-(5-(1-phenylcyclopropylthiazolo[5,4-b]pyridine-2-ylbenzoic acid

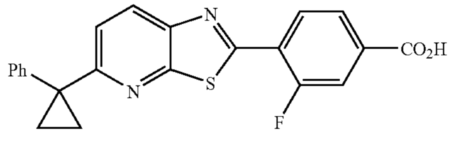

To a slurry of 3-fluoro-4-(5-(1-phenylcyclopropyl)thiazolo[5,4-b]pyridine-2-yl)-benzaldehyde (3.80 g, 10.1 mmol) and sodium dihydrogenphosphate hydrate (7.00 g, 50.7 mmol) in 40 mL 1:1 water/t-BuOH under nitrogen was added 2-methylbut-2-ene (37.6 mL, 355 mmol) and sodium chlorite (4.59 g, 50.7 mmol). The reaction mixture was allowed to stir rapidly for 3 days. The thick reaction mixture was concentrated in vacuo to remove the 2-methyl-2-butene, and the slurry diluted with water and filtered, rinsing water and MeOH. The resulting solid was dried in vacuo to give 3-fluoro-4-(5-(1-phenylcyclopropyl)thiazolo[5,4-b]pyridine-2-yl)benzoic acid as an off-white solid which was used without further purification. MS (ESI) m/z: Calculated: 390.1; Observed: 391.1 ($M^+$+1).

Reference E

Synthesis of 2-(4-(1,3-dioxan-2-yl-2-fluorophenyl-5-benzylthiazolo[5,4-b]pyridine

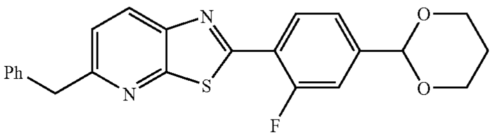

A thick slurry of 2-(4-(1,3-dioxan-2-yl)-2-fluorophenyl)-5-chlorothiazolo[5,4-b]pyridine (2.50 g, 7.1 mmol) and bis(4-(di-tert-butylphosphino)-N,N-dimethyl-benzenamine) palladium dichloride (0.10 g, 0.14 mmol) in benzylzinc(II) bromide 0.5M in THF (21 mL, 11 mmol) was flushed with argon and sealed, and heated to 70° C. All solids eventually dissolved over 1 h to give a dark brown solution. After 3 h, the reaction mixture was cooled and diluted with sat'd aq. $NH_4Cl$. Solid formed, and was taken up in EtOAc. The organic layer was washed sat'd aq. $NH_4Cl$, brine, dried over sodium sulfate, filtered, and concentrated in vacuo. The resulting solid was suspended in 50 mL MTBE and stirred for 30 min, then filtered, rinsing with a minimum amount of MTBE, and dried in vacuo to give 2-(4-(1,3-dioxan-2-yl)-2-fluorophenyl)-5-benzylthiazolo[5,4-b]pyridine as a gray solid. MS (ESI) m/z: Calculated: 406.1; Observed: 407.1 ($M^+$+1).

Reference F

Synthesis of methyl azetidine-3-carboxylate hydrochloride

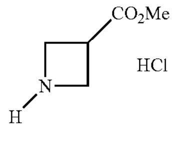

To a slurry of azetidine-3-carboxylic acid (20 g, 198 mmol) in 500 mL anhyd. MeOH under nitrogen at 0° C. was added slowly dropwise thionyl chloride (36 mL, 495 mmol) over 4 h. The resulting clear, light yellow solution was sealed and placed in a 0° C. freezer overnight. In the morning the reaction mixture was concentrated in vacuo, and the resulting oil was treated with 100 mL anhydrous benzene and concentrated in vacuo to give a solid. This was repeated anhydrous benzene. The resulting light yellow solid was dried in vacuo to give methyl azetidine-3-carboxylate hydrochloride. $^1$H NMR (400 MHz, MeOH-$d_4$) δ ppm 4.21-4.30 (m, 4H), 3.78 (s, 3H), 3.71-3.78 (m, 1H).

Reference G

Synthesis of methyl 3-hydroxyazetidine-3-carboxylate

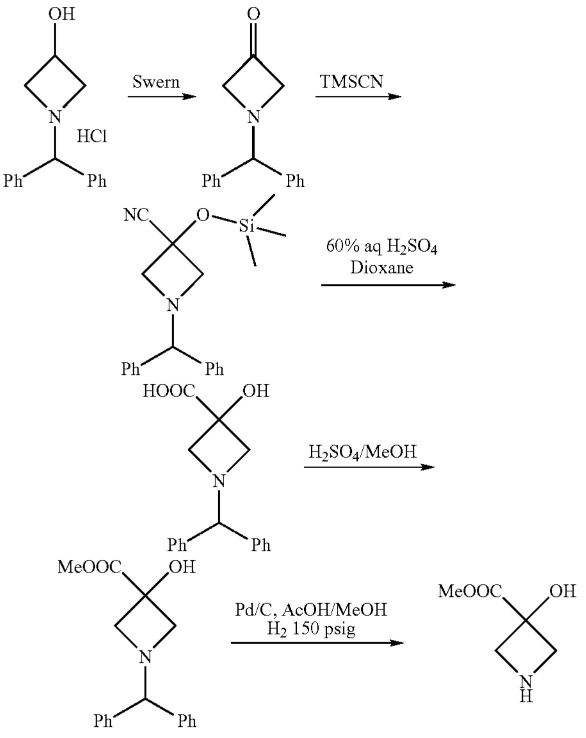

Experimental procedures can be found in patent publication WO 02/7109334.

Reference H

Synthesis of 5-(1-phenylcyclopropyl)thiazolo[5,4-b]pyridine

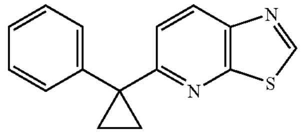

Step 1

Ethyl oxalyl chloride (27 mL, 240 mmol) was added over 30 min to a solution of 2,6-dichloropyridin-3-amine (38.8 g, 238 mmol) and triethylamine (34 mL, 240 mmol) in THF (500 mL) at 0° C. The resulting solution was stirred at 0° C. for 15 min, then allowed to warm to 25° C. and stir for 2 h. Additional $Et_3N$ (9.3 mL; 0.28 equiv) and ethyl oxalyl chloride (7.45 mL; 0.28 equiv) were sequentially added, and the resulting mixture was stirred at 25° C. for 30 min. Water (100 mL) was added to the reaction solution, and THF was removed in vacuo, affording a tan precipitate. The resulting mixture was extracted with ethyl acetate (800 mL), and the organic extract was separated, sequentially washed with water (3×200 mL) and brine, dried over sodium sulfate, filtered, and concentrated in vacuo to provide a tan solid. This solid was suspended in $Et_2O$ (100 mL) and then collected via vacuum filtration. The filter-cake was washed with $Et_2O$ (2×30 mL) and dried in vacuo to provide ethyl 2-(2,6-dichloropyridin-3-ylamino)-2-oxoacetate as a tan solid. MS (ESI) m/z: Calculated: 262.0; Observed: 262.9 ($M^+$+1).

Step 2

To a solution of ethyl 2-(2,6-dichloropyridin-3-ylamino)-2-oxoacetate (48.92 g, 186.0 mmol) in toluene (380 mL) was added Lawesson's Reagent (75.21 g, 186.0 mmol), and the resulting suspension was stirred at 90° C. for 4 h. The reaction mixture was then cooled to room temperature and filtered through Celite™, washing with 300 mL toluene. The combined filtrates were concentrated in vacuo at 40° C., and the residue was taken up in $CH_2Cl_2$ (200 mL) and filtered through a 200 g pad of silica gel, washing with additional $CH_2Cl_2$ (4×150 mL). The filtrate was concentrated in vacuo to afford ethyl 2-(2,6-dichloropyridin-3-ylamino)-2-thioxoacetate as an orange solid.

Step 3

A mixture of ethyl 2-(2,6-dichloropyridin-3-ylamino)-2-thioxoacetate (49.11 g, 175.9 mmol) and cesium carbonate (57.32 g, 175.9 mmol) in THF (350 mL) was heated at 50° C. for 6 h. The reaction suspension was then diluted with water (700 mL) and THF was removed in vacuo at 23° C. The resulting suspension was cooled to 0° C., and the precipitated solid was collected via vacuum filtration, washed with water, and dried in vacuo to provide ethyl 5-chlorothiazolo[5,4-b]pyridine-2-carboxylate as a yellow-orange solid. MS (ESI) m/z: Calculated: 242.0; Observed: 243.0 ($M^+$+1).

Step 4

A mixture of ethyl 5-chlorothiazolo[5,4-b]pyridine-2-carboxylate (500 mg, 2.06 mmol), 1-phenylvinylboronic acid (366 mg, 2.47 mmol), $Pd(Oac)_2$ (18.5 mg, 82.4 μmol), cesium carbonate (1.343 g, 4.12 mmol), and 2-dicyclohexylphosphino-2',6'-dimethoxybiphenyl (S-Phos; 33.8 mg, 82.4 μmol) in toluene (10.0 mL) was sparged with argon, then heated at 90° C. for 21.5 h. The resulting brown solution was diluted with dichloromethane (30 mL) and filtered through a pad of silica gel (washing pad with ethyl acetate (3×30 mL)). The filtrate was concentrated in vacuo, and the residue was purified via column chromatography (silica gel, 0-70% EtOAc/hexanes) to afford ethyl 5-(1-phenylvinyl)thiazolo[5,4-b]pyridine-2-carboxylate as a light yellow solid. MS (ESI) m/z: Calculated: 310.1; Observed: 311.1 ($M^+$+1).

Step 5

To a solution of ethyl 5-(1-phenylvinyl)thiazolo[5,4-b]pyridine-2-carboxylate (1.04 g, 3.35 mmol) in THF (12.9 mL) was added sodium hydroxide (1.0N, aq.) (3.35 mL, 3.35 mmol), and the resulting suspension was stirred at 25° C. for 5 min. The reaction solution was subsequently concentrated in vacuo at 25° C. to provide sodium 5-(1-phenylvinyl)thiazolo[5,4-b]pyridine-2-carboxylate as a light-orange solid.

Step 6

Potassium 2-methylpropan-2-olate (0.66 g, 5.9 mmol) was dissolved in anhydrous DMSO (19.5 mL) under argon. Trimethylsulfoxonium iodide (1.3 g, 5.9 mmol) was added to the resulting solution in one portion. After 10 min, this dissolved, and the resulting clear solution was added via cannula (over ~2 min) to a suspension of sodium 5-(1-phenylvinyl)thiazolo[5,4-b]pyridine-2-carboxylate (1.19 g, 3.9 mmol) in DMSO (5 mL) at 25° C. The resulting solution was stirred at 25° C. for 1 h. The reaction solution was then diluted with 1.0N HCl (8.0 mL) and partitioned between dichloromethane (400 mL) and water (400 mL). The organic layer was separated, and the aqueous layer was extracted with additional dichloromethane (200 mL). The combined organic extracts were dried over sodium sulfate, filtered, and concentrated in vacuo to afford crude 5-(1-phenylcyclopropyl)thiazolo[5,4-b]pyridine-2-carboxylic acid as a yellow oil. MS (ESI) m/z: Calculated: 296.1; Observed: 297.0 ($M^+$+1).

Step 7

A solution of 5-(1-phenylcyclopropyl)thiazolo[5,4-b]pyridine-2-carboxylic acid (1.16 g, 3.91 mmol) in THF (78.0 mL) was stirred at 60° C. for 30 min. The reaction solution was then concentrated in vacuo, and the residue was chromatographically purified (silica gel, 0-45% EtOAc/Hexanes) to furnish 5-(1-phenylcyclopropyl)thiazolo[5,4-b]pyridine as a light-yellow solid. MS (ESI) m/z: Calculated: 252.1; Observed: 253.0 ($M^+$+1).

Reference I

Synthesis of 2-(4-Bromo-2,6-dimethylphenyl)-1,3-dioxane

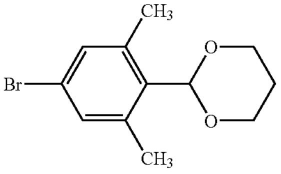

Step 1

A mixture of 4-bromo-2,6-dimethylbenzenamine (20 g, 100 mmol) and conc. HCl (100 mL) in water (100 mL) was sonicated for 5 min and then cooled to 0° C. A solution of sodium nitrite (6.9 g, 100 mmol) in water (25 mL) was added, and the resulting mixture was stirred at 0° C. for 30 min, then neutralized by the addition of solid sodium bicarbonate. The resulting mixture was slowly poured (in portions) into a solution of potassium cyanide (6.5 g, 100 mmol) and copper(I) cyanide (9.0 g, 100 mmol) in water (50 mL). The resulting mixture was heated at 70° C. for 30 min, then cooled to 25° C. and extracted with EtOAc (3×150 mL). The combined extracts were washed with brine, dried over $MgSO_4$, filtered, and concentrated in vacuo to provide 4-bromo-2,6-dimethylbenzonitrile as a brown solid. $^1H$ NMR (300 MHz, DMSO-$d_6$) δ ppm 7.56 (s, 2 H), 2.45 (s, 6 H).

Step 2

DIBAL-H (1.0M in hexanes; 22.0 mL, 22.0 mmol) was added to a solution of 4-bromo-2,6-dimethylbenzonitrile (3.87 g, 18 mmol) in $CH_2Cl_2$ (50 mL) at 0° C., and the resulting mixture stirred at 25° C. for 3 h. Saturated aqueous sodium potassium tartrate solution (75 mL) was then slowly added, and the resulting mixture was stirred vigorously for 30 min. The organic layer was separated, and the aqueous layer was extracted with $CH_2Cl_2$). The combined organic extracts were dried over $MgSO_4$, filtered, and concentrated in vacuo. Chromatographic purification of the residue (silica gel, 0-20% EtOAc/hexanes) furnished 4-bromo-2,6-dimethylbenzaldehyde as a light brown solid.

Step 3

A mixture of 4-bromo-2,6-dimethylbenzaldehyde (2.51 g, 12 mmol), 4-methyl-benzenesulfonic acid (0.20 g, 1.2 mmol), and propane-1,3-diol (1.2 mL, 16 mmol) in toluene (200 mL) was heated under nitrogen at 140° C. for 16 h, using a Dean-Stark trap to remove water. The reaction solution was then cooled to 25° C., diluted with EtOAc (200 mL), and sequentially washed with saturated aqueous sodium bicarbonate solution (100 mL) and brine (100 mL). The organic layer was separated, dried over $MgSO_4$, filtered, and concentrated in vacuo to provide a yellow-brown oil. Hexane (200 mL) was added to the oil, and the resulting mixture was stirred vigorously for 10 min, resulting in the precipitation of a solid. This solid was collected by vacuum filtration, washed with hexanes (100 mL), and dried in vacuo to provide 2-(4-bromo-2,6-dimethylphenyl)-1,3-dioxane as a tan solid.

Reference J

Synthesis of methyl 1-(3-fluoro-4-(5-(trimethylstannyl)thiazolo[5,4-b]pyridine-2-yl)benzyl)azetidine-3-carboxylate

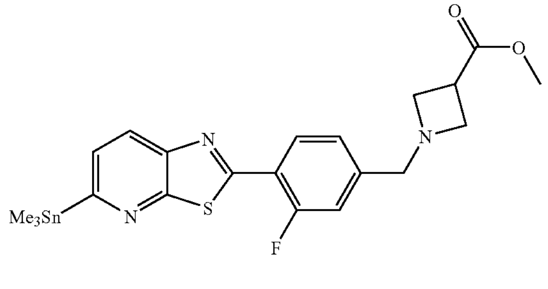

Step 1

A slurry of 2-(4-(1,3-dioxan-2-yl)-2-fluorophenyl)-5-chlorothiazolo[5,4-b]pyridine (5.00 g, 14.3 mmol) in 100 mL 1:1 THF/5N aq. HCl was heated in a sealed tube to 70° C. The thick orange mixture was cooled slightly and an additional 50 mL THF was added. The reaction mixture was sealed and heating continued. After 2 h, the reaction mixture was cooled and allowed to stir 3 days at ambient temperature. The reaction mixture was cooled and THF was removed in vacuo. The resulting yellow solid was collected by filtration through a frit, rinsing with water. The material was dried on the frit for several hours and dried in vacuo overnight to give 4-(5-chlorothiazolo[5,4-b]pyridine-2-yl)-3-fluorobenzaldehyde as a light yellow/orange solid. MS (ESI) m/z: calculated: 292.0: Observed: 292.9 ($M^+$+1).

Step 2

A mixture of 4-(5-chlorothiazolo[5,4-b]pyridine-2-yl)-3-fluorobenzaldehyde (2.08 g, 7.11 mmol), methyl azetidine-3-carboxylate hydrochloride (1.62 g, 10.7 mmol), N-ethyl-N-isopropylpropan-2-amine (1.86 mL, 10.7 mmol) in dichloromethane (40.00 mL) and methanol (30.00 mL) was stirred for 5 min. Then acetic acid (1.64 mL, 28.4 mmol) was added and the mixture was allowed to stir for 90 min at 50° C. Sodium cyanoborohydride (0.223 g, 3.55 mmol) was added. After 15 min, the solvent removed, and the mixture concentrated onto silica gel. Purification by silica gel chromatography, 120 g column, 30-40% EtOAc/hex followed by 50-60% (3% TEA in EtOAc/hex) gave methyl 1-((4-(5-chlorothiazolo[5,4-b]pyridine-2-yl)-3-fluorophenyl)methyl)azetidine-3-carboxylate. MS (ESI) m/z: calculated: 391.1; Observed: 392.0 ($M^+$+1).

Step 3

Methyl 1-((4-(5-chlorothiazolo[5,4-b]pyridine-2-yl)-3-fluorophenyl)methyl)azetidine-3-carboxylate (1.40 g, 3.57 mmol), 1,1,1,2,2,2-hexamethyldistannane (2.34 g, 7.15 mmol), and tetrakis(triphenylphosphine) palladium (0) (0.206 g, 0.179 mmol) were combined in a 75 mL sealable vessel under argon. 15 mL dioxane was added, and the reaction mixture was sealed and heated to 70° C. overnight. The reaction mixture was adsorbed onto 10 g silica gel with DCM, drying, and purified by silica gel chromatography, 0-100% EA/hexanes, to give methyl 1-((3-fluoro-4-(5-(trimethylstannyl)-thiazolo[5,4-b]pyridine-2-yl)phenyl)methyl)azetidine-3-carboxylate as a light yellow solid. MS (ESI) m/z: calculated: 521.1; Observed: 522.0 ($M^+$+1).

Reference K

Synthesis of 2-(4-(1,3-dioxan-2-yl)-2-fluorophenyl)-5-(trimethylstannyl)thiazolo[5,4-b]pyridine

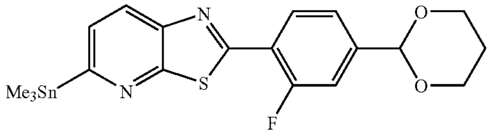

A mixture of 2-(4-(1,3-dioxan-2-yl)-2-fluorophenyl)-5-chlorothiazolo[5,4-b]pyridine (1.00 g, 2.9 mmol), hexamethylditin (1.4 g, 4.3 mmol), tetrakis(triphenylphosphine) palladium (0) (0.16 g, 0.14 mmol) in 10 mL dioxane was heated to 80° C. overnight. The dark mixture was determined by LCMS to have proceeded well to desired product. The material was transferred to a flask with DCM, and adsorbed onto 5 g silica gel, dried, and purified by ISCO 40 g, 0-30% EA/hexanes to give 2-(4-(1,3-dioxan-2-yl)-2-fluorophenyl)-5-(trimethylstannyl)thiazolo[5,4-b]pyridine as an off-white solid. MS (ESI) m/z: calculated: 480.0; Observed: 481.0 ($M^{+}$+1).

Reference L

Synthesis of 2-(2-fluoro-4-methylphenyl)-5-(1-phenylvinyl)thiazolo[5,4-b]pyridine

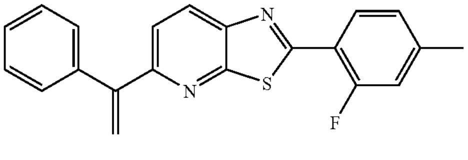

Synthesized from 1-bromo-2-fluoro-4-methylbenzene (10 g, 53 mmol) and 2,6-dichloro-3-isothiocyanatopyridine (11 g, 53 mmol) according to the procedure for the synthesis of intermediate (2-(4-(1,3-dioxan-2-yl)-2-fluorophenyl)-5-(1-phenylvinyl)-thiazolo[5,4-b]pyridine) to give 2-(2-fluoro-4-methylphenyl)-5-(1-phenylvinyl)thiazolo[5,4-b]pyridine as a tan solid. MS (ESI) m/z: calculated: 346.1; Observed: 347.1 ($M^{+}$+1).

Reference M

Synthesis of 2-(2-fluoro-4-vinylphenyl)-5-(1-phenylcyclopropyl)-thiazolo[5,4-b]pyridine

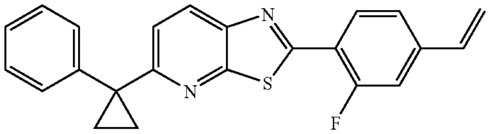

Trimethylsilylmethylmagnesium chloride, 1.1 M solution in THF (15 mL) was added dropwise to a solution at 0° C. of 3-fluoro-4-(5-(1-phenylcyclopropyl)thiazolo[5,4-b]pyridine-2-yl)benzaldehyde (4.00 g, 11 mmol) in THF (80 mL) and the reaction mixture was stirred for 30 min at 0° C. The reaction mixture was quenched with 1 N aq. HCl and extracted with EtOAc twice, dried over $MgSO_4$ and concentrated in vacuo. The residue was dissolved in THF (100 mL), and cooled to 0° C. in ice bath. The slurry of potassium t-butoxide (2.4 g, 21 mmol) in THF (12 mL) was added slowly. At the end of the addition the reaction mixture was allowed to stir for 30 min at 0° C. At this time 1 N HCl was added and the mixture was extracted with EtOAc and the organic layer was dried over $MgSO_4$. The residue was concentrated in vacuo and purified by silica gel chromatography to afford 2-(2-fluoro-4-vinylphenyl)-5-(1-phenylcyclopropyl)thiazolo[5,4-b]pyridine. MS (ESI) m/z: calculated: 372.1; Observed: 373.0 ($M^{+}$+1).

Reference N

Synthesis of 2-(4-(1,3-dioxan-2-yl)-2-fluorophenyl)-5-(trimethylstannyl)thiazolo-[5,4-b]pyridine

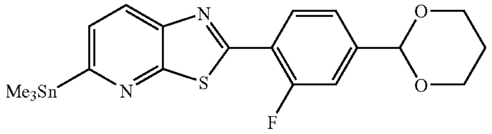

A mixture of 2-(4-(1,3-dioxan-2-yl)-2-fluorophenyl)-5-chlorothiazolo[5,4-b]pyridine (1.00 g, 2.9 mmol), hexamethylditin (1.4 g, 4.3 mmol), tetrakis(triphenylphosphine) palladium (0) (0.16 g, 0.14 mmol) in 10 mL dioxane was heated to 80° C. overnight. The dark mixture was determined by LCMS to have proceeded well to desired product. The material was transferred to a flask with DCM, and adsorbed onto 5 g silica gel, dried, and purified by ISCO 40 g, 0-30% EA/hexanes to give 2-(4-(1,3-dioxan-2-yl)-2-fluorophenyl)-5-(trimethylstannyl)thiazolo[5,4-b]pyridine as an off-white solid. MS (ESI) m/z: calculated: 480.0; Observed: 481.0 ($M^{+}$+1).

Reference O

Synthesis of 3-amino-6-(1-phenylcyclopropyl)pyridine-2(1H)-thione

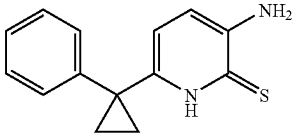

Step 1

To a 0° C. solution of methylmagnesium chloride 3.0 M in THF (99 mL, 298 mmol) in 100 mL THF under argon was added a solution of 2,6-dichloro-3-isothiocyanatopyridine (43.6 g, 213 mmol) in 100 mL THF slowly dropwise via addition funnel over 2 h. The resulting reaction mixture was allowed to stir 1 h, then was quenched by careful slow addition of sat'd aq. $NH_4Cl$. The reaction mixture was allowed to warm to ambient temperature, and was transferred to a separatory funnel with 200 mL EtOAc. The organic layer was washed with brine, dried over sodium sulfate, filtered, and concentrated in vacuo to give a thick oil. The oil was taken up in 200 mL DMF and treated with sodium carbonate (34 g, 319 mmol). The reaction flask was fitted with an air cooled reflux condenser and the reaction mixture was heated to 90° C. under nitrogen. After 1 h, the reaction mixture was cooled slightly and poured into a stirring mixture of ice and water. The resulting slurry (total volume about 1.5 L) was stirred rapidly for 30 min, then filtered through a frit, rinsing with water, then dried in air and in vacuo to give 5-chloro-2-methylthiazolo[5,4-b]pyridine as a tan solid. MS (ESI) m/z: calculated: 184.0; Observed: 185.0 ($M^{+}$+1).

Step 2

A 1000 mL rbf was charged with 1-phenylvinylboronic acid hydrate (36.7 g, 221 mmol), $(amphos)_2PdCl_2$ (3.26 g, 4.60 mmol), and 5-chloro-2-methylthiazolo[5,4-b]pyridine (34.0 g, 184 mmol) under argon. Dioxane (200 mL) was added followed by a solution of potassium carbonate (61.1 g, 442 mmol) in 60 mL water, and the reaction was fitted with a water cooled reflux condenser and flushed with argon. The resulting slurry was heated to 90° C. for 3 h. The reaction mixture was allowed to cool, and was diluted with 200 mL MTBE and water. The organic layer was washed with brine, dried over sodium sulfate, filtered, and concentrated in vacuo to give a thick brown oil. The oil was purified by silica gel chromatography, 0-30% EA/hexanes to give 2-methyl-5-(1-phenylvinyl)thiazolo[5,4-b]pyridine as a brown oil. MS (ESI) m/z: calculated: 252.1; Observed: 253.1 ($M^+$+1).

Step 3

Potassium 2-methylpropan-2-olate (32.3 g, 288 mmol) was almost completely dissolved in 250 mL DMSO under argon in a 1 L 3-necked RBF. Trimethyl sulfoxonium iodide (63.3 g, 288 mmol) was added in 2 portions, separated by 15 min. The reaction mixture became wamm after the addition. After 15 min, the reaction was fitted with a water-cooled reflux condenser and heated to 60° C., and a solution of 2-methyl-5-(1-phenylvinyl)thiazolo[5,4-b]pyridine (41.5 g, 164 mmol) in 125 mL THF was added slowly dropwise via addition funnel over 30 min. The resulting dark red reaction mixture was cooled briefly and then poured onto ice and 300 mL sat'd aq. $NH_4Cl$ was added. Ethyl acetate (500 mL) was added and the layers were separated. The aq. Layer was extracted with ethyl acetate and the combined organics were washed with brine, dried over sodium sulfate, filtered, and concentrated in vacuo. Purification by silica gel chromatography, 330 g, 0-40% EAlhexanes gave 2-methyl-5-(1-phenylcyclopropyl)thiazolo[5,4-b]pyridine as an orange solid. MS (ESI) m/z: calculated: 266.1; Observed: 267.1 ($M^+$+1).

Step 4

A slurry of 2-methyl-5-(1-phenylcyclopropyl)thiazolo[5,4-b]pyridine (17.0 g, 63.8 mmol) in 128 mL EtOH was added sodium hydroxide 10 M in water (128 mL, 1276 mmol). Argon was bubbled through the resulting slurry for 5 min, then the reaction flask was fitted with a water-cooled reflux condenser, flushed with argon, and the reaction mixture was heated to vigorous reflux under argon. After 6 h, the reaction mixture was cooled and the EtOH was removed in vacuo. The resulting slurry was poured onto ice and neutralized with 260 mL 5N aq. HCl to pH 4. A light yellow precipitate resulted. The solid was collected by filtration through a glass frit, rinsing with 2×200 mL water, and the solid was dried under a bag of nitrogen overnight. Further drying in vacuo for several hours gave 3-amino-6-(1-phenylcyclopropyl)pyridine-2(1H)-thione as a light yellow solid. MS (ESI) m/z: calculated: 242.1; Observed: 243.1 ($M^+$+1).

Reference P

Synthesis of 2-(azetidin-3-yl)acetic acid trifluoroacetic acid salt

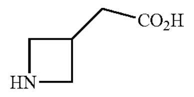

Step 1

To a solution of 1-benzhydrylazetidin-3-ol (20 g, 0.835 mol) in pyridine (167 mL) was added DMAP (12.24 g, 0.1 mM) and p-toluene sulphonylchloride at −40° C. The reaction mixture was stirred overnight. The reaction mixture was partitioned between dichloromethane (200 mL) and water. Solvent was evaporated off, purified by column chromatography using silica gel, 100-200 mesh) and 10% ethyl acetate hexane as eluent to obtain 1-benzhydryl-3-(toluene-4-sulfonyl)-azetidine. $^1$H-NMR (400 MHz, $CDCl_3$,), δ ppm 7.76-7.74 (m, 2H), 7.34-7.15 (m, 12H), 4.89-4.85 (m, 1H), 4.32 (s, 1H), 3.47-3.43 (m, 2H), 3.06-3.03 (m, 2H), 2.43 (s, 3H).

Step 2

To a suspension of sodium hydride (4.97 g, 0.129 mol) in 130 mL of anhydrous dimethyl formamide was added diethyl malonate (22.7 mL, 0.142 mol) dropwise at 0° C. and this reaction mixture was stirred at room temperature for 2 h. 1-Benzhydryl-3-(toluene-4-sulfonyl)-azetidine was added to it dropwise at 0° C. and reaction mixture was refluxed at 110° C. for 20 h. Excess sodium hydride was quenched with ammonium chloride, DMF was removed, and the reaction mixture was partitioned between chloroform and water; the aqueous layer was extracted with chloroform, the solvent was removed in vacuo, and purification by (neutral alumina) chromatography and 30% ethyl acetate/hexanes as eluent provided 2-(1-benzhydryl-azetidin-3-yl)-malonic acid diethyl ester. $^1$H-NMR (400 MHz, $CDCl_3$), δ ppm 7.41-7.17 (m, 10H), 4.34 (s, 1H), 4.25-4.09 (m, 3H), 3.66 (d, 1H, J=3.66 Hz), 3.41-3.37 (m, 2H), 3.07-2.99 (m, 1H), 2.93-2.90 (m, 2H), 1.25-1.23 (m, 6H)

Step 3

To a solution of 2-(1-benzhydryl-azetidin-3-yl)-malonic acid diethyl ester (20.2 g, 0.053 mol) in 159 mL of ethyl acetate, palladium hydroxide (0.741 g, 5.3 mmol) was added under nitrogen, followed by $Boc_2O$ (15.0 mL, 68.8 mmol). The reaction was performed under hydrogen atmosphere. The reaction mixture was passed through celite, washed with ethyl acetate, concentrated, purified by column chromatography (neutral alumina) using 4% ethyl acetate/hexanes as eluent to give 2-(1-tert-butoxycarbonyl-azetidin-3-yl)-malonic acid diethyl ester. $^1$H-NMR (400 MHz, $CDCl_3$,), δ ppm 4.23-4.17 (m, 4H), 4.16-4.06 (m, 2H), 3.73-3.69 (m, 2H), 3.62-3.59 (m, 1H), 3.12-3.10 (m, 1H), 1.42 (s, 9H), 1.28-1.24 (m, 6H).

Step 4

To a solution of 2-(1-tert-butoxycarbonyl-azetidin-3-yl)-malonic acid diethyl ester (3 g, 0.0952 mol) in 95 mL toluene was added (2.514 g, 0.0952 mol) of 18-crown-6. A solution of sodium hydroxide (0.1047 mol, 1.1 M) in ethanol was added dropwise. The reaction mixture was stirred at 25° C. for 5 h and then heated to reflux overnight. The reaction mixture was cooled, concentrated in vacuo, and partitioned between ethyl acetate and water. The organic layer was dried over sodium sulphate, solvent was evaporated off, and the residue purified by column chromatography (neutral alumina) using ethyl acetate/hexanes as eluent to give 3-ethoxycarbonyl-methyl-azetidine-1-carboxylic acid tert-butyl ester.

Step 5

To a solution of 3-ethoxycarbonylmethyl-azetidine-1-carboxylic acid tert-butyl ester (2.3 g, 0.095 mol) in 30 mL THF/MeOH/water (3:2:1) was added (0.477 g, 11.35 mmol) of LiOH*$H_2O$ at 0° C. The reaction mixture was stirred for 3 h at 25° C. Methanol and THF were removed in vacuo, and the reaction mixture was diluted with 50 mL water, and extracted with ethyl acetate. The aqueous layer was acidified with 2N HCl, extracted with ethyl acetate, and the organic layer was dried over $Na_2SO_4$, and concentrated to give 2-(1-(tert-butoxycarbonyl)-azetidin-3-yl)acetic acid. $^1$H-NMR (400 MHz, $CDCl_3$), δ ppm 4.12-4.07 (m, 2H), 3.66-3.60 (m, 2H), 2.91-2.84 (m, 1H), 2.68-2.66 (m, 2H), 1.43 (s, 9H).

Step 6

2-(1-(tert-Butoxycarbonyl)azetidin-3-yl)acetic acid (0.308 g, 1.43 mmol) was dissolved in 5 mL dichloromethane and was stirred at room temperature. Trifluoroacetic acid (1.47 mL) was added dropwise to the reaction mixture at 0° C. The reaction mixture was allowed to stir at room temperature for 2 h. Trifluoroacetic acid was removed in vacuo to give 2-(azetidin-3-yl)acetic acid trifluoroacetic acid salt. $^1$H-NMR (400 MHz, $CDCl_3$) δ ppm 4.18-4.13 (m, 2H), 3.93-3.88 (m, 2H), 3.25-3.19 (m, 1H), 2.71 (d, 2H, J=7.6 Hz).

3-Fluoro-4-(5-(1-phenylcyclopropyl)thiazolo[5,4-b]pyridine-2-yl)benzoic acid (107 mg, 0.274 mmol) was dissolved in thionyl chloride at 65° C. for 1 h before it was concentrated. The reaction mixture was dissolved in THF (1.4 mL) before ammonium hydroxide (1.07 mL, 27.40 mmol) was added and stirred at ambient temp. for 16 h. The reaction mixture was diluted with EtOAc, added to a separatory funnel, partitioned with sodium bicarbonate (saturated, aqueous), washed with sodium bicarbonate (saturated, aqueous), separated, dried over sodium sulfate, and concentrated via rotovap to give the title compound after preparatory LC. MS (ESI) m/z: Calculated: 389; Observed: 390.1 ($M^+$+1).

Reference R

General Reductive Amination and Hydrolysis Procedures

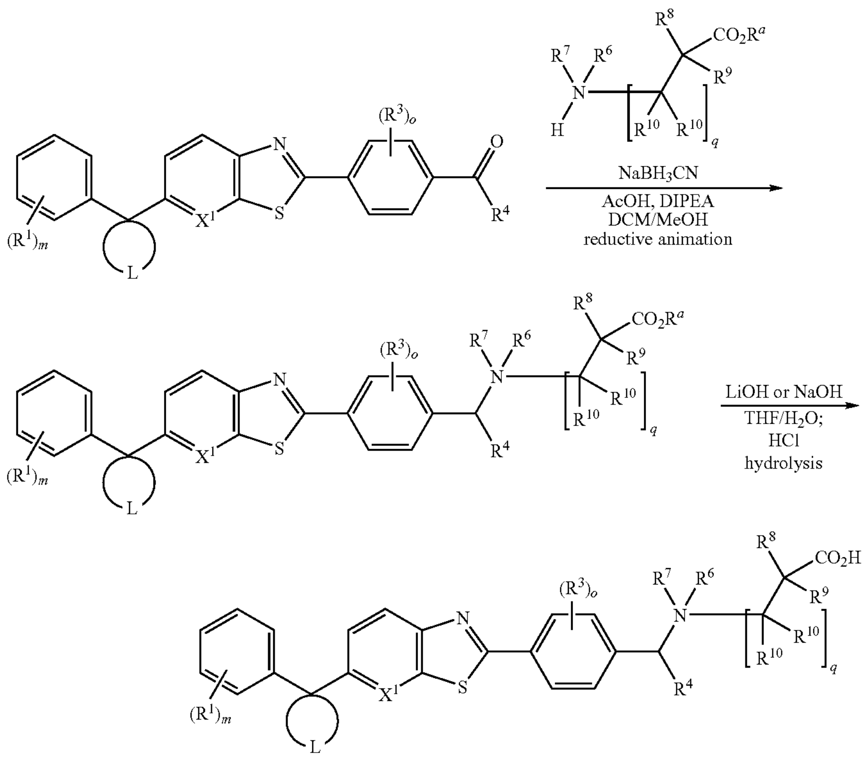

Reference Q

Synthesis of 3-fluoro-4-(5-(1-phenylcyclopropyl)[1,3]thiazolo[5,4-b]pyridine-2-yl)benzamide

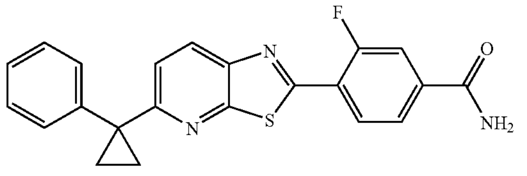

General Procedure for Reductive Amination of Aldehydes:

A mixture of aldehyde (1.0 mmol), acetic acid (1.5-5 mmol), amine (1.5-5 mmol), and DIPEA (0-5 mmol, used in 1:1 ratio with amine*HCl salts) in DCM/MeOH (1:1, 5 mL) was stirred at room temperature for 1 h. Sodium cyanoborohydride (0.5-1.0 mmol) was added and the reaction mixture was stirred for 2-3 h at room temperature. The reaction mixture was concentrated in vacuo, diluted with DCM, and the acid was quenched by addition of saturated aqueous sodium bicarbonate. The aqueous layer was extracted with DCM, and the combined organic layers were dried over sodium sulfate, filtered, and concentrated in vacuo. Purification by silica gel chromatography provided the desired products.

General Procedure for Hydrolysis of Esters:

To a solution of ester (0.5 mmol) in 2 mL THF was added sodium hydroxide (11.0M in water, 1.5 mmol). The reaction was stirred until completion. The THF was removed in vacuo, and the solid was suspended in 2 mL water. HCl (1.0N in water, 1.5 mmol) was added to neutralize the base, and the mixture was sonicated. Phosphate buffer (4 mL, 1M, pH 6) was added and the reaction was sonicated. The slurry was filtered and the solid rinsed with water and EtOH and dried in vacuo to give the desired product. Occasionally compounds were isolated as HCl salts. In these cases, the THF was removed in vacuo, and the reaction acidified with HCl until approximately pH 1-2. The solids were collected by filtration, rinsing with water and ether, and dried in vacuo to give the desired products as HCl salts.

Reference S

General Amide Formation and Ester Hydrolysis Procedures

General Procedure for Hydrolysis of Esters:

To a solution of ester (0.5 mmol) in 2 mL THF was added sodium hydroxide (1.0M in water, 1.5 mmol). The reaction was stirred until completion. The THF was removed in vacuo, and the solid was suspended in 2 mL water. HCl (1.0N in water, 1.5 mmol) was added to neutralize the base, and the mixture was sonicated. Phosphate buffer (4 mL, 1M, pH 6) was added and the reaction was sonicated. The slurry was filtered and the solid rinsed with water and EtOH and dried in vacuo to give the desired product. Occasionally compounds were isolated as HCl salts. In these cases, the THF was removed in vacuo, and the reaction acidified with HCl until approximately pH 1-2. The solids were collected by filtration, rinsing with water and ether, and dried in vacuo to give the desired products as HCl salts.

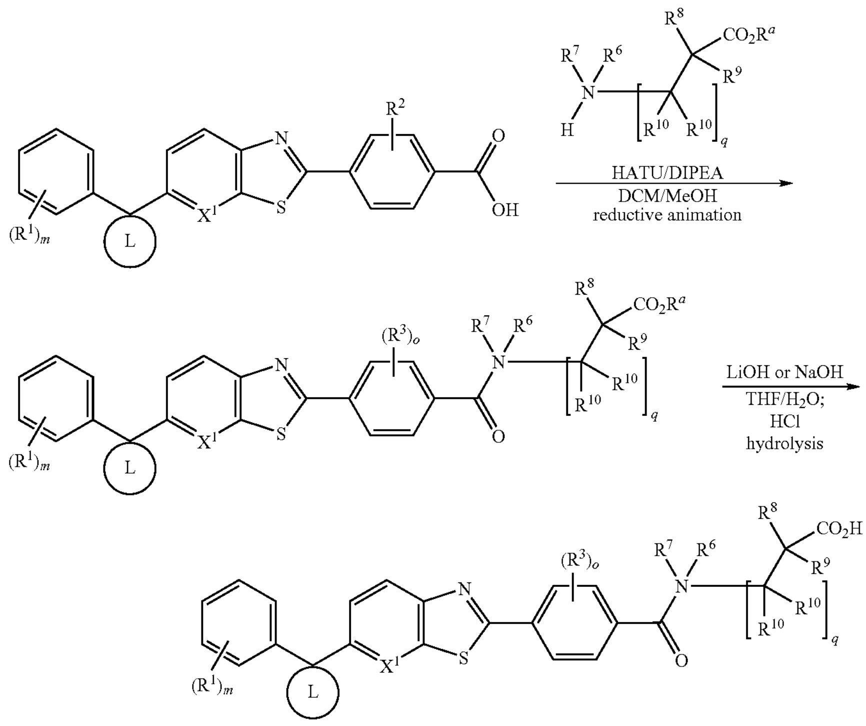

General Procedure for Amide Formation:

To 3-fluoro-4-(5-(1-phenylcyclopropyl)thiazolo[5,4-b]pyridine-2-yl)benzoic acid was added N,N-dimethylformamide, N-ethyl-N-isopropylpropan-2-amine, and HBTU or HATU and it was stirred for 5 min. The amine was then added and stirred for 1 h. The reaction mixture was diluted with EtOAc, added to a separatory funnel, partitioned with sodium bicarbonate (saturated, aqueous) or water, separated, dried over sodium sulfate, and concentrated in vacuo to give crude product. The crude product was purified via preparatory HPLC or flash chromatography to give the title compound.

Example 1

Synthesis of 1-((3-fluoro-4-(5-(1-phenylcyclopropyl)thiazolo[5,4-b]pyridin-2-yl)-phenyl)methyl)azetidine-3-carboxylic acid

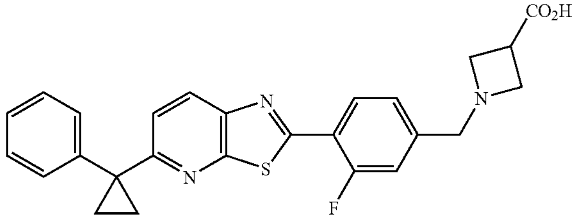

Step 1

Reaction of 3-fluoro-4-(5-(1-phenylcyclopropyl)thiazolo[5,4-b]pyridine-2-yl)-benzaldehyde (1.3 g, 3.4 mmol) and methyl azetidine-3-carboxylate hydrochloride (0.77 g, 5.1 mmol) according to Reference R and the general procedure for reductive amination gave methyl 1-((3-fluoro-4-(5-(1-phenylcyclopropyl)thiazolo[5,4-b]pyridine-2-yl)phenyl)methyl)-azetidine-3-carboxylate as a light yellow solid. MS (ESI) m/z: Calculated: 473.2; Observed: 474.1 ($M^{+}$+1).

Step 2

Hydrolysis of methyl 1-((3-fluoro-4-(5-(1-phenylcyclopropyl)thiazolo[5,4-b]pyridine-2-yl)phenyl)methyl)azetidine-3-carboxylate (1.2 g, 2.5 mmol) according to Reference R and the general procedure for ester hydrolysis gave 1-((3-fluoro-4-(5-(1-phenylcyclopropyl)-thiazolo[5,4-b]pyridine-2-yl)phenyl)methyl)azetidine-3-carboxylic acid as an off-white solid. MS (ESI) m/z: Calculated: 459.1; Observed: 460.0 ($M^{+}$+1). $^{1}$H NMR (400 MHz, DMSO-$d_6$) δ ppm 8.21-8.33 (m, 2 H), 7.28-7.49 (m, 7 H), 7.04 (d, J=8.5 Hz, 1 H), 3.65 (s, 2 H), 3.39-3.49 (m, 2 H), 3.18-3.37 (m, 3 H), 1.62-1.76 (m, 2H), 1.32-1.45 (m, 2 H)

Example 2

Synthesis of (R)-1-((3-fluoro-4-(5-(1-phenylcyclopropyl)thiazolo[5,4-b]pyridine-2-yl)-phenyl)methyl)pyrrolidine-3-carboxylic acid hydrochloride and (S)-1-((3-fluoro-4-(5-(1-phenylcyclopropyl)thiazolo[5,4-b]pyridine-2-yl)phenyl)methyl)pyrrolidine-3-carboxylic acid hydrochloride

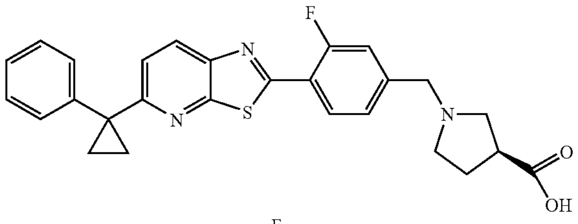

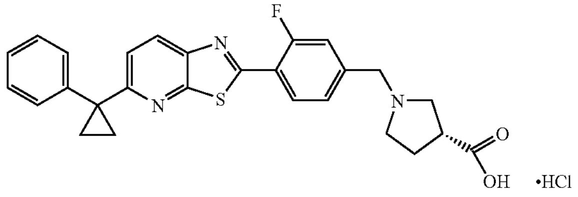

Step 1

Reaction of 3-fluoro-4-(5-(1-phenylcyclopropyl)thiazolo[5,4-b]pyridine-2-yl)-benzaldehyde (0.300 g, 0.801 mmol) and methylpyrrolidine-3-carboxylate hydrochloride (0.199 g, 1.20 mmol), according to Reference R and general procedure for reductive amination afforded the racemic mixture of methyl 1-((3-fluoro-4-(5-(1-phenylcyclopropyl)thiazolo[5,4-b]pyridine-2-yl)phenyl)methyl)pyrrolidine-3-carboxylate. MS (ESI) m/z: Calculated: 487.2; Observed: 488.0 ($M^{+}$+1). The enantiomers of methyl 1-((3-fluoro-4-(5-(1-phenylcyclopropyl)-thiazolo[5,4-b]pyridine-2-yl)phenyl)methyl)pyrrolidine-3-carboxylate were separated by SFC chromatography (Column: Chiralpak AS-H (21×250 mm, 5 um); A: Liquid $CO_2$; B: Isopropanol (0.2% DEA); Isocratic: 56:44 (A:B); Flow rate: 70 mL/min; Outlet Pressure: 100 bar) to give (R)-methyl 1-((3-fluoro-4-(5-(1-phenylcyclopropyl)thiazolo[5,4-b]pyridine-2-yl)phenyl)methyl)pyrrolidine-3-carboxylate and (S)-methyl 1-((3-fluoro-4-(5-(1-phenylcyclopropyl)thiazolo[5,4-b]pyridine-2-yl)phenyl)methyl)pyrrolidine-3-carboxylate.

Step 2

Both enantiomers of methyl 1-((3-fluoro-4-(5-(1-phenylcyclopropyl)thiazolo[5,4-b]pyridine-2-yl)phenyl)methyl)pyrrolidine-3-carboxylate were processed separately according to Reference R and the general procedure for ester hydrolysis to give (R)-1-((3-Fluoro-4-(5-(1-phenylcyclopropyl)thiazolo[5,4-b]pyridine-2-yl)phenyl)methyl)pyrrolidine-3-carboxylic acid hydrochloride and (S)-1-((3-Fluoro-4-(5-(1-phenylcyclopropyl)thiazolo[5,4-b]pyridine-2-yl)-phenyl)methyl)pyrrolidine-3-carboxylic acid hydrochloride. MS (ESI) m/z: Calculated: 473.2; Observed: 474.1 ($M^{+}$+1).

Example 3

Synthesis of 1-((3-fluoro-4-(5-(1-phenylcyclopropyl)thiazolo[5,4-b]pyridine-2-yl)-phenyl)methyl)-3-hydroxyazetidine-3-carboxylic acid hydrochloride

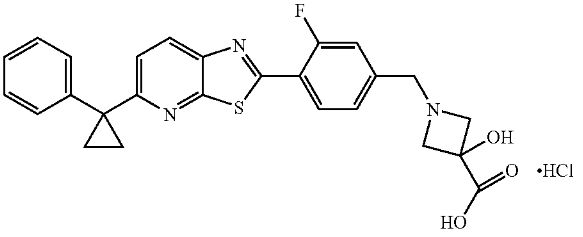

Step 1

Reaction of 3-fluoro-4-(5-(1-phenylcyclopropyl)thiazolo[5,4-b]pyridine-2-yl)-benzaldehyde (0.209 g, 0.56 mmol) and methyl 3-hydroxyazetidine-3-carboxylate acetate (0.14 g, 0.73 mmol) according to Reference R and general procedure for reductive amination afforded methyl 1-((3-fluoro-4-(5-(1-phenylcyclopropyl)thiazolo[5,4-b]pyridine-2-yl)phenyl)-methyl)-3-hydroxyazetidine-3-carboxylate. MS (ESI) m/z: Calculated: 489.2; Observed: 490.0 ($M^{+}$+1).

Step 2

Hydrolysis of methyl 1-((3-fluoro-4-(5-(1-phenylcyclopropyl)thiazolo[5,4-b]pyridine-2-yl)phenyl)methyl)-3-hydroxyazetidine-3-carboxylate (0.030 g, 0.061 mmol) according to Reference R and the general procedure for ester hydrolysis afforded 1-((3-fluoro-4-(5-(1-phenylcyclopropyl)thiazolo[5,4-b]pyridine-2-yl)phenyl)methyl)-3-hydroxyazetidine-3-carboxylic acid hydrochloride. MS (ESI) m/z: Calculated: 475.1; Observed: 476.0 ($M^{+}$+1).

Example 4

Synthesis of 3-fluoro-1-((3-fluoro-4-(5-(1-phenylcyclopropyl)thiazolo[5,4-b]pyridine-2-yl)phenyl)methyl)azetidine-3-carboxylic acid hydrochloride

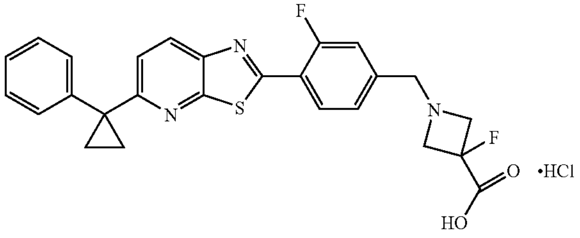

Step 1

To a solution of methyl 1-((3-fluoro-4-(5-(1-phenylcyclopropyl)thiazolo[5,4-b]pyridine-2-yl)phenyl)methyl)-3-hydroxyazetidine-3-carboxylate (0.0334 g, 0.068 mmol) at 0° C. in anhydrous DCM was added 1.0 mL was added DAST (0.011 mL, 0.082 mmol). The reaction mixture was stirred for 10 min. at which time the reaction was quenched carefully with water and extracted with DCM. The organics were dried over magnesium sulfate and concentrate in vacuo. Purification by silica gel afford methyl 3-fluoro-1-((3-fluoro-4-(5-(1-phenylcyclopropyl)thiazolo[5,4-b]pyridine-2-yl)phenyl)methyl)azetidine-3-carboxylate. MS (ESI) m/z: Calculated 491.2; Observed: 492.0 ($M^+$+1).

Step 2

Hydrolysis of methyl 3-fluoro-1-((3-fluoro-4-(5-(1-phenylcyclopropyl)thiazolo[5,4-b]pyridine-2-yl)phenyl)methyl)azetidine-3-carboxylate (0.0067 g, 0.014 mmol) according to the general procedure for ester hydrolysis afforded 3-fluoro-1-((3-fluoro-4-(5-(1-phenylcyclopropyl)thiazolo[5,4-b]pyridine-2-yl)phenyl)methyl)azetidine-3-carboxylic acid hydrochloride. MS (ESI) m/z: Calculated: 477.1; Observed: 478.0 ($M^+$+1).

Example 5

Synthesis of 1-((3-fluoro-4-(5-(1-phenylcyclopent-3-enyl)thiazolo[5,4-b]pyridine-2-yl)phenyl)methyl)azetidine-3-carboxylic acid

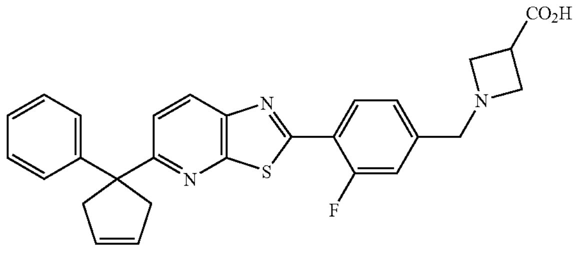

Step 1

To a slurry of 2-(4-(1,3-dioxan-2-yl)-2-fluorophenyl)-5-benzylthiazolo[5,4-b]pyridine (2.28 g, 5.6 mmol) in 40 mL DMF under argon was added lithium bis(trimethylsilyl)amide, 1.0 m solution in tetrahydrofuran (7.0 mL, 7.0 mmol). A very deep blue solution resulted. After 2 min, allyl iodide (0.77 mL, 8.4 mmol) was added via syringe and the reaction became brown. After 5 min, sat'd aq. $NH_4Cl$ was added and the reaction partitioned between water and EA. The organic was washed with water, brine, dried over sodium sulfate, filtered, and concentrated in vacuo. The resulting material was sonicated in MTBE, filtered, and dried to give 2-(4-(1,3-dioxan-2-yl)-2-fluorophenyl)-5-(1-phenylbut-3-enyl)thiazolo[5,4-b]pyridine as a yellow solid. MS (ESI) m/z: Calculated: 446.2; Observed: 447.1 ($M^+$+1).

Step 2

To a slurry of 2-(4-(1,3-dioxan-2-yl)-2-fluorophenyl)-5-(1-phenylbut-3-enyl)-thiazolo[5,4-b]pyridine (1.17 g, 2.62 mmol) in 20 mL DMF under argon was added sodium bis(trimethylsilyl)amide, 1.0M solution in tetrahydrofuran (3.28 mL, 3.28 mmol). The reaction mixture became deep blue/purple. After 2 min, allyl iodide (0.362 mL, 3.93 mmol) was added and the reaction became light orange after 1 min. After 5 min total, the reaction mixture was quenched with sat'd aq. $NH_4Cl$, EtOAc, and water. The organic layer was washed with water, brine, dried over sodium sulfate, filtered, and concentrated. The residue was purified by silica gel chromatography, ISCO, 80 g, 0-40% EA/hexanes to give 2-(4-(1,3-dioxan-2-yl)-2-fluorophenyl)-5-(4-phenylhepta-1,6-dien-4-yl)thiazolo[5,4-b]pyridine as a white foam. MS (ESI) m/z: Calculated: 486.2; Observed: 487.1 ($M^+$+1).

Step 3

To a solution of 2-(4-(1,3-dioxan-2-yl)-2-fluorophenyl)-5-(4-phenylhepta-1,6-dien-4-yl)thiazolo[5,4-b]pyridine (1.07 g, 2.20 mmol) in 44 mL DCM under argon was added tricyclohexylphosphine[1,3-bis(2,4,6-trimethylphenyl)-4,5-dihydroimidazol-2-ylidene][benzylidene]ruthenium(IV) dichloride (93.3 mg, 0.110 mmol). The reaction mixture became red-brown and was fitted with a water-cooled reflux condenser and heated to reflux. After 5 h, the reaction mixture was cooled, concentrated in vacuo, loaded onto an 80 g ISCO silica gel column, and purified with a gradient of 0-30% EA/hexanes to give 2-(4-(1,3-dioxan-2-yl)-2-fluorophenyl)-5-(1-phenylcyclopent-3-enyl)thiazolo[5,4-b]pyridine as an off-white solid. MS (ESI) m/z: Calculated: 458.2; Observed: 459.1 ($M^+$+1).

Step 4

A slurry of 2-(4-(1,3-dioxan-2-yl)-2-fluorophenyl)-5-(1-phenylcyclopent-3-enyl)-thiazolo[5,4-b]pyridine (0.550 g, 1.20 mmol) in 8 mL 1:1 THF/5N HCl was heated to 70° C. in a sealed vial. After 30 min, the reaction mixture was cooled, treated with ice, 10N NaOH until basic, and EA. The organic layer was washed with water, brine, dried over sodium sulfate, filtered, and concentrated in vacuo to give 3-fluoro-4-(5-(1-phenylcyclopent-3-enyl)-thiazolo[5,4-b]pyridine-2-yl)benzaldehyde which was used without further purification. MS (ESI) m/z: Calculated: 400.1; Observed: 401.1 ($M^+$+1).

Step 5

Reaction of 3-fluoro-4-(5-(1-phenylcyclopent-3-enyl)thiazolo[5,4-b]pyridine-2-yl)-benzaldehyde (0.48 g, 1.2 mmol), methyl azetidine-3-carboxylate hydrochloride (0.365 g, 2.41 mmol) according to Reference R and the general procedure for reductive amination gave methyl 1-((3-fluoro-4-(5-(1-phenylcyclopent-3-enyl)thiazolo[5,4-b]pyridine-2-yl)phenyl)-methyl)azetidine-3-carboxylate as an oil which partially solidified to a white solid. MS (ESI) m/z: Calculated: 499.0; Observed: 500.1 ($M^{+}$+1).

Step 6

Hydrolysis of methyl 1-((3-fluoro-4-(5-(1-phenylcyclopent-3-enyl)thiazolo[5,4-b]pyridine-2-yl)phenyl)methyl) azetidine-3-carboxylate (0.086 g, 0.17 mmol) according to Referenc F and the general procedure for ester hydrolysis to give 1-((3-fluoro-4-(5-(1-phenylcyclopent-3-enyl)thiazolo [5,4-b]pyridine-2-yl)phenyl)methyl)azetidine-3-carboxylic acid as a white solid. MS (ESI) m/z: Calculated: 485.2; Observed: 486.1 ($M^{+}$+1).

Example 6

Synthesis of 1-((3-fluoro-4-(5-(1-phenylcyclopentyl) thiazolo[5,4-b]pyridine-2-yl)-phenyl)methyl)azetidine-3-carboxylic acid

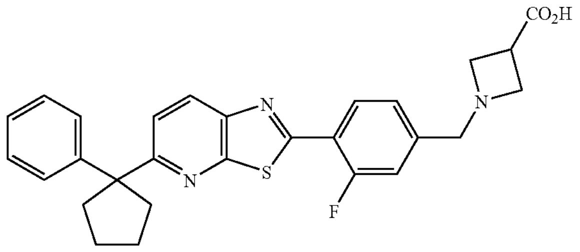

Step 1

To a mixture of methyl 1-((3-fluoro-4-(5-(1-phenylcyclopent-3-enyl)thiazolo[5,4-b]pyridine-2-yl)phenyl)methyl) azetidine-3-carboxylate (0.333 g, 0.667 mmol) and 10% Pd/C, 50% water (0.355 g, 0.333 mmol) under nitrogen was added 5 mL MeOH and 5 mL THF. The resulting mixture was stirred rapidly under an $H_2$ balloon for 4 h. The reaction mixture was flushed with nitrogen, filtered, rinsing with DCM, and concentrated in vacuo. The resulting oil was purified by silica gel chromatography, ISCO 0-100% EA/hexanes, to give methyl 1-((3-fluoro-4-(5-(1-phenylcyclopentyl) thiazolo[5,4-b]pyridine-2-yl)phenyl)methyl)azetidine-3-carboxylate as a clear and colorless oil. MS (ESI) m/z: Calculated: 501.2; Observed: 502.1 ($M^{+}$+1).

Step 2

Hydrolysis of methyl 1-((3-fluoro-4-(5-(1-phenylcyclopentyl)thiazolo[5,4-b]pyridine-2-yl)phenyl)methyl)azetidine-3-carboxylate (0.32 g, 0.64 mmol) according to Reference R and the general procedure for ester hydrolysis to give 1-((3-fluoro-4-(5-(1-phenylcyclopentyl)-thiazolo[5,4-b]pyridine-2-yl)phenyl)methyl)azetidine-3-carboxylic acid as a white solid. MS (ESI) m/z: Calculated: 487.2; Observed: 488.1 ($M^{+}$+1).

Example 7

Synthesis of 1-((3-fluoro-4-(5-(1-phenylcyclohexyl) thiazolo[5,4-b]pyridine-2-yl)-phenyl)methyl)azetidine-3-carboxylic acid

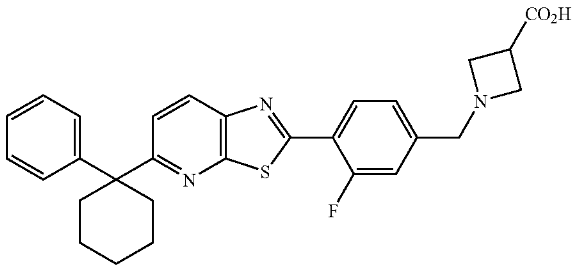

Step 1

Argon was bubbled through a slurry of 2-(4-(1,3-dioxan-2-yl)-2-fluorophenyl)-5-benzylthiazolo[5,4-b]pyridine (1.00 g, 2.46 mmol) in 20 mL DMF for 5 min. To the rapidly stirring reaction mixture was added LiHMDS 1.0M in THF (2.71 mL, 2.71 mmol) rapidly dropwise. The resulting deep blue reaction mixture was stirred for 2 min, at which point 4-bromo-1-butene (0.499 mL, 4.92 mmol) was added rapidly via syringe. The color of the reaction slowly became purple over 5 min, then brown over about 10-15 min additional. After 1.5 h, the reaction mixture was quenched with sat'd aq. $NH_4Cl$ and MTBE. The organic layer was washed with water, brine, dried over sodium sulfate, filtered, and concentrated in vacuo to give 2-(4-(1,3-dioxan-2-yl)-2-fluorophenyl)-5-(1-phenylpent-4-enyl)thiazolo[5,4-b]pyridine as an orange solid MS (ESI) m/z: Calculated: 460.2; Observed: 461.1 ($M^{+}$+1).

Step 2

Argon was bubbled through a slurry of 2-(4-(1,3-dioxan-2-yl)-2-fluorophenyl)-5-(1-phenylpent-4-enyl)thiazolo[5,4-b]pyridine (1.02 g, 2.21 mmol) in 20 mL DMF for 5 min. The slurry was treated with sodium bis(trimethylsilyl)amide, 1.0M solution in tetrahydrofuran (2.66 mL, 2.66 mmol) rapidly via syringe, to give a dark blue solution. After 2 min, allyl iodide (0.306 mL, 3.32 mmol) was added via syringe, and the color gradually faded from blue to light brown. After 1 h, the reaction mixture was quenched with sat'd aq. $NH_4Cl$ and MTBE. The organic layer was washed with water, brine, dried over sodium sulfate, filtered, and concentrated in vacuo. The resulting oil was dissolved in DCM, adsorbed onto 7 g silica gel, dried, and purified by silica gel chromatography ISCO, 40 g, gradient, 0-50% EA/hexanes, to give 2-(4-(1,3-dioxan-2-yl)-2-fluorophenyl)-5-(4-phenylocta-1,7-dien-4-yl)thiazolo[5,4-b]pyridine as a light yellow foam MS (ESI) m/z: Calculated: 500.2; Observed: 501.1 ($M^{+}$+1).

Step 3

To a solution of 2-(4-(1,3-dioxan-2-yl)-2-fluorophenyl)-5-(4-phenylocta-1,7-dien-4-yl)thiazolo[5,4-b]pyridine (0.580 g, 1.16 mmol) in 22 mL DCM under argon was added tricyclohexylphosphine[1,3-bis(2,4,6-trimethylphenyl)-4,5-dihydroimidazol-2-ylidene][benzylidene]ruthenium(IV) dichloride (0.0492 g, 0.0579 mmol). The flask was fitted with a water-cooled reflux condenser and heated to reflux. The reaction was checked after 4 h and judged complete. Silica gel (4 g) was added and the reaction mixture was dried, purified by ISCO, gradient, 0-100% EA/hexanes, to give 2-(4-(1,3-dioxan-2-yl)-2-fluorophenyl)-5-(1-phenylcyclohex-3-enyl)

thiazolo[5,4-b]pyridine as a foam/oil which solidified to an off-white solid. MS (ESI) m/z: Calculated: 472.2; Observed: 473.2 ($M^{+}$+1).

Step 4

A mixture of 10% palladium on carbon, 50% water wet (0.33 g, 0.31 mmol) and 2-(4-(1,3-dioxan-2-yl)-2-fluorophenyl)-5-(1-phenylcyclohex-3-enyl)thiazolo[5,4-b]pyridine (0.492 g, 1.0 mmol) under nitrogen was treated with 10 mL THF and exposed to 1 atm $H_2$ gas via balloon. The reaction mixture was allowed to stir 36 h, then flush with nitrogen, filter, rinsing with DCM. The filtrate was concentrated in vacuo to give 2-(4-(1,3-dioxan-2-yl)-2-fluorophenyl)-5-(1-phenylcyclohexyl)thiazolo[5,4-b]pyridine as a light yellow solid. MS (ESI) m/z: Calculated: 474.2; Observed: 475.1 ($M^{+}$+1).

Step 5

A slurry of 2-(4-(1,3-dioxan-2-yl)-2-fluorophenyl)-5-(1-phenylcyclohexyl)thiazolo[5,4-b]pyridine (0.467 g, 0.984 mmol) in 5 mL 1:1 THF/5N HCl was sealed and heated to 80° C. The resulting yellow solution was allowed to stir 3 h, was cooled, and then was treated with ice and 10N NaOH until basic. The reaction mixture was partitioned between EA and water, washed with water, brine, dried over sodium sulfate, filter, concentrate in vacuo to give 3-fluoro-4-(5-(1-phenylcyclohexyl)thiazolo[5,4-b]pyridine-2-yl)benzaldehyde as an oil/solid that contained some starting material. This material was carried on without further pyrification. MS (ESI) m/z: Calculated: 416.1; Observed: 417.1 ($M^{+}$+1).

Step 6

Reaction of 3-fluoro-4-(5-(1-phenylcyclohexyl)thiazolo[5,4-b]pyridine-2-yl)-benzaldehyde (0.36 g, 0.85 mmol), methyl azetidine-3-carboxylate hydrochloride (0.388 g, 2.56 mmol) according to Reference R and the general procedure for reductive amination to give methyl 1-((3-fluoro-4-(5-(1-phenylcyclohexyl)thiazolo[5,4-b]pyridine-2-yl)phenyl)-methyl)azetidine-3-carboxylate as an oil which solidified to a white solid. MS (ESI) m/z: Calculated: 515.2; Observed: 516.1 ($M^{+}$+1).

Step 7

The title compound was synthesized according to Reference R and the general procedure for ester hydrolysis from 1-((3-fluoro-4-(5-(1-phenylcyclohexyl)thiazolo[5,4-b]pyridine-2-yl)phenyl)methyl)azetidine-3-carboxylate (0.290 g, 0.562 mmol) to give 1-((3-fluoro-4-(5-(1-phenylcyclohexyl)thiazolo[1,4-b]pyridine-2-yl)phenyl)methyl)azetidine-3-carboxylic acid as a white solid. MS (ESI) m/z: Calculated: 501.2; Observed: 502.1 ($M^{+}$+1).

Example 8

Synthesis of (1R,3S)-3-carboxy-1-(3-fluoro-4-(5-(1-phenylcyclopropyl)thiazolo[5,4-b]pyridin-2-yl)benzyl)azetidine 1-oxide and (1S,3R)-3-carboxy-1-(3-fluoro-4-(5-(1-phenylcyclopropyl)thiazolo[5,4-b]pyridin-2-yl)benzyl)azetidine 1-oxide

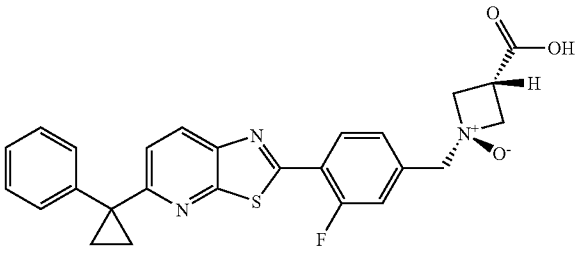

-continued

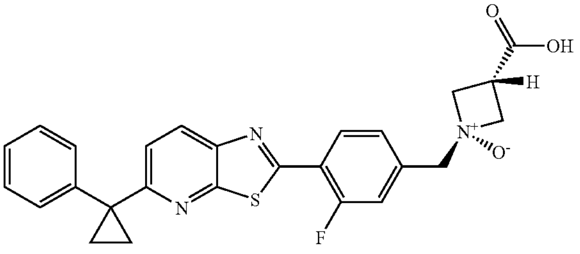

A slurry of 1-((3-fluoro-4-(5-(1-phenylcyclopropyl)thiazolo[5,4-b]pyridine-2-yl)-phenyl)methyl)azetidine-3-carboxylic acid (0.084 g, 0.18 mmol) and mCPBA (0.063 g, 0.37 mmol) in 5 mL 10% MeOH/DCM was stirred rapidly at ambient temperature. After about 10 min, the reaction mixture became clear. After 10 additional minutes precipitates formed. After 10 additional minutes, the reaction mixture was filtered, rinsing with DCM. The solid was collected and dried in vacuo to give 1-((3-fluoro-4-(5-(1-phenylcyclopropyl)thiazolo[5,4-b]pyridine-2-yl)phenyl)methyl)azetidine-3-carboxylic acid N-oxide as a mixture of isomers. The isomers were separated by RPHPLC (A=0.2% formic acid in water; B=0.04% formic acid in acetonitirle; 30×100, Gemini Axia, 5um) to give (1r,3s)-3-carboxy-1-(3-fluoro-4-(5-(1-phenylcyclopropyl)thiazolo[5,4-b]pyridin-2-yl)benzyl)azetidine 1-oxide and (1s,3r)-3-carboxy-1-(3-fluoro-4-(5-(1-phenylcyclopropyl)thiazolo[5,4-b]pyridin-2-yl)benzyl)azetidine 1-oxide. MS (ESI) m/z: Calculated: 475.1; Observed: 476.1 ($M^{+}$+1).

Example 9

Synthesis of 1-((3-fluoro-4-(5-(2-phenyloxetan-2-yl)thiazolo[5,4-b]pyridine-2-yl)-phenyl)methyl)azetidine-3-carboxylic acid

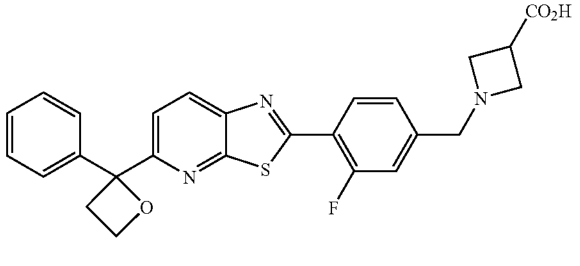

Step 1

A solution of 2-(4-(1,3-dioxan-2-yl)-2-fluorophenyl)-5-(1-phenylvinyl)thiazolo[5,4-b]pyridine (2.66 g, 6.4 mmol) in 3:1 $CH_2Cl_2$/MeOH (128 mL) at −78° C. was treated with ozone for 15 min. The solution was then sparged with $O_2$, dimethyl sulfide (18 mL) was added, and the bath was allowed to expire. The resulting solution was stirred at 25° C. for 3 d and then concentrated in vacuo. This residue was taken up in $CH_2Cl_2$ (400 mL) and sequentially washed with water and brine, then concentrated in vacuo to provide (2-(4-(1,3-dioxan-2-yl)-2-fluorophenyl)thiazolo[5,4-b]pyridine-5-yl)(phenyl)methanone as a yellow solid. MS (ESI) m/z: Calculated: 420.1; Observed: 421.1 ($M^{+}$+1).

Step 2

To a suspension of (2-(4-(1,3-dioxan-2-yl)-2-fluorophenyl)thiazolo[5,4-b]pyridine-5-yl)(phenyl)methanone (718.0 mg, 1708 μmol) in methanol (12.0 mL) and THF (4.8 mL) was added sodium borohydride (64.6 mg, 1708 μmol), and the resulting solution was stirred at 25° C. for 10 min. Saturated aqueous $NH_4Cl$ (10 mL) was then added, and MeOH and THF were removed in vacuo. The resulting suspension was partitioned between ethyl acetate and water). The organic layer was separated and washed with brine, and the aqueous layer was extracted with EtOAc. The combined organic extracts were dried over sodium sulfate, filtered, and concentrated in vacuo to provide (2-(4-(1,3-dioxan-2-yl)-2-fluorophenyl)thiazolo[5,4-b]pyridine-5-yl)(phenyl)methanol as a yellow solid. MS (ESI) m/z: Calculated: 422.1; Observed: 423.0 ($M^+$+1).

Step 3

Hydrochloric acid (5.0N, aq., 5.3 mL, 26500 μmol) was added to (2-(4-(1,3-dioxan-2-yl)-2-fluorophenyl)thiazolo[5,4-b]pyridine-5-yl)(phenyl)methanol (590 mg, 1397 μmol) in THF (28.0 mL), and the resulting solution was stirred at 60° C. for 3 h. 5.0N NaOH (aq) (5.3 mL) and sat. aq. $NaHCO_3$ (20 mL) were then sequentially added, and THF was removed in vacuo. The resulting mixture was partitioned between EtOAc and half-saturated aq. $NaHCO_3$. The organic layer was separated, sequentially washed with water and brine, dried over sodium sulfate, filtered, and concentrated in vacuo to provide 3-fluoro-4-(5-(pyridine(phenyl)-methyl)thiazolo[5,4-b]pyridine-2-yl)benzaldehyde as a light orange solid. MS (ESI) m/z: Calculated: 364.1; Observed: 365.0 ($M^+$+1).

Step 4

Reaction of 3-fluoro-4-(5-(pyridine(phenyl)methyl)thiazolo[5,4-b]□yridine-2-yl)-benzaldehyde (550.0 mg, 1509 μmol) and methyl azetidine-3-carboxylate hydrochloride (229 mg, 1509 μmol) according to Reference R and the general procedure for reductive amination gave methyl 1-((3-fluoro-4-(5-(pyridine(phenyl)methyl)thiazolo[5,4-b]pyridine-2-yl)phenyl)-methyl)azetidine-3-carboxylate as a light-yellow foam. MS (ESI) m/z: Calculated: 463.1; Observed: 464.1 ($M^+$+1).

Step 5

A mixture of methyl 1-((3-fluoro-4-(5-(pyridine(phenyl)methyl)thiazolo[5,4-b]pyridine-2-yl)phenyl)methyl)azetidine-3-carboxylate (340 mg, 734 μmol) and manganese dioxide (1275 mg, 14670 μmol) in $CH_2Cl_2$ (49.0 mL) was stirred at 25° C. for 1.5 h. The resulting solution was filtered through Celite™, washing with $CH_2Cl_2$ (40 mL). The combined filtrates were concentrated in vacuo to yield methyl 1-((4-(5-benzoylthiazolo[5,4-b]pyridine-2-yl)-3-fluorophenyl)methyl)azetidine-3-carboxylate as an off-white solid. MS (ESI) m/z: Calculated: 461.1; Observed: 462.0 ($M^+$+1).

Step 6

A mixture of lithium hydroxide hydrate (66.4 mg, 1582 μmol) and methyl 1-((4-(5-benzoylthiazolo[5,4-b]pyridine-2-yl)-3-fluorophenyl)methyl)azetidine-3-carboxylate (233.0 mg, 505 μmol) in THF (12.6 mL) and water (1.7 mL) was stirred at 25° C. for 1.5 h. The reaction mixture was then diluted with water (1.0 mL), acidified with 1.0N HCl (1.58 mL), brought to pH 6 with 0.05M phosphate buffer (1.0 mL), and partially concentrated in vacuo. The resulting precipitate was collected by vacuum filtration, washed with water (3.0 mL), and dried in vacuo to afford 1-((4-(5-benzoylthiazolo[5,4-b]pyridine-2-yl)-3-fluorophenyl)methyl)-azetidine-3-carboxylic acid as a colorless solid. MS (ESI) m/z: Calculated: 447.1; Observed: 448.0 ($M^+$+1).

Step 7

A mixture of trimethylsulfoxonium iodide (230 mg, 1047 μmol) and potassium t-butoxide (1.0M in t-BuOH) (1.047 ml, 1.047 mmol) in t-BuOH (1.0 mL) was stirred at 50° C. for 30 min. 1-((4-(5-Benzoylthiazolo[5,4-b]pyridine-2-yl)-3-fluorophenyl)methyl)azetidine-3-carboxylic acid (93.7 mg, 0.209 mmol) was added in one portion, and the resulting suspension was stirred at 50° C. for 20 h. The reaction mixture was then diluted with 0.05M pH 6 phosphate buffer (2.0 mL), acidified with 1.0N HCl (750 μL), diluted with water (15 mL), and partially concentrated in vacuo. The resulting precipitate was collected by vacuum filtration, washed with water (3.0 mL), and dried in vacuo. Reverse-phase HPLC of this solid ($C_{18}$, $CH_3CN/H_2O$+0.1% ammonium formate) afforded 1-((3-fluoro-4-(5-(2-phenyloxetan-2-yl)-thiazolo[5,4-b]pyridine-2-yl)phenyl)methyl)azetidine-3-carboxylic acid as a colorless solid. MS (ESI) m/z: Calculated: 475.1; Observed: 476.1 ($M^+$+1).

Example 10

Synthesis of 1-((3-fluoro-4-(6-(1-phenylcyclopropyl)benzo[d]thiazol-2-yl)phenyl)-methyl)azetidine-3-carboxylic acid hydrochloride

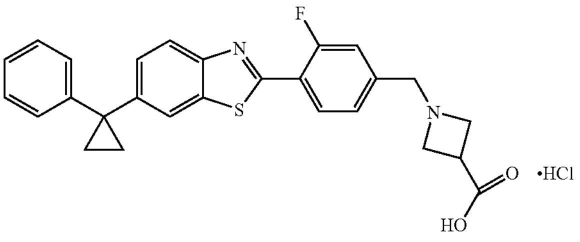

Step 1

Thiophosgene (22 mL, 289 mmol) was added to a suspension of sodium carbonate (61.0 g, 579 mmol) and 4-bromo-2-fluoroaniline (50.0 g, 263 mmol) in $CHCl_3$ (1 L). The reaction mixture was stirred overnight at RT, the inorganic salts were filtered off, and the filtrate was concentrated to give 4-bromo-2-fluoro-1-isothio-cyanatobenzene as a tan solid which was converted to 2-(4-(1,3-dioxan-2-yl)-2-fluorophenyl)-6-bromobenzo[d]thiazole as described in Reference A above.

Step 2

A slurry of $(amphos)_2PdCl_2$ (0.114 g, 0.161 mmol), potassium carbonate (2.85 g, 20.6 mmol), 1-phenylvinylboronic acid (2.10 g, 14.2 mmol), 2-(4-(1,3-dioxan-2-yl)-2-fluorophenyl)-6-bromobenzo[d]thiazole (2.54 g, 6.44 mmol) in 20 mL dioxane/4 mL water was flushed with argon and sealed, and heated at 90° C. overnight. In the morning the reaction mixture was cooled and judged complete by LCMS. The reaction mixture was partitioned between EA/$H_2O$ and the organic layer was washed with brine, dried over sodium sulfate, filtered, and concentrated to give a solid. The material was suspended in MeOH, and filtered. The resulting solid was dried in vacuo to give 2-(4-(1,3-dioxan-2-yl)-2-fluorophenyl)-6-(1-phenylvinyl)benzo[d]thiazole as a dull yellow solid. MS (ESI) m/z: Calculated: 417.1; Observed: 418.0 ($M^+$+1).

Step 3

In a reactor bottle (trimethylsilyl)diazomethane, 2.0 M in diethyl ether (2.4 mL, 4.8 mmol) was added to a mixture of 2-(4-(1,3-dioxan-2-yl)-2-fluorophenyl)-6-(1-phenylvinyl)-benzo[d]thiazole (0.650 g, 1.6 mmol), in anhydrous dioxane 15.00 mL. The reaction mixture was heated to 150° C. for 18 h. At which time the crude reaction mixture was concentrate in vacuo and purified by silica gel chromatography to afford as a mixture of isomers 2-(4-(1,3-dioxan-2-yl)-2-fluorophenyl)-6-(1-phenyl-2 (trimethylsilyl)cyclopropyl)benzo[d]thiazole. MS (ESI) m/z: Calculated: 503.2; Observed: 504.0 ($M^+$+1).

Step 4

In a reactor bottle were combined 2-(4-(1,3-dioxan-2-yl)-2-fluorophenyl)-6-(1-phenyl-2-(trimethylsilyl)cyclopropyl) benzo[d]thiazole (1.305 g, 2.6 mmol) and neat tetrabutylammonium fluoride (25 mL, 25 mmol). The reaction mixture was heated to 110° C. in an oil bath and allowed to stir for 2 h. The mixture was cooled and extracted with EtOAc and water, dried over $MgSO_4$ and concentrate in vacuo. Purification by silica gel chromatography afforded 2-(4-(1,3-dioxan-2-yl)-2-fluorophenyl)-6-(1-phenylcyclopropyl)-benzo[d] thiazole. MS (ESI) m/z: Calculated: 431.1; Observed: 432.1 ($M^+$+1).

Step 5

A mixture of 2-(4-(1,3-dioxan-2-yl)-2-fluorophenyl)-6-(1-phenylcyclopropyl)-benzo[d]thiazole (0.061 g, 0.14 mmol) and 5N HCl (3.50 mL, 0.14 mmol) in THF (7.0 mL) was heated to 70° C. for 3 h. The reaction was cooled and concentrated in vacuo, placed in an ice bath, and basified with 5 N aq. NaOH. The solid was collected by filtration, rinsed with water and MeOH, and was dried in vacuo to afford 3-fluoro-4-(6-(1-phenylcyclopropyl)-benzo[d]thiazol-2-yl) benzaldehyde. MS (ESI) m/z: Calculated: 373.1; Observed: 374.0 ($M^+$+1).

Step 6

Reaction of 3-fluoro-4-(6-(1-phenylcyclopropyl)benzo[d] thiazol-2-yl)benzaldehyde (0.050 g, 0.13 mmol) and methyl azetidine-3-carboxylate hydrochloride (0.030 g, 0.20 mmol) according to Reference R and general procedure for reductive amination afforded methyl 1-((3-fluoro-4-(6-(1-phenylcyclopropyl)benzo[d]thiazol-2-yl)phenyl)methyl)azetidine-3-carboxylate. MS (ESI) m/z: Calculated: 472.2; Observed: 473.1 ($M^+$+1).

Step 7

Hydrolysis of methyl 1-((3-fluoro-4-(6-(1-phenylcyclopropyl)benzo[d]thiazol-2-yl)-phenyl)methyl)azetidine-3-carboxylate (0.0562 g, 0.12 mmol) according to Reference R and the general procedure for ester hydrolysis to afford 1-((3-fluoro-4-(6-(1-phenylcyclopropyl)-benzo[d]thiazol-2-yl) phenyl)methyl)azetidine-3-carboxylic acid hydrochloride. MS (ESI) m/z: Calculated: 458.2; Observed: 459.1 ($M^+$+1).

Example 11

Synthesis of (R)-1-(3-fluoro-4-(5-(1-phenylcyclopropyl)thiazolo[5,4-b]pyridine-2-yl)-phenyl)ethyl)azetidine-3-carboxylic acid and (S)-1-(3-fluoro-4-(5-(1-phenylcyclopropyl)-thiazolo[5,4-b]pyridine-2-yl) phenyl)ethyl)azetidine-3-carboxylic acid

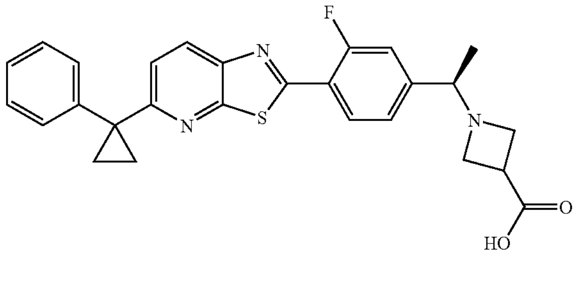

-continued

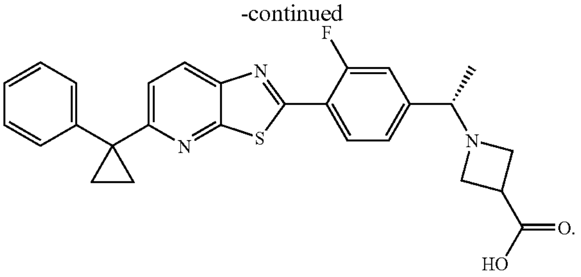

Step 1

Reaction of 1-(3-fluoro-4-(5-(1-phenylcyclopropyl)thiazolo[5,4-b]pyridin-2-yl)phenyl)ethanone (1.76 g, 4.53 mmol) and methyl azetidine-3-carboxylate hydrochloride (1.03 g, 6.80 mmol) according to reference R and the general procedure for reductive amination gave racemic methyl 1-(1-(3-fluoro-4-(5-(1-phenylcyclopropyl)thiazolo[5,4-b]pyridine-2-yl)phenyl)ethyl)azetidine-3-carboxylate. Separation of enantiomers was accomplished by SFC chromatography (Column: Chiralcel OJ-H (21×250 mm, 5 um)×2; A: Liquid $CO_2$; B: Ethanol (0.2% IPA); Isocratic: 80:20 (A:B); Flow Rate: 70 mL/min; Outlet Pressure: 100 bar) to give (R)-methyl 1-(1-(3-fluoro-4-(5-(1-phenylcyclopropyl)-thiazolo [5,4-b]pyridine-2-yl)phenyl)ethyl)azetidine-3-carboxylate and (S)-methyl 1-(1-(3-fluoro-4-(5-(1-phenylcyclopropyl) thiazolo[5,4-b]pyridine-2-yl)phenyl)ethyl)azetidine-3-carboxylate. MS (ESI) m/z: Calculated: 487.2; Observed: 488.1 ($M^+$+1).

Step 2

Separately, (R)-methyl 1-(1-(3-fluoro-4-(5-(1-phenylcyclopropyl)thiazolo[5,4-b]pyridine-2-yl)phenyl)ethyl)azetidine-3-carboxylate and (S)-methyl 1-(1-(3-fluoro-4-(5-(1-phenylcyclopropyl)thiazolo[5,4-b]pyridine-2-yl)phenyl) ethyl)azetidine-3-carboxylate were processed according to Reference R and the general procedure for ester hydrolysis to afford (R)-1-(1-(3-fluoro-4-(5-(1-phenylcyclopropyl)thiazolo[5,4-b]pyridine-2-yl)phenyl)ethyl)-azetidine-3-carboxylic acid hydrochloride and (S)-1-(1-(3-fluoro-4-(5-(1-phenylcyclopropyl)-thiazolo[5,4-b]pyridine-2-yl)phenyl) ethyl)azetidine-3-carboxylic acid hydrochloride. MS (ESI) m/z: Calculated: 473.2; Observed: 474.0 ($M^+$+1). $^1$H NMR (400 MHz, DMSO-$d_6$) δ ppm 12.38 (br. s., 1 H), 8.11-8.48 (m, 2 H), 7.22-7.55 (m, 7 H), 7.03 (d, J=8.5 Hz, 1 H), 2.90-3.69 (m, 6 H), 1.58-1.80 (m, 2 H), 1.33-1.47 (m, 2 H), 1.09-1.19 (m, 3 H)

Example 12

Synthesis of 3-((3-fluoro-4-(5-(1-phenylcyclopropyl) thiazolo[5,4-b]pyridine-2-yl)-phenyl)methylamino) propanoic acid hydrochloride

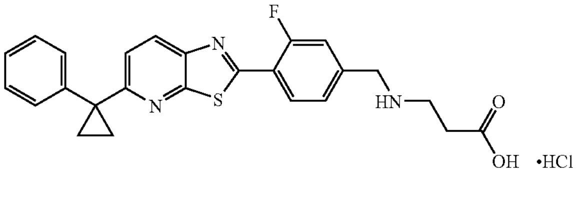

Step 1

Reaction of 3-fluoro-4-(5-(1-phenylcyclopropyl)thiazolo[5,4-b]pyridine-2-yl)-benzaldehyde (0.100 g, 0.27 mmol) and beta-alanine ethyl ester hydrochloride (0.062 g, 0.40 mmol) according to the Reference R and the general procedure for reductive amination gave ethyl 3-((3-fluoro-4-(5-(1-phenylcyclopropyl)thiazolo[5,4-b]pyridine-2-yl)phenyl)-methylamino)propanoate. MS (ESI) m/z: Calculated: 475.2; Observed: 476.1 ($M^{+}$+1).

Step 2

Hydrolysis of ethyl 3-((3-fluoro-4-(5-(1-phenylcyclopropyl)thiazolo[5,4-b]pyridine-2-yl)phenyl)methylamino)propanoate (0.0909 g, 0.19 mmol) according to Reference R and the general procedure for ester hydrolysis gave 3-((3-fluoro-4-(5-(1-phenylcyclopropyl)-thiazolo[5,4-b]-pyridin-2-yl)phenyl)methylamino)propanoic acid hydrochloride. MS (ESI) m/z: Calculated: 447.1; Observed: 448.1 ($M^{+}$+1). $^{1}$H NMR (300 MHz, DMSO-$d_6$) δ ppm 12.27 (br. s., 1H), 8.76-8.91 (m, 1 H), 8.42 (dd, J=7.9, 7.9 Hz, 1 H), 8.31 (d, J=8.6 Hz, 1 H), 7.83-7.98 (m, 2 H), 7.23-7.54 (m, 5 H), 7.06 (d, J=8.8 Hz, 1 H), 3.43-3.57 (m, 2 H), 2.46-2.64 (m, 2 H), 1.56-1.78 (s, 2 H), 1.40 (s, 2 H)

Example 13

Synthesis of (R)-3-(1-(3-fluoro-4-(5-(1-phenylcyclopropyl)thiazolo[5,4-b]pyridine-2-yl)phenyl)ethylamino)propanoic acid hydrochloride and (S)-3-(1-(3-fluoro-4-(5-(1-phenylcyclopropyl)thiazolo[5,4-b]pyridine-2-yl)phenyl)ethylamino)propanoic acid hydrochloride

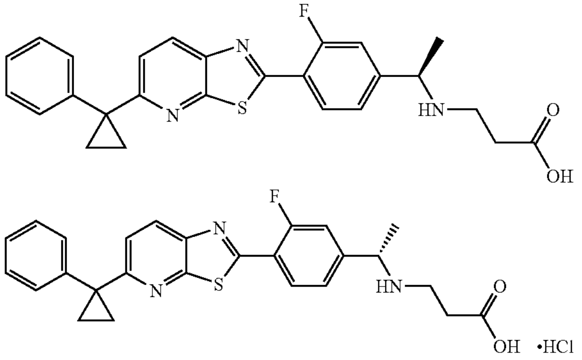

Step 1

A solution of 1-(3-fluoro-4-(5-(1-phenylcyclopropyl)thiazolo[5,4-b]pyridine-2-yl)-phenyl)ethanone (0.212 g, 0.546 mmol), beta-alanine ethyl ester hydrochloride (0.126 g, 0.819 mmol), N-ethyl-N-isopropylpropan-2-amine (0.143 mL, 0.819 mmol) in dichloromethane (5.00 mL) and methanol (5.00 mL). The reaction mixture was allowed to stir for 5 min before acetic acid (0.126 mL, 2.18 mmol) was added, the solution was stirred for 3 h at 50° C. At which time the reaction mixture was cooled to rt and was treated with $NaCNBH_3$ (0.0171 g, 0.273 mmol), the reaction mixture was stirred for 3 h at 85° C. The crude was fused into silica and purified by silica gel chromatography to afford a mixture of ethyl 3-(1-(3-fluoro-4-(5-(1-phenylcyclopropyl)thiazolo[5,4-b]pyridine-2-yl)phenyl)ethylamino)propanoate and methyl 3-(1-(3-fluoro-4-(5-(1-phenylcyclopropyl)thiazolo[5,4-b]pyridine-2-yl)phenyl)ethylamino)-propanoate. MS (ESI) m/z: Calculated: 489.2; Observed: 490.1 (($M^{+}$+1). MS (ESI) m/z: Calculated: 475.2; Observed: 476.1 ($M^{+}$+1).

Step 2

The mixture of ethyl 3-(1-(3-fluoro-4-(5-(1-phenylcyclopropyl)thiazolo[5,4-b]pyridine-2-yl)phenyl)ethylamino)propanoate and methyl 3-(1-(3-fluoro-4-(5-(1-phenylcyclopropyl)-thiazolo[5,4-b]pyridine-2-yl)phenyl)ethylamino)propanoate was hydrolyzed according to Reference R and the general procedure for ester hydrolysis to afford racemic 3-(1-(3-fluoro-4-(5-(1-phenylcyclopropyl)thiazolo[5,4-b]pyridine-2-yl)phenyl)ethylamino)propanoic acid hydrochloride. The enantiomers were separated by SFC (Column: Chiralpak AD-H (21×250 mm, 5 um)×2; A: Liquid $CO_2$; B: Methanol (0.2% DEA); Isocratic: 70:30 (A:B); Flow Rate: 55 mL/min; Outlet Pressure: 100 bar) to give (R)-3-(1-(3-fluoro-4-(5-(1-phenylcyclopropyl)thiazolo[5,4-b]pyridine-2-yl)phenyl)ethylamino)propanoic acid hydrochloride and (S)-3-(1-(3-fluoro-4-(5-(1-phenylcyclopropyl)thiazolo[5,4-b]pyridine-2-yl)phenyl)ethylamino)propanoic acid hydrochloride. MS (ESI) m/z: Calculated: 461.2; Observed: 462.0 ($M^{+}$+1).

Example 14

Synthesis of 3-(3-fluoro-4-(5-(1-phenylcyclopropyl)thiazolo[5,4-b]pyridine-2-yl)-benzamido)propanoic acid

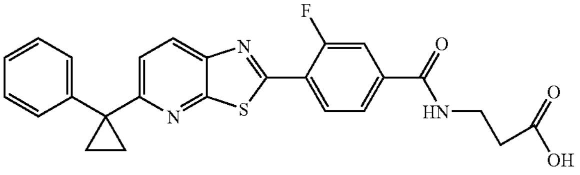

Step 1

Reaction of 3-fluoro-4-(5-(1-phenylcyclopropyl)thiazolo[5,4-b]pyridine-2-yl)benzoic acid (0.080 g, 0.20 mmol) and beta-alanine ethyl ester hydrochloride, according to Reference S and the general procedure for amide formation afforded ethyl 3-(3-fluoro-4-(5-(1-phenylcyclopropyl)thiazolo[5,4-b]pyridine-2-yl)benzamido)propanoate. MS (ESI) m/z: Calculated: 489.2; Observed: 490.0 ($M^{+}$+1).

Step 2

Hydrolysis of ethyl 3-(3-fluoro-4-(5-(1-phenylcyclopropyl)thiazolo[5,4-b]pyridine-2-yl)benzamido)propanoate, according to Reference S and the general procedure for ester hydrolysis afforded 3-(3-fluoro-4-(5-(1-phenylcyclopropyl)thiazolo[5,4-b]pyridine-2-yl)-benzamido)propanoic acid. MS (ESI) m/z: Calculated: 461.1; Observed: 462.0 ($M^{+}$+1).

Example 15

Synthesis of 2-(3-fluoro-4-(5-(1-phenylcyclopropyl) thiazolo[5,4-b]pyridine-2-yl)-benzamido)acetic acid

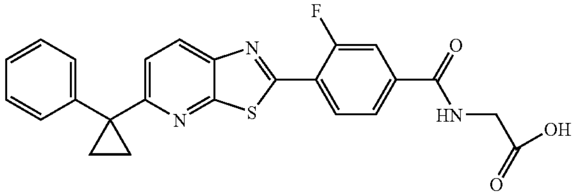

Step 1

Reaction of 3-fluoro-4-(5-(1-phenylcyclopropyl)thiazolo [5,4-b]pyridine-2-yl)benzoic acid (0.050 g, 0.13 mmol) and glycine methyl ester hydrochloride (0.019 g, 0.15 mmol), according to Reference S and the general procedure for amide formation afforded methyl 2-(3-fluoro-4-(5-(1-phenylcyclopropyl)thiazolo[5,4-b]pyridine-2-yl)benzamido)acetate. MS (ESI) m/z: Calculated: 461.1; Observed: 462.0 ($M^+$+1).

Step 2

Hydrolysis of methyl 2-(3-fluoro-4-(5-(1-phenylcyclopropyl)thiazolo[5,4-b]pyridine-2-yl)benzamido)acetate (0.0395 g, 0.086 mmol), according to Reference S and the general procedure for ester hydrolysis afforded 2-(3-fluoro-4-(5-(1-phenylcyclopropyl)thiazolo[5,4-b]pyridine-2-yl)benzamido)acetic acid. MS (ESI) m/z: Calculated: 447.1; Observed: 448.0 ($M^+$+1).

Example 16

Synthesis of 4-(3-fluoro-4-(5-(1-phenylcyclopropyl) thiazolo[5,4-b]pyridine-2-yl)-benzamido)butanoic acid

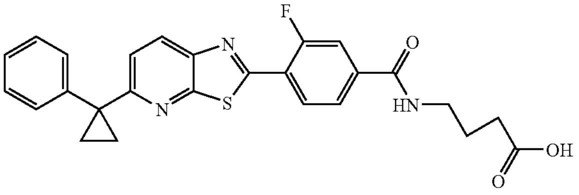

Step 1

Reaction of 3-fluoro-4-(5-(1-phenylcyclopropyl)thiazolo [5,4-b]pyridine-2-yl)benzoic acid (0.080 g, 0.20 mmol) and ethyl 4-aminobutyrate hydrochloride, according to Reference S and the general procedure for amide formation afforded ethyl 4-(3-fluoro-4-(5-(1-phenylcyclopropyl)thiazolo[5,4-b] pyridine-2-yl)benzamido)butanoate. MS (ESI) m/z: Calculated: 503.2; Observed: 504.1 ($M^+$+1).

Step 2

Hydrolysis of ethyl 4-(3-fluoro-4-(5-(1-phenylcyclopropyl)thiazolo[5,4-b]pyridine-2-yl)benzamido)butanoate (0.0945 g, 0.19 mmol), according to Reference S and the general procedure for ester hydrolysis afforded 4-(3-fluoro-4-(5-(1-phenylcyclopropyl)thiazolo[5,4-b]pyridine-2-yl) benzamido)butanoic acid. MS (ESI) m/z: Calculated: 475.1; Observed: 476.0 ($M^+$+1).

Example 17

Synthesis of 1-((2,6-dimethyl-4-(5-(1-phenylcyclopropyl)thiazolo[5,4-b]-pyridin-2-yl)phenyl)methyl) azetidine-3-carboxylic acid

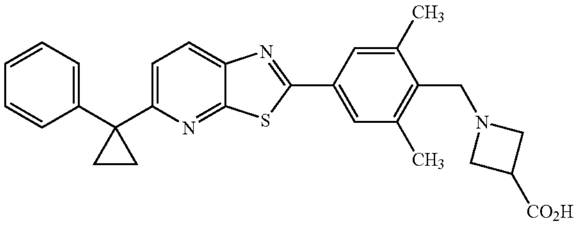

Step 1

A mixture of 5-(1-phenylcyclopropyl)thiazolo[5,4-b]pyridine (23.2 mg, 92 μmol), 2-(4-bromo-2,6-dimethylphenyl)-1,3-dioxane (25 mg, 92 μmol), $PdCl_2(AmPhos)_2$ (4.8 mg, 7.7 μmol), and cesium carbonate (90 mg, 276 μmol) in DMF (1.0 mL) was heated (microwave) at 190° C. under argon for 30 min, then at 200° C. for 30 min. The reaction mixture was then partitioned between EtOAc (40 mL) and water (10 mL). The organic layer was separated and sequentially washed with water (2×10 mL) and brine (10 mL), then dried over sodium sulfate, filtered, and concentrated in vacuo. Chromatographic purification of the residue (silica gel, 0-70% EtOAc/Hex,) furnished 2-(4-(1,3-dioxan-2-yl)-3,5-dimethylphenyl)-5-(1-phenylcyclopropyl)-thiazolo[5,4-b]pyridine as a yellow solid. MS (ESI) m/z: Calculated: 442.2; Observed: 443.2 ($M^+$+1).

Step 2

A mixture of 2-(4-(1,3-dioxan-2-yl)-3,5-dimethylphenyl)-5-(1-phenyl-cyclopropyl)thiazolo[5,4-b]pyridine (96.0 mg, 217 μmol) and hydrochloric acid (5.0M, aq; 1.5 mL, 7500 μmol) in THF (3.0 mL) was heated at 60° C. in a sealed flask under argon. After 2 h, the reaction mixture was allowed to cool to 25° C. The resulting mixture was diluted with EtOAc (50 mL) and water (20 mL), neutralized with 5.0N NaOH (1.5 mL), and saturated aqueous sodium bicarbonate (10 mL) was added. The organic layer was then separated, sequentially washed with water (20 mL) and brine (15 mL), dried over sodium sulfate, filtered, and concentrated in vacuo to provide 2,6-dimethyl-4-(5-(1-phenylcyclopropyl)thiazolo[5,4-b]-pyridine-2-yl)benzaldehyde as a yellow-orange solid. MS (ESI) m/z: Calculated: 384.1; Observed: 385.1 ($M^+$+1).

Step 3

A mixture of 2,6-dimethyl-4-(5-(1-phenylcyclopropyl) thiazolo[5,4-b]pyridine-2-yl)benzaldehyde (22.4 mg, 58.3 μmol), azetidine-3-carboxylic acid (29.5 mg, 291 μmol), and acetic acid (26.9 μl, 466 μmol) in 1:1 $CH_2Cl_2$/MeOH (2.0 mL) was stirred at 25° C. for 1 h. Sodium cyanoborohydride (6.59 mg, 105 μmol) was then added, and the resulting mixture was stirred at 25° C. for 15 h. The reaction mixture was then concentrated in vacuo, dissolved in 2 mL DMSO+20 μL trifluoroacetic acid, filtered, and purified by rpHPLC (10-100% acetonitrile/water+0.1% TFA) to provide 1-((2,6-dimethyl-4-(5-(1-phenylcyclopropyl)thiazolo[5,4-b]pyridine-2- yl)phenyl)methyl)-azetidine-3-carboxylic acid as a light yellow solid. MS (ESI) m/z: Calculated: 469.2; Observed: 470.1 ($M^{+}$+1).

Example 18

Synthesis of 1-((2-methyl-4-(5-(1-phenylcyclopropyl)thiazolo[5,4-b]pyridine-2-yl)phenyl)methyl)azetidine-3-carboxylic acid

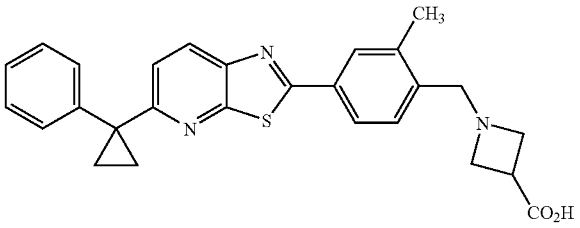

Step 1

A mixture of 5-(1-phenylcyclopropyl)thiazolo[5,4-b]pyridine (50.6 mg, 201 μmol), 4-bromo-2-methylbenzonitrile (47 mg, 241 μmol), $PdCl_2(AmPhos)_2$ (7.1 mg, 10 μmol), and cesium carbonate (196 mg, 602 μmol) in DMF (1.6 mL) was heated (microwave) under argon at 190° C. for 30 min. The reaction mixture was then partitioned between EtOAc (40 mL) and water (15 mL). The organic layer was separated, washed with water and brine (10 mL), dried over sodium sulfate, filtered and concentrated in vacuo. Chromatographic purification of the residue (silica gel, 10% EtOAc/hexanes) provided 2-methyl-4-(5-(1-phenyl-cyclopropyl)thiazolo[5,4-b]pyridine-2-yl)benzonitrile as a light-yellow solid. MS (ESI) m/z: Calculated: 367.1; Observed: 368.1 ($M^{+}$+1).

Step 2

DIBAL-H (1.0M in hexanes; 132 μL, 132 μmol) was added to a solution of 2-methyl-4-(5-(1-phenylcyclopropyl)thiazolo[5,4-b]pyridine-2-yl)benzonitrile (44.2 mg, 120 μmol) in $CH_2Cl_2$ (2.0 mL) at 25° C., and the resulting solution was stirred at 25° C. for 45 min. Saturated aqueous Na/K tartrate solution (2.0 mL) was then added, and the resulting mixture was stirred for 15 min, then partitioned between $CH_2Cl_2$ (20 mL) and water (10 mL). The organic layer was separated, and the aqueous layer was extracted with $CH_2Cl_2$. The combined organic extracts were dried over $MgSO_4$, filtered, and concentrated in vacuo. Chromatographic purification of the residue (silica gel, 15% EtOAc/hexanes) provided 2-methyl-4-(5-(1-phenylcyclopropyl)thiazolo[5,4-b]pyridine-2-yl) benzaldehyde as a light yellow solid. MS (ESI) m/z: Calculated: 370.1; Observed: 371.2 ($M^{+}$+1).

Step 3

A mixture of 2-methyl-4-(5-(1-phenylcyclopropyl)thiazolo[5,4-b]pyridine-2-yl)benzaldehyde (22.6 mg, 61 μmol), azetidine-3-carboxylic acid (31 mg, 305 μmol), and acetic acid (28 μL, 488 μmol) in 1:1 $CH_2Cl_2$/MeOH (2.0 mL) was stirred at 25° C. for 1 h. Sodium cyanoborohydride (6.9 mg, 110 μmol) was then added, and the resulting mixture was stirred at 25° C. for 16 h. The reaction mixture was then concentrated in vacuo, dissolved in 2 mL DMSO+20 μL trifluoroacetic acid, filtered, and purified by rpHPLC (10-100% acetonitrile/water+0.1% TFA) to provide 1-((2-methyl-4-(5-(1-phenylcyclopropyl)thiazolo[5,4-b]pyridine-2-yl)-phenyl)methyl)-azetidine-3-carboxylic acid as a white solid. MS (ESI) m/z: Calculated: 455.2; Observed: 456.1 ($M^{+}$+1).

Example 19

Synthesis of 1-((3-methyl-4-(5-(1-phenylcyclopropyl)thiazolo[5,4-b]pyridine-2-yl)phenyl)methyl)azetidine-3-carboxylic acid

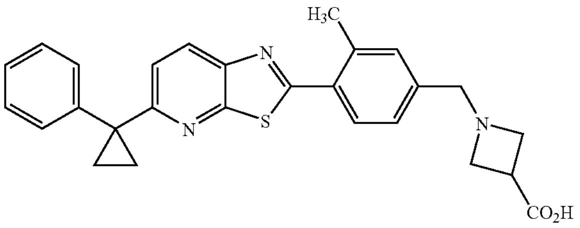

Step 1

A mixture of 5-(1-phenylcyclopropyl)thiazolo[5,4-b]pyridine (48.3 mg, 191 μmol), 4-bromo-3-methylbenzonitrile (45.0 mg, 230 μmol), $PdCl_2(AmPhos)_2$ (6.78 mg, 9.57 μmol), and cesium carbonate (187 mg, 574 μmol) in DMF (1.6 mL) was heated (microwave) under argon at 190° C. for 40 min. The reaction mixture was then partitioned between EtOAc (40 mL) and water (15 mL). The organic layer was separated, washed with water and brine, dried over sodium sulfate, filtered, and concentrated in vacuo. Chromatographic purification of the residue (silica gel, 0-100% EtOAc/hexanes) furnished 3-methyl-4-(5-(1-phenylcyclopropyl)thiazolo[5,4-b] pyridine-2-yl)benzonitrile as a light-yellow solid. MS (ESI) m/z: Calculated: 367.1; Observed: 368.1 ($M^{+}$+1).

Step 2

DIBAL-H (11.0M in hexanes; 315 μl, 315 μmol) was added to a solution of 3-methyl-4-(5-(1-phenylcyclopropyl) thiazolo[5,4-b]pyridine-2-yl)benzonitrile (105.2 mg, 286 μmol) in $CH_2Cl_2$ (4.5 mL) at 25° C., and the resulting solution was stirred at 25° C. for 45 min. Additional DIBAL-H (1.0M in hexanes; 86 μL, 86 μmol) was then added, and the resulting solution was stirred at 25° C. for 30 min. Saturated aqueous Na/K tartrate solution (4.0 mL) was added, and the resulting mixture was vigorously stirred for 15 min, then partitioned between $CH_2Cl_2$ (40 mL) and saturated. Aqueous Na/K tartrate solution (10 mL). The organic layer was separated, and the aqueous layer was extracted with $CH_2Cl_2$. The combined organic extracts were dried over $MgSO_4$, filtered, and concentrated in vacuo. Chromatographic purification of the residue (silica gel, 0-40% EtOAc/hexanes) provided 3-methyl-4-(5-(1-phenylcyclopropyl)-thiazolo[5,4-b]pyridine-2-yl)-benzaldehyde as a light-yellow foam. MS (ESI) m/z: Calculated: 370.1; Observed: 371.1 ($M^{+}$+1).

Step 3

A mixture of 3-methyl-4-(5-(1-phenylcyclopropyl)thiazolo[5,4-b]pyridine-2-yl)-benzaldehyde (85.0 mg, 229 μmol), azetidine-3-carboxylic acid (116 mg, 1147 μmol), and acetic acid (106 μL, 1836 μmol) in 1:1 $CH_2Cl_2$/MeOH (7.0 mL) was stirred at 25° C. for 1 h. Sodium cyanoborohydride (26 mg, 413 μmol) was then added, and the resulting mixture was stirred at 25° C. for 16 h. The reaction mixture was then concentrated in vacuo, dissolved in 2 mL DMSO+20 μL trifluoroacetic acid, filtered, and purified by rpHPLC (10-100% acetonitrile/water+0.1% TFA) to provide 1-((3-methyl-4-(5-(1-phenylcyclopropyl)-thiazolo[5,4-b]pyridine-2-yl)phenyl)methyl)-azetidine-3-carboxylic acid as a white solid. MS (ESI) m/z: Calculated: 455.2; Observed: 456.1

(M+1). $^1$H NMR (400 MHz, MeOH) δ ppm 8.11 (d, J=8.6 Hz, 1 H), 7.88 (d, J=7.8 Hz, 1 H), 7.35-7.55 (m, 6 H), 7.27-7.34 (m, 1 H), 7.11 (d, J=8.6 Hz, 1 H), 4.47 (s, 2 H), 4.32-4.42 (m, 4 H), 3.63-3.81 (m, 1 H), 2.67 (s, 3 H), 1.70-1.77 (m, 2 H), 1.36-1.47 (m, 2 H)

Example 20

Synthesis of 1-(3-fluoro-4-(5-(1-phenylcyclopropyl) thiazolo[5,4-b]pyridine-2-yl)phenyl)cyclopropanamine

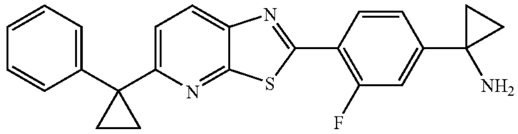

Step 1

To a stirred solution of 3-fluoro-4-(5-(1-phenylcyclopropyl)thiazolo[5,4-b]pyridine-2-yl)benzoic acid (0.222 g, 0.569 mmol) in 1,2-dichloroethane (1.5 mL, 19 mmol) and acetonitrile (1.5 mL, 29 mmol) under argon were added chlorosulfonyl isocyanate (0.074 mL, 0.853 mmol) and triethylamine (0.12 mL, 0.853 mmol). The reaction mixture was stirred at 90° C. for 18 h. The cooled reaction mixture was diluted with $CH_2Cl_2$ and washed with saturated aqueous $NaHCO_3$ solution and brine; dried ($MgSO_4$). ISCO purification (with 10% to 50% EtOAc/hexanes) afforded 3-fluoro-4-(5-(1-phenylcyclopropyl)-thiazolo[5,4-b]pyridine-2-yl)benzonitrile as an off-white solid. MS (ESI) m/z: Calculated: 371.1; Observed: 372.0 ($M^+$+1).

Step 2

Ethylmagnesium bromide (1 M solution in t-butyl methyl ether) (0.764 mL, 0.764 mmol) was added at −78° C. to a solution of 3-fluoro-4-(5-(1-phenylcyclopropyl)-thiazolo[5,4-b]pyridine-2-yl)benzonitrile (0.113 g, 0.306 mmol) and titanium (iv) isopropoxide (0.098 mL, 0.336 mmol) in ethyl ether (3 mL) and toluene (3 mL) under argon. After stirring at −78° C. for 10 min, the yellow solution was allowed to warm to room temperature (1 h), during which boron trifluoride diethyl etherate (0.023 mL, 0.187 mmol) was added. After the reaction mixture was stirred for 1 h, 1 N HCl (ca. 0.5 mL) and $CH_2Cl_2$ were added. NaOH (10% aq, ca. 1 mL) was added to the resulting two clear phases and the mixture was extracted with $CH_2Cl_2$. The combined $CH_2Cl_2$ layers were dried ($MgSO_4$), filtered, and concentrated in vacuo. ISCO purification with 10% MeOH/$CH_2Cl_2$ failed to give a pure batch of 1-(3-fluoro-4-(5-(1-phenyl-cyclopropyl)thiazolo-[5,4-b]pyridine-2-yl)phenyl)cyclopropanamine. Further purification on the reverse phase prep. HPLC provided the title compound as an off-white solid. MS (ESI) m/z: Calculated: 401.1; Observed: 402.1 ($M^+$+1).

Example 21

Synthesis of 3-(1-(3-fluoro-4-(5-(1-phenylcyclopropyl)thiazolo[5,4-b]pyridine-2-yl)phenyl)cyclopropylamino)propanoic acid

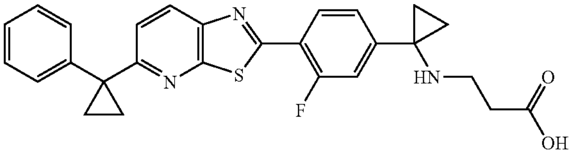

Step 1

1-(3-Fluoro-4-(5-(1-phenylcyclopropyl)thiazolo[5,4-b]pyridine-2-yl)phenyl)-cyclopropanamine (0.067 g, 0.167 mmol) and methyl acrylate (0.5 mL, 5.5 mmol) were combined in a sealed tube and heated neat at 100° C. for 1 day, during which LC-MS indicated completion of reaction. The cooled reaction mixture was diluted with $CH_2Cl_2$ and washed with aqueous saturated $NaHCO_3$ solution and brine. The organic layer was dried ($MgSO_4$), filtered, and concentrated in vacuo. ISCO purification with 5% to 20% EtOAc/Hexanes afforded methyl 3-(1-(3-fluoro-4-(5-(1-phenylcyclopropyl) thiazolo[5,4-b]pyridine-2-yl)phenyl)cyclopropylamino)propanoate as a light golden yellow oil. MS (ESI) m/z: Calculated: 487.6; Observed: 488.1 ($M^+$+1).

Step 2

A solution of methyl 3-(1-(3-fluoro-4-(5-(1-phenylcyclopropyl)thiazolo[5,4-b]pyridine-2-yl)phenyl)cyclopropylamino)propanoate (0.031 g, 0.064 mmol) in tetrahydrofuran (0.2 mL) and methanol (0.1 mL) was added 1 M lithium hydroxide solution (0.19 mL, 0.19 mmol) and stirred at room temperature for 3 hours. The reaction mixture was concentrated in vacuo and the resulting slurry was diluted with water and neutralized (to pH=~7) with aqueous 1 N HCl solution. The aqueous suspension was extracted with 15% MeOH/$CHCl_3$; the organic extracts were combined, dried ($K_2CO_3$), filtered, and concentrated in vacuo. Purification via reverse phase prep. HPLC afforded the title compound as an off-white amorphous solid. MS (ESI) m/z: Calculated: 473.2; Observed: 474.1 ($M^+$+1).

Example 22

Synthesis of 2-(3-fluoro-4-(5-(1-phenylcyclopropyl) thiazolo[5,4-b]pyridine-2-yl)phenyl)-propan-2-amine

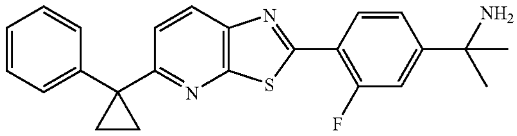

Step 1

To 1-(3-fluoro-4-(5-(1-phenylcyclopropyl)thiazolo[5,4-b]pyridine-2-yl)phenyl)ethanone (0.732 g, 1.88 mmol) in diethyl ether (15.7 mL) and toluene (14.7 mL) at 0° C. under argon was added methylmagnesium chloride, 3.0 M solution in THF (1.38 mL, 4.14 mmol). After stirring at 0° C. for 10 minutes, the reaction mixture was allowed to warm to room temperature and stirred for another 1 hour. The reaction mixture was quenched with saturated $NH_4Cl$ solution and diluted with $CH_2Cl_2$; the aqueous layer was back-extracted with $CH_2Cl_2$. The combined organic extracts were dried ($MgSO_4$), filtered, and concentrated in vacuo. ISCO purification with 10% to 30% EtOAc/Hexanes afforded 2-(3-fluoro-4-(5-(1-phenylcyclopropyl)thiazolo[5,4-b]pyridine-2-yl)phenyl)propan-2-ol as a colorless foam. MS (ESI) m/z: Calculated: 404.1; Observed: 405.1 ($M^+$+1).

Step 2

To 2-(3-fluoro-4-(5-(1-phenylcyclopropyl)thiazolo[5,4-b]pyridine-2-yl)phenyl)propan-2-ol (0.715 g, 1.77 mmol) at 0° C. under argon was added 2-chloroacetonitrile (0.67 mL, 10.6 mmol), followed by acetic acid (1.4 mL) and sulfuric acid (0.90 mL). The resulting yellow reaction mixture was warmed to room temperature and stirred for 4 hours, during which LC-MS indicated completion of reaction. The reaction mixture was diluted with $CH_2Cl_2$ and washed with saturated $NaHCO_3$ solution and brine; dried ($MgSO_4$). The organic layer was filtered and concentrated in vacuo. ISCO purification with 10% to 40% EtOAc/Hexanes afforded 2-chloro-N-(2-(3-fluoro-4-(5-(1-phenylcyclopropyl)-thiazolo[5,4-b]pyridine-2-yl)phenyl)propan-2-yl)acetamide as a white amorphous solid. MS (ESI) m/z: Calculated: 480.0; Observed: 481.1 ($M^+$+1).

Step 3

To a solution of 2-chloro-N-(2-(3-fluoro-4-(5-(1-phenylcyclopropyl)-thiazolo[5,4-b]pyridine-2-yl)phenyl)propan-2-yl)acetamide (0.51 g, 1.0 mmol) in ethanol (10 mL) and acetic acid (2 mL) was added thiourea (0.12 g, 1.58 mmol). The reaction mixture was heated to reflux for 18 hours. The reaction mixture was diluted with $CH_2Cl_2$ and washed with saturated $NaHCO_3$ solution and brine. The organic layer was dried ($MgSO_4$), filtered, and concentrated in vacuo. ISCO purification with 1% to 10% MeOH/$CH_2Cl_2$ afforded a crude crop of the desired product. Trituration with $CH_2Cl_2$ afforded 2-(3-fluoro-4-(5-(1-phenylcyclopropyl)thiazolo[5,4-b]pyridine-2-yl)phenyl)-propan-2-amine as a white amorphous solid. MS (ESI) m/z: Calculated: 403.2; Observed: 404.1 ($M^+$+1).

Example 23

Synthesis of 3-(2-(3-fluoro-4-(5-(1-phenylcyclopropyl)thiazolo[5,4-b]pyridine-2-yl)phenyl)propan-2-ylamino)propanoic acid

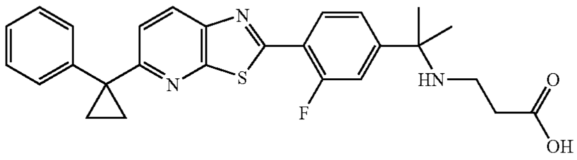

Step 1

2-(3-Fluoro-4-(5-(1-phenylcyclopropyl)thiazolo[5,4-b]pyridine-2-yl)phenyl)-propan-2-amine (0.081 g, 0.20 mmol) and methyl acrylate (0.18 mL, 2.00 mmol) were combined in a sealed tube and heated neat at 100° C. for 1 day, during which LC-MS indicated completion of reaction. The cooled reaction mixture was diluted with $CH_2Cl_2$ and washed with aqueous saturated $NaHCO_3$ solution and brine. The organic layer was dried ($MgSO_4$), filtered, and concentrated in vacuo.

ISCO purification with 5% to 25% EtOAc/Hexanes afforded methyl 3-(2-(3-fluoro-4-(5-(1-phenylcyclopropyl)thiazolo[5,4-b]pyridine-2-yl)phenyl)propan-2-ylamino)propanoate as a white amorphous solid. MS (ESI) m/z: Calculated: 489.2; Observed: 490.1 ($M^+$+1).

Step 2

A solution of methyl 3-(2-(3-fluoro-4-(5-(1-phenylcyclopropyl)thiazolo[5,4-b]pyridine-2-yl)phenyl)propan-2-ylamino)propanoate (0.067 g, 0.137 mmol) in tetrahydrofuran (1 mL) and methanol (0.5 mL) was added 1 M lithium hydroxide solution (0.4 mL, 0.4 mmol) and stirred at room temperature for 3 hours. The reaction mixture was concentrated in vacuo and the resulting slurry was diluted with water and neutralized (to pH=~7) with aqueous 1 N HCl solution. The aqueous suspension was extracted with 15% MeOH/$CHCl_3$; the organic extracts were combined, dried ($K_2CO_3$), filtered, and concentrated in vacuo to give a crude golden yellow solid (~0.040 g). Trituration with MeOH afforded the title compound as an off-white amorphous solid. MS (ESI) m/z: Calculated: 475.5; Observed: 476.1 ($M^+$+1).

Example 24

Synthesis of 1-((2,6-dimethyl-4-(5-(1-phenylcyclopropyl)thiazolo[5,4-b]pyridin-2-yl)phenyl)methyl)azetidine-3-carboxylic acid

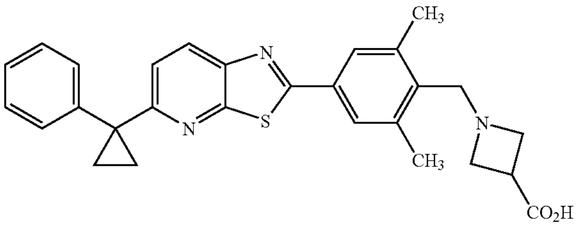

Step 1

Synthesized from 5-(1-phenylcyclopropyl)thiazolo[5,4-b]pyridine (23.2 mg, 92 μmol) and 2-(4-bromo-2,6-dimethylphenyl)-1,3-dioxane (25 mg, 92 μmol) according to Reference T and the general procedure for azabenzothiazole 2-arylation to give 2-(4-(1,3-dioxan-2-yl)-3,5-dimethylphenyl)-5-(1-phenylcyclopropyl)thiazolo[5,4-b]pyridine as a yellow solid. MS (ESI) m/z: Calculated: 442.2; Observed: 443.2 ($M^+$+1).

Step 2

A mixture of 2-(4-(1,3-dioxan-2-yl)-3,5-dimethylphenyl)-5-(1-phenylcyclopropyl)-thiazolo[5,4-b]pyridine (96.0 mg, 0.217 mmol) and hydrochloric acid (5.0M, aq; 1.5 mL, 7.50 mmol) in THF (3.0 mL) was heated at 60° C. in a sealed flask under argon. After 2 h, the reaction was allowed to cool to 25° C. The resulting mixture was diluted with EtOAc (50 mL) and water (20 mL), neutralized with 5.0N NaOH (1.5 mL), and saturated aqueous sodium bicarbonate (10 mL) was added. The organic layer was then separated, sequentially washed with water and brine, dried over sodium sulfate, filtered, and concentrated in vacuo to provide 2,6-dimethyl-4-(5-(1-phenylcyclopropyl)thiazolo[5,4-b]pyridine-2-yl)-benzaldehyde as a yellow-orange solid. MS (ESI) m/z: Calculated: 384.1; Observed: 385.1 ($M^+$+1).

Step 3

A mixture of 2,6-dimethyl-4-(5-(1-phenylcyclopropyl)thiazolo[5,4-b]pyridine-2-yl)benzaldehyde (22.4 mg, 0.058 mmol), azetidine-3-carboxylic acid (29.5 mg, 0.29 mmol), and acetic acid (26.9 μl, 0.466 mmol) in 1:1 $CH_2Cl_2$/MeOH (2.0 mL) was stirred at 25° C. for 1 h. Sodium cyanoborohydride (6.59 mg, 0.105 mmol) was then added, and the resulting mixture was stirred at 25° C. for 15 h. The reaction mixture was then concentrated in vacuo, dissolved in DMSO (2 mL)+trifluoroacetic acid (20 μL), filtered, and purified by rpHPLC (10-100% acetonitrile/water+0.1% TFA) to provide 1-((2,6-dimethyl-4-(5-(1-phenylcyclopropyl)thiazolo[5,4-b]pyridine-2-yl)phenyl)methyl)azetidine-3-carboxylic acid as a light yellow solid. MS (ESI) m/z: Calculated: 469.2; Observed: 470.1 ($M^+$+1). (2,6-

Dimethyl-4-(5-(1-phenylcyclopropyl)thiazolo[5,4-b]pyridine-2-yl)phenyl)methanol was also obtained from this reaction as a white solid. MS (ESI) m/z: Calculated: 386.1; Observed: 387.1 ($M^+$+1).

Example 25

Synthesis of 1-((2-methyl-4-(5-(1-phenylcyclopropyl)thiazolo[5,4-b]pyridine-2-yl)phenyl)methyl)azetidine-3-carboxylic acid

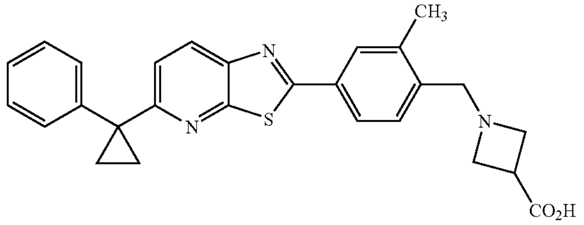

Step 1

2-Methyl-4-(5-(1-phenylcyclopropyl)thiazolo[5,4-b]□yridine-2-yl)benzonitrile was synthesized from 5-(1-phenylcyclopropyl)thiazolo[5,4-b]pyridine (50.6 mg, 201 μmol) and 4-bromo-2-methylbenzonitrile (47.0 mg, 241 μmol) according to Reference T and the general procedure for azabenzothiazole 2-arylation as a light yellow solid. MS (ESI) m/z: Calculated: 367.1; Observed: 368.1 ($M^+$+1).

Step 2

DIBAL-H (1.0M in hexanes; 0.132 mL, 0.132 mmol) was added to a solution of 2-methyl-4-(5-(1-phenylcyclopropyl)thiazolo[5,4-b]pyridine-2-yl)benzonitrile (44.2 mg, 0.120 mmol) in $CH_2Cl_2$ (2.0 mL) at 25° C., and the resulting solution was stirred at 25° C. for 45 min. Saturated aqueous Na/K tartrate solution (2.0 mL) was then added, and the resulting mixture was stirred for 15 min, then partitioned between $CH_2Cl_2$ (20 mL) and water (10 mL). The organic layer was separated, and the aqueous layer was extracted with $CH_2Cl_2$. The combined organic extracts were dried over $MgSO_4$, filtered, and concentrated in vacuo. Chromatographic purification of the residue (silica gel, 15% EtOAc/hexanes) provided 2-methyl-4-(5-(1-phenylcyclopropyl)thiazolo[5,4-b]pyridine-2-yl)benzaldehyde as a light yellow solid. MS (ESI) m/z: Calculated: 370.1; Observed: 371.2 ($M^+$+1).

Step 3

A mixture of 2-methyl-4-(5-(1-phenylcyclopropyl)thiazolo[5,4-b]pyridine-2-yl)benzaldehyde (22.6 mg, 0.061 mmol), azetidine-3-carboxylic acid (31 mg, 0.305 mmol), and acetic acid (28 μL, 0.488 mmol) in 1:1 $CH_2Cl_2$/MeOH (2.0 mL) was stirred at 25° C. for 1 h. Sodium cyanoborohydride (6.9 mg, 0.110 mmol) was then added, and the resulting mixture was stirred at 25° C. for 16 h. The reaction mixture was then concentrated in vacuo, dissolved in DMSO (2 mL)+trifluoroacetic acid (20 μL), filtered, and purified by rpHPLC (10-100% acetonitrile/water+0.1% TFA) to provide 1-((2-methyl-4-(5-(1-phenyl-cyclopropyl)thiazolo[5,4-b]pyridine-2-yl)phenyl)methyl)azetidine-3-carboxylic acid as a white solid. MS (ESI) m/z: Calculated: 455.2; Observed: 456.1 ($M^+$+1).

(2-Methyl-4-(5-(1-phenylcyclopropyl)thiazolo[5,4-b]pyridine-2-yl)phenyl)methanol was also obtained from this reaction as a white solid. MS (ESI) m/z: Calculated: 372.1; Observed: 373.1 ($M^+$+1).

Example 26

Synthesis of 1-((3-methyl-4-(5-(1-phenylcyclopropyl)thiazolo[5,4-b]pyridine-2-yl)phenyl)methyl)azetidine-3-carboxylic acid

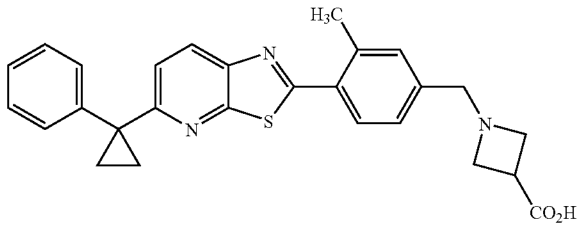

Step 1

3-Methyl-4-(5-(1-phenylcyclopropyl)thiazolo[5,4-b]pyridine-2-yl)benzonitrile was synthesized from 5-(1-phenylcyclopropyl)thiazolo[5,4-b]pyridine (48.3 mg, 191 μmol) and 4-bromo-3-methylbenzonitrile (45.0 mg, 230 μmol) according to Reference T and the general procedure for azabenzothiazole 2-arylation as a light yellow solid. MS (ESI) m/z: Calculated: 367.1; Observed: 368.1 ($M^+$+1).

Step 2

DIBAL-H (11.0M in hexanes; 0.315 mL, 0.315 mmol) was added to a solution of 3-methyl-4-(5-(1-phenylcyclopropyl)thiazolo[5,4-b]pyridine-2-yl)benzonitrile (105.2 mg, 0.286 mmol) in $CH_2Cl_2$ (4.5 mL) at 25° C., and the resulting solution was stirred at 25° C. for 45 min. Additional DIBAL-H (1.0M in hexanes; 86 μL, 86 μmol) was then added, and the resulting solution was stirred at 25° C. for 30 min. Saturated aqueous Na/K tartrate solution (4.0 mL) was added, and the resulting mixture was vigorously stirred for 15 min, then partitioned between $CH_2Cl_2$ (40 mL) and saturated aqueous Na/K tartrate solution (10 mL). The organic layer was separated, and the aqueous layer was extracted with $CH_2Cl_2$. The combined organic extracts were dried over $MgSO_4$, filtered, and concentrated in vacuo. Chromatographic purification of the residue (silica gel, 0-40% EtOAc/hexanes) provided 3-methyl-4-(5-(1-phenylcyclopropyl)thiazolo[5,4-b]pyridine-2-yl)benzaldehyde as a light-yellow foam. MS (ESI) m/z: Calculated: 370.1; Observed: 371.1 ($M^+$+1).

Step 3

A mixture of 3-methyl-4-(5-(1-phenylcyclopropyl)thiazolo[5,4-b]pyridine-2-yl)benzaldehyde (85.0 mg, 0.229 mmol), azetidine-3-carboxylic acid (116 mg, 1.147 mmol), and acetic acid (106 µL, 1.836 mmol) in 1:1 $CH_2Cl_2$/MeOH (7.0 mL) was stirred at 25° C. for 1 h. Sodium cyanoborohydride (26 mg, 0.413 mmol) was then added, and the resulting mixture was stirred at 25° C. for 16 h. The reaction mixture was then concentrated in vacuo, dissolved in DMSO (2 mL)+ trifluoroacetic acid (20 µL), filtered, and purified by rpHPLC (10-100% acetonitrile/water+0.1% TFA) to provide 1-((3-methyl-4-(5-(1-phenyl-cyclopropyl)thiazolo[5,4-b]pyridine-2-yl)phenyl)methyl)azetidine-3-carboxylic acid as a white solid. MS (ESI) m/z: Calculated: 455.2; Observed: 456.1 ($M^+$+1).

3-Methyl-4-(5-(1-phenylcyclopropyl)thiazolo[5,4-b]pyridine-2-yl)phenyl)methanol was also obtained from this reaction as a light yellow solid. MS (ESI) m/z: Calculated: 372.1; Observed: 373.1 ($M^+$+1).

Example 27

Synthesis of 3-(3-fluoro-4-(5-(1-phenylcyclopropyl) thiazolo[5,4-b]pyridine-2-yl)-phenyl)propanoic acid

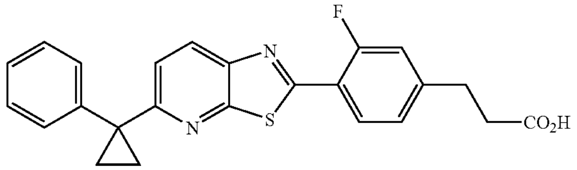

Step 1

A dark brown solution of methyl(triphenylphosphoranylidene) acetate (0.418 g, 1.25 mmol) and 3-fluoro-4-(5-(1-phenylcyclopropyl)thiazolo[5,4-b]pyridine-2-yl)benzaldehyde (0.426 g, 1.14 mmol) in 4 mL DCM was allowed to stir rapidly over the weekend. A bright orange precipitate was evident. The reaction mixture was adsorbed onto silica gel (2.5 g), dried, and purified by ISCO, 0-20% EA/hexanes to give (E)-methyl 3-(3-fluoro-4-(5-(1-phenylcyclopropyl)thiazolo[5,4-b]pyridine-2-yl)phenyl)acrylate. MS (ESI) m/z; calculated: 430.1; Observed: 431.1 ($M^+$+1).

Step 2

A slurry of (E)-methyl 3-(3-fluoro-4-(5-(1-phenylcyclopropyl)thiazolo[5,4-b]pyridine-2-yl)phenyl)acrylate (0.116 g, 0.269 mmol) and Pd/C 10%, 50% water (0.115 g, 0.108 mmol) in 2 mL THF was treated with a hydrogen balloon with rapid stirring for 3 h. The reaction mixture was flushed with nitrogen, diluted with DCM, filtered through celite, rinsing with DCM. The filtrate was concentrated in vacuo to give methyl 3-(3-fluoro-4-(5-(1-phenylcyclopropyl)thiazolo[5,4-b]pyridine-2-yl)phenyl)propanoate as a white solid. MS (ESI) m/z; calculated: 432.1; Observed: 433.1 ($M^+$+1).

Step 3

To a slurry of methyl 3-(3-fluoro-4-(5-(1-phenylcyclopropyl)thiazolo[5,4-b]pyridine-2-yl)phenyl)propanoate (0.114 g, 0.26 mmol) in 3 mL THF/1 mL water was added sodium hydroxide (0.53 mL, 0.53 mmol). The reaction mixture became light yellow and was still heterogeneous. After stirring overnight, the slightly milky solution was treated with a stream of nitrogen to remove the THF, then 0.53 mL 1N HCl to neutralize base, at which point a white precipitate formed, and diluted with 3 mL 3M pH 4.8 sodium acetate buffer. The reaction mixture was filtered and the solid rinsed with water and MeOH. The solid was collected and dried in vacuo to give 3-(3-fluoro-4-(5-(1-phenylcyclopropyl)thiazolo[5,4-b]pyridine-2-yl)phenyl)propanoic acid as a white solid. MS (ESI) m/z; calculated: 418.1; Observed: 419.1 ($M^+$+1).

Example 28

Synthesis of (3-fluoro-4-(5-(1-phenylcyclopropyl) thiazolo[5,4-b]pyridine-2-yl)phenyl)methanol

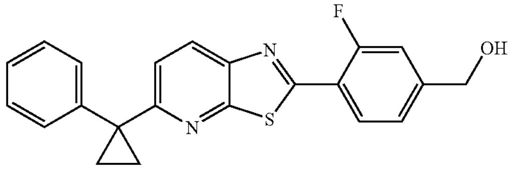

To a solution at 0° C. of 3-fluoro-4-(5-(1-phenylcyclopropyl)thiazolo[5,4-b]pyridine-2-yl)benzaldehyde (2.00 g, 5.34 mmol) in THF (50 mL) and MeOH (25 mL) was added sodium borohydride (0.188 mL, 5.34 mmol). The reaction mixture was allowed to warm up to ambient temperature. The crude reaction mixture, after 1 h, was concentrated in vacuo and purified by silica gel chromatography to afford (3-fluoro-4-(5-(1-phenylcyclopropyl)thiazolo[5,4-b]pyridine-2-yl) phenyl)methanol. MS (ESI) m/z: calculated: 376.1: Observed: 377.0 ($M^+$+1).

Example 29

Synthesis of 2-(3-fluoro-4-(5-(1-phenylcyclopropyl) thiazolo[5,4-b]pyridine-2-yl)benzyl)propane-1,3-diol

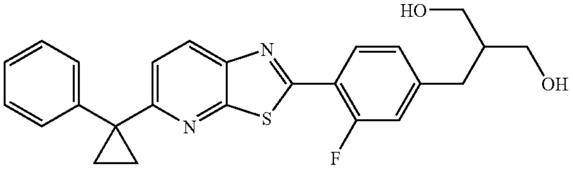

Step 1

To a slurry of (3-fluoro-4-(5-(1-phenylcyclopropyl)thiazolo[5,4-b]pyridine-2-yl)phenyl)methanol (2.05 g, 5.45 mmol), triphenylphosphine (1.64 mL, 7.08 mmol) in DCM (25 mL) at 0° C. under $N_2$, carbon tetrabromide (0.634 mL, 6.53 mmol) was added. The reaction mixture was allowed to warm up to ambient temperature. The crude reaction mixture after 1 h, was concentrate in vacuo and purified by silica gel chromatography to afford 2-(4-(bromomethyl)-2-fluorophenyl)-5-(1-phenylcyclopropyl)thiazolo[5,4-b]pyridine. MS (ESI) m/z; calculated: 438.0; Observed: 438.9 ($M^+$+1).

Step 2

To a slurry of NaH (0.55 g, 14 mmol) in 40 mL DME under nitrogen was added diethyl malonate (2.1 mL, 14 mmol) slowly dropwise. After addition of 1 mL, the reaction mixture was warm, so cooled to 0° C. and continued addition. To the resulting clear solution was added a slurry of 2-(4-(bromomethyl)-2-fluorophenyl)-5-(1-phenylcyclopropyl)-thiazolo[5,4-b]pyridine (3.00 g, 6.8 mmol) as a solid. After 1 h, the reaction mixture was quenched with sat'd aq. Ammonium chloride and DCM, and the aq. Layer was extracted with DCM, and the combined organics were dried over sodium sulfate, filtered, and concentrated in vacuo. The resulting oil was purified by silica gel chromatography, 40 g, 0-30% EA/hexanes. Product containing fractions were combined and concentrated and triturated with hexanes to give diethyl 2-((3-fluoro-4-(5-(1-phenyl-cyclopropyl)thiazolo[5,4-b]pyridine-2-yl)phenyl)methyl)malonate as an off-white solid. MS (ESI) m/z: calculated: 518.2; Observed: 519.1 ($M^{+}$+1).

Step 3

To a slurry of lithium aluminum hydride, 1.0 m solution in tetrahydrafuran (1.39 mL, 1.39 mmol) in 4 mL THF at 0° C. under nitrogen was added diethyl 2-((3-fluoro-4-(5-(1-phenyl-cyclopropyl)thiazolo[5,4-b]pyridine-2-yl)phenyl)methyl)malonate (0.240 g, 0.463 mmol) as a solution in 4 mL THF slowly dropwise via syringe, with 1 mL THF rinse. The slightly yellow reaction mixture was allowed to stir 1 h, then the bath was removed. After 4 h at ambient temperature, the reaction was judged complete. Water (0.05 mL) was added carefully dropwise under nitrogen, followed by 0.10 mL 5 N NaOH, followed by 0.15 mL water. After 1 h, the reaction mixture was filtered to remove a solid, rinsing with THF, and concentrated in vacuo. The material was adsorbed onto 2 g silica gel from DCM/MeOH and purify by silica gel chromatography, 12 g, 20-100% EA/hexanes to give 2-((3-fluoro-4-(5-(1-phenylcyclopropyl)-thiazolo[5,4-b]pyridine-2-yl)phenyl)methyl)propane-1,3-diol as a light yellow solid. MS (ESI) m/z: calculated: 434.2; Observed: 435.1 ($M^{+}$+1).

Example 30

Synthesis of 3-(3-fluoro-4-(5-(1-phenylcyclopropyl) thiazolo[5,4-b]pyridine-2-yl)benzyl)cyclobutane-1,1-dicarboxylic acid

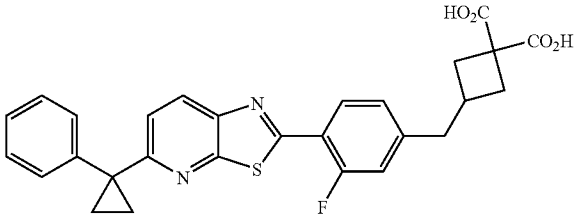

Step 1

To a thick slurry of 2-((3-fluoro-4-(5-(1-phenylcyclopropyl)thiazolo[5,4-b]pyridine-2-yl)phenyl)methyl)propane-1, 3-diol (0.992 g, 2.3 mmol) and triphenylphosphine (1.3 g, 5.0 mmol) in 30 mL DCM at 0° C. under nitrogen was added solid $CBr_4$ (1.6 g, 4.8 mmol). The reaction mixture was allowed to stir rapidly for 1 h, and was then treated with silica gel and concentrated in vacuo. Purification by silica gel chromatography, 40 g, 0-100% EA/hexanes provided 2-(4-(3-bromo-2-(bromomethyl)propyl)-2-fluorophenyl)-5-(1-phenylcyclopropyl)thiazolo[5,4-b]pyridine as a yellow/brown solid. MS (ESI) m/z: calculated: 558.0; Observed: 559.0 ($M^{+}$+1).

Step 2

To a slurry of sodium hydride (0.206 g, 5.14 mmol) in 7 mL DMF was added diethyl malonate (0.690 mL, 4.57 mmol) dropwise via syringe (bubbling). After 3 min, the reaction mixture was clear, and solid 2-(4-(3-bromo-2-(bromomethyl) propyl)-2-fluorophenyl)-5-(1-phenylcyclopropyl)thiazolo [5,4-b]pyridine (0.640 g, 1.14 mmol) was added, the reaction mixture was sealed, and heated to 100° C. After 1 h, the reaction mixture was partitioned between sat'd aq. $NH_4Cl$ and EtOAc. The org layer was washed with water, brine, dried over anhydrous sodium sulfate, filtered, and concentrated in vacuo. The resulting material was purified by silica gel chromatography, EA/hexanes gradient, to give diethyl 3-((3-fluoro-4-(5-(1-phenylcyclopropyl)thiazolo[5,4-b]pyridine-2-yl)phenyl)methyl)cyclobutane-1,1-dicarboxylate as a white solid. MS (ESI) m/z: calculated: 558.2; Observed: 559.1 ($M^{+}$+1).

Step 3

To a mixture of diethyl 3-((3-fluoro-4-(5-(1-phenylcyclopropyl)thiazolo[5,4-b]pyridine-2-yl)phenyl)methyl)cyclobutane-1,1-dicarboxylate (0.533 g, 0.954 mmol) in 10 mL EtOH was added KOH (0.187 g, 3.34 mmol) in 5 mL water. The reaction flask was fitted with a water-cooled reflux condenser and heated to reflux over the weekend. The solvent all evaporated, and the solid was determined to be a mixture of diacid and monoacid. The solid was treated with water, 3.3 mL 1 N HCl, and NaOH 10 M (0.572 mL, 5.72 mmol), and 5 mL THF. The nearly clear solution was heated to reflux for 4 h. The Oyridine mixture was cooled, treated with 1.2 mL 5N HCl, to give a thick white mixture (pH$<$2). The reaction mixture was heated to reflux for several hours. The reaction mixture was partitioned between water and EtOAc. The organic layer was washed with sat'd NaCl once and the organics were dried over anhydrous sodium sulfate, filtered, and concentrated in vacuo to give 3-((3-fluoro-4-(5-(1-phenylcyclopropyl)thiazolo[5,4-b]pyridine-2-yl)phenyl)methyl)cyclobutane-1,1-dicarboxylic acid as a white solid. MS (ESI) m/z: calculated: 502.1; Observed: 503.1 ($M^{+}$+1).

Example 31

Synthesis of (cis)-3-(3-fluoro-4-(5-(1-phenylcyclopropyl)thiazolo[5,4-b]pyridine-2-yl)benzyl)cyclobutanecarboxylic acid

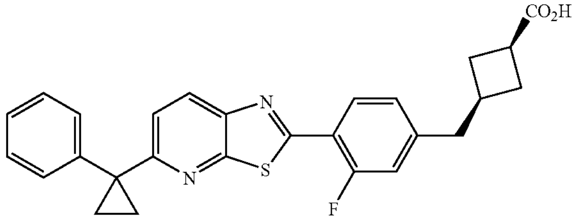

3-((3-Fluoro-4-(5-(1-phenylcyclopropyl)thiazolo[5,4-b] pyridine-2-yl)phenyl)-methyl)cyclobutane-1,1-dicarboxylic acid (0.360 g, 0.716 mmol) treated with 4 mL DMSO, fitted with a water cooled reflux condenser, and heated to 160° C. After 4 h, the reaction mixture was cooled to rt. The reaction mixture was partitioned between water and EtOAc. The organic layer was washed with water once, satd NaCl once and the organics were dried over anhydrous sodium sulfate, filtered, and concentrated in vacuo to give a light yellow solid, as an approximately 2:1 mixture of isomers. Separation by SFC (Gradient with Chiralpak IC (21×250 mm, 5 micron), pure methanol with $CO_2$ 70 mL/min) gave (cis)-3-(3-fluoro-4-(5-(1-phenylcyclopropyl)-thiazolo[5,4-b]pyridine-2-yl)

benzyl)cyclobutanecarboxylic acid as a white solid. MS (ESI) m/z: calculated: 458.2; Observed: 459.1 ($M^+$+1).

Example 32

Synthesis of (trans)-3-(3-fluoro-4-(5-(1-phenylcyclopropyl)thiazolo[5,4-b]pyridine-2-yl)benzyl)cyclobutanecarboxylic acid

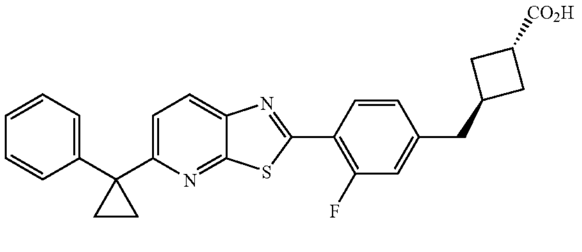

3-((3-Fluoro-4-(5-(1-phenylcyclopropyl)thiazolo[5,4-b]pyridine-2-yl)phenyl)methyl)-cyclobutane-1,1-dicarboxylic acid (0.360 g, 0.716 mmol) was treated with 4 mL DMSO, fitted with a water cooled reflux condenser, and heated to 160° C. After 4 h, the reaction mixture was cooled to rt. The reaction mixture was partitioned between water and EtOAc. The organic layer was washed with water once, satd NaCl once and the organics were dried over anhydrous sodium sulfate, filtered, and concentrated in vacuo to give a light yellow solid, as an approximately 2:1 mixture of isomers. Separation by SFC (Gradient with Chiralpak IC (21×250 mm, 5 micron), pure methanol with $CO_2$ 70 mL/min) gave (trans)-3-(3-fluoro-4-(5-(1-phenylcyclopropyl)-thiazolo[5,4-b]pyridine-2-yl)benzyl)cyclobutanecarboxylic acid as a white solid. MS (ESI) m/z: calculated: 458.2; Observed: 459.1 ($M^+$+1).

Example 33

Synthesis of (R)-2,2,2-trifluoro-1-(3-fluoro-4-(5-(1-phenylcyclopropyl)-thiazolo[5,4-b]pyridine-2-yl)phenyl)ethanol and (S)-2,2,2-trifluoro-1-(3-fluoro-4-(5-(1-phenylcyclopropyl)thiazolo[5,4-b]pyridine-2-yl)phenyl)ethanol

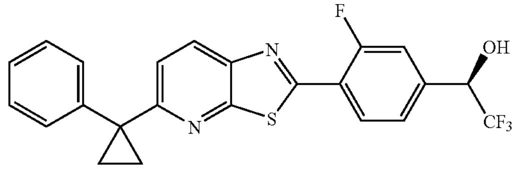

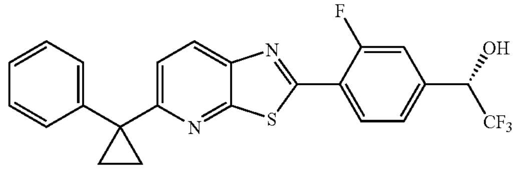

To a mixture of 3-fluoro-4-(5-(1-phenylcyclopropyl)thiazolo[5,4-b]pyridine-2-yl)benzaldehyde (2.00 g, 5.34 mmol) and trimethyl(trifluoromethyl)silane (0.911 g, 6.41 mmol) in 20 mL THF under nitrogen at 0° C. was added TBAF 1.0 M in THF (0.534 mL, 0.534 mmol). The reaction mixture became immediately dark brown and homogeneous. The water bath was removed and the reaction mixture was allowed to stir for 3 h. 1N aq. HCl (20 mL) was added and the reaction mixture allowed to stir overnight. The reaction mixture was partitioned between water and DCM. The aqueous layer was extracted with DCM, and the combined organics were dried over anhydrous sodium sulfate, filtered, and concentrated in vacuo. The material was treated with DCM and passed through a Redi-Sep® pre-packed silica gel column (40 g) using 0-20% EtOAc/hexane. The product-containing fractions were concentrated to afford racemic 2,2,2-trifluoro-1-(3-fluoro-4-(5-(1-phenylcyclopropyl)thiazolo[5,4-b]pyridine-2-yl)phenyl)ethanol as a pale yellow foam. The racemic mixture were separated by Multigram II SFC (Column: Chiralpak ADH (21×250 mm, 5 um); A=supercritical $CO_2$; B=Isopropanol; 30% B, 65 mL/min total flow, 40° C., 100 bar outlet pressure) to give (R)-2,2,2-trifluoro-1-(3-fluoro-4-(5-(1-phenylcyclopropyl)thiazolo[5,4-b]pyridine-2-yl)phenyl)ethanol and (S)-2,2,2-trifluoro-1-(3-fluoro-4-(5-(1-phenylcyclopropyl)-thiazolo[5,4-b]pyridine-2-yl)phenyl)ethanol. MS (ESI) m/z: calculated: 444.1; Observed: 445.1 ($M^+$+1).

Example 34

Synthesis of 2(rac)-2,2,2-trifluoro-1-(3-fluoro-4-(5-(1-phenylcyclopropyl)thiazolo[5,4-b]pyridine-2-yl)phenyl)ethanamine trifluoroacetic acid salt

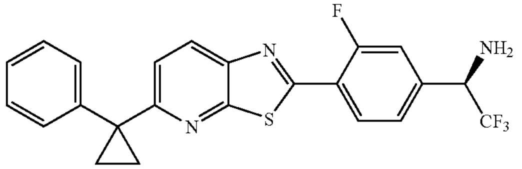

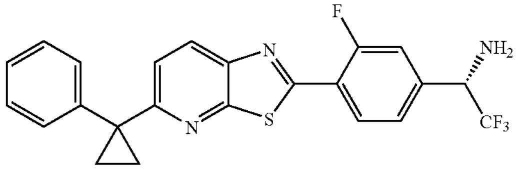

Step 1

To a solution of 2,2,2-trifluoro-1-(3-fluoro-4-(5-(1-phenylcyclopropyl)thiazolo-[5,4-b]pyridine-2-yl)phenyl)ethanol (1.15 g, 2.6 mmol) in 25 mL DCM under nitrogen was added Dess-Martin Periodinane (2.0 g, 4.7 mmol) in one portion. The reaction mixture was allowed to stir for 3 h. The reaction mixture was quenched with sat'd aq. Sodium thiosulfate (2 mL) and 25 mL sat'd aq. Sodium bicarbonate and allowed to stir rapidly for 30 min. The organic layer was separated and the aq. Layer was extracted with DCM, combined organics were dried over sodium sulfate, filtered, and concentrated in vacuo to give a yellow foam. The material was treated with DCM and passed through a Redi-Sep® pre-packed silica gel column (40 g) using 0-60% EtOAc/hexane. The product-containing fractions were concentrated to afford 2,2,2-trifluoro-1-(3-fluoro-4-(5-(1-phenylcyclopropyl)-thiazolo[5,4-b]pyridine-2-yl)phenyl)ethanone as a yellowish foam. The foam was treated with hexanes and concentrated in vacuo a few times to give a nice light yellow solid. MS (ESI) m/z: calculated: 442.1; Observed: 461.0 ($M^+$+$H_2O$+1).

Step 2

To a slurry of 2,2,2-trifluoro-1-(3-fluoro-4-(5-(1-phenylcyclopropyl)thiazolo-[5,4-b]pyridine-2-yl)phenyl)ethanone (0.300 g, 0.68 mmol) in 2.2 mL toluene under nitrogen was added slowly dropwise lithium bis(trimethylsilyl)amide, 1.0 m solution in tetrahydrofuran (0.75 mL, 0.75 mmol) over 2-3 min. The reaction mixture became clear and yellow. After 15 min, borane-methyl sulfide complex, 2.0 M sol in THF (0.68 mL, 1.4 mmol) was added dropwise. The reaction mixture became dark red, and was allowed to stir 40 min. The reaction mixture was cooled to 0° C. and 1 mL 2 N NaOH was added very cautiously dropwise via syringe (gas evolution). The resulting yellow mixture was allowed to stir overnight, and then the reaction mixture was partitioned between water and EA. The organic layer was washed with sat'd aq. Sodium bicarbonate, 1× brine, dried over sodium sulfate, filtered, and purified in vacuo to give a yellow oil. The material was treated with DCM and passed through a Redi-Sep® pre-packed silica gel column (40 g) using 0-100% EtOAc/hexane. Product-containing fractions were combined and concentrated in vacuo, and the resulting material was purified by RPHPLC, 10-100% TFA/ACN in TFA/$H_2O$. The purified fractions were combined and concentrated in vacuo to give racemic 2,2,2-trifluoro-1-(3-fluoro-4-(5-(1-phenylcyclopropyl)thiazolo[5,4-b]pyridine-2-yl)phenyl-)ethanamine trifluoroacetic acid salt as a white solid. MS (ESI) m/z: calculated: 443.1; Observed: 444.1 ($M^+$+1).

Example 35

Synthesis of 1-(3-fluoro-4-(5-(1-phenylcyclopropyl)thiazolo[5,4-b]pyridin-2-yl)benzyl)-azetidin-3-ol

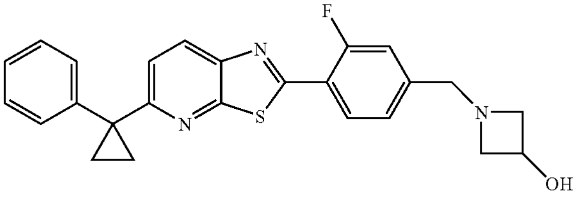

Synthesized from 3-fluoro-4-(5-(1-phenylcyclopropyl)thiazolo[5,4-b]pyridine-2-yl)benzaldehyde (0.500 g, 1.34 mmol) and 3-hydroxyazetidine hydrochloride (0.293 g, 2.67 mmol) according to the general procedure for reductive amination to afford 1-((3-fluoro-4-(5-(1-phenylcyclopropyl)thiazolo[5,4-b]pyridine-2-yl)phenyl)methyl)azetidin-3-ol as a pale yellow solid. MS (ESI) m/z: Calculated: 431.2; Observed: 432.1 ($M^+$+1).

Example 36

Synthesis of 2-(4-((3,3-difluoroazetidin-1-yl)methyl)-2-fluorophenyl)-5-(1-phenylcyclopropyl)-thiazolo[5,4-b]pyridine

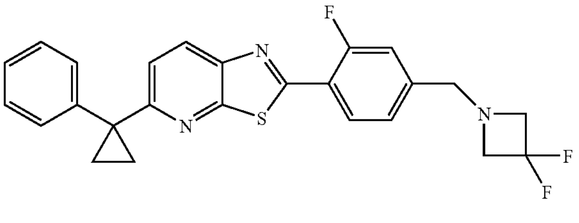

Synthesized from 3-fluoro-4-(5-(1-phenylcyclopropyl)thiazolo[5,4-b]pyridine-2-yl)benzaldehyde (0.200 g, 0.534 mmol) and 3,3-difluoroazetidine hydrochloride (0.138 g, 1.07 mmol) according to the general procedure for reductive amination to afford 2-(4-((3,3-difluoroazetidin-1-yl)methyl)-2-fluorophenyl)-5-(1-phenylcyclopropyl)thiazol-[5,4-b]pyridine as a pale yellow solid. MS (ESI) m/z: Calculated: 451.1; Observed: 452.1 ($M^+$+1).

Example 37

Synthesis of (R)-1-(1-(3-fluoro-4-(5-(1-phenylcyclopropyl)thiazolo[5,4-b]pyridin-2-yl)phenyl)propyl)azetidine-3-carboxylic acid hydrochloride and (S)-1-(1-(3-fluoro-4-(5-(1-phenylcyclopropyl)thiazolo[5,4-b]pyridin-2-yl)phenyl)propyl)azetidine-3-carboxylic acid hydrochloride

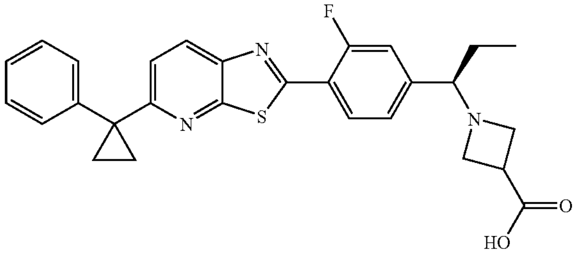

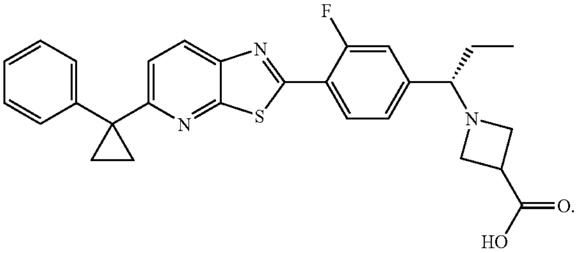

Step 1

To a mixture of 3-fluoro-4-(5-(1-phenylcyclopropyl)thiazolo[5,4-b]pyridin-2-yl)benzaldehyde (1.00 g, 2.7 mmol) in tetrahydrofuran (20 ml) at 0° C. was added ethylmagnesium bromide soln in t-butylmethyl ether. (4.0 ml, 4.0 mmol) dropwise over 5 min. The reaction was allowed to stir 20 min at 0° C. The reaction was quenched with $NH_4Cl$ aq. sat soln. The solid was removed by filtration. The filtrate was concentrated and purified by silica gel chromatography: ISCO, 120 g column, 20-30% EtOAc/Hex, followed by 40% (3% EtN3 in EtOAc)/Hex to give 1-(3-fluoro-4-(5-(1-phenylcyclopropyl)thiazolo[5,4-b]pyridin-2-yl)phenyl)propan-1-ol. MS (ESI) m/z: Calculated: 404.1; Observed: 405.1 ($M^+$+H).

Step 2

Dess-Martin periodinane (0.524 g, 1.24 mmol) was added to a solution of 1-(3-fluoro-4-(5-(1-phenylcyclopropyl)thiazolo[5,4-b]pyridin-2-yl)phenyl)propan-1-ol (0.500 g, 1.24 mmol) in dichloromethane (25.00 ml, 1.24 mmol), and the reaction was stirred at ambient temperature for 60 min. Saturated aq. NaHCO3 was added and the reaction stirred for 5 min. The organic layer was dried, filtered, and concentrated in vacuo and the residue purified by silica gel chromatography: ISCO 120 g column, 20-30% (3% Et3N in EtOAc)/Hex to give 1-(3-fluoro-4-(5-(1-phenylcyclopropyl)thiazolo[5,4-b]pyridin-2-yl)phenyl)propan-1-one. MS (ESI) m/z: Calculated: 402.1; Observed: 403.0 ($M^+$+H).

Step 3

Reaction of 1-(3-fluoro-4-(5-(1-phenylcyclopropyl)thiazolo[5,4-b]pyridin-2-yl)phenyl)propan-1-one (0.200 g, 0.497 mmol) and methyl azetidine-3-carboxylate hydrochloride (0.113 g, 0.745 mmol), according to reference R and the general procedure for reductive amination gave racemic methyl 1-(1-(3-fluoro-4-(5-(1-phenylcyclopropyl)thiazolo[5,4-b]pyridin-2-yl)phenyl)propyl)azetidine-3-carboxylate. Separation of enantiomers was accomplished by SFC chromatography (Column: Chiralpak AD-H (21×250 mm, 5 um); A: Liquid $CO_2$; B: Isopropanol (0.2% DEA); Isocratic: 79:21 (A:B); Flow Rate: 70 mL/min; Outlet Pressure: 100 bar) to give (R)-methyl 1-(1-(3-fluoro-4-(5-(1-phenylcyclopropyl)thiazolo[5,4-b]pyridin-2-yl)phenyl)propyl)azetidine-3-carboxylate and (S)-methyl 1-(1-(3-fluoro-4-(5-(1-phenylcyclopropyl)thiazolo[5,4-b]pyridin-2-yl)phenyl)propyl)azetidine-3-carboxylate. MS (ESI) m/z: Calculated: 501.2; Observed: 502.1 ($M^+$+1).

Step 4

Separately, (give (R)-methyl 1-(1-(3-fluoro-4-(5-(1-phenylcyclopropyl)thiazolo[5,4-b]pyridin-2-yl)phenyl)propyl)azetidine-3-carboxylate and (S)-methyl 1-(1-(3-fluoro-4-(5-(1-phenylcyclopropyl)thiazolo[5,4-b]pyridin-2-yl)phenyl)propyl)azetidine-3-carboxylate were processed according to Reference R and the general procedure for ester hydrolysis to afford (R)-1-(1-(3-fluoro-4-(5-(1-phenylcyclopropyl)thiazolo[5,4-b]pyridin-2-yl)phenyl)propyl)azetidine-3-carboxylic acid hydrochloride and (S)-1-(1-(3-fluoro-4-(5-(1-phenylcyclopropyl)thiazolo[5,4-b]pyridin-2-yl)phenyl)propyl)azetidine-3-carboxylic acid hydrochloride. MS (ESI) m/z: Calculated: 487.2; Observed: 488.1 ($M^+$+1).

Example 38

Synthesis of 1-(3-fluoro-4-(5-(1-(2-fluorophenyl)cyclopropyl)thiazolo[5,4-b]pyridine-2-yl)-benzyl)azetidine-3-carboxylic acid

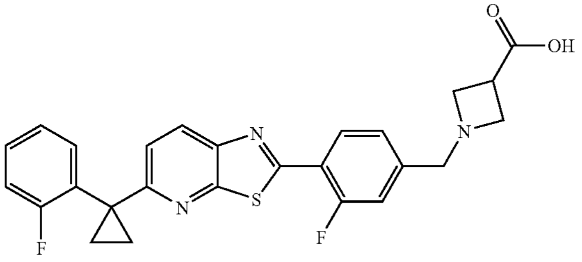

Step 1

To a mixture of 1-(2-fluorophenyl)ethanone (2.00 g, 14.5 mmol) and sodium carbonate (2.46 g, 23.2 mmol) in 30 mL anhyd. DCM was added triflic anhydride (4.89 mL, 29.0 mmol) in 15 mL DCM slowly, dropwise. Upon complete addition the reaction mixture was light yellow. The reaction mixture was allowed to stir over the weekend, at which point it became dark brown. The reaction mixture was filtered through a frit, rinsing with DCM and the filtrate was washed with sat'd aq. NaHCO3, water, dried over sodium sulfate, filtered, and concentrated in vacuo. The residue was purified by silica gel chromatography, 0-10% EA/hexanes. The product-containing fractions were concentrated in vacuo to give 1-(2-fluorophenyl)vinyl trifluoromethanesulfonate as a yellow oil. $^1$H NMR (400 MHz, CHLOROFORM-d) δ ppm 7.48-7.56 (m, 1 H), 7.36-7.46 (m, 1 H), 7.22 (dd, J=7.8, 7.8 Hz, 1 H), 7.15 (dd, J=10.8, 8.8 Hz, 1 H), 5.76 (d, J=3.5 Hz, 1 H), 5.59-5.65 (m, 1 H).

Step 2

A sealable tube was charged with Cu(I) iodide (7.32 mg, 0.0384 mmol), cesium fluoride (0.117 g, 0.769 mmol), 1-(2-fluorophenyl)vinyl trifluoromethane-sulfonate (0.208 g, 0.769 mmol), tetrakis(triphenylphosphine) palladium (0) (0.0222 g, 0.0192 mmol), methyl 1-((3-fluoro-4-(5-(trimethylstannyl)-thiazolo[5,4-b]pyridine-2-yl)phenyl)methyl)azetidine-3-carboxylate (0.200 g, 0.384 mmol), flushed with argon, diluted with 0.8 mL DMF, sealed, and heated to 45° C. overnight. The reaction mixture was partitioned between EA, water, saturated sodium bicarbonate. The organic layer was washed with water, brine, dried over sodium sulfate, filtered, and concentrated in vacuo. Purification by silica gel chromatography, 12 g, 0-100% EA/hexanes provided methyl 1-((3-fluoro-4-(5-(1-(2-fluorophenyl)vinyl)thiazolo[5,4-b]pyridine-2-yl)phenyl)methyl)azetidine-3-carboxylate as an oil which slowly solidified to a tan solid. MS (ESI) m/z: calculated: 477.1; Observed: 478.1 ($M^+$+1).

Step 3

To a solution of potassium tert-butoxide (0.063 g, 0.56 mmol) and trimethylsulfoxonium iodide (0.12 g, 0.52 mmol) in 2 mL DMSO under nitrogen was added dropwise a solution of methyl 1-((3-fluoro-4-(5-(1-(2-fluorophenyl)vinyl-thiazolo[5,4-b]pyridine-2-yl)phenyl)methyl)azetidine-3-carboxylate (0.192 g, 0.40 mmol) in 2 mL THF. The reaction mixture became deep blue and then very dark. After 1 h, the reaction mixture was quenched with sat'd aq. $NH_4Cl$ and EtOAc. A thick emulsion formed, which was treated with sat'd aq. $NaHCO_3$ until basic, and diluted with copious amounts of EA and water. The aq. Layer was washed with water, brine, dried over sodium sulfate, filtered, and concentrated in vacuo. The material was treated with DCM and passed through a Redi-Sep® pre-packed silica gel column (40 g) using 0-100% EtOAc/hexane. The product-containing fractions were concentrated to afford methyl 1-((3-fluoro-4-(5-(1-(2-fluorophenyl)cyclopropyl)thiazolo[5,4-b]pyridine-2-yl)phenyl)-methyl)azetidine-3-carboxylate as a off-white solid. MS (ESI) m/z: calculated: 491.2; Observed: 492.1 ($M^+$+1).

Step 4

Synthesized from methyl 1-((3-fluoro-4-(5-(1-(2-fluorophenyl)cyclopropyl)-thiazolo[5,4-b]pyridine-2-yl)phenyl)methyl)azetidine-3-carboxylate (0.074 g, 0.15 mmol) according to the general procedure for ester hydrolysis to give 1-((3-fluoro-4-(5-(1-(2-fluorophenyl)-cyclopropyl)thiazolo[5,4-b]pyridine-2-yl)phenyl)methyl)azetidine-3-carboxylic acid as a white solid. MS (ESI) m/z: calculated: 477.1; Observed: 478.1 ($M^+$+1).

Example 39

Synthesis of 1-(3-fluoro-4-(5-(1-(4-hydroxyphenyl)cyclopropyl)thiazolo[5,4-b]pyridine-2-yl)benzyl)azetidine-3-carboxylic acid

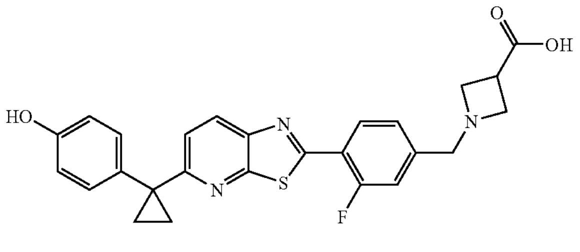

Step 1

To a solution of diisopropylamine (1.4 mL, 10 mmol) in 20 mL THF at 0° C. was added butyllithium (4.0 mL, 10 mmol).

After 10 min, tributylstannane (2.4 mL, 9.2 mmol) was added. After 10 min, the reaction mixture was cooled to −78° C. and a solution of 1-(4-(benzyloxy)-phenyl)ethanone (2.05 g, 9.1 mmol) in 10 mL THF was added slowly by syringe in portions over 10 min. After 10 min, triethylamine (9.4 mL, 68 mmol) and methanesulfonyl chloride (2.8 mL, 36 mmol) was added and the bath allowed to expire overnight. The reaction mixture was treated with 50 mL hexanes and filtered, rinsing with hexanes. The filtrate was extracted with ACN, and the hexanes layer was dried over sodium sulfate, filtered, and concentrated. The resulting oil was purified by reverse-phase MPLC with a C-18 derivitized column, loading with 1:1 DCM/ACN and eluting with 0-50% DCM/ACN. The resulting light yellow oil, containing (1-(4-(benzyloxy)phenyl)vinyl)-tributylstannane was used without further purification.

Step 2

A slurry of cesium fluoride (0.325 g, 2.14 mmol), CuI 0.0271 g, 0.143 mmol), tetrakis(triphenylphosphine) palladium (0) (0.0824 g, 0.0713 mmol), 2-(4-(1,3-dioxan-2-yl)-2-fluorophenyl)-5-chlorothiazolo[5,4-b]pyridine (0.500 g, 1.43 mmol), and crude (1-(4-(benzyloxy)-phenyl)vinyl)tributylstannane (1.07 g, 2.14 mmol) in 5 mL DMF was flushed with argon, sealed, and heated to 55° C. overnight. The reaction mixture was diluted with EA, filtered through celite, rinsing with EA. The filtrate was washed with water, brine, dried over sodium sulfate, filtered, and concentrated. The residue was adsorbed onto 4 g silica gel from DCM, concentrated, and purified by ISCO 40 g, 0-100% EA/hexanes to give 2-(4-(1,3-dioxan-2-yl)-2-fluorophenyl)-5-(1-(4-(benzyloxy)phenyl)vinyl)thiazolo[5,4-b]pyridine as an orange solid. MS (ESI) m/z: calculated: 524.2; Observed: 525.1 ($M^+$+1).

Step 3

A solution of potassium tert-butoxide (0.206 g, 1.83 mmol) and trimethylsulfoxonium iodide (0.404 g, 1.83 mmol) in 5 mL DMSO under nitrogen was added 2-(4-(1,3-dioxan-2-yl)-2-fluorophenyl)-5-(1-(4-(benzyloxy)phenyl)vinyl)-thiazolo[5,4-b]pyridine (0.385 g, 0.734 mmol) as a solution in 6 mL THF (min volume to dissolve) slowly dropwise via addition funnel over 1 h. The cloudy reaction mixture was allowed to stir for 4 h and was quenched with ice. The reaction mixture was partitioned between water and EtOAc. The organic layer was washed with water, brine, dried, and concentrated in vacuo to give an oil/solid which was purified by silica gel chromatography 0-100% EA/hexanes to give 2-(4-(1,3-dioxan-2-yl)-2-fluorophenyl)-5-(1-(4-(benzyloxy)phenyl)cyclopropyl)thiazolo[5,4-b]pyridine as a yellow solid. The aqueous suspension from the extraction was further extracted with DCM, the combined org extracts were dried over sodium sulfate, filtered, and concentrated in vacuo to give additional 2-(4-(1,3-dioxan-2-yl)-2-fluorophenyl)-5-(1-(4-(benzyloxy)phenyl)-cyclopropyl)thiazolo[5,4-b]pyridine. MS (ESI) m/z: calculated: 538.2; Observed: 539.1 ($M^+$+1).

Step 4

A suspension of 2-(4-(1,3-dioxan-2-yl)-2-fluorophenyl)-5-(1-(4-(benzyloxy)-phenyl)cyclopropyl)thiazolo[5,4-b]pyridine (0.305 g, 0.566 mmol) in 5 mL THF and 5 mL 5N aq. HCl was heated in a sealed vial to 65° C. for 1 h. The reaction mixture was cooled, poured onto ice, quenched with 10 N NaOH, sonicated in 5 mL MTBE, filtered, and rinsed with 1 mL MTBE. The solid was collected to give 4-(5-(1-(4-(benzyloxy)-phenyl)cyclopropyl)thiazolo[5,4-b]pyridine-2-yl)-3-fluorobenzaldehyde as an orange solid. MS (ESI) m/z: calculated: 480.1; Observed: 481.1 ($M^+$+1).

Step 5

Synthesized from 4-(5-(1-(4-(benzyloxy)phenyl)cyclopropyl)thiazolo[5,4-b]pyridine-2-yl)-3-fluorobenzaldehyde (0.224 g, 0.466 mmol) and methyl azetidine-3-carboxylate hydrochloride (0.177 g, 1.17 mmol) according to the general procedure for reductive amination to give methyl 1-(4-(5-(1-(4-(benzyloxy)phenyl)cyclopropyl)-thiazolo[5,4-b]pyridine-2-yl)-3-fluorobenzyl)azetidine-3-carboxylate as a yellow solid. MS (ESI) m/z: calculated: 579.2; Observed: 580.1 ($M^+$+1).

Step 6

A slurry of palladium 10% on carbon, 50% water (0.26 g), methyl 1-(4-(5-(1-(4-(benzyloxy)phenyl)cyclopropyl)thiazolo[5,4-b]pyridine-2-yl)-3-fluorobenzyl)azetidine-3-carboxylate (0.144 g, 0.25 mmol), triethylamine (0.087 mL, 0.62 mmol) in 4 mL of 3:1 THF/MeOH was stirred rapidly under an atmosphere of hydrogen (balloon) for 36 h. The reaction mixture was diluted with DCM, and filtered through celite and concentrated in vacuo. The resulting solid was adsorbed onto 1.4 g silica gel and purified by silica gel chromatography 0-100% EA/hexanes, to give methyl 1-((3-fluoro-4-(5-(1-(4-hydroxyphenyl)cyclopropyl)thiazolo[5,4-b]pyridine-2-yl)phenyl)methyl)-azetidine-3-carboxylate as a white solid. MS (ESI) m/z: calculated: 489.2; Observed: 490.1 ($M^+$+1).

Step 7

Synthesized from methyl 1-((3-fluoro-4-(5-(1-(4-hydroxyphenyl)cyclopropyl)-thiazolo[5,4-b]pyridine-2-yl)phenyl)methyl)azetidine-3-carboxylate (0.043 g, 0.088 mmol) according to the general method for ester hydrolysis to give 1-((3-fluoro-4-(5-(1-(4-hydroxyphenyl)cyclopropyl)thiazolo[5,4-b]pyridine-2-yl)phenyl)methyl)azetidine-3-carboxylic acid as a white solid. MS (ESI) m/z: calculated: 475.1; Observed: 476.1 ($M^+$+1).

Example 40

Synthesis of 1-(3-fluoro-4-(5-(1-(4-fluorophenyl)cyclopropyl)thiazolo[5,4-b]pyridine-2-yl)benzyl)azetidine-3-carboxylic acid

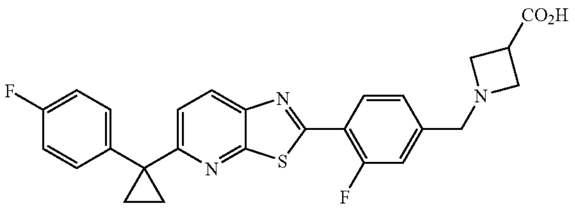

Step 1

To a solution of diisopropylamine (1.39 mL, 10.1 mmol) in 20 mL THF at 0° C. was added butyllithium (4.02 mL, 10.0 mmol). After 10 min, tributylstannane (2.45 mL, 9.23 mmol) was added. After 10 min, the reaction mixture was cooled to −78° C. and a solution of 1-(4-fluorophenyl)ethanone (1.09 mL, 9.05 mmol) in 10 mL THF was added slowly by syringe in portions over 10 min. After 10 min, triethylamine (9.43 mL, 67.9 mmol) and methanesulfonyl chloride (2.80 mL, 36.2 mmol) was added and the bath allowed to expire overnight. The reaction mixture was treated with 50 mL hexanes and filtered, rinsing with hexanes. The filtrate was extracted with ACN, and the hexanes layer was dried over sodium sulfate, filtered, and concentrated. Purification with C-18 silica gel, eluting with DCM/ACN, gave tributyl(1-(4-fluorophenyl)vinyl)stannane as an oil.

Step 2

A slurry of cesium fluoride (0.310 g, 2.04 mmol), copper(I) iodide (0.0194 g, 0.102 mmol), tetrakis(triphenylphosphine) palladium (0) (0.0590 g, 0.0510 mmol), methyl 1-((4-(5-chlorothiazolo[5,4-b]pyridine-2-yl)-3-fluorophenyl)methyl) azetidine-3-carboxylate (0.400 g, 1.02 mmol), tributyl(1-(4-fluorophenyl)-vinyl)stannane (0.504 g, 1.22 mmol) in 2 mL DMF was sealed and heated to 45° C. overnight. The reaction mixture became purple/black and was allowed to stir at ambient temperature for 24 h. The reaction mixture was diluted with EtOAc and filtered through celite, then the filtrate was washed with water. The water layer was removed, and the EA layer was treated with DCM until only slightly cloudy, the organics were dried over magnesium sulfate, filtered, and concentrated in vacuo. The resulting material was purified by silica gel chromatography, 0-100% EA/hexanes to give methyl 1-((3-fluoro-4-(5-(1-(4-fluorophenyl)vinyl)thiazolo[5,4-b]pyridine-2-yl)phenyl)methyl)azetidine-3-carboxylate as an orange solid. MS (ESI) m/z: calculated: 477.1; Observed: 478.1 ($M^{+}$+1).

Step 3

To a solution of potassium tert-butoxide (0.080 g, 0.71 mmol) and trimethylsulfoxonium iodide (0.16 g, 0.71 mmol) in 2 mL DMSO was added slowly dropwise a solution of methyl 1-((3-fluoro-4-(5-(1-(4-fluorophenyl)vinyl)thiazolo[5,4-b]pyridine-2-yl)phenyl)methyl)azetidine-3-carboxylate (0.170 g, 0.36 mmol) in 2 mL THF, with 1 mL rinse. The solution became colored. After 30 min, the reaction mixture was quenched with sat'd aq. $NH_4Cl$ and EtOAc. The organic layer was washed with water, then brine, dried over sodium sulfate, filtered, and concentrated in vacuo. The material was treated with DCM and adsorbed onto 1.5 g silica gel and passed through a Redi-Sep® pre-packed silica gel column (12 g) using 0-100% EtOAc/hexane. The product-containing fractions were concentrated to afford methyl 1-((3-fluoro-4-(5-(1-(4-fluorophenyl)-cyclopropyl)thiazolo[5,4-b]pyridine-2-yl)phenyl)methyl)azetidine-3-carboxylate as a yellow solid. MS (ESI) m/z: calculated: 491.2; Observed: 492.1 ($M^{+}$+1).

Step 4

Synthesized from methyl 1-((3-fluoro-4-(5-(1-(4-fluorophenyl)cyclopropyl)-thiazolo[5,4-b]pyridine-2-yl)phenyl) methyl)azetidine-3-carboxylate (0.064 g, 0.13 mmol) according to the general method for ester hydrolysis to give 1-((3-fluoro-4-(5-(1-(4-fluorophenyl)cyclopropyl)-thiazolo[5,4-b]pyridine-2-yl)phenyl)methyl)azetidine-3-carboxylic acid as a yellow solid. MS (ESI) m/z: calculated: 477.1; Observed: 478.1 ($M^{+}$+1).

Example 41

Synthesis of 1-(3-fluoro-4-(5-(1-phenylcyclobutyl)thiazolo[5,4-b]pyridine-2-yl)benzyl)azetidine-3-carboxylic acid

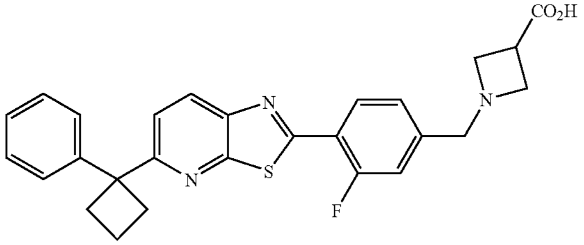

Step 1

A solution of N,Ndimethylacetamide (0.320 mL, 3.46 mmol) in 30 mL anhyd. 1,2-DCE in a 3-neck flask under argon fitted with addition funnel was cooled to −17° C. with ice/salt. Trifluoromethanesulfonic anhydride (0.679 mL, 4.04 mmol) was added over 2 min by syringe, and the reaction mixture became yellow and the temperature rose to −13° C. After 5 min, a solution of 2,6-di-tert-butylpyridine (0.893 mL, 4.04 mmol) and 2-(2-fluoro-4-methylphenyl)-5-(1-phenylvinyl)thiazolo[5,4-b]pyridine (1.00 g, 2.89 mmol) in 15 mL DCE was added slowly dropwise via addition funnel over 10 min. The reaction was fitted with a water-cooled reflux condenser and placed in a 110° C. oil bath. After 1 h, the reaction mixture was allowed to cool to ambient temperature overnight. 45 mL water was added and the reaction mixture reheated to 110° C. After 7 h, the reaction mixture was cooled, layers separated, and the aqueous layer was extracted with DCM. The combined organics were dried over sodium sulfate, filtered, and concentrated. The crude material was adsorbed onto 5 g silica gel and purify by silica gel chromatography, 0-100% EA/hexanes to give a yellow solid containing the desired product. This was further purified by trituration with diethyl ether to give 3-(2-(2-fluoro-4-methylphenyl)-thiazolo[5,4-b]pyridine-5-yl)-3-phenylcyclobutanone as a light yellow solid. MS (ESI) m/z: calculated: 388.1; Observed: 389.1 ($M^{+}$+1).

Step 2

To a thick slurry of p-methylbenzenesulfonylhydrazine (0.036 g, 0.19 mmol) and 3-(2-(2-fluoro-4-methylphenyl) thiazolo[5,4-b]pyridine-5-yl)-3-phenylcyclobutanone (0.050 g, 0.13 mmol) in 0.3 mL MeOH under nitrogen was added a pre-mixed suspension of sodium cyanoborohydride (0.016 g, 0.26 mmol) and zinc chloride, 0.5 M solution in THF (0.26 mL, 0.13 mmol) in 0.26 mL MeOH, via pipette. The reaction mixture was sealed and heated to 70° C. for 3 h. The reaction mixture was adsorbed onto 600 mg silica gel and dried. Purification by silica gel chromatography, 12 g, 0-50% EA/hexanes provided 2-(2-fluoro-4-methylphenyl)-5-(1-phenylcyclobutyl)-thiazolo[5,4-b]pyridine as a light yellow oil that slowly solidified. MS (ESI) m/z: calculated: 374.1; Observed: 375.1 ($M^{+}$+1).

Step 3

A slurry of 2-(2-fluoro-4-methylphenyl)-5-(1-phenylcyclobutyl)thiazolo[5,4-b]pyridine (0.059 g, 0.16 mmol), AIBN (0.013 g, 0.079 mmol), and N-bromosuccinimide (0.034 g, 0.19 mmol) in 1 mL $CCl_4$ in a sealed tube was heated to 100° C. for 30 min. The reaction mixture became clear, then a precipitate formed. Allowed to stir 30 min longer, then cooled and allowed to stand overnight. The solvent was removed and the crude material treated with methyl azetidine-3-carboxylate hydrochloride (0.14 g, 0.95 mmol) and N,N-diisopropylethylamine (0.27 mL, 1.6 mmol), and 1 mL DMF. The solution was sealed and heated to 100° C. for 30 min. The reaction mixture was cooled to 0° C. and quenched with sat'd aq. $NaHCO_3$. The reaction mixture was partitioned between sat'd aq. $NaHCO_3$ and EA, and the organic layer was washed with water, brine, dried over sodium sulfate, filtered, and concentrated in vacuo. The resulting material was dissolved in 2 mL THF and treated with NaOH 1.0 M (0.47 mL, 0.47 mmol). After 1 h, the reaction mixture was concentrated under nitrogen stream, and treated with 2 mL DMSO and TFA until a solution resulted. The solution was filtered and purified by RPHPLC, 10-100% TFA/ACN in TFA/H2O to give 1-(3-fluoro-4-(5-(1-phenylcyclobutyl)thiazolo[5,4-b]pyridine-2- yl)benzyl)azetidine-3-carboxylic acid trifluoroacetic acid salt as an off-white solid. MS (ESI) m/z: calculated: 473.2; Observed: 474.1 ($M^{+}$+1).

Example 42

Synthesis of 2-amino-2-(3-fluoro-4-(5-(1-phenylcyclopropyl)thiazolo[5,4-b]pyridin-2-yl)phenethyl) propane-1,3-diol hydrochloride

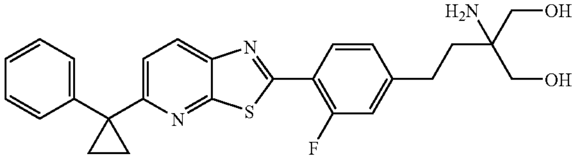

Step 1

A slurry of $CsCO_3$ (0.420 g, 1.29 mmol) and acetamidomalonic acid diethyl ester (0.560 g, 2.58 mmol) in 6 mL DMSO under argon was allowed to stir for 2 h. 2-(2-Fluoro-4-vinylphenyl)-5-(1-phenylcyclopropyl)thiazolo[5,4-b]pyridine (0.400 g, 1.07 mmol) was added as a solid and the reaction mixture sealed and heated to 35° C. for 3 h. The clear, red reaction mixture was quenched with ice and 1N aq. HCl until acidic, and partitioned between water and EA. The organic layer was washed with water, brine, dried over sodium sulfate, filtered, and concentrated in vacuo. The material was treated with DCM and passed through a Redi-Sep® pre-packed silica gel column (40 g) using 0-60% EtOAc/hexane. The product-containing fractions were concentrated to afford diethyl 2-acetamido-2-(2-(3-fluoro-4-(5-(1-phenylcyclopropyl)thiazolo[5,4-b]pyridine-2-yl)phenyl)ethyl)malonate as a white solid. MS (ESI) m/z: calculated: 589.2; Observed: 590.1 ($M^{+}$+1).

Step 2

To solution of $CaCl_2$ (0.188 g, 1.70 mmol) in 1.3 mL water was added a slurry of diethyl 2-acetamido-2-(2-(3-fluoro-4-(5-(1-phenylcyclopropyl)thiazolo[5,4-b]pyridine-2-yl)phenyl)ethyl)malonate (0.400 g, 0.678 mmol) in about 15 mL EtOH total. To this slurry was added $NaBH_4$ (0.128 g, 3.39 mmol). The mixture bubbled and became warm, and was cooled briefly with an ice bath, then allowed to stir at ambient temperature overnight. 10 mL THF was added, followed by additional $NaBH_4$ (0.128 g, 3.39 mmol). After 5 h, the reaction mixture was concentrated in vacuo, partitioned between DCM and 1N aq. HCl, and extracted with DCM. The combined organics were dried over sodium sulfate, filtered, and concentrated in vacuo. The material was treated with 10% MeOH in DCM and adsorbed onto 2 g silica gel, dried, and passed through a Redi-Sep® pre-packed silica gel column (40 g) using 0-10% MeOH/DCM. The product-containing fractions were concentrated to give N-(4-(3-fluoro-4-(5-(1-phenyl-cyclopropyl)thiazolo[5,4-b]pyridine-2-yl)phenyl)-1-hydroxy-2-(hydroxymethyl)butan-2-yl)acetamide as a white solid. MS (ESI) m/z: calculated: 505.2; Observed: 506.0 ($M^{+}$+1).

Step 3

A slurry of N-(4-(3-fluoro-4-(5-(1-phenylcyclopropyl)thiazolo[5,4-b]pyridine-2-yl)phenyl)-1-hydroxy-2-(hydroxymethyl)butan-2-yl)acetamide (0.205 g, 0.405 mmol) in 6 mL 5N aq. HCl was heated to 120° C. in a sealed tube. A clear yellow solution resulted, with a white precipitate forming after 1 h. The mixture was heated overnight to give a gray mixture, which was cooled and filtered through a glass frit, rinsing with water and EtOH, and the solid was dried in vacuo to give 2-amino-2-(2-(3-fluoro-4-(5-(1-phenylcyclopropyl)thiazolo[5,4-b]pyridine-2-yl)phenyl)ethyl)propane-1,3-diol hydrochloride as an off-white solid. MS (ESI) m/z: calculated: 463.2; Observed: 464.1 ($M^{+}$+1).

Example 43

Synthesis of (rac)-2-amino-4-(3-fluoro-4-(5-(1-phenylcyclopropyl)thiazolo[5,4-b]pyridine-2-yl)phenyl)-2-(hydroxymethyl)butyl dihydrogen phosphate

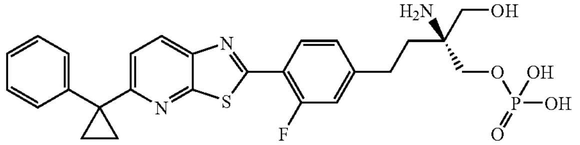

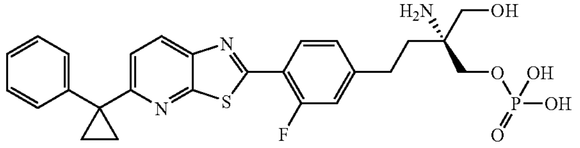

A slurry of 2-amino-2-(2-(3-fluoro-4-(5-(1-phenylcyclopropyl)thiazolo[5,4-b]pyridine-2-yl)phenyl)ethyl)propane-1,3-diol hydrochloride (0.075 g, 0.15 mmol), N,N-diisopropylethylamine (0.065 mL, 0.37 mmol), and 1,1,1-triethoxyethane (0.041 mL, 0.22 mmol) in 0.75 mL DMF was heated in a sealed tube for 3 h. The brown solution was cooled and partitioned between EA/water, and the organic layer was washed with 1N aq. HCl, sat'd aq. $NaHCO_3$, brine, and dried over sodium sulfate, filtered, and concentrated in vacuo. The HCl layer was neutralized with 1N aq NaOH and extracted with DCM, and the combined organics were dried, and concentrated in vacuo to give additional material, which was combined with the EA extract to give a brown oil. Purification by silica gel chromatography, 12 g, 0-10% MeOH/DCM provided an impure mixture. This was treated with 1.2 mL DCM and 1H-tetrazole 3 wt % solution in ACN (0.82 mL, 0.28 mmol) at 0° C. under nitrogen was added di-tert-butyl diisopropylphosphoramidite (0.087 mL, 0.28 mmol). The reaction mixture was allowed to warm to ambient temperature. After 1 h, the reaction mixture was cooled to 0° C. and treated with m-CPBA (77% by weight) (0.083 g, 0.37 mmol). The reaction mixture became immediately clear. After 30 min the reaction mixture was quenched with sat'd aq. $NaHCO_3$ and EA. The organic layer was washed with brine, dried over sodium sulfate, filtered, and concentrated in vacuo to a yellow oil. The oil was taken up in 2 mL EtOH and 0.5 mL conc HCl was added with rapid stirring at ambient temperature. The reaction was sealed and heated to 80° C. for 20 min and then cooled to ambient temperature. The solvent was removed and the resulting solid was taken up in MeOH and purified by HPLC, 5-100% ACN/TFA in H2O/TFA; The product-containing fractions were combined and concentrated in vacuo to give a white solid, which was sonicated briefly in MeOH, filtered, rinsing with MeOH followed by DCM. The resulting white solid was dried in vacuo to give (rac)-2-amino-4-(3-fluoro-4-(5-(1-phenylcyclopropyl)thiazolo[5,4-b]pyridine- 2-yl)phenyl)-2-(hydroxymethyl)butyl dihydrogen phosphate MS (ESI) m/z: calculated: 543.1; Observed: 544.0 ($M^{+}$+1).

Example 44

Synthesis of 1-(3-fluoro-4-(5-(1-phenylcyclopropyl) thiazolo[4,5-b]pyridin-2-yl)-benzyl)azetidine-3-carboxylic acid trifluoroacetic acid salt

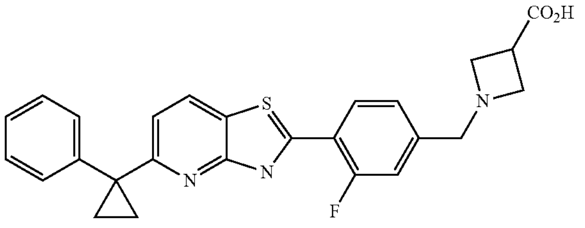

Step 1

To 6-chloropyridin-2-amine (20.0 g, 156 mmol) and triethylamine (23.7 mL, 171 mmol) in 100 mL toluene at 50° C. was added pivaloyl chloride (19.6 mL, 163 mmol) dropwise via syringe. The reaction mixture was allowed to stir, and eventually became a solid mass. 50 mL toluene was added. The reaction mixture was heated overnight, and cooled to ambient temperature. The reaction mixture was quenched with 400 mL 2N aq. HCl, and diluted with 300 mL EtOAc. The organic layer was washed with water, brine, dried over sodium sulfate, filtered, and concentrated to a solid. The solid was dissolved in a min. volume of hot MTBE (50° C.), and approx. 300 mL hexanes was added with swirling. On standing, crystals form, which were collected by filtration, rinsing with hexanes to give a total of N-(6-chloropyridin-2-yl)pivalamide. MS (ESI) m/z: calculated: 212.1; Observed: 213.2 ($M^{+}$+1).

Step 2

To a solution of N-(6-chloropyridin-2-yl)pivalamide (2.00 g, 9.40 mmol) in 25 mL THF at −78° C. was added butyllithium 2.5 M in hexanes (9.40 mL, 23.5 mmol) slowly dropwise over 2 min After 5 min, the reaction mixture was warmed to 0° C., then back to −10° C. (ice/brine) and to −20° C. (ice/salt). The reaction mixture was allowed to stir at this temp for 1.5 h. The reaction mixture was cooled to −78° C. and a solution of hexachloroethane (3.34 g, 14.1 mmol) in 7.5 mL THF was added dropwise via syringe. The bath was removed and the reaction mixture warmed to ambient temperature. The reaction mixture was partitioned between satd $NH_4Cl$ and $Et_2O$. The organic layer was washed with water once, brine once, and the organics were dried over anhydrous sodium sulfate, filtered, and concentrated in vacuo. The material was dissolved in DCM and purified by silica gel chromatography, 80 g, 5-50% EA/hexanes. Product-containing fractions were combined and concentrated to give N-(3,6-dichloropyridin-2-yl)pivalamide as a solid. MS (ESI) m/z: calculated: 246.0; Observed: 247.0 ($M^{+}$+1).

Step 3

A slurry of N-(3,6-dichloropyridin-2-yl)pivalamide (1.83 g, 7.41 mmol) in 75 mL 5N aq HCl with water cooled reflux pyridine was heated in a 115° C. bath overnight, to give a clear yellow solution. The reaction mixture was cooled and poured onto ice, and was basified with 10 N NaOH. The resulting white precipitate was extracted with DCM, and the combined organics were dried over anhydrous sodium sulfate, filtered, and concentrated in vauco to give 3,6-dichloropyridin-2-amine as an off-white solid. MS (ESI) m/z: calculated: 162.0; Observed: 163.0 ($M^{+}$+1).

Step 4

A mixture of 3,6-dichloropyridin-2-amine (0.772 g, 4.74 mmol), sodium carbonate (2.01 g, 18.9 mmol), and thiophosgene (0.726 mL, 9.47 mmol) in 6 mL DCM was heated to 55° C. in a sealed tube for 36 h. The reaction was filtered through a frit, rinsing with DCM, and the material was adsorbed onto 6 g silica gel and dried. The material was purified by silica gel chromatography, 40 g, 0-100% EA/hexanes to give 3,6-dichloro-2-isothiocyanatopyridine. $^{1}H$ NMR (400 MHz, DMSO-$d_6$) δ ppm 8.19 (d, J=8.5 Hz, 1 H), 7.59 (d, J=9.5 Hz, 1 H).

Step 5

To a solution of 2-(4-bromo-3-fluorophenyl)-1,3-dioxane (0.900 g, 3.45 mmol) in 10 mL THF at −78° C. was added 1-butyllithium 2.5 M in hexanes (1.52 mL, 3.79 mmol) slowly dropwise. After 30 min, a solution of 2,6-dibromo-3-isothiocyanato-pyridine (2.25 g, 7.66 mmol) in 3 mL THF was added slowly dropwise via syringe. The dark brown reaction mixture was stirred for 15 min and was quenched by sat'd aq. $NH_4Cl$ and warmed to ambient temp. The reaction mixture was partitioned between satd $NH_4Cl$ and DCM. The aqueous layer was extracted with DCM, and the combined organics were dried over anhydrous sodium sulfate, filtered, and concentrated in vacuo. The material was treated with 10 mL DMF and $Na_2CO_3$ (0.731 g, 6.89 mmol) heated to 100° C. overnight in a sealed tube. The reaction mixture was cooled and partitioned between water and DCM. The aqueous layer was extracted with DCM, and the combined organics were washed with water, then dried over anhydrous sodium sulfate, filtered, and concentrated in vacuo. Residual DMF was removed in vacuo, and the material was suspended in MTBE, filtered, rinsed and dried in vacuo to give 2-(4-(1,3-dioxan-2-yl)-2-fluorophenyl)-5-chlorothiazolo[4,5-b]pyridine as a light orange solid. MS (ESI) m/z: calculated: 350.0; Observed: 351.0 ($M^{+}$+1).

Step 6

A slurry of $(amphos)_2PdCl_2$ (0.0333 g, 0.0470 mmol), potassium carbonate (0.442 g, 3.20 mmol), 1-phenylvinylboronic acid (0.306 g, 2.07 mmol), and 2-(4-(1,3-dioxan-2-yl)-2-fluorophenyl)-5-chlorothiazolo[4,5-b]pyridine (0.330 g, 0.941 mmol) in 4.5 mL dioxane and 1 mL water was flushed with argon and sealed, and heated to 80° C. overnight. The reaction mixture was cooled and treated with water and DCM. The aq. Layer was extracted with DCM, and the combined organics were dried over sodium sulfate, filtered, and concentrated in vacuo. The residue was suspended in 2 mL MTBE and filtered, rinsing with 1 mL MTBE, to give 2-(4-(1,3-dioxan-2-yl)-2-fluorophenyl)-5-(1-phenylvinyl)thiazolo[4,5-b]pyridine as a gray solid. MS (ESI) m/z: calculated: 418.1; Observed: 419.0 ($M^{+}$+1).

Step 7

Trimethylsulfoxonium iodide (0.16 g, 0.72 mmol) and potassium tert-butoxide (0.080 g, 0.72 mmol) were combined in 1.5 mL DMSO to give a clear solution. A slurry of 2-(4-(1,3-dioxan-2-yl)-2-fluorophenyl)-5-(1-phenylvinyl)thiazolo[4,5-b]pyridine (0.200 g, 0.48 mmol) in 4 mL THF was added dropwise, rinsing with 1 mL THF. The reaction mixture was stirred overnight, and was then quenched with sat'd aq. $NH_4Cl$ and EtOAc. The organic layer was washed with water, brine, dried over sodium sulfate, filtered and concentrated in vacuo. The material was treated with DCM and passed through a Redi-Sep® pre-packed silica gel column (12 g) using 0-70% EtOAc/hexane. The product-containing fractions were concentrated to afford 2-(4-(1,3-dioxan-2-yl)-2-fluorophenyl)-5-(1-phenylcyclopropyl)thiazolo[4,5-b]pyridine as a pale yellow solid. MS (ESI) m/z: calculated: 432.1; Observed: 433.1 ($M^{+}$+1).

Step 8

2-(4-(1,3-Dioxan-2-yl)-2-fluorophenyl)-5-(1-phenylcyclopropyl)thiazolo[4,5-b]pyridine (0.064 g, 0.15 mmol) was dissolved in 1 mL THF and 1 mL 5N aq HCl and heated to 80° C. for 1 h. The reaction mixture was cooled and a precipitate formed. The reaction mixture was treated with ice and 10 N NaOH, then extracted with DCM. The combined organics were dried over sodium sulfate, filtered, and concentrated in vacuo to give a light orange solid. This was dissolved in 1 mL DCM and treated with azetidine-3-carboxylic acid (0.045 g, 0.44 mmol), acetic acid (0.043 mL, 0.74 mmol), and 1 mL MeOH. After 1 h, sodium cyanoborohydride (0.0093 g, 0.15 mmol) was added. After 30 min, the reaction mixture was concentrated under a stream of nitrogen, dissolved in DMSO+TFA and purified by RPHPLC, 15-100% ACN/TFA in $H_2O$/TFA, and the product-containing fractions were combined and concentrated to give 1-(3-fluoro-4-(5-(1-phenylcyclopropyl)thiazolo[4,5-b]pyridine-2-yl)benzyl)azetidine-3-carboxylic acid trifluoroacetic acid salt as a white solid. MS (ESI) m/z: calculated: 388.1; Observed: 389.1 ($M^{+}$+1).

Example 45

Synthesis of 1-(3-fluoro-4-(6-(1-phenylcyclopropyl) thiazolo[4,5-c]pyridine-2-yl)benzyl)azetidine-3-carboxylic acid trifluoroacetic acid salt

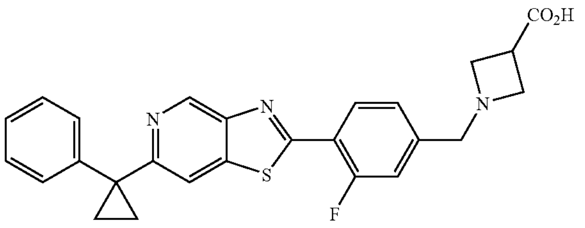

Step 1

To a stirring slurry of 4,6-dichloropyridin-3-amine (2.00 g, 12 mmol) and sodium carbonate (3.4 g, 32 mmol) in 10 mL DCM was added thiophosgene (1.2 mL, 16 mmol). The orange mixture was sealed and allowed to stir at ambient temperature overnight. The reaction mixture was filtered, rinsing with DCM, and the filtrate concentrated in vacuo to give 2,4-dichloro-5-isothiocyanatopyridine as an orange solid. MS (ESD m/z: calculated: 203.9; Observed: 204.9 ($M^{+}$+1).

Step 2

To a solution of 2-(4-bromo-3-fluorophenyl)-1,3-dioxane (3.12 g, 11.9 mmol) in 40 mL THF at −78° C. under argon was added butyllithium, 2.5 M solution in hexanes (5.26 mL, 13.1 mmol) slowly dropwise. The resulting solution was allowed to stir 1 h at −78° C., at which point a solution at ambient temp of 2,4-dichloro-5-isothiocyanatopyridine (2.45 g, 11.9 mmol) in 10 mL THF was added slowly via cannula. The dark red reaction mixture was allowed to stir 15 min, and was then removed from the bath and quenched by slow addition of sat'd aq. $NH_4Cl$. The reaction mixture was diluted with 40 mL MTBE, and the organic layer washed with water, brine, dried over sodium sulfate, filtered, and concentrated in vacuo. The resulting material was treated with sodium carbonate (1.90 g, 17.9 mmol) and 10 mL DMF. The reaction was heated under nitrogen to 80° C. An additional 5 mL DMF was added to give a stirrable slurry. After 30 min additional, the reaction mixture was cooled slightly and treated with 100 mL water. After 10 min stirring, the mixture was filtered, rinsing with water and MeOH. The solid was collected and dried in vacuo overnight to give 2-(4-(1,3-dioxan-2-yl)-2-fluorophenyl)-6-chlorothiazolo[4,5-c]pyridine as a tan solid. MS (ESI) m/z: calculated: 350.0; Observed: 351.0 ($M^{+}$+1).

Step 3

A slurry of 2-(4-(1,3-dioxan-2-yl)-2-fluorophenyl)-6-chlorothiazolo[4,5-c]pyridine (1.00 g, 2.85 mmol), $(Amphos)_2PdCl_2$ (0.0505 g, 0.0713 mmol), potassium carbonate (1.34 g, 9.69 mmol), 1-phenylvinylboronic acid (0.928 g, 6.27 mmol) in 12 mL dioxane and 3 mL water was heated to 60° C. overnight in a sealed tube. Additional $(Amphos)_2PdCl_2$ (0.0505 g, 0.0713 mmol) was added and the temperature raised to 90° C. After 3 h, the homogeneous reaction mixture was cooled and treated with water and DCM. The organic layer was extracted with DCM, and combined organics were dried over sodium sulfate, filtered, and concentrated in vacuo. The solid was suspended in MTBE and filtered to give 2-(4-(1,3-dioxan-2-yl)-2-fluorophenyl)-6-(1-phenylvinyl)-thiazolo[4,5-c]pyridine as an off-white solid. MS (ESI) m/z: calculated: 418.1; Observed: 419.0 ($M^{+}$+1).

Step 4

To a clear solution of potassium tert-butoxide (0.201 g, 1.79 mmol) and trimethylsulfoxonium iodide (0.394 g, 1.79 mmol) in 5 mL DMSO was added a cloudy mixture of 2-(4-(1,3-dioxan-2-yl)-2-fluorophenyl)-6-(1-phenylvinyl)thiazolo[4,5-c]pyridine (0.500 g, 1.19 mmol) in 20 mL THF rapidly. After 4 h, the reaction mixture was partitioned between EA and sat'd aq $NH_4Cl$, and the organic layer was washed with water, brine, dried over sodium sulfate, filtered, and concentrated in vacuo. The resulting material was taken up in DCM and was filtered. The filtrate was collected and adsorbed onto 2 g silica gel and dried in vacuo. The resulting material was purified by silica gel chromatography, 40 g, 0-100% EA/hexanes to give 2-(4-(1,3-dioxan-2-yl)-2-fluorophenyl)-6-(1-phenylcyclopropyl)thiazolo[4,5-c]pyridine as a white solid. MS (ESI) m/z: calculated: 432.1; Observed: 433.0 ($M^{+}$+1).

Step 5

A slurry of 2-(4-(1,3-dioxan-2-yl)-2-fluorophenyl)-6-(1-phenylcyclopropyl)-thiazolo[4,5-c]pyridine (0.142 g, 0.33 mmol) in 2 mL THF and 2 mL 5N HCl was heated to 70° C. for 2 h. The reaction mixture was cooled and treated with ice and 10 N NaOH until basic. The mixture was extracted with DCM, and the combined organics were dried over sodium sulfate, filtered, and concentrated in vacuo to give a yellow solid. This material was combined with azetidine-3-carboxylic acid (0.100 g, 0.98 mmol) 1.5 mL DCM, acetic acid (0.099 g, 1.6 mmol) and 1.5 mL MeOH and stirred overnight. Sodium cyanoborohydride (0.021 g, 0.33 mmol) was added, and after 30 min the reaction mixture was concentrated, dissolved in DMSO and TFA, filtered and purified by RPHPLC, 10-100% ACN/TFA in water/TFA. Product-containing fractions were combined and concentrated in vacuo to give 1-(3-fluoro-4-(6-(1-phenylcyclopropyl)thiazolo[4,5-c]pyridine- 2-yl)benzyl)azetidine-3-carboxylic acid trifluoroacetic acid salt as a white solid. MS (ESI) m/z: calculated: 459.1; Observed: 460.1 ($M^+$+1).

Example 46

Synthesis of 1-(3-amino-4-(5-(1-phenylcyclopropyl) thiazolo[5,4-b]pyridin-2-yl)benzyl)azetidine-3-carboxylic acid

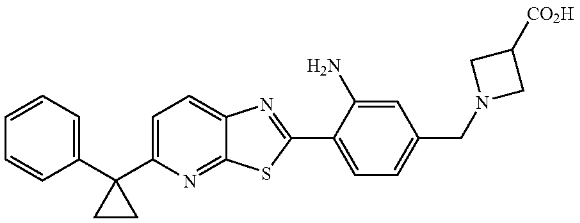

Step 1

A slurry of 3-amino-6-(1-phenylcyclopropyl)pyridine-2(1H)-thione (1.00 g, 4.13 mmol) and methyl 4-(chlorocarbonyl)-3-nitrobenzoate (1.11 g, 4.54 mmol) in 10 mL toluene was heated under nitrogen with a water cooled reflux condenser was heated in a 120° C. oil bath. After bubbling had subsided, ((1S,4R)-7,7-dimethyl-2-oxobicyclo[2.2.1]heptan-1-yl)methanesulfonic acid (0.479 g, 2.06 mmol) was added through the condenser and heating continued for 30 min. The slurry was treated with 5 mL toluene to and heating continued overnight to give a dark brown solution. The reaction mixture was cooled to ambient temperature, then diluted with EtOAc, washed with water, sat'd aq. Bicarbonate, and brine. The organic layer was dried over sodium sulfate, filtered, and concentrated in vacuo to give a brown oil. Purification by silica gel chromatography, 40 g, 0-30% EA/hexanes gave methyl 3-nitro-4-(5-(1-phenylcyclopropyl)thiazolo[5,4-b]pyridine-2-yl)benzoate as a light brown solid. MS (ESI) m/z: Calculated: 431.1; Observed: 432.0 ($M^+$+1).

Step 2

To a 0° C. solution of methyl 3-nitro-4-(5-(1-phenylcyclopropyl)thiazolo[5,4-b]pyridine-2-yl)benzoate (1.10 g, 2.5 mmol) in THF and methanol (0.31 mL, 7.6 mmol) was added lithium borohydride, 2.0 M solution in tetrahydrofuran (1.9 mL, 3.8 mmol). The reaction mixture was stirred at ambient temp, and upon completion the reaction mixture was cooled to 0° C. was quenched with ice and sat'd aq. $NH_4Cl$ carefully. The reaction mixture was partitioned between DCM and sat'd aq. $NH_4Cl$ and extracted with DCM. The combined organics were purified by silica gel chromatography, EA/hexanes gradient, to give (3-nitro-4-(5-(1-phenylcyclopropyl)thiazolo[5,4-b]pyridine-2-yl)phenyl)methanol as an orage solid. MS (ESI) m/z: Calculated: 403.1; Observed: 403.8 ($M^+$+1).

Step 3

To a nearly clear solution of (3-nitro-4-(5-(1-phenylcyclopropyl)thiazolo[5,4-b]pyridine-2-yl)phenyl)methanol (0.394 g, 0.977 mmol) and triphenyl phosphine (0.294 mL, 1.27 mmol) in 10 mL DCM at 0° C. was added carbon tetrabromide (0.114 mL, 1.17 mmol) in one portion. The reaction mixture was allowed to stir 1 h, then was treated with 3.5 g silica gel and dried. Purification by silica gel chromatography, 40 g, 0-30% EA/hexanes gave 2-(4-(bromomethyl)-2-nitrophenyl)-5-(1-phenylcyclopropyl)thiazolo-[5,4-b]pyridine as an orange-yellow solid. MS (ESI) m/z: Calculated: 467.0; Observed: 467.6 ($M^+$+1).

Step 4

A mixture of 2-(4-(bromomethyl)-2-nitrophenyl)-5-(1-phenylcyclopropyl)-thiazolo[5,4-b]pyridine (0.363 g, 0.778 mmol), methyl azetidine-3-carboxylate hydrochloride (0.354 g, 2.34 mmol), N,N-diisopropylethylamine (0.812 mL, 4.67 mmol) in 3 mL DMF was heated in a sealed vial to 80° C. for 1 h. The reaction mixture was cooled and allowed to stand overnight. In the morning the reaction mixture was treated with ice, sat'd aq. $NaHCO_3$, and EA. The organic layer was washed with water, brine, dried over sodium sulfate, filtered, and concentrated in vacuo. Purification by silica gel chromatography, 40 g, 0-10% MeOH/DCM gave methyl 1-((3-nitro-4-(5-(1-phenylcyclopropyl)thiazolo[5,4-b]pyridine-2-yl) phenyl)methyl)azetidine-3-carboxylate as a yellow oil. MS (ESI) m/z: Calculated: 500.2; Observed: 500.7 ($M^+$+1).

Step 5

A slurry of methyl 1-((3-nitro-4-(5-(1-phenylcyclopropyl) thiazolo[5,4-b]pyridine-2-yl)phenyl)methyl)azetidine-3-carboxylate (0.390 g, 0.78 mmol) and 10% palladium on carbon, 50% water, (0.41 g) and N,N-diisopropylethylamine (0.27 mL, 1.6 mmol) was treated with a hydrogen balloon and stirred rapidly for 2 h, then was flushed with nitrogen, filtered through celite, rinsing with MeOH/DCM. The filtrate was concentrated in vacuo and the residue purified by silica gel chromatography 40 g, 20-100% EA/hexanes to give methyl 1-((3-amino-4-(5-(1-phenylcyclopropyl)thiazolo[5,4-b]pyridine-2-yl)phenyl)methyl)azetidine-3-carboxylate as a yellow solid. MS (ESI) m/z: Calculated: 470.2; Observed: 470.8 ($M^+$+1).

Step 6

Synthesized from methyl 1-((3-amino-4-(5-(1-phenylcyclopropyl)thiazolo[5,4-b]pyridine-2-yl)phenyl)methyl)azetidine-3-carboxylate (0.100 g, 0.21 mmol) according to the general procedure for ester hydrolysis to give 1-(3-amino-4-(5-(1-phenyl-cyclopropyl)thiazolo[5,4-b]pyridine-2-yl)benzyl)azetidine-3-carboxylic acid as a yellow solid. MS (ESI) m/z: Calculated: 456.2; Observed: 457.1 ($M^+$+1).

Example 47

Synthesis of 1-(4-(5-(1-cyclohexylcyclopropyl)thiazolo[5,4-b]pyridine-2-yl)-3-fluorobenzyl)azetidine-3-carboxylic acid trifluoroacetic acid salt

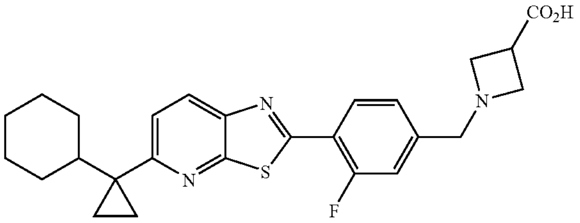

Step 1

To a solution of 9-bromo-9-bora-bicyclo[3.3.1]nonane 1 M in DCM (33 mL, 33 mmol) at 0° C. was added ethynylcyclohexane (3.6 mL, 28 mmol) under argon via syringe slowly dropwise in portions over 10 min. The reaction mixture was allowed to stir 3 h, at which point acetic acid (4.8 mL, 83 mmol) was added dropwise in portions over 20 min. After 1 h additional, sodium hydroxide (17 mL, 166 mmol) was added slowly, followed by cautious addition of hydrogen peroxide (8.5 mL, 83 mmol). The reaction mixture was allowed to stir rapidly 1 h, then was warmed to ambient temperature. The reaction mixture was partitioned between hexanes and water, and the organic layer was washed with saturated aq. Sodium bicarbonate, and brine, dried over sodium sulfate, filtered, and concentrated in vacuo. The resulting liquid was filtered through a 3 cm pad of silica gel, rinsing with 200 mL hexanes, and the filtrate was concentrated in vacuo to give crude (1-bromovinyl)-cyclohexane as a clear/colorless oil which was used without further purification.

Step 2

A mixture of copper(I) iodide (0.0159 g, 0.0835 mmol), cesium fluoride (0.380 g, 2.50 mmol), (1-bromovinyl)cyclohexane (0.947 g, 5.01 mmol), tetrakis(triphenylphosphine) palladium (0) (0.0965 g, 0.0835 mmol), and 2-(4-(1,3-dioxan-2-yl)-2-fluorophenyl)-5-(trimethylstannyl)-thiazolo[5,4-b]pyridine (0.800 g, 1.67 mmol) in 7.5 mL DMF was heated at 55° C. for several hours. The reaction mixture was cooled, diluted with EA, and filtered through celite. The organic layer was washed with water, brine, dried over sodium sulfate, filtered, and concentrated in vacuo to give a solid, which was adsorbed onto silica gel and purified by silica gel chromatography, 0-40-100% EA/hexanes to give 2-(4-(1,3-dioxan-2-yl)-2-fluorophenyl)-5-(1-cyclohexylvinyl)thiazolo[5,4-b]pyridine as an off white solid. MS (ESI) m/z: calculated: 424.2; Observed: 425.1 ($M^{+}$+1).

Step 3

To a solution of trimethylsulfoxonium iodide (0.385 g, 1.75 mmol) and potassium tert-butoxide (0.196 g, 1.75 mmol) in 4 mL DMSO was added 2-(4-(1,3-dioxan-2-yl)-2-fluorophenyl)-5-(1-cyclohexylvinyl)thiazolo[5,4-b]pyridine (0.371 g, 0.874 mmol) rapidly as a solution in THF (8 mL min volume). The reaction mixture became a light purple color. The reaction was sealed and heated to 60° C. After 4 h, the reaction mixture was cooled, quenched with ice and sat'd aq. $NH_4Cl$, diluted with EtOAc and the organic layer was washed with water, brine, dried over sodium sulfate, filtered, and concentrated in vacuo. The resulting orange oil/solid was purified by silica gel chromatography 40 g, 0-40% EA/hexanes to give 2-(4-(1,3-dioxan-2-yl)-2-fluorophenyl)-5-(1-cyclohexylcyclopropyl)thiazolo[5,4-b]pyridine as a white solid. MS (ESI) m/z: calculated: 438.2; Observed: 439.1 ($M^{+}$+1).

Step 4

A mixture of 2-(4-(1,3-dioxan-2-yl)-2-fluorophenyl)-5-(1-cyclohexyl-cyclopropyl)-thiazolo[5,4-b]pyridine (0.157 g, 0.36 mmol) in 4 mL 1:1 THF/5N aq. HCl was sealed and heated to 70° C. for 1 h. The reaction mixture was cooled, quenched with ice and 10 N NaOH, and partitioned between DCM/water. The aq. Layer was extracted with DCM, and the combined organics were dried over sodium sulfate, filtered, and concentrated in vacuo. The resulting brown solid was treated with azetidine-3-carboxylic acid (0.11 g, 1.1 mmol), 2 mL DCM, acetic acid (0.10 mL, 1.8 mmol), and 2 mL MeOH and allowed to stir 1 h. Sodium cyanoborohydride (0.022 g, 0.36 mmol) was added and the reaction mixture stirred for 30 min, then concentrated in vacuo. The resulting solid was dissolved in ~3 mL DMSO+TFA, and purified by RPHPLC, 10-100% TFA/ACN in H2O/TFA. The product-containing fractions were concentrated in vacuo to give 1-(4-(5-(1-cyclohexyl-cyclopropyl)thiazolo[5,4-b]pyridine-2-yl)-3-fluorobenzyl)azetidine-3-carboxylic acid trifluoroacetic acid salt as a light yellow solid. MS (ESI) m/z: calculated: 465.2; Observed: 466.2 ($M^{+}$+1). $^{1}$H NMR (400 MHz, DMSO-$d_6$) δ ppm 8.31-8.47 (m, 2 H), 7.63 (d, J=11.5 Hz, 1 H), 7.57 (d, J=8.5 Hz, 1 H), 7.53 (d, J=8.0 Hz, 1 H), 4.48 (s, 2 H), 4.12-4.33 (m, 4 H), 3.57-3.71 (m, 1 H), 1.49-1.83 (m, 6 H), 1.21 (m, 2 H), 0.82-1.04 (m, 7 H)

Example 48

Synthesis of 1-(4-(5-(1-cyclopentylcyclopropyl)thiazolo[5,4-b]pyridin-2-yl)-3-fluorobenzyl)azetidine-3-carboxylic acid diethylamine salt

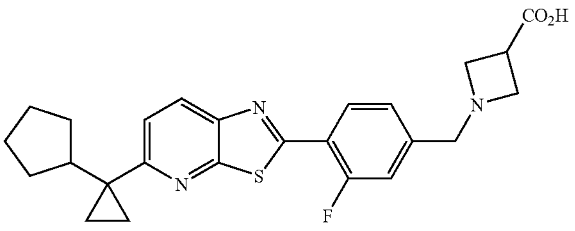

Synthesized from ethynyl cyclopentane and 2-(4-(1,3-dioxan-2-yl)-2-fluorophenyl)-5-(trimethylstannyl)thiazolo[5,4-b]pyridine (0.800 g, 1.67 mmol) according to the procedures used for the synthesis of preceding Example 47 to give 1-(4-(5-(1-cyclopentylcyclopropyl)thiazolo-[5,4-b]pyridine-2-yl)-3-fluorobenzyl)-azetidine-3-carboxylic acid diethylamine salt. MS (ESI) m/z: calculated: 451.2; Observed: 451.8 ($M^{+}$+1).

Example 49

Synthesis of 1-(4-(5-bi(cycloprop)ylthiazolo[5,4-b]pyridine-2-yl)-3-fluorobenzyl)-azetidine-3-carboxylic acid trifluoroacetic acid salt

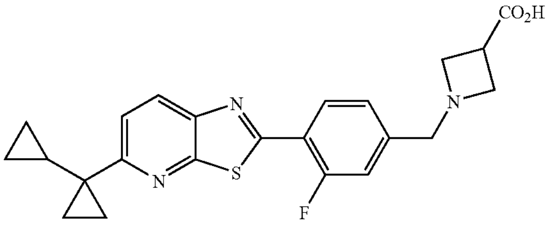

Synthesized from ethynyl cyclopropane and 2-(4-(1,3-dioxan-2-yl)-2-fluorophenyl)-5-(trimethylstannyl)thiazolo[5,4-b]pyridine (0.875 g, 1.83 mmol) according to the procedures used for the synthesis of preceding Example 47 to give 1-(4-(5-bi(cycloprop)ylthiazolo[5,4-b]pyridine-2-yl)-3-fluorobenzyl)azetidine-3-carboxylic acid trifluoroacetic acid salt. MS (ESI) m/z: calculated: 423.1; Observed: 423.8 ($M^{+}$+1).

Example 50

Synthesis of 1-(4-(5-(1-(4,4-difluorocyclohexyl)cyclopropyl)thiazolo[5,4-b]pyridine-2-yl)-3-fluorobenzyl)azetidine-3-carboxylic acid trifluoroacetic acid salt

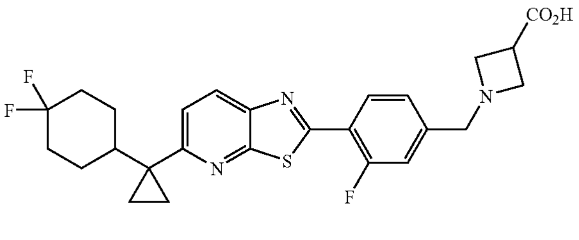

Step 1

To a clear solution of 4,4-difluorocyclohexanecarboxylic acid (2.00 g, 12.18 mmol) in 100 mL THF at 0° C. was added slowly dropwise methyllithium, 1.6M solution in diethyl ether (30.5 mL, 48.7 mmol) from an addition funnel. The resulting cloudy mixture was allowed to stir 2 h, then was treated with chlorotrimethyl silane (24.74 mL, 195 mmol) dropwise over 10 min. The bath was removed and the clear solution allowed to stir 1 h. 5 mL 1M HCl aq. Was added and the reaction mixture stirred an additional hour. The reaction mixture was then concentrated in vacuo to a small volume, diluted with $Et_2O$, and the organic layer was washed with water, sat'd aq. $NaHCO_3$, brine, dried over magnesium sulfate, filtered, and concentrated in vacuo to give impure 1-(4,4-difluorocyclohexyl)-ethanone as a clear/colorless oil, which was used without further purification.

Step 2

To NaHMDS 1.0 M in THF (8.41 mL, 8.41 mmol) in 8 mL THF at −78° C. under argon was added 1-(4,4-difluorocyclohexyl)ethanone (1.24 g, 7.65 mmol) in 3 mL THF dropwise via syringe. After 15 min, N-phenyl bis-trifluoromethanesulfonimide (2.73 g, 7.65 mmol) in 8 mL THF was added slowly via cannula. The light yellow reaction mixture was allowed to stir 3 h, at which point the bath was removed and sat'd aq. $NaHCO_3$ was added, followed by diethyl ether. The organic layer was washed with brine, dried over magnesium sulfate, filtered, and concentrated down to about 5 mL volume, then purified by silica gel chromatography (load with DCM) 40 g, 0-20% EA/hexanes, to give impure 1-(4,4-difluorocyclohexyl)vinyl trifluoromethanesulfonate, which was used without further purification.

Step 3

Synthesized from 2-(4-(1,3-dioxan-2-yl)-2-fluorophenyl)-5-(trimethylstannyl)-thiazolo[5,4-b]pyridine (1.00 g, 2.087 mmol), 1-(4,4-difluorocyclohexyl)vinyl trifluoromethanesulfonate (0.921 g, 3.13 mmol) according to the procedures used for the synthesis of preceding Example 47, Steps 2-4 to give 1-(4-(5-(1-(4,4-difluorocyclohexyl)-cyclopropyl)thiazolo[5,4-b]pyridine-2-yl)-3-fluorobenzyl)azetidine-3-carboxylic acid trifluoroacetic acid salt. MS (ESI) m/z: calculated: 501.2; Observed: 502.1 ($M^+$+1).

Example 51

Synthesis of (R)-1-(4-(5-(1-(3,3-difluorocyclopentyl)cyclopropyl)thiazolo[5,4-b]pyridine-2-yl)-3-fluorobenzyl)azetidine-3-carboxylic acid and (S)-1-(4-(5-(1-(3,3-difluorocyclopentyl)cyclopropyl)thiazolo[5,4-b]pyridine-2-yl)-3-fluorobenzyl)azetidine-3-carboxylic acid

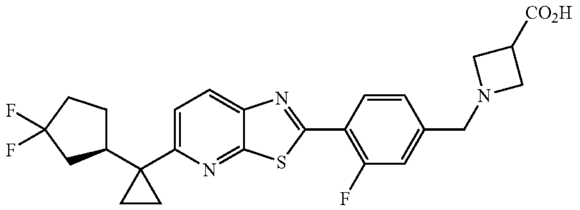

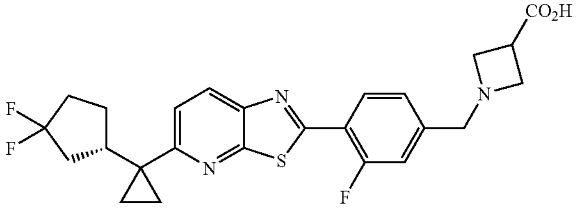

Step 1

To a slurry of 1-hydroxybenzotriazole (7.91 g, 58.5 mmol), 3-oxo-1-cyclopentanecarboxylic acid (5.00 g, 39.0 mmol), 1-(3-dimethylaminopropyl)-3-ethylcarbodiimide hydrochloride (11.22 g, 58.5 mmol) in 44 mL DCM under nitrogen was added N,O-dimethylhydroxylamine hydrochloride (5.71 g, 58.5 mmol) followed by triethylamine (8.16 mL, 58.5 mmol) in portions. The reaction mixture became warm and was cooled with an ice bath for the remainder of TEA addition, then stirred at ambient temp under nitrogen for 2 d. The reaction mixture was concentrated in vacuo, and taken up in EA (300 mL), washed with water, sat'd aq. Sodium bicarbonate, brine, and the organic layer was dried over sodium sulfate, filtered, and concentrated in vacuo, to give (rac)-N-methoxy-N-methyl-3-oxocyclopentanecarboxamide as a yellow oil which was used without further purification. $^1H$ NMR (400 MHz, $CDCl_3$-d) δ ppm 3.74 (s, 3 H), 3.41-3.61 (m, 1 H), 3.23 (s, 3 H), 2.52-2.64 (m, 1 H), 2.34-2.50 (m, 2 H), 2.08-2.31 (m, 3 H).

Step 2

To a solution of N-methoxy-N-methyl-3-oxocyclopentanecarboxamide (2.43 g, 14.19 mmol) in 30 mL toluene under nitrogen was added deoxo-fluor® (7.05 mL, 38.3 mmol) followed by trifluoroacetic acid (0.219 mL, 2.84 mmol). The reaction was sealed and heated to 40° C. overnight. The reaction mixture was cooled, diluted with $Et_2O$, cooled to 0° C. in an ice bath and quenched slowly with 75 mL 2N NaOH with rapid stirring. The aq. Layer was separated and extracted once with $Et_2O$. The combined organics were washed with brine, dried over magnesium sulfate, filtered, and concentrated in vacuo. Purified by silica gel chromatography (50% EA/hexanes) gave (rac)-3,3-difluoro-N-methoxy-N-methylcyclopentanecarboxamide as a light yellow oil. $^1H$ NMR (400 MHz, $CDCl_3$-d) δ ppm 3.71 (s, 3 H), 3.29-3.43 (m, 1 H), 3.21 (s, 3 H), 2.17-2.54 (m, 3 H), 1.93-2.15 (m, 3 H).

Step 3

To a solution of (rac)-3,3-difluoro-N-methoxy-N-methylcyclopentane-carboxamide (1.90 g, 9.83 mmol) in 20 mL THF at 0° C. was added methylmagnesium bromide 3.0 m in diethyl ether (6.56 mL, 19.67 mmol) slowly dropwise. The reaction mixture became white and cloudy. After 1.5 h, the reaction mixture was quenched carefully with ice and 1N HCl, and diluted with $Et_2O$. The organic layer was washed with brine, dried over magnesium sulfate, filtered, and concentrated in vacuo to give (rac)-1-(3,3-difluorocyclopentyl) ethanone as a light yellow oil. $^1$H NMR (400 MHz, $CDCl_3$-d) δ ppm 3.03-3.19 (m, 1 H), 2.22-2.48 (m, 2 H), 2.20 (s, 3 H), 2.03-2.16 (m, 3 H), 1.90-1.99 (m, 1 H).

Step 4

To a solution of sodium hexamethyldisilylazide (1.0 M in THF) (9.36 mL, 9.36 mmol) in 10 mL THF at −78° C. was added (rac)-1-(3,3-difluorocyclopentyl)ethanone (1.26 g, 8.50 mmol) in THF slowly dropwise via cannula. After 15 min, a solution of 1,1,1-trifluoro-N-phenyl-N-(trifluoromethylsulfonyl)methanesulfonamide (3.04 g, 8.50 mmol) in THF was added dropwise via cannula. After 3 h, the reaction mixture was quenched with saturated aq. $NaHCO_3$ and diluted with $Et_2O$. The organic layer was washed with brine, dried over magnesium sulfate, filtered, and concentrated in vacuo to give an oil. Purification by silica gel chromatography, 0-10% EA/hexanes, gave impure (rac)-1-(3,3-difluorocyclopentyl)vinyl trifluoromethanesulfonate which was used in the next step without further purification.

Step 5

A slurry of cesium fluoride (1.664 g, 10.96 mmol), copper (I) iodide (0.042 g, 0.219 mmol), tetrakis(triphenylphosphine) palladium (0) (0.253 g, 0.219 mmol), 2-(4-(1,3-dioxan-2-yl)-2-fluorophenyl)-5-(trimethylstannyl)thiazolo[5,4-b]pyridine (2.10 g, 4.38 mmol), 1-(3,3-difluorocyclopentyl)-vinyl trifluoromethanesulfonate (1.842 g, 6.57 mmol) were combined in 10 mL DMF, sealed, and heated to 50° C. The reaction mixture became homogeneous and then a thick precipitate formed. The reaction mixture was cooled, diluted with DCM, filtered through celite, and concentrated onto 16 g silica gel. Purification by silica gel chromatography 30% EA/hexanes gave 1.5 g of an orange solid that contained impure (rac)-2-(4-(1,3-dioxan-2-yl)-2-fluorophenyl)-5-(1-(3,3-difluorocyclopentyl)vinyl)thiazolo[5,4-b]pyridine. MS (ESI) m/z: Calculated: 446.1; Observed: 447.1 ($M^+$+1).

Step 6

(rac)-2-(4-(1,3-Dioxan-2-yl)-2-fluorophenyl)-5-(1-(3,3-difluorocyclopentyl)-vinyl)thiazolo[5,4-b]pyridine was taken up in 15 mL THF under nitrogen and to this was added a solution of trimethylsulfoxonium iodide (1.479 g, 6.72 mmol) and potassium tert-butoxide (0.754 g, 6.72 mmol) in 10 mL DMSO via syringe. The resulting red solution was sealed and heated to 70° C. for 1 h. The reaction mixture was cooled, quenched with ice and sat'd aq. $NH_4Cl$. The reaction mixture was diluted with DCM, and extracted with DCM. The combined organics were dried over sodium sulfate, filtered, and concentrated in vacuo. The solid was adsorbed onto 11 g silica gel and dried, and purified by silica gel chromatography, eluting with 0-70% EA/hexanes. Product containing fractions were combined and concentrated to give 0.61 g of an impure yellow solid containing 2-(4-(1,3-dioxan-2-yl)-2-fluorophenyl)-5-(1-(3,3-difluorocyclopentyl)-cyclopropyl)thiazolo[5,4-b]pyridine. MS (ESI) m/z: Calculated: 460.1; Observed: 461.1 ($M^+$+1).

Step 7

2-(4-(1,3-Dioxan-2-yl)-2-fluorophenyl)-5-(1-(3,3-difluorocyclopentyl)-cyclopropyl)thiazolo[5,4-b]pyridine was treated with 5 mL THF and 5N HCl was sealed and heated to 70° C. for 1 h. The reaction mixture was cooled, quenched with ice and 10 N NaOH until basic, and diluted with water and DCM. The aq. Layer was extracted with DCM, and the combined organics were dried over sodium sulfate, filtered, and concentrated in vacuo to give a brown oil. The oil was adsorbed onto 5 g silica gel and dried, purified by silica gel chromatography, 0-40% EA/hexanes, to give (rac)-4-(5-(1-(3,3-difluorocyclopentyl)-cyclopropyl)thiazolo[5,4-b]pyridine-2-yl)-3-fluorobenzaldehyde as a solid. MS (ESI) m/z: Calculated: 402.1; Observed: 403.0 ($M^+$+1).

Step 8

Reaction of 4-(5-(1-(3,3-difluorocyclopentyl)cyclopropyl)thiazolo[5,4-b]pyridine-2-yl)-3-fluorobenzaldehyde (0.268 g, 0.666 mmol) and methyl azetidine-3-carboxylate hydrochloride (0.202 g, 1.332 mmol) according to the general method for reductive amination provided methyl(rac)-1-(4-(5-(1-(3,3-difluorocyclopentyl)cyclopropyl)-thiazolo[5,4-b]pyridine-2-yl)-3-fluorobenzyl)azetidine-3-carboxylic acid. This racemic material was separated by chiral SFC (Column: Phenomenex Cellulose 2 (250×21 mm, 5 micron); Mobile Phase: 85:15 (A:B); A: Liquid $CO_2$; B: Isopropanol (0.2% DEA); Flow Rate: 70 mL/min; Oven/column temp: 35° C.) to give both (rac)-methyl 1-(4-(5-(1-(3,3-difluorocyclopentyl)-cyclopropyl)thiazolo[5,4-b]pyridine-2-yl)-3-fluorobenzyl)-azetidine-3-carboxylate and (S)-methyl 1-(4-(5-(1-(3,3-difluorocyclopentyl)-cyclopropyl)thiazolo-[5,4-b]pyridine-2-yl)-3-fluorobenzyl)azetidine-3-carboxylate. MS (ESI) m/z: Calculated: 501.2; Observed: 502.0 ($M^+$+1).

Step 9

Separately, the enantiomers of methyl 1-(4-(5-(1-(3,3-difluorocyclopentyl)-cyclopropyl)thiazolo[5,4-b]pyridine-2-yl)-3-fluorobenzyl)azetidine-3-carboxylate were processed according to the general procedure for ester hydrolysis to give both (R)-1-(4-(5-(1-(3,3-difluorocyclopentyl)cyclopropyl) thiazolo[5,4-b]pyridine-2-yl)-3-fluoro-benzyl)azetidine-3-carboxylic acid and (S)-1-(4-(5-(1-(3,3-difluorocyclopentyl)-cyclopropyl)thiazolo[5,4-b]pyridine-2-yl)-3-fluorobenzyl)azetidine-3-carboxylic acid. MS (ESI) m/z: Calculated: 487.2; Observed: 487.8 ($M^+$+1).

Example 52

Synthesis of 1-(3-fluoro-4-(5-(1-(tetrahydro-2H-pyran-4-yl)cyclopropyl)thiazolo[5,4-b]pyridine-2-yl) benzyl)azetidine-3-carboxylic acid trifluoroacetic acid salt

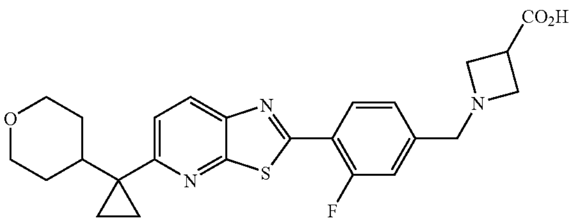

Step 1

A solution of 2-(4-(1,3-dioxan-2-yl)-2-fluorophenyl)-5-(trimethylstannyl)-thiazolo[5,4-b]pyridine (1.00 g, 2.087 mmol) and tetrahydro-2H-pyran-4-carbonyl chloride (0.434 mL, 2.92 mmol) in 15 mL toluene was sealed and heated to 80° C. After 4 h a precipitate formed. The reaction mixture was cooled and filtered, rinsing with $Et_2O$, and the solid was dried in vacuo to give (2-(4-(1,3-dioxan-2-yl)-2-fluorophenyl)-thiazolo[5,4-b]pyridine-5-yl)(tetrahydro-2H-pyran-4-yl)methanone as a white solid. MS (ESI) m/z: Calculated: 428.1; Observed: 428.8 ($M^+$+1).

Step 2

To a slurry of (2-(4-(1,3-dioxan-2-yl)-2-fluorophenyl)thiazolo[5,4-b]pyridine-5-yl)(tetrahydro-2H-pyran-4-yl)methanone (0.408 g, 0.952 mmol) in 20 mL THF at ambient temp was added trimethylsilylmethylmagnesium chloride, 1.1 M solution in THF (1.472 mL, 1.619 mmol) dropwise via syringe. The reaction mixture became clear and dark brown. After 10 min, the reaction mixture became light orange and was cooled to 0° C. and was quenched by careful dropwise addition of sat'd aq $NH_4Cl$. The reaction mixture was partitioned between satd $NH_4Cl$ and DCM. The aqueous layer was extracted with DCM 3 times, and the combined organics were dried over anhydrous sodium sulfate, filtered, and concentrated in vacuo to give an orange solid. The crude was taken up in 10 mL THF and potassium tert-butoxide (0.128 g, 1.143 mmol) was added. The reaction mixture became dark brown. After 2 h, additional potassium tert-butoxide (0.128 g, 1.143 mmol) was added. After 2 h, the reaction mixture was partitioned between sat'd aq. $NH_4Cl$ and DCM. The aqueous layer was extracted with DCM, and the combined organics were dried over anhydrous sodium sulfate, filtered, and concentrated in vacuo. The solid was suspended in a minimum amount of MeOH and filtered, rinsing with MeOH to give 2-(4-(1,3-dioxan-2-yl)-2-fluorophenyl)-5-(1-(tetrahydro-2H-pyran-4-yl)vinyl)thiazolo[5,4-b]pyridine as a white solid. MS (ESI) m/z: Calculated: 426.1; Observed: 427.1 ($M^+$+1).

Step 2

To a slurry of 2-(4-(1,3-dioxan-2-yl)-2-fluorophenyl)-5-(1-(tetrahydro-2H-pyran-4-yl)vinyl)thiazolo[5,4-b]pyridine (0.201 g, 0.471 mmol) in 2.5 mL THF was added a solution of trimethylsulfoxonium iodide (0.207 g, 0.943 mmol) and potassium tert-butoxide (0.106 g, 0.943 mmol) in 2.5 mL DMSO. The yellow slurry was sealed and heated to 60° C. After 6 h, the reaction mixture was cooled, quenched with ice and sat'd aq. $NH_4Cl$. The reaction mixture was partitioned between satd aq $NH_4Cl$ and DCM. The aqueous layer was extracted with DCM 3 times, and the combined organics were dried over anhydrous sodium sulfate, filtered, and concentrated in vacuo. The material was purified by silica gel chromatography, 0-50% EA/hexanes, to give 2-(4-(1,3-dioxan-2-yl)-2-fluorophenyl)-5-(1-(tetrahydro-2H-pyran-4-yl)cyclopropyl)thiazolo[5,4-b]pyridine as a solid. MS (ESI) m/z: Calculated: 440.2; Observed: 441.1 ($M^+$+1).

Step 3

A slurry of 2-(4-(1,3-dioxan-2-yl)-2-fluorophenyl)-5-(1-(tetrahydro-2H-pyran-4-yl)cyclopropyl)thiazolo[5,4-b]pyridine (0.068 g, 0.154 mmol) in 2 mL 1:1 THF/5N HCl was sealed and heated to 70° C. for 2 h. The reaction mixture was cooled, quenched with ice and 10 N NaOH until basic, and diluted with water and DCM. The aq. Layer was extracted with DCM, and the combined organics were dried over sodium sulfate, filtered, and concentrated in vacuo to give a yellow solid. This material was treated with azetidine-3-carboxylic acid (0.047 g, 0.463 mmol), acetic acid (0.044 mL, 0.772 mmol), 1.5 mL DCM and 1.5 mL MeOH and allowed to stir 30 min. sodium cyanoborohydride (9.70 mg, 0.154 mmol) was added and allowed to stir 30 min. The reaction mixture was concentrated, taken up in 1 mL DMSO+TFA, filtered, and purified by RPHPLC, gradient of TFA/ACN in TFA/$H_2O$. Product containing fractions were concentrated to give 1-(3-fluoro-4-(5-(1-(tetrahydro-2H-pyran-4-yl)cyclopropyl)-thiazolo[5,4-b]pyridine-2-yl)benzyl)azetidine-3-carboxylic acid trifluoroacetic acid salt. MS (ESI) m/z: Calculated: 467.2; Observed: 468.1 ($M^+$+1).

Example 53

Synthesis of (2S,4R)-4-(3-fluoro-4-(5-(1-phenylcyclopropyl)thiazolo[5,4-b]pyridine-2-yl)phenyl)-4-hydroxypyrrolidine-2-carboxylic acid

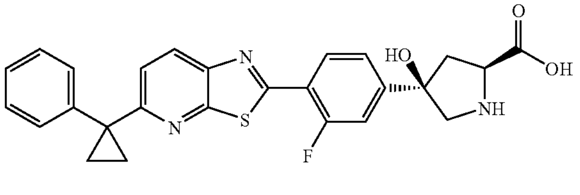

A solution of 2-(4-bromo-2-fluorophenyl)-5-(1-phenylcyclopropyl)thiazolo[5,4-b]pyridine (1.00 g, 2.35 mmol) in 25 mL THF was cooled to −78° C. Butyllithium 2.5 M in hexanes (1.03 mL, 2.59 mmol) was added dropwise over 2 min to give a deep red solution. After 30 seconds, a solution of (S)-di-tert-butyl 4-oxopyrrolidine-1,2-dicarboxylate (0.738 g, 2.59 mmol) in 3 mL THF was added dropwise via syringe over 2-3 min, and the red color faded to yellow brown. After 20 min, the reaction mixture was placed in a 0° C. bath; after 10 min, was quenched with sat'd aq. $NH_4Cl$ and diluted with DCM. The aq. Layer was extracted with DCM, and the combined extracts were dried over sodium sulfate, filtered, and concentrated in vacuo. Purification by silica gel chromatography, 40 g, gave 0.400 g of an impure yellow oil. A portion of this material (0.313 g) was dissolved in trifluoroacetic acid (0.99 mL, 13 mmol) to give a yellow solution. After 5 min, triethylsilane (1.0 mL, 6.4 mmol) was added. The reaction mixture was biphasic and was stirred rapidly. After 15 min, the reaction mixture was diluted with 2 mL DCM and stirring was continued overnight. The reaction mixture was concentrated, diluted with 3 mL DMSO, filtered, and purified by RPHPLC, 10-100% TFA/ACN in $H_2O$/ACN, and the combined product-containing fractions were concentrated in vacuo to give (2S,4R)-4-(3-fluoro-4-(5-(1-phenylcyclopropyl)-thiazolo[5,4-b]pyridine-2-yl)phenyl)-4-hydroxypyrrolidine-2-carboxylic acid as an off-white solid. MS (ESI) m/z: Calculated: 475.1; Observed: 476.0 ($M^+$+1).

Example 54

Synthesis of (2S,4R)-4-(3-fluoro-4-(5-(1-phenylcyclopropyl)thiazolo[5,4-b]pyridine-2-yl)phenyl)pyrrolidine-2-carboxylic acid trifluoroacetic acid salt

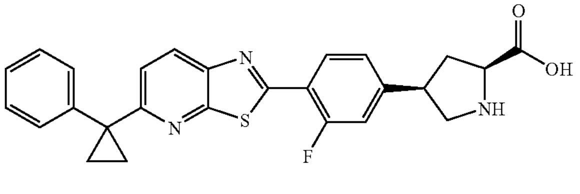

Step 1

A slurry of potassium phosphate (2.50 g, 11.8 mmol), $(Amphos)_2PdCl_2$ (0.125 g, 0.177 mmol), 2-(2-fluoro-4-(4,4, 5,5-tetramethyl-1,3,2-dioxaborolan-2-yl)phenyl)-5-(1-phenylcyclopropyl)thiazolo[5,4-b]pyridine (2.78 g, 5.89 mmol) and (S)-1-tert-butyl 2-methyl 4-(trifluoromethylsulfonyloxy)-1H-pyrrole-1,2(2H,5H)-dicarboxylate (2.21 g, 5.89 mmol, synthesized according to literature reference: Bioorganic and Medicinal Chemistry Letters, 2007, 2715) in 15 mL DMF was flushed with argon, sealed, and heated to 80° C. After 6 h, the reaction was judged complete, cooled, and filtered through celite, rinsing with 200 mL EtOAc. The filtrate was washed with water, brine, dried over sodium sulfate, filtered, and concentrated in vacuo. Purification by silica gel chromatography, EA/hexanes gradient, gave (2S)-1-tert-butyl 2-methyl 4-(3-fluoro-4-(5-(1-phenylcyclopropyl)thiazolo[5,4-b]pyridine-2-yl)phenyl)-2H-pyrrole-1,2(5H)-dicarboxylate as a light yellow solid. MS (ESI) m/z: Calculated: 571.2; Observed: 572.1 ($M^+$+1).

Step 2

(2S)-1-tert-Butyl 2-methyl 4-(3-fluoro-4-(5-(1-phenylcyclopropyl)thiazolo[5,4-b]pyridine-2-yl)phenyl)-2H-pyrrole-1,2(5H)-dicarboxylate (0.618 g, 1.1 mmol) and 10% palladium on carbon, 50% water (0.58 g) were combined in a flask and treated with nitrogen and 10 mL THF. The reaction mixture was stirred rapidly under $H_2$ balloon for 48 h. The reaction mixture was flushed with nitrogen, filtered, rinsing with DCM and concentrated in vacuo. Purification by silica gel chromatography, 40 g, 0-30% EA/hexanes gave (2S,4R)-1-tert-butyl 2-methyl 4-(3-fluoro-4-(5-(1-phenyl-cyclopropyl)thiazolo[5,4-b]pyridine-2-yl)phenyl)pyrrolidine-1,2-dicarboxylate as a yellow foam. MS (ESI) m/z: Calculated: 573.2; Observed: 573.7 ($M^+$+1).

Step 3

To a solution of (2S,4R)-1-tert-butyl 2-methyl 4-(3-fluoro-4-(5-(1-phenylcyclopropyl)-thiazolo[5,4-b]pyridine-2-yl)phenyl)pyrrolidine-1,2-dicarboxylate (0.100 g, 0.17 mmol) in 2 mL THF was added sodium hydroxide (0.70 mL, 0.70 mmol). The yellow cloudy reaction mixture was diluted with 0.7 mL water, and stirred rapidly at ambient temperature. After 6 h, the reaction mixture was quenched with ice and 5 N HCl until slightly acidic. The aq. Layer was extracted with DCM and the combined extracts were dried over sodium sulfate, filtered, and concentrated in vacuo to give (2S,4R)-1-(tert-butoxycarbonyl)-4-(3-fluoro-4-(5-(1-phenylcyclopropyl)thiazolo-[5,4-b]pyridine-2-yl)phenyl)pyrrolidine-2-carboxylic acid as a white solid. MS (ESI) m/z: Calculated: 559.2; Observed: 559.7 ($M^+$+1).

Step 4

To a slurry of (2S,4R)-1-(tert-butoxycarbonyl)-4-(3-fluoro-4-(5-(1-phenyl-cyclopropyl)-thiazolo[5,4-b]pyridine-2-yl)phenyl)pyrrolidine-2-carboxylic acid (0.091 g, 0.16 mmol) in 2 mL DCM was added trifluoroacetic acid (0.13 mL, 1.6 mmol) to give a yellow solution. Upon completion the reaction mixture was concentrated in vacuo and the material was triturated with MTBE to give (2S,4R)-4-(3-fluoro-4-(5-(1-phenylcyclopropyl)-thiazolo[5,4-b]pyridine-2-yl)phenyl)pyrrolidine-2-carboxylic acid trifluoroacetic acid salt. MS (ESI) m/z: Calculated: 459.1; Observed: 459.8 ($M^+$+1). $^1$H NMR (400 MHz, DMSO-$d_6$) δ ppm 8.22-8.36 (m, 2 H), 7.57 (d, J=13.1 Hz, 1 H), 7.27-7.49 (m, 8 H), 7.05 (d, J=8.6 Hz, 1 H), 4.42 (dd, J=10.0, 7.6 Hz, 1 H), 3.59-3.81 (m, 2 H), 3.24-3.34 (m, 1 H), 2.72-2.85 (m, 1 H), 2.06-2.22 (m, 1 H), 1.62-1.74 (m, 2 H), 1.34-1.45 (m, 2 H)

Example 55

Synthesis of (2S,4R)-4-(3-fluoro-4-(5-(1-phenylcyclopropyl)thiazolo[5,4-b]pyridine-2-yl)phenyl)-1-methylpyrrolidine-2-carboxylic acid trifluoroacetic acid salt

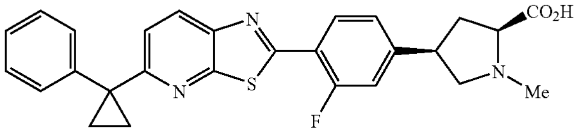

To a slurry of (2S,4R)-4-(3-fluoro-4-(5-(1-phenylcyclopropyl)thiazolo[5,4-b]pyridine-2-yl)phenyl)pyrrolidine-2-carboxylic acid trifluoroacetic acid salt (0.048 g, 0.084 mmol) formaldehyde (0.050 mL, 0.67 mmol) acetic acid (0.048 mL, 0.84 mmol) in 2 mL ACN was added sodium cyanoborohydride (0.011 g, 0.17 mmol). After 1 h, the reaction mixture was concentrated, dissolved in DMSO/TFA, and purified by RPHPLC, gradient of ACN/TFA in $H_2O$/TFA to give (2S,4R)-4-(3-fluoro-4-(5-(1-phenylcyclopropyl)thiazolo[5,4-b]pyridine-2-yl)phenyl)-1-methylpyrrolidine-2-carboxylic acid trifluoroacetic acid salt as a solid. MS (ESI) m/z: Calculated: 473.2; Observed: 474.1 ($M^+$+1).

Example 56

Synthesis of ((2S,4S)-4-(3-fluoro-4-(5-(1-phenylcyclopropyl)thiazolo[5,4-b]pyridine-2-yl)phenyl)pyrrolidin-2-yl)methanol trifluoroacetic acid salt

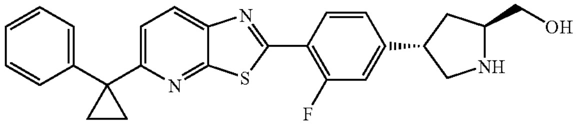

Step 1

To a solution of lithium aluminum hydride, 1.0 M solution in tetrahydrafuran (1.165 mL, 1.165 mmol) in 7 mL THF at 0° C. was added a solution of (S)-1-tert-butyl 2-methyl 4-(3-fluoro-4-(5-(1-phenylcyclopropyl)thiazolo[5,4-b]pyridine-2-yl)phenyl)-1H-pyrrole-1,2(2H,5H)-dicarboxylate (0.555 g, 0.971 mmol) dropwise via syringe, over 5 min. The reaction mixture became a deep purple color. The bath was removed, and after 30 min, the reaction mixture was re-cooled, and treated with ice carefully. 6 mL 1N aq. HCl was added and the aq. Layer was extracted with DCM. The combined organics were dried over sodium sulfate, filtered, and concentrated in vacuo. Purification by silica gel chromatography, 0-100% EA/hexanes gradient gave (2S,4S)-tert-butyl 4-(3-fluoro-4-(5-(1-phenylcyclopropyl)-thiazolo[5,4-b]pyridine-2-yl)phenyl)-2-(hydroxymethyl)pyrrolidine-1-carboxylate. MS (ESI) m/z: Calculated: 545.2; Observed: 546.1 ($M^+$+1).

Step 2

(2S,4S)-tert-butyl 4-(3-fluoro-4-(5-(1-phenylcyclopropyl)thiazolo[5,4-b]pyridine-2-yl)phenyl)-2-(hydroxymethyl)pyrrolidine-1-carboxylate (0.084 g, 0.154 mmol) in 2 mL DCM was added trifluoroacetic acid (0.200 mL) After 3 d, the reaction mixture was concentrated, dissolved in DMSO, filtered, and purified by RPHPLC, gradient, 10-100% ACN/TFA in $H_2O$/TFA. Product-containing fractions were concentrated in vacuo to give ((2S,4S)-4-(3-fluoro-4-(5-(1-phenylcyclopropyl)thiazolo[5,4-b]pyridine-2-yl)phenyl)pyrrolidin-2-yl)methanol. MS (ESI) m/z: Calculated: 445.2; Observed: 445.8 ($M^+$+1).

Example 57

Synthesis of ((2-(3-fluoro-4-(5-(1-phenylcyclopropyl)[1,3]thiazolo[5,4-b]pyridin-2-yl)phenyl)ethyl)amino)(oxo)acetic acid

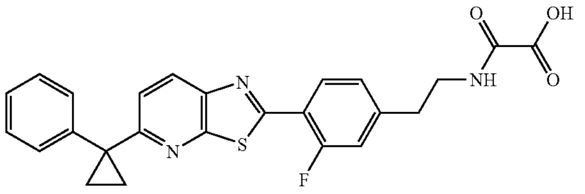

Step 1

2-(3-Fluoro-4-(5-(1-phenylcyclopropyl)thiazolo[5,4-b]pyridin-2-yl)phenyl)-ethanamine (112 mg, 0.29 mmol) was dissolved in toluene (2.9 mL) before diethyl oxalate (0.39 mL, 2.88 mmol) was added and stirred at 110° C. for 16 h. The reaction mixture was diluted with 75 mL of DCM, added to a separatory funnel, partitioned with sodium bicarbonate (saturated, aqueous), washed with sodium bicarbonate (saturated, aqueous), separated, dried over sodium sulfate, and concentrated via rotovap to give ethyl 2-(2-(3-fluoro-4-(5-(1-phenylcyclopropyl)thiazolo[5,4-b]pyridin-2-yl)phenyl)ethylamino)-2-oxoacetate after flash chromatography. MS (ESI) m/z: Calculated: 489.2; Observed: 490.4 ($M^+$+H).

Step 2

Ethyl 2-(2-(3-fluoro-4-(5-(1-phenylcyclopropyl)thiazolo[5,4-b]pyridin-2-yl)phenyl)ethylamino)-2-oxoacetate (100 mg, 0.20 mmol) was dissolved in ethanol (2.0 mL) before crushed potassium hydroxide (23 mg, 0.41 mmol) was added and stirred at ambient temperature for 30 min. The reaction mixture was concentrated, suspended in water, acidified with 2 N HCl, filtered, and washed with water. The title compound was obtained after purification via preparatory LC. MS (ESI) m/z: Calculated: 461.1; Observed: 462.0 ($M^+$+H).

Example 58

Synthesis of 2-(2-fluoro-4-((3-fluoroazetidin-1-yl)methyl)-phenyl)-5-(1-phenylcyclopropyl)thiazolo[5,4-b]pyridine

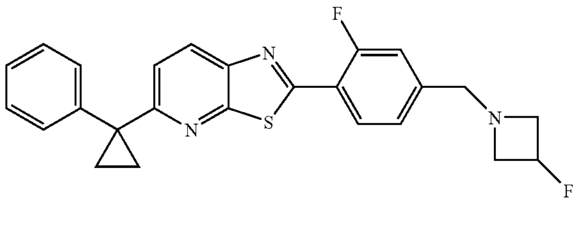

To a slurry of 1-((3-fluoro-4-(5-(1-phenylcyclopropyl)thiazolo[5,4-b]pyridin-2-yl)phenyl)methyl)azetidin-3-ol (0.100 g, 0.2 mmol) in 1 mL DCM under nitrogen at 0° C. was added (diethylamino)sulfur trifluoride (0.05 ml, 0.3 mmol). Upon consumption of starting material, the reaction was quenched with ice and 1 N NaOH. The reaction mixture was partitioned between water and DCM. The aqueous layer was extracted with DCM 3, and the combined cloudy organics were treated with a small amount of MeOH to give a solution, were dried over anhydrous sodium sulfate, filtered, and concentrated in vacuo. Purification by RPHPLC, gradient, TFA/ACN in TFA/$H_2O$ provided material that was taken up in DCM and washed with saturated aq. NaHCO3, dried over sodium sulfate, filtered, and concentrated in vacuo to give 2-(2-fluoro-4-((3-fluoroazetidin-1-yl)methyl)-phenyl)-5-(1-phenylcyclopropyl)thiazolo[5,4-b]pyridine as a solid. MS (ESI) m/z: Calculated: 433.1; Observed: 434.1 ($M^+$+1).

Example 59

Synthesis of 2-amino-2-(3-fluoro-4-(5-(1-phenylcyclopropyl)thiazolo[5,4-b]pyridin-2-yl)benzyl)propane-1,3-diol

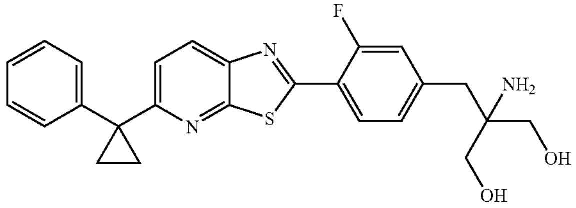

Step 1

In a sealable bottle, sodium tert-butoxide (0.120 g, 1.25 mmol) was added to a mixture of acetamidomalonic acid diethyl ester (0.272 g, 1.25 mmol) in THF (10.00 ml)/DMF (2.00 ml). The reaction was heated to 80° C. for 20 min., cooled to ambient temperature, and a solution of 2-(4-(bromomethyl)-2-fluorophenyl)-5-(1-phenylcyclopropyl)thiazolo[5,4-b]pyridine (0.500 g, 1.14 mmol) in THF 4 ml was added slowly dropwise. The resulting mixture was heated to reflux (90 deg. C.) for 1.5 h, and the color changed from orange to yellow. The reaction was cooled, poured over ice water, and treated with EtOAc. The organic layer was washed with water, NaCl, dried over $MgSO_4$, filtered, and concentrated in vacuo. Purification by silica gel chromatography, 40 g column, 10-30% EtOAc/hexanes, followed by 30-50% (3% $Et_3N$ in EtOAc)/hexanes provided diethyl 2-acetamido-2-(3-fluoro-4-(5-(1-phenylcyclopropyl)thiazolo[5,4-b]pyridin-2-yl)benzyl)malonate. MS (ESI) m/z: calculated: 575.2; Observed: 576.1 ($M^+$+1).

Step 2

A solution of $CaCl_2$ (0.159 g, 1.43 mmol) in 1.00 ml of water was added to a solution of diethyl 2-acetamido-2-((3-fluoro-4-(5-(1-phenylcyclopropyl)thiazolo[5,4-b]pyridin-2-yl)phenyl)methyl)malonate (0.330 g, 0.573 mmol) in THF (10.00 ml) and ethanol (10.00 ml). The reaction was cooled to 0° C. in ice bath before the addition of sodium borohydride (0.108 g, 2.87 mmol) was added and the solution became a yellow mixture. The reaction mixture was allowed to stir at ambient temperature for 2 h. DCM (5 ml) and additional sodium borohydride (0.108 g, 2.87 mmol) was added. After 18 h, the reaction was poured over DCM/1 N HCl, and the organic layer was washed with 1 N HCl, dried over $MgSO_4$, filtered, and concentrated in vacuo. The residue was purified by silica gel chromatography, 40 g column, 0-15% MeOH/DCM to give N-(2-(3-fluoro-4-(5-(1-phenylcyclopropyl)thiazolo[5,4-b]pyridin-2-yl)benzyl)-1,3-dihydroxypropan-2-yl)acetamide. MS (ESI) m/z: calculated: 491.2; Observed: 492.1 ($M^+$+1).

Step 3

In a sealable tube a slurry of N-(3-(3-fluoro-4-(5-(1-phenylcyclopropyl)thiazolo[5,4-b]pyridin-2-yl)phenyl)-1-hydroxy-2-(hydroxymethyl)propan-2-yl)acetamide (0.14 g, 0.28 mmol) in hydrochloric acid, 5 N (5.00 ml, 165 mmol) was heated to 120° C. The heterogeneous reaction mixture turned light green after 2 h of heating. The reaction mixture was cooled, filtered through a glass frit, and the solid was rinsed with water, EtOH, and $CHCl_3$. The EtOH and $CHCl_3$ filtrate was combined and concentrated, and this was combined with the isolated solid, and the material was purified by SFC (Sepapak 2 (250×21 mm, 5 micron) column using 50% methanol with 0.2% DEA as additive in supercritical $CO_2$ with a flow rate of 60 ml/min) to give 2-amino-2-(3-fluoro-4-(5-(1-phenylcyclopropyl)thiazolo[5,4-b]pyridin-2-yl)benzyl)propane-1,3-diol. MS (ESI) m/z: calculated: 449.2; Observed: 450.0 ($M^+$+1). Also isolated was (rac)-2-amino-3-(3-fluoro-4-(5-(1-phenylcyclopropyl)thiazolo[5,4-b]pyridin-2-yl)phenyl)propan-1-ol. MS (ESI) m/z: calculated: 419.2; Observed: 420.1 ($M^+$+1).

Example 60

Synthesis of N-benzyl-2-(3-fluoro-4-(5-(1-phenylcyclopropyl)[1,3]thiazolo[5,4-b]pyridin-2-yl)phenyl)ethanamine

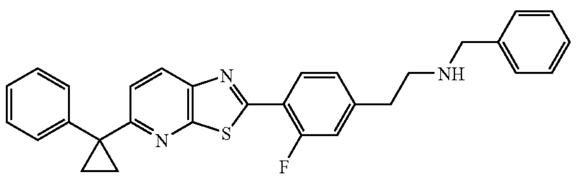

Step 1

To (methoxymethyl)triphenylphosphonium chloride (1.0 g, 2.93 mmol) was added THF (26 mLl) before it was cooled to 0° C.; butyllithium (2.5 M in hexanes, 1.28 ml, 3.20 mmol) was then added and stirred for 15 min before 3-fluoro-4-(5-(1-phenylcyclopropyl)thiazolo[5,4-b]pyridin-2-yl)benzaldehyde (1.00 g, 2.67 mmol) in THF (26 ml) was added to the reaction mixture. The reaction mixture was allowed to warm to ambient temperature and stir for 1 h to give 2-(2-fluoro-4-(2-methoxyvinyl)phenyl)-5-(1-phenylcyclopropyl)thiazolo[5,4-b]pyridine after flash chromatography. MS (ESI) m/z: Calculated: 402.1; Observed: 403.1 ($M^+$+H).

Step 2

2-(2-Fluoro-4-(2-methoxyvinyl)phenyl)-5-(1-phenylcyclopropyl)thiazolo[5,4-b]pyridine (570 mg, 1.42 mmol) was dissolved in 1,4-dioxane (14 mL) before concentrated hydrochloric acid (1.18 mL, 14.16 mmol) was added and stirred at 65° C. for 1 h. The reaction mixture was diluted with 100 mL of DCM, added to a separatory funnel, partitioned with 1 N NaOH (aqueous), washed with sodium bicarbonate (saturated, aqueous), separated, dried over sodium sulfate, and concentrated via rotovap to give 2-(3-fluoro-4-(5-(1-phenylcyclopropyl)thiazolo[5,4-b]pyridin-2-yl)phenyl)acetaldehyde after flash chromatography. MS (ESI) m/z: Calculated: 388.1; Observed: 389.0 ($M^+$+H).

Step 3

2-(3-Fluoro-4-(5-(1-phenylcyclopropyl)thiazolo[5,4-b]pyridin-2-yl)phenyl)acetaldehyde (44 mg, 0.113 mmol) was dissolved in chloroform (1.1 mL) before it was stirred at ambient temperature with benzylamine (62 μl, 0.57 mmol) and PTSA (1 mg) for 16 h. Methanol (1.1 mL) and sodium cyanoborohydride (7.1 mg, 0.113 mmol) were then added and allowed to stir in the reaction mixture over 3 d. The reaction mixture was diluted with DCM, added to a separatory funnel, partitioned with sodium bicarbonate (saturated, aqueous), washed with sodium bicarbonate (saturated, aqueous), separated, dried over sodium sulfate, and concentrated via rotovap to give the title compound after flash chromatography. MS (ESI) m/z: Calculated: 479.2; Observed: 480.1 ($M^+$+H).

Example 61

Synthesis of N-(2-(3-fluoro-4-(5-(1-phenylcyclopropyl)[1,3]thiazolo[5,4-b]pyridin-2-yl)phenyl)ethyl)methanesulfonamide

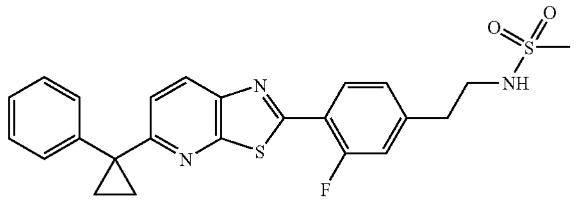

2-(3-Fluoro-4-(5-(1-phenylcyclopropyl)thiazolo[5,4-b]pyridin-2-yl)phenyl)ethanamine (100 mg, 0.257 mmol) was dissolved in dichloromethane (2.6 mL) and pyridine (0.208 mL, 2.57 mmol) before methanesulfonyl chloride (30 μl, 0.385 mmol) was added and stirred at ambient temperature for 3 h. The reaction mixture was diluted with 100 mL of DCM, added to a separatory funnel, partitioned with 1 N HCl (aqueous), washed with 1 N HCl (aqueous), separated, dried over sodium sulfate, and concentrated via rotovap to give the title compound after purification via preparatory LC. MS (ESI) m/z: Calculated: 467.1; Observed: 468.1 ($M^+$+H).

Example 62

Synthesis of 1-((3-fluoro-4-(6-(1-(pyridine-2-yl)cyclopropyl)benzo[d]thiazol-2-yl)-phenyl)methyl)azetidine-3-carboxylic acid

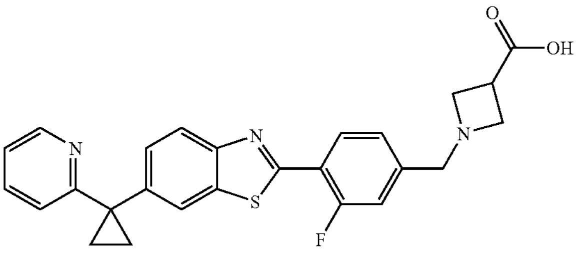

Step 1

Triethylamine (0.32 mL, 2.28 mmol), 1,3-(bis[diphenylphosphino]propane) dichloropalladium(II) (0.051 g, 0.076 mmol), and 2-(4-(1,3-dioxan-2-yl)-2-fluorophenyl)-6- bromobenzo[d]thiazole (0.75 g, 1.90 mmol) were mixed in DMF:THF:MeOH (2:7:2, 11 mL total volume) in a heavy-walled pressure tube. The tube was placed under CO atmosphere (20 psi) and then heated to 95° C. for 16 h. The mixture was cooled to RT and EtOAc (5 mL) was added. The suspension was filtered and the collected solid was washed with EtOAc. The solid obtained was then partitioned between DCM and water, the layers were separated, and the organic layer was dried ($MgSO_4$) and concentrated under vacuum to give methyl 2-(4-(1,3-dioxan-2-yl)-2-fluorophenyl)benzo[d]thiazole-6-carboxylate as a white solid.

Step 2

Lithium hydroxide (1M in $H_2O$, 0.80 mL, 0.80 mmol) and methyl 2-(4-(1,3-dioxan-2-yl)-2-fluorophenyl)benzo[d]thiazole-6-carboxylate (0.25 g, 0.67 mmol) were stirred in THF (5 mL) for 3 d. The reaction mixture was concentrated under vacuum, the resulting oil was dissolved in a minimum amount of water, and the solution was made acidic with 5 N HCl (aq). The resulting suspension was filtered and the collected solid was dried to give 2-(4-(1,3-dioxan-2-yl)-2-fluorophenyl) benzo[d]thiazole-6-carboxylic acid an off-white solid. MS (ESI) m/z: Calculated: 359.1; Observed: 360.4 ($M^+$+1).

Step 3

HBTU (0.80 g, 2.11 mmol) was added to a solution of di-isopropylethylamine (0.61 mL, 3.52 mmol), N,O-dimethylhydroxylamine hydrochloride (0.21 g, 2.11 mmol), and 2-(4-(1,3-dioxan-2-yl)-2-fluorophenyl)benzo[d]thiazole-6-carboxylic acid (0.51 g, 1.41 mmol) in DMF (7 mL). The reaction mixture was stirred for 30 min, diluted with water, and extracted with EtOAc three times. The combined extracts were dried ($MgSO_4$), concentrated under vacuum, and purified by silica gel chromatography to give 2-(4-(1,3-dioxan-2-yl)-2-fluorophenyl)-N-methoxy-N-methylbenzo[d]thiazole-6-carboxamide as an oil. MS (ESI) m/z: Calculated: 402.1; Observed: 403.1 ($M^+$+1).

Step 4

2-Pyridylmagnesium chloride (3.92 mL, 2.84 mmol, solution in THF) was added to a solution of 2-(4-(1,3-dioxan-2-yl)-2-fluorophenyl)-N-methoxy-N-methylbenzo[d]thiazole-6-carboxamide (0.52 g, 1.29 mmol) in THF (2 mL) and the reaction mixture was stirred for 30 min. Satd. $NH_4Cl$ (aq) was added and the mixture was extracted with DCM three times. The combined extracts were dried ($MgSO_4$) and concentrated under vacuum to give (2-(4-(1,3-dioxan-2-yl)-2-fluorophenyl)benzo[d]thiazol-6-yl)(pyridine-2-yl)methanone as a yellow solid. MS (ESI) m/z: Calculated: 420.1; Observed: 421.0 ($M^+$+1).

Step 4 n-Butyllithium (2.5 M in hexanes, 1.80 mL, 4.50 mmol) was added to a suspension of methyltriphenylphosphonium bromide (1.78 g, 5.00 mmol) in THF (10 mL) at −78° C. and the mixture was warmed to 0° C. over 30 min. The suspension (1 mL, about 3 equiv Wittig reagent) was added to a suspension of (2-(4-(1,3-dioxan-2-yl)-2-fluorophenyl)-benzo[d]thiazol-6-yl)(pyridine-2-yl)methanone (0.09 g, 0.21 mmol) in THF (1 mL) and the mixture was stirred for 16 h at RT. The solvent was remove under vacuum and the resulting oil was purified by silica gel chromatography to give 2-(4-(1,3-dioxan-2-yl)-2-fluorophenyl)-6-(1-(pyridin-2-yl)vinyl)benzo[d]thiazole as a white solid. MS (ESI) m/z: Calculated: 418.1; Observed: 419.1 ($M^+$+1).

Step 5

Potassium t-butoxide (36 mg, 0.32 mmol) was added to a solution of trimethyl-sulfoxonium iodide (440 mg, 0.48 mmol) in DMSO to make a 1M solution of ylide. This reaction mixture was stirred for 10 min at RT, then a portion of it (0.64 mL, 0.64 mmol) was added to a solution of 2-(4-(1,3-dioxan-2-yl)-2-fluorophenyl)-6-(1-(pyridine-2-yl)vinyl)-benzo[d]thiazole (134 mg, 0.32 mmol) in THF (0.5 mL). The reaction mixture was stirred overnight, EtOAc was added, and the mixture was washed with water several times, then dried over $MgSO_4$. After concentrating under vacuum, the resulting oil was purified by silica gel chromatography to give 2-(4-(1,3-dioxan-2-yl)-2-fluorophenyl)-6-(1-(pyridine-2-yl)-cyclopropyl)benzo[d]thiazole. MS (ESI) m/z: Calculated: 432.1; Observed: 433.1 ($M^+$+1).

Step 6

2-(4-(1,3-Dioxan-2-yl)-2-fluorophenyl)-6-(1-(pyridine-2-yl)cyclopropyl)benzo[d]-thiazole (38 mg, 0.088 mmol) was stirred in THF (1 mL) and 5 N HCl (aq., 0.2 mL) at 50° C. for 2 h. The reaction mixture was cooled to RT, neutralized with satd. $NaHCO_3$, and extracted with EtOAc three times. The organic extracts were dried ($MgSO_4$) and concentrated to give 3-fluoro-4-(6-(1-(pyridine-2-yl)cyclopropyl)benzo[d]thiazol-2-yl)benzaldehyde as a yellow solid. MS (ESI) m/z: Calculated: 374.1; Observed: 375.0 ($M^+$+1).

Step 7

Methyl 1-((3-fluoro-4-(6-(1-(pyridin-2-yl)cyclopropyl)benzo[d]thiazol-2-yl)phenyl)-methyl)azetidine-3-carboxylate was prepared according to general procedure for reductive amination of aldehydes. Light yellow solid. MS (ESI) m/z: Calculated: 473.2; Observed: 474.1 ($M^+$+1).

Step 8

1-((3-Fluoro-4-(6-(1-(pyridin-2-yl)cyclopropyl)benzo[d]thiazol-2-yl)phenyl)methyl)-azetidine-3-carboxylic acid was prepared according to general procedure for hydrolysis of esters except lithium hydroxide was used as base. White solid. MS (ESI) m/z: Calculated: 459.1; Observed: 460.1 ($M^+$+1).

Reference T

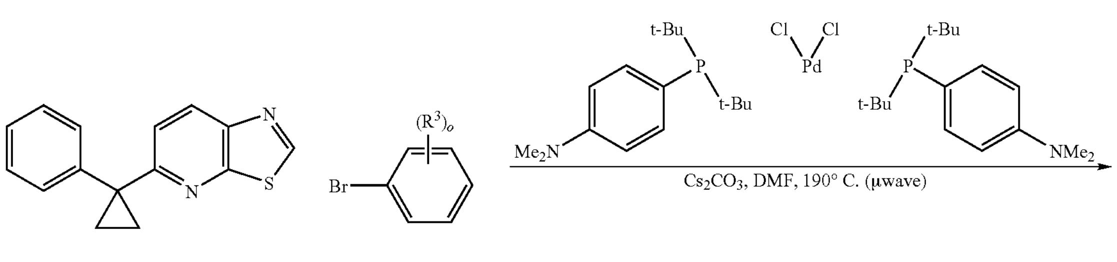

-continued

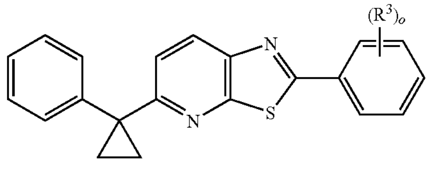

General Procedure for azabenzothiazole 2-arylation:

A mixture of 5-(1-phenylcyclopropyl)thiazolo[5,4-b]pyridine (1 mmol), aryl bromide (1.2-2.2 mmol), $PdCl_2$(AmPhos)$_2$ (0.05 mmol), and cesium carbonate (3.0 mmol) in a microwave vial was taken up in DMF (10 mL). The resulting suspension was sparged with argon, the tube was sealed, and the reaction mixture was heated at 190° C. for 0.5-1.5 h. The reaction mixture was then partitioned between EtOAc (100 mL) and water (20 mL). The organic layer was separated and sequentially washed with water and brine, then dried over sodium sulfate, filtered, and concentrated in vacuo. Purification by silica gel chromatography or HPLC provided the desired product.

Reference U

Oxidative Condensation of 3-Aminopyridine-2-thione with Aryl Aldehydes

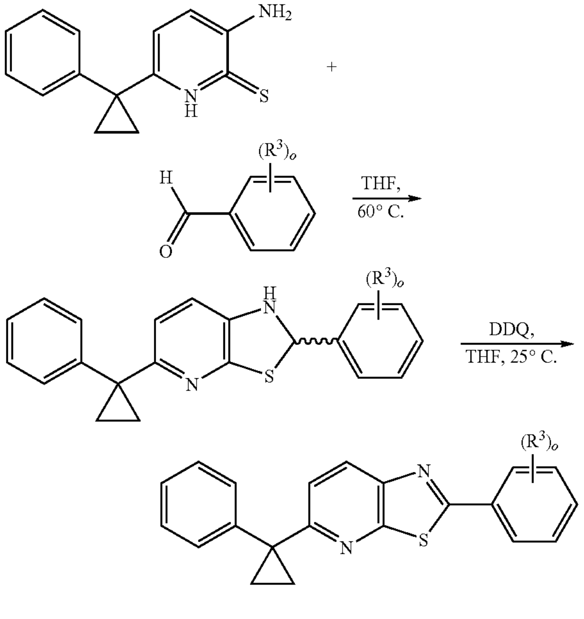

General procedure for Oxidative Condensation of 3-aminopyridine-2-thione with Aryl Aldehydes:

A mixture of 3-amino-6-(1-phenylcyclopropyl)pyridine-2(1H)-thione (1 mmol) and aryl aldehyde (0.95-1 mmol) in THF (10 mL) was stirred at 25° C. for 1 h. DDQ (1.05 mmol) was then added, and the resulting solution was stirred at 25° C. for 10 min. The reaction solution was then partitioned between EtOAc (100 mL) and sat. aq. $NaHCO_3$ (40 mL). The organic layer was separated and sequentially washed with sat. aq. $NaHCO_3$ (40 mL) and brine (40 mL), then dried over $Na_2SO_4$ and concentrated in vacuo. Purification by silica gel chromatography provided the desired product.

Reference V

Condensation of 3-Aminopyridine-2-thione with Aryl Acid Chlorides

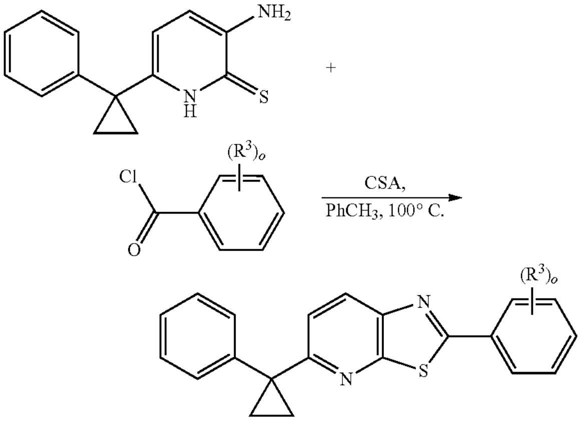

General Procedure for the Condensation of 3-aminopyridine-2-thione with Aryl Acid Chlorides:

Aryl acid chloride (1 mmol) was added to a suspension of 3-amino-6-(1-phenylcyclopropyl)pyridine-2(1H)-thione (1 mmol) in $PhCH_3$ (10 mL), and the resulting reaction mixture was stirred at 100° C. for 10 min. (±)-10-Camphorsulfonic acid (0.1-0.5 mmol) was then added, and the resulting mixture was heated at 100° C. for 4 h. The reaction solution was then cooled to 25° C. and concentrated onto silica gel. Purification by silica gel chromatography provided the desired product.

Example 63

Synthesis of 2-(4-(azetidin-1-ylmethyl)-3,5-dimethylphenyl)-5-(1-phenyl-cyclopropyl)thiazolo[5,4-b]pyridine

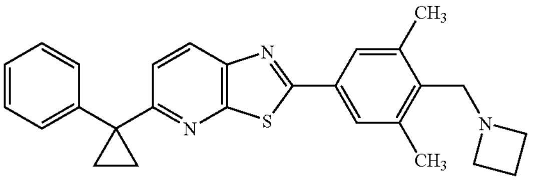

Reaction of 2,6-dimethyl-4-(5-(1-phenylcyclopropyl)thiazolo[5,4-b]pyridin-2-yl)benzaldehyde (29.3 mg, 76 μmol) and azetidine (18 μL, 267 μmol) according to Reference R and the general procedure for reductive amination gave 2-(4-(azetidin-1-ylmethyl)-3,5-dimethylphenyl)-5-(1-phenylcyclopropyl)thiazolo[5,4-b]pyridine as a light yellow solid. MS (ESI) m/z: Calculated: 425.2; Observed: 426.1 ($M^{+}$+1). 3-(Azetidin-1-yl)-N-(2,6-dimethyl-4-(5-(1-phenylcyclopropyl)thiazolo[5,4-b]pyridin-2-yl)benzyl)propan-1-amine was also obtained from this reaction as a light yellow solid. MS (ESI) m/z: Calculated: 482.3; Observed: 483.2 ($M^{+}$+1).

Example 64

Synthesis of 1-(4-(5-(1-phenylcyclopropyl)thiazolo[5,4-b]pyridin-2-yl)benzyl)azetidine-3-carboxylic acid

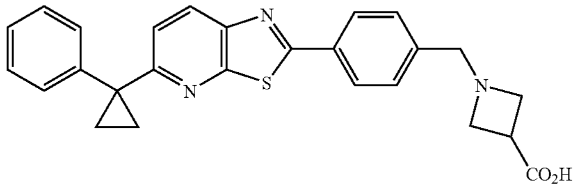

Step 1

Reaction of 3-amino-6-(1-phenylcyclopropyl)pyridine-2(1H)-thione (55.6 mg, 229 μmol) and 4-formylbenzonitrile (29 mg, 218 μmol) according to Reference U and the general procedure for oxidative condensation of 3-aminopyridine-2-thione with aryl aldehydes gave 4-(5-(1-phenylcyclopropyl)thiazolo[5,4-b]pyridin-2-yl)benzonitrile as a light yellow solid. MS (ESI) m/z: Calculated: 353.1; Observed: 354.1 ($M^{+}$+1).

Step 2

DIBAL-H (1.0M in hexanes) (185 μl, 0.185 mmol) was added to a solution of 4-(5-(1-phenylcyclopropyl)thiazolo[5,4-b]pyridin-2-yl)benzonitrile (59.6 mg, 0.169 mmol) in DCM (2.7 mL) at 25° C., and the resulting solution was stirred at 25° C. for 45 min. Sat. aq. Na/K tartrate solution (3.0 mL) was added, and the resulting mixture was vigorously stirred for 15 min, then partitioned between DCM (40 mL) and sat. aq. Na/K tartrate solution (10 mL). The organic layer was separated, and the aqueous layer was extracted with DCM. The combined organic extracts were dried over $MgSO_4$, filtered, and concentrated in vacuo. Chromatographic purification of the residue (silica gel, 0-100% EtOAc/Hexanes) provided 4-(5-(1-phenylcyclopropyl)thiazolo[5,4-b]pyridin-2-yl)benzaldehyde as a light yellow solid. MS (ESI) m/z: Calculated: 356.1; Observed: 357.1 ($M^{+}$+1).

Step 3

Reaction of 4-(5-(1-phenylcyclopropyl)thiazolo[5,4-b]pyridin-2-yl)benzaldehyde (38.9 mg, 0.109 mmol) and azetidine-3-carboxylic acid (55 mg, 0.546 mmol) according to Reference R and the general procedure for reductive amination to give 1-(4-(5-(1-phenylcyclopropyl)-thiazolo[5,4-b]pyridin-2-yl)benzyl)azetidine-3-carboxylic acid as a white solid. MS (ESI) m/z: Calculated: 441.2; Observed: 442.1 ($M^{+}$+1).

(4-(5-(1-Phenylcyclopropyl)thiazolo[5,4-b]pyridin-2-yl)phenyl)methanol was also obtained from this reaction as a white solid. MS (ESI) m/z: Calculated: 358.1; Observed: 359.1 ($M^{+}$+1)

Example 65

Synthesis of 3-(3-fluoro-4-(5-(1-phenylcyclopropyl)thiazolo[5,4-b]pyridin-2-yl)phenylamino)propanoic acid

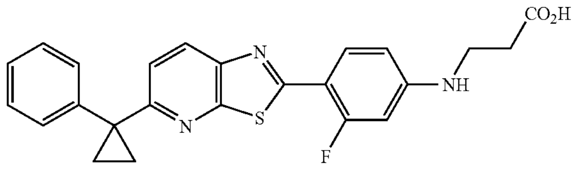

Step 1

Reaction of 3-amino-6-(1-phenylcyclopropyl)pyridine-2(1H)-thione (50.0 mg, 206 μmol) and 4-bromo-2-fluorobenzaldehyde (44.0 mg, 217 μmol) according to Reference U and the general procedure for oxidative condensation of 3-aminopyridine-2-thione with aryl aldehydes gave 2-(4-bromo-2-fluorophenyl)-5-(1-phenylcyclopropyl)thiazolo[5,4-b]pyridine as a light yellow solid. MS (ESI) m/z: Calculated: 424.0; Observed: 424.9 ($M^{+}$+1).

Step 2

A mixture of 2-(4-bromo-2-fluorophenyl)-5-(1-phenylcyclopropyl)thiazolo[5,4-b]pyridine (76.8 mg, 0.181 mmol), tert-butyl 3-aminopropanoate hydrochloride (43 mg, 0.235 mmol), $Pd_2(dba)_3$ (4.1 mg, 4.5 μmol), Xantphos (10 mg, 18 μmol) and sodium tert-butoxide (45 mg, 0.469 mmol) in toluene (1.9 mL) was heated under argon at 80° C. for 18 h, then at 130° C. (microwave) for 30 min, then at 150° C. (microwave) for 30 min. The reaction mixture was then cooled to 25° C. and concentrated onto silica gel. Chromatographic purification (silica gel, 0-50% EtOAc/hexanes) furnished tert-butyl 3-(3-fluoro-4-(5-(1-phenylcyclopropyl)thiazolo[5,4-b]pyridin-2-yl)phenylamino)-propanoate as a yellow solid. MS (ESI) m/z: Calculated: 489.2; Observed: 490.1 ($M^{+}$+1).

Step 3

2,2,2-Trifluoroacetic acid (360 μl, 4.67 mmol) was added to a solution of tert-butyl 3-(3-fluoro-4-(5-(1-phenylcyclopropyl)thiazolo[5,4-b]pyridin-2-yl)phenylamino)propanoate (46.5 mg, 0.095 mmol) in DCM (2.0 mL) at 25° C., and the resulting solution was stirred at 25° C. for 19 h. The reaction solution was then concentrated in vacuo, and the residue was taken up in DMSO (2.0 mL) and purified by rpHPLC (10-100% $CH_3CN$/water+0.1% TFA) to provide 3-(3-fluoro-4-(5-(1-phenylcyclopropyl)thiazolo[5,4-b]pyridin-2-yl)phenylamino)propanoic acid as a yellow solid. MS (ESI) m/z: Calculated: 433.1; Observed: 434.0 ($M^{+}$+1).

Example 66

Synthesis of 4-(3-fluoro-4-(5-(1-phenylcyclopropyl) thiazolo[5,4-b]pyridin-2-yl)phenylamino)butanoic acid

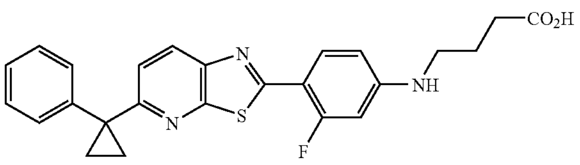

Step 1

Reaction of 3-amino-6-(1-phenylcyclopropyl)pyridine-2(1H)-thione (27.3 mg, 113 μmol) and 2,4-difluorobenzoyl chloride (13.8 μl, 113 μmol) according to Reference V and the general procedure for the condensation of 3-aminopyridine-2-thione with aryl acid chlorides to give 2-(2,4-difluorophenyl)-5-(1-phenylcyclopropyl)thiazolo[5,4-b]pyridine as a white solid. MS (ESI) m/z: Calculated: 364.1; Observed: 365.0 ($M^+$+1).

Step 2

Sodium hydride (60% w/w in mineral oil) (3.7 mg, 93 μmol) was added to a mixture of 2-(2,4-difluorophenyl)-5-(1-phenylcyclopropyl)thiazolo[5,4-b]pyridine (28.2 mg, 77 μmol) and pyrrolidin-2-one (5.9 μl, 77 μmol) in DMF (0.8 mL) and the resulting mixture was stirred at 25° C. for 30 min, then heated at 40° C. for 15 h. Additional pyrrolidin-2-one (5.9 μl, 77 μmol) and sodium hydride (60% w/w in mineral oil) (3.7 mg, 93 μmol) were then added, and the resulting mixture was heated at 60° C. for 1 h. The reaction mixture was then cooled to 25° C. and partitioned between EtOAc (70 mL) and sat. aq. ammonium chloride (30 mL). The organic layer was separated and sequentially washed with water and brine, then dried over sodium sulfate, filtered, and concentrated in vacuo. Chromatographic purification of the residue (silica gel, 0-100% EtOAc-Hexanes) provided 4-(3-fluoro-4-(5-(1-phenylcyclopropyl)thiazolo[5,4-b]pyridin-2-yl)phenylamino)butanoic acid as a light yellow solid. MS (ESI) m/z: Calculated: 447.1; Observed: 448.2 ($M^+$+1).

Example 67

Synthesis of (R)-3-(2,6-dimethyl-4-(5-(1-phenylcyclopropyl)thiazolo[5,4-b]pyridin-2-yl)phenoxy)propane-1,2-diol

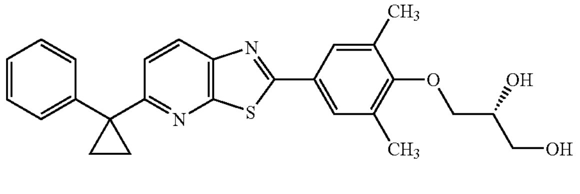

Step 1

2-Methyl-2-butene (3.31 mL, 31.2 mmol) and sodium chlorite (282 mg, 3.12 mmol) were sequentially added to a mixture of 4-(benzyloxy)-3,5-dimethyl-benzaldehyde (455 μl, 2.081 mmol) and potassium dihydrogen phosphate (425 mg, 3.12 mmol) in 1:1 water/t-BuOH (8.0 mL), and the resulting mixture was stirred at 25° C. for 4 h. Additional potassium dihydrogen phosphate (991 mg, 7.28 mmol) and sodium chlorite (659 mg, 7.28 mmol) were then sequentially added, and the resulting mixture was stirred at 25° C. for 15 h. The reaction mixture was subsequently partitioned between EtOAc (120 mL) and 0.02N aq. HCl (50 mL). The aqueous layer was extracted with EtOAc and the combined organic layers were dried over $Na_2SO_4$, filtered, and concentrated in vacuo. Chromatographic purification of the residue (silica gel, 0-100% EtOAc/Hexanes) gave 4-(benzyloxy)-3,5-dimethylbenzoic acid as a white solid. MS (ESI) m/z: Calculated: 256.1; Observed: 257.2 ($M^+$+1).

Step 2

A mixture of 4-(benzyloxy)-3,5-dimethylbenzoic acid (238.0 mg, 929 μmol) and thionyl chloride (2.5 mL, 34.25 mmol) was heated at 70° C. for 1 h and then concentrated in vacuo. 3-Amino-6-(1-phenylcyclopropyl)pyridine-2(1H)-thione (225 mg, 0.929 mmol) was added to the residue, and the resulting mixture was and heated in toluene (9.0 mL) at 100° C. for 10 min. (±)-10-Camphorsulfonic acid (194 mg, 836 μmol) was subsequently added, and the resulting mixture was heated at 100° C. for 30 min. The reaction solution was then cooled to 25° C. and concentrated onto silica gel. Chromatographic purification (silica gel, 0-40% ethyl ether/hexanes) provided 2-(4-(benzyloxy)-3,5-dimethylphenyl)-5-(1-phenylcyclopropyl)thiazolo[5,4-b]pyridine as a white solid. MS (ESI) m/z: Calculated: 462.2; Observed: 463.2 ($M^+$+1).

Step 3

Boron tribromide (1.0M in DCM; 963 μl, 0.963 mmol) was added to a solution of 2-(4-(benzyloxy)-3,5-dimethylphenyl)-5-(1-phenylcyclopropyl)thiazolo[5,4-b]pyridine (247.4 mg, 0.535 mmol) in DCM (24.0 mL) at −78° C., and the resulting solution was stirred at −78° C. for 5 min. Excess $BBr_3$ was then quenched by the addition of water (50 mL), and the resulting mixture was diluted with DCM (100 mL) and allowed to warm to 25° C. The organic layer was separated, dried over sodium sulfate, filtered, and concentrated in vacuo. Chromatographic purification of the residue (silica gel, 0-100% ethyl ether/hexanes) afforded 2,6-dimethyl-4-(5-(1-phenyl-cyclopropyl)thiazolo[5,4-b]pyridin-2-yl)phenol as a white solid. MS (ESI) m/z: Calculated: 372.1; Observed: 373.2 ($M^+$+1).

Step 4

A mixture of 2,6-dimethyl-4-(5-(1-phenylcyclopropyl) thiazolo[5,4-b]pyridin-2-yl)phenol (35.1 mg, 94 μmol) and cesium fluoride (0.72 mg, 4.7 μmol) in anhydrous DMF (0.5 mL) was stirred at 25° C. for 1 h. (R)-(+)-glycidol (98% ee) (6.6 μl, 99 μmol) was then added, and the resulting mixture was heated under argon at 80° C. for 2 d. Additional (R)-(+)-glycidol (6.56 μl, 98.9 μmol) was then added, and the reaction mixture was heated at 80° C. for 18 h. The reaction mixture was subsequently cooled to 25° C., filtered through Celite, diluted with DMSO (1.5 mL), and purified by rpHPLC (10-100% $CH_3CN$/water+0.1% TFA) to provide (R)-3-(2,6-dimethyl-4-(5-(1-phenylcyclopropyl)thiazolo[5,4-b]pyridin-2-yl)phenoxy)propane-1,2-diol as a white solid. MS (ESI) m/z: Calculated: 446.2; Observed: 447.0 ($M^+$+1).

Example 68

Synthesis of (S)-3-(2,6-dimethyl-4-(5-(1-phenylcyclopropyl)thiazolo[5,4-b]pyridin-2-yl)phenoxy)propane-1,2-diol

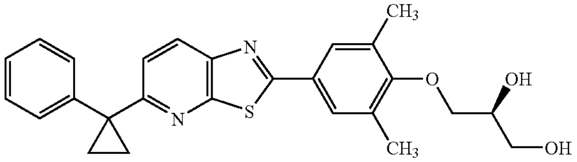

A mixture of 2,6-dimethyl-4-(5-(1-phenylcyclopropyl)thiazolo[5,4-b]pyridin-2-yl)phenol (36.7 mg, 99 μmol) and cesium fluoride (1.5 mg, 9.9 μmol) in anhydrous DMF (0.5 mL) was stirred at 25° C. for 1 h. (S)-(−)-glycidol (14 μl, 207 μmol) was then added, and the resulting mixture was heated under argon at 80° C. for 7 d. The reaction mixture was subsequently cooled to 25° C., filtered through Celite, diluted with DMSO (1.5 mL), and purified by rpHPLC (10-100% $CH_3CN$/water+0.1% TFA) to provide (S)-3-(2,6-dimethyl-4-(5-(1-phenylcyclopropyl)-thiazolo[5,4-b]pyridin-2-yl)phenoxy)-propane-1,2-diol as a light yellow solid. MS (ESI) m/z: Calculated: 446.2; Observed: 447.2 ($M^+$+1).

Example 69

Synthesis of 3-(4-(5-(1-phenylcyclopropyl)thiazolo[5,4-b]pyridin-2-yl)phenylamino)-propanoic acid

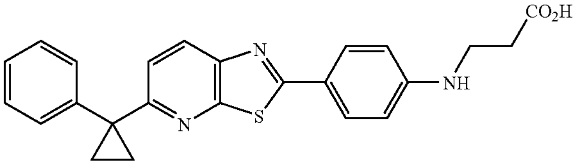

Step 1

Reaction of 3-amino-6-(1-phenylcyclopropyl)pyridine-2(1H)-thione (503.8 mg, 2.079 mmol) and 4-iodobenzoyl chloride (554 mg, 2.079 mmol) according to Reference V and the general procedure for the condensation of 3-aminopyridine-2-thione with aryl acid chlorides gave 2-(4-iodophenyl)-5-(1-phenylcyclopropyl)thiazolo[5,4-b]pyridine as a white solid. MS (ESI) m/z: Calculated: 454.0; Observed: 454.9 ($M^+$+1).

Step 2

Sodium tert-butoxide (21 mg, 0.213 mmol) was added to a mixture of 2-(4-iodophenyl)-5-(1-phenylcyclopropyl)thiazolo[5,4-b]pyridine (40.4 mg, 0.089 mmol), tert-butyl 3-aminopropanoate hydrochloride (19 mg, 0.107 mmol), $Pd_2(dba)_3$ (2.0 mg, 2.2 μmol), and Xantphos (5.1 mg, 8.9 μmol) in toluene (1.0 mL), and the resulting mixutre was heated under argon at 80° C. for 15 h. The reaction mixture was then cooled to 25° C. and concentrated onto silica gel. Chromatographic purificaiton (silica gel, 0-50% EtOAc/hexanes) furnished tert-butyl 3-(4-(5-(1-phenylcyclopropyl)-thiazolo[5,4-b]pyridin-2-yl)phenylamino)propanoate as a yellow oil. MS (ESI) m/z: Calculated: 471.2; Observed: 472.1 ($M^+$+1).

Step 3

2,2,2-Trifluoroacetic acid (217 μl, 2.82 mmol) was added to a solution oftert-butyl 3-(4-(5-(1-phenylcyclopropyl)thiazolo[5,4-b]pyridin-2-yl)phenylamino)propanoate (26.6 mg, 56 μmol) in DCM (1.0 mL) at 25° C., and the resulting solution was stirred at 25° C. for 3.5 h. The reaction mixture was then concentrated in vacuo, and the residue was taken up in DMSO (2.0 mL) and purified by rpHPLC (10-100% $CH_3CN$/water+0.1% TFA) to provide 3-(4-(5-(1-phenylcyclopropyl)thiazolo[5,4-b]pyridin-2-yl)phenylamino)propanoic acid as a yellow solid. MS (ESI) m/z: Calculated: 415.1; Observed: 416.1 ($M^+$+1).

Example 70

Synthesis of (S)-2-(3-fluoro-4-(5-(1-phenylcyclopropyl)thiazolo[5,4-b]pyridin-2-yl)benzylamino)propanoic acid

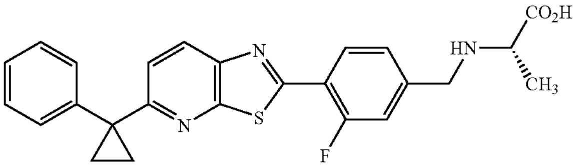

Step 1

Reaction of 3-fluoro-4-(5-(1-phenylcyclopropyl)thiazolo[5,4-b]pyridin-2-yl)benzaldehyde (105.5 mg, 0.282 mmol) and L-alanine tert-butyl ester hydrochloride (51.2 mg, 0.282 mmol) according to Reference R and the general procedure for reductive amination to give (S)-tert-butyl 2-(3-fluoro-4-(5-(1-phenylcyclopropyl)thiazolo[5,4-b]pyridin-2-yl)benzylamino)propanoate as a yellow-orange solid. MS (ESI) m/z: Calculated: 503.2; Observed: 503.8 ($M^+$+1).

Step 2

Trifluoroacetic acid (1.0 mL, 12.98 mmol) was added to a solution of (S)-tert-butyl 2-((3-fluoro-4-(5-(1-phenylcyclopropyl)thiazolo[5,4-b]pyridin-2-yl)phenyl)methylamino)propanoate (140.6 mg, 0.279 mmol) in DCM (2.1 mL) at 25° C., and the resulting mixture was stirred at 25° C. for 16 h. The reaction mixture was then concentrated in vacuo and the brown residue was taken up in DMSO (2.0 mL) and purified by rpHPLC (10-100% $CH_3CN$/water+0.1% TFA) to provide (S)-2-((3-fluoro-4-(5-(1-phenylcyclopropyl)thiazolo[5,4-b]pyridin-2-yl)phenyl)methylamino)-propanoic acid as a light yellow solid. MS (ESI) m/z: Calculated: 447.1; Observed: 448.2 ($M^+$+1).

Example 71

Synthesis of (R)-2-(3-fluoro-4-(5-(1-phenylcyclopropyl)thiazolo[5,4-b]pyridin-2-yl)benzylamino)propanoic acid

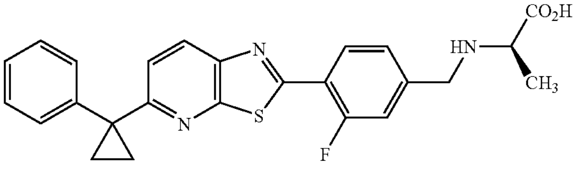

Step 1

Reaction of 3-fluoro-4-(5-(1-phenylcyclopropyl)thiazolo[5,4-b]pyridin-2-yl)benzaldehyde (101.1 mg, 0.270 mmol) and D-alanine tert-butyl ester hydrochloride (49.1 mg, 0.270 mmol) according to Reference R and the general procedure for reductive amination to give (R)-tert-butyl 2-(3-fluoro-4-(5-(1-phenylcyclopropyl)thiazolo[5,4-b]pyridin-2-yl)benzylamino)propanoate as a yellow-orange solid. MS (ESI) m/z: Calculated: 503.2; Observed: 503.8 ($M^+$+1).

Step 2

Trifluoroacetic acid (1.0 mL, 12.98 mmol) was added to a solution of (R)-tert-butyl 2-((3-fluoro-4-(5-(1-phenylcyclopropyl)thiazolo[5,4-b]pyridin-2-yl)phenyl)methylamino) propanoate (135.0 mg, 0.268 mmol) in DCM (2.0 mL) at 25° C., and the resulting mixture was stirred at 25° C. for 16 h. The reaction solution was then concentrated in vacuo, and the brown residue was taken up in DMSO (2.0 mL) and purified by rpHPLC (10-100% $CH_3CN$/water+0.1% TFA) to provide (R)-2-((3-fluoro-4-(5-(1-phenylcyclopropyl)thiazolo[5,4-b]pyridin-2-yl)phenyl)-methylamino)propanoic acid as a light yellow solid. MS (ESI) m/z: Calculated: 447.1; Observed: 448.1 ($M^+$+1).

Example 72

Synthesis of (2S,4R)-4-(4-(5-(1-phenylcyclopropyl)thiazolo[5,4-b]pyridin-2-yl)phenoxy)pyrrolidine-2-carboxylic acid

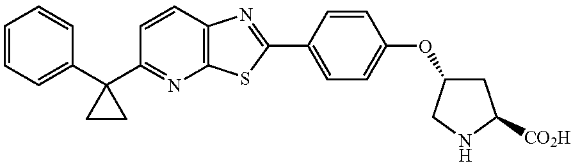

Step 1

Reaction of 3-amino-6-(1-phenylcyclopropyl)pyridine-2(1H)-thione (52.6 mg, 0.217 mmol) and 4-fluorobenzaldehyde (22 µl, 0.206 mmol) according to Reference V and the general procedure for the condensation of 3-aminopyridine-2-thione with aryl acid chlorides gave 2-(4-fluorophenyl)-5-(1-phenylcyclopropyl)thiazolo[5,4-b]pyridine as a white solid. MS (ESI) m/z: Calculated: 346.1; Observed: 347.1 ($M^+$+1).

Step 2

A solution of (2S,4R)-1-(tert-butoxycarbonyl)-4-hydroxypyrrolidine-2-carboxylic acid (162.1 mg, 0.701 mmol) in DMF (4.0 mL) was slowly added to a suspension of sodium hydride (60% w/w in mineral oil) (58 mg, 1.45 mmol) in DMF (4.0 mL), and the resulting mixture was heated at 95° C. for 5 min. 2-(4-Fluorophenyl)-5-(1-phenylcyclopropyl)-thiazolo[5,4-b]pyridine (75.3 mg, 0.217 mmol) was then added, and the resulting solution was heated at 95° C. for 18 h. The reaction mixture was subsequently cooled to 25° C. and diluted with EtOAc (5 mL). Excess NaH was quenched with water (5 mL), and the resulting mixture was diluted with 0.1N aq. HCl (40 mL) and extracted with EtOAc. The combined extracts were sequentially washed with water (50 mL) and brine (50 mL), dried over sodium sulfate, filtered, and concentrated in vacuo to provide (2S,4R)-1-(tert-butoxycarbonyl)-4-(4-(5-(1-phenylcyclopropyl)thiazolo[5,4-b]pyridin-2-yl)phenoxy)pyrrolidine-2-carboxylic acid as a yellow solid. MS (ESI) m/z: Calculated: 557.2; Observed: 557.8 ($M^+$+1).

Step 3

2,2,2-Trifluoroacetic acid (0.5 mL, 6.49 mmol) was added to a solution of (2S,4R)-1-(tert-butoxycarbonyl)-4-(4-(5-(1-phenylcyclopropyl)thiazolo[5,4-b]pyridin-2-yl)phenoxy) pyrrolidine-2-carboxylic acid (130.0 mg, 0.233 mmol) in DCM (4.5 mL) and the resulting solution was stirred at 25° C. for 2 h. The reaction mixture was then concentrated in vacuo, and the residue was taken up in DMSO (2.0 mL) and purified by rpHPLC (10-100% $CH_3CN/H_2O$+0.1% TFA) to provide (2S,4R)-4-(4-(5-(1-phenylcyclopropyl)thiazolo[5,4-b]pyridin-2-yl)phenoxy)pyrrolidine-2-carboxylic acid as a white solid. MS (ESI) m/z: Calculated: 457.1; Observed: 458.1 ($M^+$+1).

Example 73

Synthesis of 1-(3-fluoro-4-(5-(1-phenylcyclopropyl)thiazolo[5,4-b]pyridin-2-yl)benzylamino)cyclopropanecarboxylic acid

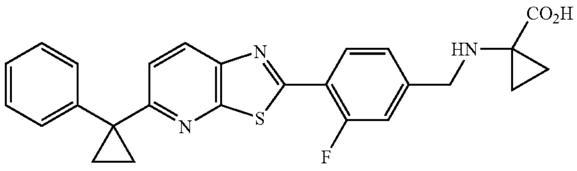

Step 1

Reaction of 3-fluoro-4-(5-(1-phenylcyclopropyl)thiazolo[5,4-b]pyridin-2-yl)benzaldehyde (98.0 mg, 0.262 mmol) and methyl 1-aminocyclopropanecarboxylate hydrochloride (40 mg, 0.262 mmol) according to Reference R and the general procedure for reductive amination to give methyl 1-(3-fluoro-4-(5-(1-phenylcyclopropyl)-thiazolo[5,4-b]pyridin-2-yl)benzylamino)-cyclopropanecarboxylate as a tan solid. MS (ESI) m/z: Calculated: 473.2; Observed: 474.1 ($M^+$+1).

Step 2

Synthesized from methyl 1-((3-fluoro-4-(5-(1-phenylcyclopropyl)thiazolo[5,4-b]pyridin-2-yl)phenyl)methylamino) cyclopropanecarboxylate (117.2 mg, 0.247 mmol) according to Reference R and the general procedure for ester hydrolysis to give 1-(3-fluoro-4-(5-(1-phenylcyclopropyl)thiazolo[5,4-b]pyridin-2-yl)benzylamino)-cyclopropanecarboxylic acid as a light yellow solid. MS (ESI) m/z: Calculated: 459.1; Observed: 460.1 ($M^+$+1).

Example 74

Synthesis of 2-(3-fluoro-4-(5-(1-phenylcyclopropyl)thiazolo[5,4-b]pyridin-2-yl)-benzylamino)-2-methylpropanoic acid

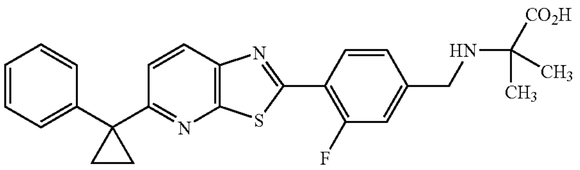

Step 1

Reaction of 3-fluoro-4-(5-(1-phenylcyclopropyl)thiazolo[5,4-b]pyridin-2-yl)benzaldehyde (100.3 mg, 0.268 mmol) and methyl 2-amino-2-methylpropanoate hydrochloride (41 mg, 0.268 mmol) according to Reference R and the general procedure for reductive amination to give methyl 2-(3-fluoro-4-(5-(1-phenylcyclopropyl)-thiazolo[5,4-b]pyridin-2-yl)benzylamino)-2-methylpropanoate as a yellow-orange oil. MS (ESI) m/z: Calculated: 475.2; Observed: 476.1 ($M^{+}$+1).

Step 2

Synthesized from methyl 2-((3-fluoro-4-(5-(1-phenylcyclopropyl)thiazolo[5,4-b]pyridin-2-yl)phenyl)methylamino)-2-methylpropanoate (122.8 mg, 258 μmol) according to Reference R and the general procedure for ester hydrolysis to give 2-(3-fluoro-4-(5-(1-phenylcyclopropyl)thiazolo[5,4-b]pyridin-2-yl)benzylamino)-2-methylpropanoic acid as a white solid. MS (ESI) m/z: Calculated: 461.1; Observed: 462.0 ($M^{+}$+1).

Example 75

Synthesis of (S)-1-(3-fluoro-4-(5-(1-phenylcyclopropyl)thiazolo[5,4-b]pyridin-2-yl)benzyl)azetidine-2-carboxylic acid

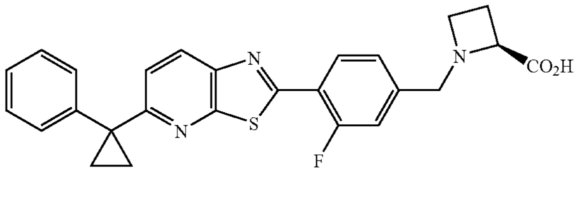

Reaction of 3-fluoro-4-(5-(1-phenylcyclopropyl)thiazolo[5,4-b]pyridin-2-yl)benzaldehyde (93.3 mg, 0.249 mmol) and L-azetidine-2-carboxylic acid (76 mg, 0.748 mμmol) according to Reference R and the general procedure for reductive amination gave (S)-1-(3-fluoro-4-(5-(1-phenylcyclopropyl)thiazolo[5,4-b]pyridin-2-yl)benzyl)-azetidine-2-carboxylic acid as a light yellow solid. MS (ESI) m/z: Calculated: 459.1; Observed: 460.0 ($M^{+}$+1).

Example 76

Synthesis of (R)-1-(3-fluoro-4-(5-(1-phenylcyclopropyl)thiazolo[5,4-b]pyridin-2-yl)-benzyl)azetidine-2-carboxylic acid

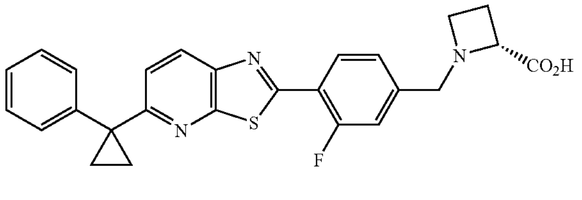

Reaction of 3-fluoro-4-(5-(1-phenylcyclopropyl)thiazolo[5,4-b]pyridin-2-yl)benzaldehyde (106.1 mg, 0.283 mmol) and (R)-azetidine-2-carboxylic acid (86 mg, 0.850 mmol) according to Reference R and the general procedure for reductive amination gave (R)-1-(3-fluoro-4-(5-(1-phenylcyclopropyl)thiazolo[5,4-b]pyridin-2-yl)benzyl)azetidine-2-carboxylic acid as a brown solid. MS (ESI) m/z: Calculated: 459.1; Observed: 460.1 ($M^{+}$+1).

Example 77

Synthesis of (s)-1-(3-fluoro-4-(5-(1-phenylcyclopropyl)thiazolo[5,4-b]pyridin-2-yl)-benzyl)pyrrolidine-2-carboxylic acid

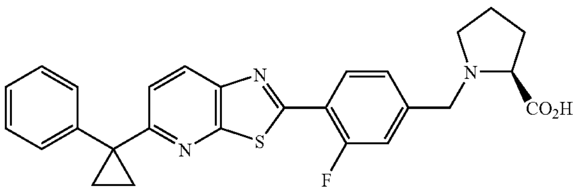

Reaction of 3-fluoro-4-(5-(1-phenylcyclopropyl)thiazolo[5,4-b]pyridin-2-yl)benzaldehyde (101.1 mg, 0.270 mmol) and L-(−)-proline (93.3 mg, 0.810 mμmol) according to Reference R and the general procedure for reductive amination to give (S)-1-(3-fluoro-4-(5-(1-phenylcyclopropyl)thiazolo[5,4-b]pyridin-2-yl)benzyl)pyrrolidine-2-carboxylic acid as a light yellow solid. MS (ESI) m/z: Calculated: 473.2; Observed: 474.2 ($M^{+}$+1).

Example 78

Synthesis of (R)-1-(3-fluoro-4-(5-(1-phenylcyclopropyl)thiazolo[5,4-b]pyridin-2-yl)-benzyl)pyrrolidine-2-carboxylic acid

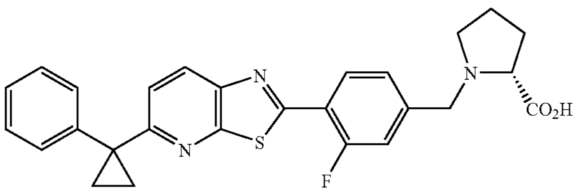

Reaction of 3-fluoro-4-(5-(1-phenylcyclopropyl)thiazolo[5,4-b]pyridin-2-yl)benzaldehyde (96.1 mg, 0.257 mmol) and D-(+)-proline (88.6 mg, 0.770 mmol) according to Reference R and the general procedure for reductive amination to give (R)-1-(3-fluoro-4-(5-(1-phenylcyclopropyl)thiazolo[5,4-b]pyridin-2-yl)benzyl)pyrrolidine-2-carboxylic acid as a light yellow solid. MS (ESI) m/z: Calculated: 473.2; Observed: 474.2 ($M^{+}$+1).

Example 79

Synthesis of 2-(1-(3-fluoro-4-(5-(1-phenylcyclopropyl)thiazolo[5,4-b]pyridin-2-yl)-benzyl)azetidin-3-yl)acetic acid

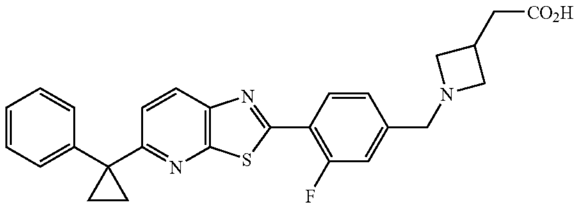

Reaction of 3-fluoro-4-(5-(1-phenylcyclopropyl)thiazolo[5,4-b]pyridin-2-yl)benzaldehyde (100.0 mg, 0.267 mmol) and 2-(azetidin-3-yl)acetic acid trifluoroacetic acid (88.1 mg, 0.384 mmol) according to Reference R and the general procedure for reductive amination to give 2-(1-(3-fluoro-4-(5-(1-phenylcyclopropyl)thiazolo[5,4-b]pyridin-2-yl)benzyl)azetidin-3-yl)acetic acid as a tan solid. MS (ESI) m/z: Calculated: 473.2; Observed: 474.1 ($M^+$+1).

Example 80

Synthesis of 5-(1-phenylcyclopropyl)-2-(1,2,3,4-tetrahydroisoquinolin-6-yl)thiazolo-[5,4-b]pyridine

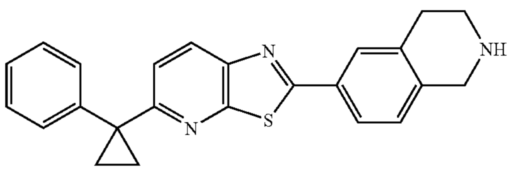

DMF (27.8 μL, 0.358 mmol) was added to a solution of 2-(tert-butoxycarbonyl)-1,2,3,4-tetrahydroisoquinoline-6-carboxylic acid (198.6 mg, 0.716 mmol) and oxalyl chloride (66 μL, 0.757 mmol) in DCM (7.0 mL), and the resulting mixture was stirred at 25° C. for 4 h. The reaction mixture was then concentrated in vacuo and 3-amino-6-(1-phenylcyclopropyl)pyridine-2(1H)-thione (175 mg, 0.720 mmol) was added. The resulting mixture was taken up in toluene (7.0 mL) and stirred at 25° C. for 5 min then at 100° C. for 1.5 h. (±)-10-camphorsulfonic acid (184 mg, 0.792 mmol) was then added, and the resulting mixture was heated at 100° C. for 1.5 h. The reaction mixture was subsequently cooled to 25° C. and purified by column chromatography (silica gel, 0-10% MeOH/DCM) to provide crude product, which was taken up in DCM (100 mL) and sequentially washed with sat. aq. $NaHCO_3$ and brine. The organic layer was separated, dried over sodium sulfate, filtered, and concentrated in vacuo to provide 5-(1-phenylcyclopropyl)-2-(1,2,3,4-tetrahydroisoquinolin-6-yl)thiazolo[5,4-b]pyridine as a light yellow solid. MS (ESI) m/z: Calculated: 383.1; Observed: 384.1 ($M^+$+1).

Example 81

Synthesis of 3-(6-(5-(1-phenylcyclopropyl)thiazolo[5,4-b]pyridin-2-yl)-3,4-dihydroisoquinolin-2(1H)-yl)propanoic acid

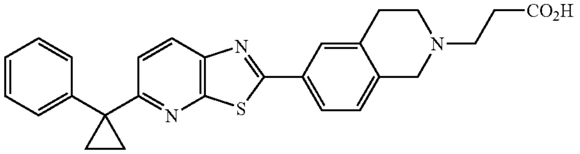

A mixture of 5-(1-phenylcyclopropyl)-2-(1,2,3,4-tetrahydroisoquinolin-6-yl)thiazolo[5,4-b]pyridine (28.1 mg, 0.073 mmol), acrylic acid (7.54 μl, 0.110 mmol), and DIPEA (1.276 μl, 7.33 μmol) in methanol (0.80 mL) was stirred at 63° C. for 1 d. The resulting suspension was then concentrated in vacuo, and the residue was taken up in DMSO (2.0 mL)+TFA (50 μL) and purified by rpHPLC (10-100% $CH_3CN/H_2O$+0.1% TFA) to provide 3-(6-(5-(1-phenylcyclopropyl)thiazolo[5,4-b]pyridin-2-yl)-3,4-dihydroisoquinolin-2(1H)-yl)propanoic acid as a yellow solid. MS (ESI) m/z: Calculated: 455.2; Observed: 456.1 ($M^+$+1).

Example 82

Synthesis of 2-(6-(5-(1-phenylcyclopropyl)thiazolo[5,4-b]pyridin-2-yl)-3,4-dihydroisoquinolin-2(1H)-yl)acetic acid

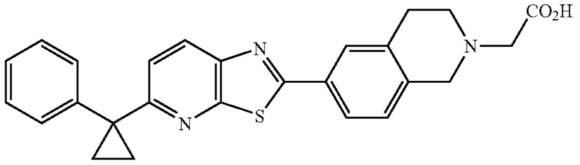

Step 1

A mixture of 5-(1-phenylcyclopropyl)-2-(1,2,3,4-tetrahydroisoquinolin-6-yl)thiazolo[5,4-b]pyridine (97 mg, 0.252 mmol), triethylamine (0.053 mL, 0.377 mmol), and methyl 2-bromoacetate (0.024 mL, 0.254 mmol) in DCM (2.0 mL) was stirred at 25° C. for 30 min. Additional methyl 2-bromoacetate (0.024 mL, 0.254 mmol) was then added, and the resulting mixture was stirred at 25° C. for 30 min. The resulting suspension was then concentrated onto silica gel and chromatographically purified (0-100% EtOAc/hexanes) to provide methyl 2-(6-(5-(1-phenylcyclopropyl)thiazolo[5,4-b]pyridin-2-yl)-3,4-dihydroisoquinolin-2(1H)-yl)acetate as a white solid. MS (ESI) m/z: Calculated: 455.2; Observed: 456.0 ($M^+$+1).

Step 2

Hydrolysis of methyl 2-(6-(5-(1-phenylcyclopropyl)thiazolo[5,4-b]pyridin-2-yl)-3,4-dihydroisoquinolin-2(1H)-yl)acetate (96.5 mg, 0.212 mmol) according to Reference R and the general procedure for ester hydrolysis to give 2-(6-(5-(1-phenylcyclopropyl)-thiazolo[5,4-b]pyridin-2-yl)-3,4-dihydroisoquinolin-2(1H)-yl)acetic acid as a light yellow solid. MS (ESI) m/z: Calculated: 441.2; Observed: 442.0 ($M^+$+1).

Example 83

Synthesis of 1-(4-(5-(1-cyclobutylcyclopropyl)thiazolo[5,4-b]pyridin-2-yl)-3-fluorobenzyl)azetidine-3-carboxylic acid

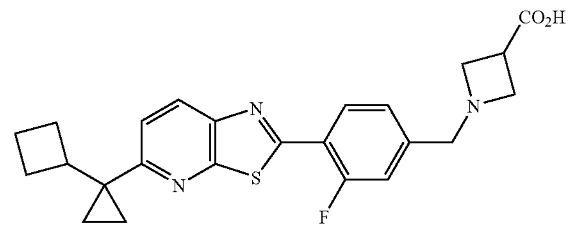

Step 1

A solution of 2-(4-(1,3-dioxan-2-yl)-2-fluorophenyl)-5-(trimethylstannyl)-thiazolo[5,4-b]pyridine (515.5 mg, 1.076 mmol) and cyclobutanecarbonyl chloride (0.147 mL, 1.291 mmol) in toluene (10.0 mL) was stirred under argon at 80° C. for 22 h. The reaction mixture was then concentrated onto silica gel and chromatographically purified (0-50% EtOAc/hexanes) to provide (2-(4-(1,3-dioxan-2-yl)-2-fluorophenyl)-thiazolo[5,4-b]pyridin-5-yl)(cyclobutyl)methanone as an off-white solid. MS (ESI) m/z: Calculated: 398.1; Observed: 398.9 ($M^+$+1).

Step 2

Trimethylsilylmethylmagnesium chloride (1.1M solution in THF; 1.12 mL, 1.23 mmol) was added to a solution of (2-(4-(1,3-dioxan-2-yl)-2-fluorophenyl)thiazolo[5,4-b]pyridin-5-yl)(cyclobutyl)methanone (327.0 mg, 0.821 mmol) in THF (15 mL) at 25° C., and the resulting solution was stirred at 25° C. for 5 min. Excess Grignard reagent was quenched by the careful addition of sat. aq. $NH_4Cl$ (5 mL), water was added to dissolve precipitated salts, and THF was then removed in vacuo. The resulting solution was partitioned between EtOAc (100 mL) and sat. aq. $NH_4Cl$ (20 mL), and the organic layer was separated and washed with brine. The organic layer was then dried over sodium sulfate, filtered, and concentrated in vacuo to provide 1-(2-(4-(1,3-dioxan-2-yl)-2-fluorophenyl)thiazolo[5,4-b]pyridin-5-yl)-1-cyclobutyl-2-(trimethylsilyl)ethanol as a yellow oil. MS (ESI) m/z: Calculated: 486.2; Observed: 487.1 ($M^+$+1).

Step 3

1-(2-(4-(1,3-Dioxan-2-yl)-2-fluorophenyl)thiazolo[5,4-b]pyridin-5-yl)-1-cyclobutyl-2-(trimethylsilyl)ethanol (355.8 mg, 0.731 mmol) in THF (10.0 mL) was carefully added dropwise to potassium hydride (30 wt % in mineral oil; 293 mg, 2.193 mmol) (washed with hexanes (1×5 mL) to remove mineral oil) at 0° C. The resulting solution was heated at 65° C. for 3 h, and excess potassium hydride was then quenched by the sequential addition of water (4 mL) and sat. aq. $NH_4Cl$ (4 mL). THF was removed in vacuo, and the resulting mixture was diluted with EtOAc (100 mL) and sequentially washed with sat. aq. $NH_4Cl$ and brine. The combined aqueous layers were extracted with EtOAc, and all organic layers were then combined, dried over sodium sulfate, filtered, and concentrated in vacuo. Chromatographic purification of the residue (silica gel, 0-30% EtOAc/hexanes) furnished 2-(4-(1,3-dioxan-2-yl)-2-fluorophenyl)-5-(1-cyclobutylvinyl)-thiazolo[5,4-b]pyridine as a white solid. MS (ESI) m/z: Calculated: 396.1; Observed: 397.1 ($M^+$+1).

Step 4

A solution of 2-(4-(1,3-dioxan-2-yl)-2-fluorophenyl)-5-(1-cyclobutylvinyl)-thiazolo[5,4-b]pyridine (167.1 mg, 0.421 mmol) in THF (8.0 mL) was added a solution of trimethylsulfoxonium iodide (557 mg, 2.53 mmol) and potassium 2-methylpropan-2-olate (284 mg, 2.53 mmol) in DMSO (4.80 mL) under argon, and the resulting solution was stirred at 60° C. for 2.5 h. The reaction mixture was then cooled to 25° C., THF was removed in vacuo, and the residual mixture was diluted with DCM (100 mL). The resulting solution was sequentially washed with sat. aq. $NH_4Cl$ (50 mL) and brine (20 mL). The combined aqueous layers were extracted with DCM (2×50 mL), and the combined organic layers were then dried over sodium sulfate, filtered, and concentrated in vacuo. Chromatographic purification of the residue (silica gel, 0-30% EtOAc/hexanes) furnished 2-(4-(1,3-dioxan-2-yl)-2-fluorophenyl)-5-(1-cyclobutyl-cyclopropyl)thiazolo[5,4-b]pyridine as a white solid. MS (ESI) m/z: Calculated: 410.1; Observed: 411.1 ($M^+$+1).

Step 5

A mixture of 2-(4-(1,3-dioxan-2-yl)-2-fluorophenyl)-5-(1-cyclobutyl-cyclopropyl)-thiazolo[5,4-b]pyridine (85.7 mg, 0.209 mmol) and hydrochloric acid (5.0N, aq.) (2.00 mL, 10.02 mmol) in THF (4.0 mL) was stirred at 65° C. for 3 h. The reaction mixture was then cooled on an ice bath, and NaOH (5.0N, aq., 2.0 mL) was added. THF was removed in vacuo, and the resulting mixture was partitioned between EtOAc and water. The organic layer was separated, sequentially washed with water and brine, dried over sodium sulfate, filtered, and concentrated in vacuo. Chromatographic purification of the residue (silica gel, 0-30% EtOAc/hexanes) furnished 4-(5-(1-cyclobutylcyclopropyl)thiazolo[5,4-b]pyridin-2-yl)-3-fluorobenzaldehyde as a light yellow solid. MS (ESI) m/z: Calculated: 352.1; Observed: 353.1 ($M^+$+1).

Step 6

Reaction of 4-(5-(1-cyclobutylcyclopropyl)thiazolo[5,4-b]pyridin-2-yl)-3-fluorobenzaldehyde (66.2 mg, 0.188 mmol) and methyl azetidine-3-carboxylate hydrochloride (42.7 mg, 0.282 mmol) according to Reference R and the general procedure for reductive amination to give methyl 1-(4-(5-(1-cyclobutylcyclopropyl)thiazolo[5,4-b]pyridin-2-yl)-3-fluorobenzyl)azetidine-3-carboxylate as a white solid. MS (ESI) m/z: Calculated: 451.2; Observed: 451.9 ($M^+$+1).

Step 7

Hydrolysis of methyl 1-(4-(5-(1-cyclobutylcyclopropyl)thiazolo[5,4-b]pyridin-2-yl)-3-fluorobenzyl)azetidine-3-carboxylate (47.0 mg, 0.104 mmol) according to Reference R and the general procedure for ester hydrolysis gave 1-(4-(5-(1-cyclobutylcyclopropyl)-thiazolo[5,4-b]pyridin-2-yl)-3-fluorobenzyl)azetidine-3-carboxylic acid as a white solid. MS (ESI) m/z: Calculated: 437.2; Observed: 438.0 ($M^+$+1).

Example 84

Synthesis of 1-(4-(5-(1-(3,3-difluorocyclobutyl)cyclopropyl)thiazolo[5,4-b]pyridin-2-yl)-3-fluorobenzyl)azetidine-3-carboxylic acid

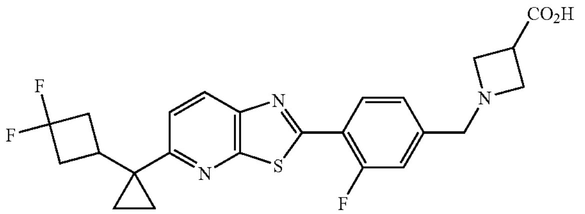

Step 1

A solution of 3,3-difluorocyclobutanecarboxylic acid (542.6 mg, 3.99 mmol) in thionyl chloride (5.24 mL, 71.8 mmol) was heated at 70° C. for 1 h and then concentrated in vacuo. 2-(4-(1,3-Dioxan-2-yl)-2-fluorophenyl)-5-(trimethylstannyl)thiazolo[5,4-b]pyridine (1.08 g, 2.254 mmol) was added to the residue, and the mixture was taken up in toluene (20.0 mL) and stirred under argon at 80° C. for 16 h. The reaction mixture was then concentrated onto silica gel and chromatographically purified (0-60% EtOAc/hexanes) to provide (2-(4-(1,3-dioxan-2-yl)-2-fluorophenyl)thiazolo[5,4-b]pyridin-5-yl)(3,3-difluorocyclobutyl)methanone as an off-white solid. MS (ESI) m/z: Calculated: 434.1; Observed: 435.0 ($M^{+}$+1).

Step 2

Trimethylsilylmethylmagnesium chloride (1.1M solution in THF; 2.24 mL, 2.47 mmol) was added to a solution of (2-(4-(1,3-dioxan-2-yl)-2-fluorophenyl)thiazolo[5,4-b]pyridin-5-yl)(3,3-difluorocyclobutyl)methanone (630 mg, 1.450 mmol) in THF (30.0 mL) at 25° C., and the resulting solution was stirred at 25° C. for 10 min. Excess Grignard reagent was quenched by the careful addition of sat. aq. $NH_4Cl$ (10 mL), water was added to dissolve the precipitated salts, and THF was then removed in vacuo. The resulting mixture was partitioned between EtOAc (250 mL) and sat. aq. $NH_4Cl$ (50 mL), and the organic layer was separated and washed with brine (50 mL). The organic layer was then dried over sodium sulfate, filtered, and concentrated in vacuo to provide 1-(2-(4-(1,3-dioxan-2-yl)-2-fluorophenyl)thiazolo[5,4-b]pyridin-5-yl)-1-(3,3-difluoro-cyclobutyl)-2-(trimethylsilyl)ethanol as a yellow foam. MS (ESI) m/z: Calculated: 522.2; Observed: 522.8 ($M^{+}$+1).

Step 3

1-(2-(4-(1,3-Dioxan-2-yl)-2-fluorophenyl)thiazolo[5,4-b]pyridin-5-yl)-1-(3,3-difluorocyclobutyl)-2-(trimethylsilyl)ethanol (600.0 mg, 1.148 mmol) in THF (16.0 mL) was carefully added dropwise to potassium hydride (35 wt % in mineral oil; 395 mg, 3.44 mmol) at 0° C. The resulting brown solution was heated at 65° C. for 3 h. Excess potassium hydride was then quenched by the sequential addition of water (4 mL) and sat. aq. $NH_4Cl$ (4 mL). THF was removed in vacuo, and the resulting mixture was then diluted with EtOAc (150 mL) and sequentially washed with sat. aq. $NH_4Cl$ and brine. The combined aqueous layers were extracted with EtOAc), and all organic layers were then combined, dried over sodium sulfate, filtered, and concentrated in vacuo. Chromatographic purification of the residue (silica gel, 0-70% EtOAc/hexanes) furnished 2-(4-(1,3-dioxan-2-yl)-2-fluorophenyl)-5-(1-(3,3-difluorocyclobutyl)vinyl)-thiazolo[5,4-b]pyridine as a light yellow solid. MS (ESI) m/z: Calculated: 432.1; Observed: 433.0 ($M^{+}$+1).

Step 4

A solution of 2-(4-(1,3-dioxan-2-yl)-2-fluorophenyl)-5-(1-(3,3-difluoro-cyclobutyl)vinyl)thiazolo[5,4-b]pyridine (299.1 mg, 0.692 mmol) in THF (13.33 mL) was added a solution of trimethylsulfoxonium iodide (913 mg, 4.15 mmol) and potassium 2-methylpropan-2-olate (466 mg, 4.15 mmol) in DMSO (8.0 mL) under argon, and the resulting solution was stirred at 60° C. for 2.5 h. The reaction mixture was then cooled to 25° C., THF was removed in vacuo, and the residual mixture was diluted with DCM (200 mL). The resulting solution was sequentially washed with sat. aq. $NH_4Cl$ and brine). The combined aqueous layers were extracted with DCM, and the combined organic layers were then dried over sodium sulfate, filtered, and concentrated in vacuo. Chromatographic purification of the residue (silica gel, 0-70% EtOAc/hexanes) furnished 2-(4-(1,3-dioxan-2-yl)-2-fluorophenyl)-5-(1-(3,3-difluoro-cyclobutyl)cyclopropyl)thiazolo[5,4-b]pyridine as a light yellow solid. MS (ESI) m/z: Calculated: 446.1; Observed: 447.1 ($M^{+}$+1).

Step 5

A mixture of 2-(4-(1,3-dioxan-2-yl)-2-fluorophenyl)-5-(1-(3,3-difluoro-cyclobutyl)cyclopropyl)thiazolo[5,4-b]pyridine (151.5 mg, 0.339 mmol) and hydrochloric acid (5.0N, aq.) (3.0 mL, 15.00 mmol) in THF (6.7 mL) was stirred at 65° C. for 3 h. Ther reaction mixture was then cooled on an ice bath, and NaOH (5.0N, aq.; 3.0 mL) was added. THF was removed in vacuo, and the resulting mixture was partitioned between EtOAc (100 mL) and water (30 mL). The organic layer was separated, sequentially washed with water (30 mL) and brine (20 mL), dried over sodium sulfate, filtered, and concentrated in vacuo. Chromatographic purification of the residue (silica gel, 0-60% EtOAc/hexanes) furnished 4-(5-(1-(3,3-difluoro-cyclobutyl)cyclopropyl)thiazolo[5,4-b]pyridin-2-yl)-3-fluorobenzaldehyde as a light-yellow solid. MS (ESI) m/z: Calculated: 388.1; Observed: 389.0 ($M^{+}$+1).

Step 6

Reaction of 4-(5-(1-(3,3-difluorocyclobutyl)cyclopropyl)thiazolo[5,4-b]pyridin-2-yl)-3-fluorobenzaldehyde (112.0 mg, 0.288 mmol) and methyl azetidine-3-carboxylate hydrochloride (65.6 mg, 0.433 mmol) according to Reference R and the general procedure for reductive amination gave methyl 1-(4-(5-(1-(3,3-difluorocyclobutyl)cyclopropyl)-thiazolo[5,4-b]pyridin-2-yl)-3-fluorobenzyl)azetidine-3-carboxylate as a white solid. MS (ESI) m/z: Calculated: 487.2; Observed: 487.8 ($M^{+}$+1).

Step 7

Hydrolysis of methyl 1-(4-(5-(1-(3,3-difluorocyclobutyl)cyclopropyl)thiazolo[5,4-b]pyridin-2-yl)-3-fluorobenzyl)azetidine-3-carboxylate (111.5 mg, 0.229 mmol) according to Reference R and the general procedure for ester hydrolysis gave 1-(4-(5-(1-(3,3-difluorocyclobutyl)cyclopropyl)thiazolo[5,4-b]pyridin-2-yl)-3-fluorobenzyl)azetidine-3-carboxylic acid as an off-white solid. MS (ESI) m/z: Calculated: 473.1; Observed: 473.8 ($M^{+}$+1).

Example 85

Synthesis of 2-(3-fluoro-4-(5-(1-phenylcyclopropyl) thiazolo[5,4-b]pyridin-2-yl)benzyloxy)acetic acid

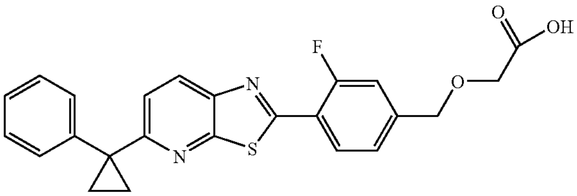

Step 1

Sodium hydride (0.015 mL, 0.35 mmol) was added to a light yellow solution of (3-fluoro-4-(5-(1-phenylcyclopropyl)thiazolo[5,4-b]pyridin-2-yl)phenyl)methanol (0.110 g, 0.29 mmol) in DMF (3.00 mL); the color changed to dark brown. The reaction mixture was treated with methyl 2-bromoacetate (0.032 mL, 0.35 mmol), and the color changed to green, then yellow, and then became cloudy. After 15 min, additional methyl 2-bromoacetate (0.032 mL, 0.35 mmol) was added, and after 15 min, the reaction mixture was quenched with $NH_4Cl$, extracted with EtOAc, and the organic layer was dried over $MgSO_4$, filtered, and concentrated in vacuo. The residue was purified by silica gel chromatography, eluting with 15-20% EtOAc/hexanes to give methyl 2-(3-fluoro-4-(5-(1-phenylcyclopropyl)thiazolo[5,4-b]pyridin-2-yl)benzyloxy)acetate. MS (ESI) m/z: calculated: 448.1; Observed: 449.0 ($M^+$+1).

Step 2

To a solution of methyl 2-((3-fluoro-4-(5-(1-phenylcyclopropyl)thiazolo[5,4-b]pyridin-2-yl)phenyl)methoxy)acetate (0.040 g, 0.089 mmol) in THF (2.00 mL) was added a solution of lithium hydroxide (0.011 g, 0.45 mmol) in 1.0 mL of water. The reaction mixture was stirred for 10 min. The THF was removed, and the reaction mixture acidified to pH 1 with 5N HCl. The resulting solid was rinsed with water and diethyl ether, and the solid was dried in vacuo at 50° C. for 2 h to give 2-(3-fluoro-4-(5-(1-phenylcyclopropyl)thiazolo[5,4-b]pyridin-2-yl)benzyloxy)acetic acid. MS (ESI) m/z: calculated: 434.1; Observed: 435.0 ($M^+$+1).

Example 86

Synthesis of 2-(4-(1-azetidinylmethyl)-2-fluorophenyl)-5-(1-phenyl-cyclopropyl)-[1,3]thiazolo[5,4-b] pyridine

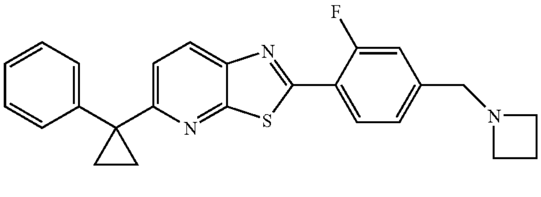

A solution of 3-fluoro-4-(5-(1-phenylcyclopropyl)thiazolo[5,4-b]pyridin-2-yl)benzaldehyde (0.102 g, 0.27 mmol), azetidine (0.037 mL, 0.54 mmol) and acetic acid (0.063 mL, 1.1 mmol) in dichloromethane (3.00 mL, 0.27 mmol) and methanol (2.00 mL, 0.27 mmol), was stirred for 60 min at ambient temperature. The reaction mixture was treated with sodium cyanoborohydride (0.0086 g, 0.14 mmol) and was stirred for 10 min, concentrated in vacuo, and adsorbed onto silica gel. Silica gel chromatography (20-30% EtOAc/hexanes, followed by 40% (3% $Et_3N$/EtOAc)/hexanes gave the title compound. MS (ESI) m/z: Calculated: 415.2; Observed: 416.1 ($M^+$+1).

Example 87

Synthesis of 3-(3-fluoro-4-(5-(1-phenylcyclopropyl) thiazolo[5,4-b]pyridin-2-yl)-benzylamino)-3-methylbutanoic acid hydrochloride

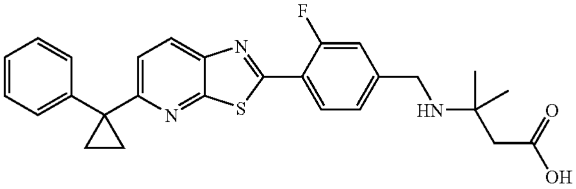

Reaction of 3-fluoro-4-(5-(1-phenylcyclopropyl)thiazolo[5,4-b]pyridin-2-yl)benzaldehyde (0.100 g, 0.267 mmol) and 3-amino-3-methylbutanoic acid (0.0469 g, 0.401 mmol) according to Reference R and general procedure for reductive amination afforded 3-(3-fluoro-4-(5-(1-phenylcyclopropyl) thiazolo[5,4-b]pyridin-2-yl)benzylamino)-3-methylbutanoic acid hydrochloride. MS (ESI) m/z: calculated: 475.2; Observed: 476.1 ($M^+$+1).

Example 88

Synthesis of 4-(3-fluoro-4-(5-(1-phenylcyclopropyl) thiazolo[5,4-b]pyridin-2-yl)benzylamino)butanoic acid hydrochloride

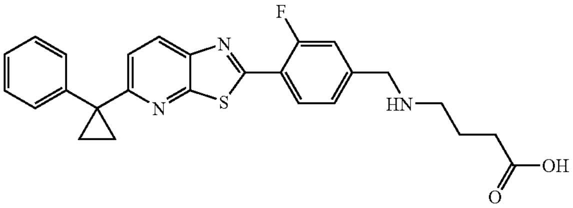

Reaction of 3-fluoro-4-(5-(1-phenylcyclopropyl)thiazolo[5,4-b]pyridin-2-yl)benzaldehyde (0.100 g, 0.267 mmol) and 4-aminobutanoic acid (0.0413 g, 0.401 mmol) according to Reference R and general procedure for reductive amination afforded 4-(3-fluoro-4-(5-(1-phenylcyclopropyl)thiazolo[5,4-b]pyridin-2-yl)benzylamino)butanoic acid hydrochloride. MS (ESI) m/z: calculated: 461.2; Observed: 462.0 ($M^+$+1).

Example 89

Synthesis of (rac)-3-(3-fluoro-4-(5-(1-phenylcyclopropyl)thiazolo[5,4-b]pyridin-2-yl)benzylamino) butanoic acid hydrochloride

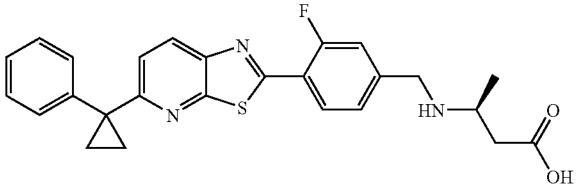

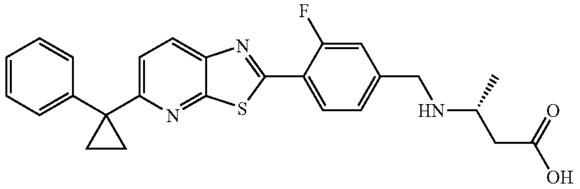

Reaction of 3-fluoro-4-(5-(1-phenylcyclopropyl)thiazolo [5,4-b]pyridin-2-yl)benzaldehyde (0.040 g, 0.11 mmol) and racemic 3-aminobutanoic acid (0.011 g, 0.11 mmol) according to Reference R and general procedure for reductive amination afforded racemic3-(3-fluoro-4-(5-(1-phenylcyclopropyl)thiazolo[5,4-b]pyridin-2-yl)benzylamino)butanoic acid hydrochloride. MS (ESI) m/z: calculated: 461.2; Observed: 462.0 ($M^{+}$+1).

Example 90

Synthesis of (S)-3-(3-fluoro-4-(5-(1-phenylcyclopropyl)thiazolo[5,4-b]pyridin-2-yl)benzylamino)butanoic acid hydrochloride

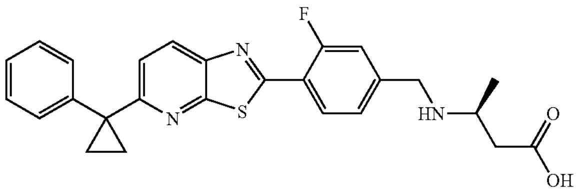

Reaction of 3-fluoro-4-(5-(1-phenylcyclopropyl)thiazolo [5,4-b]pyridin-2-yl)benzaldehyde (0.040 g, 0.11 mmol) and (S)-3-aminobutanoic acid (0.057 g, 0.41 mmol) according to Reference R and general procedure for reductive amination afforded (S)-3-(3-fluoro-4-(5-(1-phenylcyclopropyl)thiazolo[5,4-b]pyridin-2-yl)benzylamino)butanoic acid hydrochloride. MS (ESI) m/z: calculated: 461.2; Observed: 462.1 ($M^{+}$+1).

Example 91

Synthesis of (R)-3-(3-fluoro-4-(5-(1-phenylcyclopropyl)thiazolo[5,4-b]pyridin-2-yl)benzylamino)butanoic acid hydrochloride

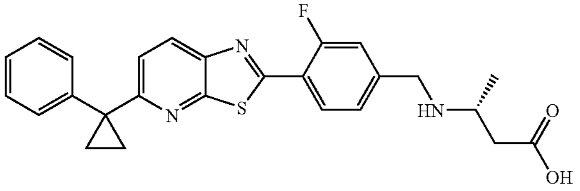

Reaction of 3-fluoro-4-(5-(1-phenylcyclopropyl)thiazolo [5,4-b]pyridin-2-yl)benzaldehyde (0.040 g, 0.11 mmol) and (R)-3-aminobutanoic acid hydrochloride (0.056 g, 0.40 mmol) according to Reference R and general procedure for reductive amination afforded (R)-3-(3-fluoro-4-(5-(1-phenylcyclopropyl)thiazolo[5,4-b]pyridin-2-yl)benzylamino) butanoic acid hydrochloride. MS (ESI) m/z: calculated: 461.2; Observed: 462.1 ($M^{+}$+1).

Example 92

Synthesis of 3-(1-(3-fluoro-4-(5-(1-phenylcyclopropyl)thiazolo[5,4-b]pyridin-2-yl)phenyl)ethylamino) butanoic acid hydrochloride

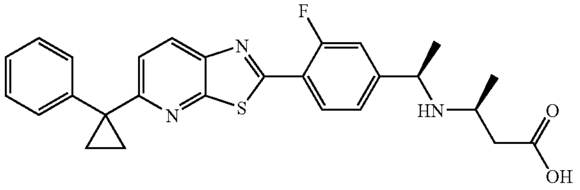

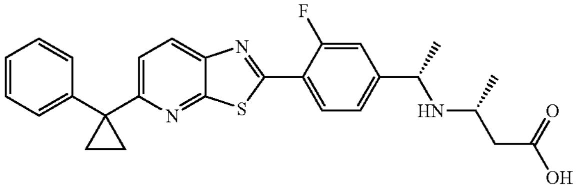

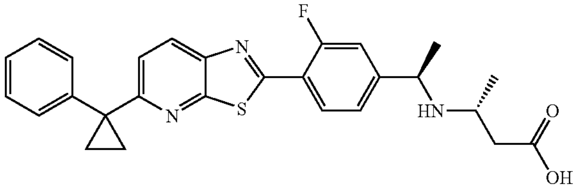

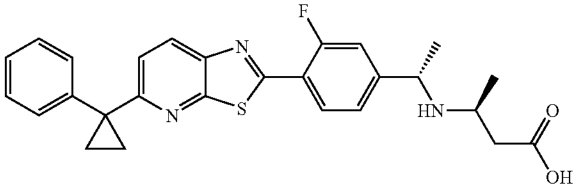

Reaction of 1-(3-fluoro-4-(5-(1-phenylcyclopropyl)thiazolo[5,4-b]pyridin-2-yl)phenyl)ethanone acetate (0.055 g, 0.14 mmol) and 3-aminobutanoic acid (0.022 g, 0.21 mmol) according to Reference R and general procedure for reductive amination afforded 3-(1-(3-fluoro-4-(5-(1-phenylcyclopropyl)thiazolo[5,4-b]pyridin-2-yl)phenyl)ethylamino)-butanoic acid hydrochloride as a mixture of isomers. MS (ESI) m/z: calculated: 475.2: Observed: 476.1 ($M^{+}$+1). Alternatively, (R)-3-aminobutanoic acid or (S)-3-aminobutanoic acid could be used to prepare mixtures enriched in isomers with (R)— or (S)— configuration, respectively, at C3. The isomers were separated by SFC (Column: Chiralpak AD-H (4.6×150 mm, 5 um); A: Liquid $CO_2$; B: Methanol (0.2% DEA); Isocratic: 88:22 (A:B); Flow rate: 4 mL/min; Outlet Pressure: 100 bar) to give the four possible isomers of 3-(1-(3-fluoro-4-(5-(1-phenylcyclopropyl)thiazolo[5,4-b]pyridin-2-yl)phenyl)ethylamino)butanoic acid. MS (ESI) m/z: calculated: 475.2: Observed: 476.1 ($M^{+}$+1).

Example 93

Synthesis of (R)-1-(3-fluoro-4-(5-(1-phenylcyclopropyl)thiazolo[5,4-b]pyridin-2-yl)phenyl)ethanamine

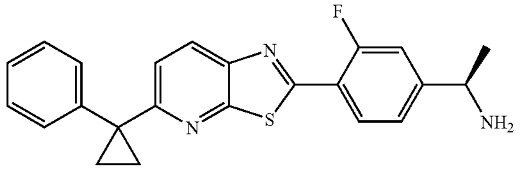

Step 1

1-(3-Fluoro-4-(5-(1-phenylcyclopropyl)thiazolo[5,4-b]pyridin-2-yl)phenyl)ethanone (0.577 g, 2.49 mmol) was added to a solution of (R)-(+)-2-methyl-2-propanesulfinamide (0.150 g, 1.24 mmol), titanium (iv) ethoxide (0.510 mL, 2.48 mmol) in THF (5 mL). The reaction mixture was heated to 70° C. for 23 h, At which time was cooled to −50° C. To the reaction mixture was added a suspension of sodium borohydride (0.187 g, 4.95 mmol) in 0.5 mL of THF also at −50° C., allowed to stir for 18 h at −50° C. The reaction mixture was warmed to 0° C. and MeOH was added dropwise until gas evolution was no longer observed. The crude reaction mixture was poured into an equal volume of brine while being stirred rapidly. The resulting suspension was filtered through a plug of celite, the cake rinsed with EtOAc and MeOH. The filtrate was reduced in vacuo, the residue diluted with EtOAc, extracted with brine and dried over $MgSO_4$. The crude reaction mixture was concentrated in vacuo and purified by silica gel chromatography to afford (R)-N-(1-(3-fluoro-4-(5-(1-phenylcyclopropyl)thiazolo[5,4-b]pyridin-2-yl)phenyl)ethyl)-2-methylpropane-2-sulfinamide. MS (ESI) m/z: calculated: 493.2; Observed: 494.0 ($M^{+}$+1).

Step 2

Hydrogen chloride 4.0 M in 1,4-dioxane (0.04 mL, 0.2 mmol) was added to a solution of (R)-N-((R)-1-(3-fluoro-4-(5-(1-phenylcyclopropyl)thiazolo[5,4-b]pyridin-2-yl)phenyl)-ethyl)-2-methylpropane-2-sulfinamide (0.0301 g, 0.06 mmol) in MeOH (5 mL). The yellow reaction mixture was allowed to stir at ambient temperature for 18 h. The crude reaction mixture was concentrated in vacuo and purified by silica gel chromatography to afford (R)-1-(3-fluoro-4-(5-(1-phenylcyclopropyl)thiazolo[5,4-b]pyridin-2-yl)phenyl)ethanamine. MS (ESI) m/z: calculated: 389.1; Observed: 390.1 ($M^{+}$+1).

Example 94

Synthesis of (S)-1-(3-fluoro-4-(5-(1-phenylcyclopropyl)thiazolo[5,4-b]pyridin-2-yl)phenyl)ethanamine

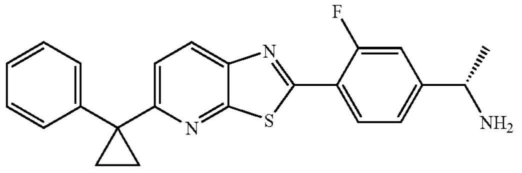

Step 1

1-(3-Fluoro-4-(5-(1-phenylcyclopropyl)thiazolo[5,4-b]pyridin-2-yl)phenyl)ethanone (0.48 g, 1.2 mmol) was added to a solution of (R)-(+)-2-methyl-2-propanesulfinamide ((0.150 g, 1.2 mmol), titanium (iv) ethoxide (0.510 mL, 2.48 mmol) in THF (5 mL). The reaction mixture was heated to 70° C. for 2 h at which point additional (R)-(+)-2-methyl-2-propanesulfinamide (0.150 g, 1.2 mmol) and titanium (iv) ethoxide (0.51 mL, 2.48 mmol) were added and the reaction mixture was allowed to stir for 18 h at 70° C. The reaction mixture was cooled to ambient temperature and then to −50° C. To the reaction mixture was added dropwise 1 M solution of L-Selectride (3.7 mL, 3.7 mmol) also at −50° C., and allowed to stir for 5 h at −50° C. The reaction mixture was warmed to 0° C. and MeOH was added dropwise until gas evolution was no longer observed. The crude reaction mixture was poured into an equal volume of brine while being stirred rapidly. The resulting suspension was filtered through a plug of celite, the cake rinsed with EtOAc and MeOH. The filtrate was reduced in vacuo, the residue diluted with EtOAc, extracted with brine and dried over $MgSO_4$. The crude reaction mixture was concentrated in vacuo and purified by silica gel chromatography to afford (S)-N-(1-(3-fluoro-4-(5-(1-phenylcyclopropyl)-thiazolo[5,4-b]pyridin-2-yl)phenyl)-ethyl)-2-methylpropane-2-sulfinamide. MS (ESI) m/z: calculated: 493.2; Observed: 494.0 ($M^{+}$+1).

Step 2

Hydrogen chloride, 4.0 M solution in 1,4-dioxane (0.63 mL, 2.5 mmol) was added to a suspension of (R)-N-((S)-1-(3-fluoro-4-(5-(1-phenylcyclopropyl)thiazolo[5,4-b]pyridin-2-yl)phenyl)ethyl)-2-methylpropane-2-sulfinamide. (0.413 g, 0.84 mmol)) in methanol (60.00 mL). The yellow reaction mixture was allowed to stir at ambient temperature for 4 h. The crude reaction mixture was concentrated in vacuo and purified by silica gel chromatography to afford (S)-1-(3-fluoro-4-(5-(1-phenylcyclopropyl)thiazolo[5,4-b]pyridin-2-yl)phenyl)ethanamine. MS (ESI) m/z: calculated: 389.1; Observed: 390.1 ($M^{+}$+1).

Example 95

Synthesis of 4-(3-fluoro-4-(5-(1-phenylcyclopropyl) thiazolo[5,4-b]pyridin-2-yl)phenyl)butanoic acid

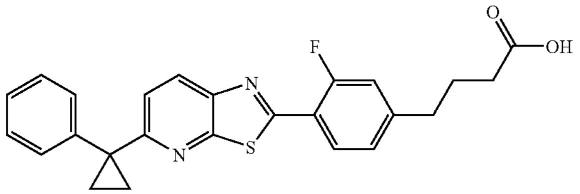

Step 1

In reactor bottle under $N_2$ were combined fine cesium carbonate (0.209 g, 0.644 mmol) and diethyl malonate (0.195 mL, 1.29 mmol) in DMF (3 mL). The resulting slurry was allowed to stir for 1 h at ambient temperature. To the mixture was added 2-(2-fluoro-4-vinylphenyl)-5-(1-phenylcyclopropyl)thiazolo[5,4-b]pyridine (0.200 g, 0.537 mmol) and the reaction mixture was heated to 35° C. for 1.5 h. The reaction mixture was cooled to 0° C. and acidified using 1 N aq. HCl, extracted with EtOAc, and the organic layer was dried over $MgSO_4$, filtered, and concentrated in vacuo. Purification by silica gel chromatography provided diethyl 2-(3-fluoro-4-(5-(1-phenylcyclopropyl)thiazolo[5,4-b]pyridin-2-yl)phenethyl)malonate. MS (ESI) m/z: calculated: 532.2; Observed: 533.1 ($M^+$+1).

Step 2

In reactor bottle, hydrochloric acid, 5N aq. (3 mL) was added to diethyl 2-(2-(3-fluoro-4-(5-(1-phenylcyclopropyl) thiazolo[5,4-b]pyridin-2-yl)phenyl)ethyl)malonate (0.257 g, 0.48 mmol), and the mixture heated to 120° C. for 6 h. The crude reaction mixture was concentrated in vacuo and purified by silica gel chromatography to afford 4-(3-fluoro-4-(5-(1-phenylcyclopropyl)thiazolo[5,4-b]pyridin-2-yl)phenyl) butanoic acid. MS (ESI) m/z: calculated: 432.1; Observed: 433.0 ($M^+$+1).

Example 96

Synthesis of 1-(3-fluoro-4-(5-(1-phenylcyclopropyl) thiazolo[5,4-b]pyridin-2-yl)benzyl)-1H-imidazole-4-carboxylic acid hydrochloride

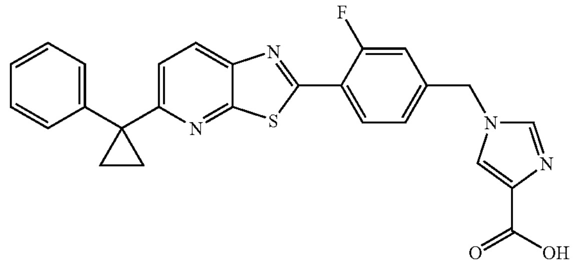

Step 1

In a reactor tube was dissolved methyl 4-imidazolecarboxylate (0.047 g, 0.37 mmol) in ethyl alcohol (2 mL). To the solution was added sodium tert-butoxide (0.035 g, 0.37 mmol) followed by 2-(4-(bromomethyl)-2-fluorophenyl)-5-(1-phenylcyclopropyl)thiazolo[5,4-b]pyridine (0.081 g, 0.18 mmol) and the reaction mixture was heated to 70° C. for 1 h. The crude reaction mixture was concentrated in vacuo and purified by silica gel chromatography to afford pure ethyl 1-(3-fluoro-4-(5-(1-phenylcyclopropyl)thiazolo[5,4-b]pyridin-2-yl)benzyl)-1H-imidazole-4-carboxylate and ethyl 1-(3-fluoro-4-(5-(1-phenylcyclopropyl)thiazolo[5,4-b]pyridin-2-yl)benzyl)-1H-imidazole-5-carboxylate. MS (ESI) m/z: calculated: 498.2; Observed: 499.0.

Step 2

To a solution of ethyl 1-((3-fluoro-4-(5-(1-phenylcyclopropyl)thiazolo[5,4-b]pyridin-2-yl)phenyl)methyl)-1H-imidazole-4-carboxylate (0.034 g, 0.068 mmol) in THF was added a solution of lithium hydroxide (0.0082 g, 0.34 mmol) in 1.0 mL of water. The reaction mixture was heated to 100° C. for 18 h. The crude reaction mixture was concentrated in vacuo. The residue was diluted with water and the pH was adjusted to 1 with aq. HCl. The solid was collected by filtration, rinsed with water and $Et_2O$, and dried in vacuo at 50° C. for 2 h to afford 1-(3-fluoro-4-(5-(1-phenylcyclopropyl)thiazolo[5,4-b]pyridin-2-yl)benzyl)-1H-imidazole-4-carboxylic acid. MS (ESI) m/z: calculated: 470.1; Observed: 471.0 ($M^+$+1).

Example 97

Synthesis of 1-(3-fluoro-4-(5-(1-phenylcyclopropyl) thiazolo[5,4-b]pyridin-2-yl)benzyl)-1H-imidazole-5-carboxylic acid hydrochloride

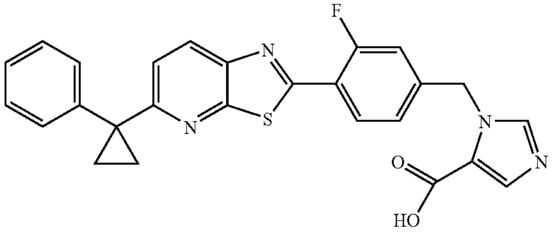

To a solution of ethyl 1-(3-fluoro-4-(5-(1-phenylcyclopropyl)thiazolo[5,4-b]pyridin-2-yl)benzyl)-1H-imidazole-5-carboxylate (0.016 g, 0.032 mmol) in THF was added a solution of lithium hydroxide (0.00077 g, 0.032 mmol) in 1.0 mL of water. The reaction mixture was heated to 100° C. for 18 h. The crude reaction mixture was concentrated in vacuo. The residue was diluted with water and the pH was adjusted to 1 with aq. HCl. The solid observed was collected by filtration, rinsed with water and $Et_2O$, and dried in vacuo at 50° C. for 2 h to afford 1-(3-fluoro-4-(5-(1-phenylcyclopropyl)thiazolo [5,4-b]pyridin-2-yl)benzyl)-1H-imidazole-5-carboxylic acid hydrochloride. MS (ESI) m/z: calculated: 470.1; Observed: 471.0 ($M^+$+1).

Example 98

Synthesis of 1-(3-fluoro-4-(5-(1-phenylcyclopropyl) thiazolo[5,4-b]pyridin-2-yl)benzyl)-1H-pyrazole-4-carboxylic acid hydrochloride

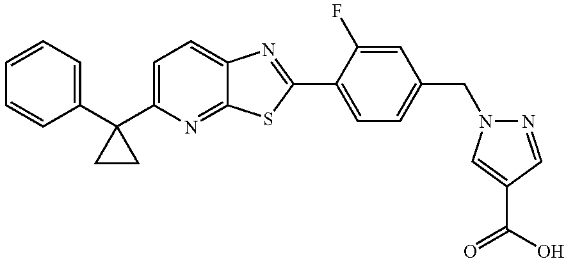

Step 1

In a reactor tube was dissolved ethyl 4-pyrazolecarboxylate (0.0957 g, 0.683 mmol) methyl 4-imidazolecarboxylate (0.047 g, 0.37 mmol) in ethyl alcohol (2 mL). To this solution was added tert-butoxide (0.0656 g, 0.683 mmol) followed by 2-(4-(bromomethyl)-2-fluorophenyl)-5-(1-phenylcyclopropyl)thiazolo[5,4-b]pyridine (0.150 g, 0.341 mmol) and the reaction mixture was heated to 70° C. for 90 min. The solid observed was collected by filtration, rinsed with $Et_2O$ to afford ethyl 1-(3-fluoro-4-(5-(1-phenylcyclopropyl)thiazolo [5,4-b]pyridin-2-yl)benzyl)-1H-pyrazole-4-carboxylate. MS (ESI) m/z: calculated: 498.2; Observed: 499.0 ($M^{+}$+1).

Step 2

To a solution of ethyl 1-((3-fluoro-4-(5-(1-phenylcyclopropyl)thiazolo[5,4-b]pyridin-2-yl)phenyl)methyl)-1H-pyrazole-4-carboxylate (0.145 g, 0.29 mmol) in THF (5 mL) was added a solution of lithium hydroxide (0.014 mL, 1.5 mmol) in 2.0 mL of water. The reaction mixture was heated to 100° C. for 18 h. The crude reaction mixture was concentrate in vacuo. The residue was diluted with water and the pH was adjusted to 1. The solid observed was collected by filtration, rinsed with water and $Et_2O$, and dried in vacuo at 50° C. for 3 h to afford 1-(3-fluoro-4-(5-(1-phenylcyclopropyl)thiazolo [5,4-b]pyridin-2-yl)benzyl)-1H-pyrazole-4-carboxylic acid hydrochloride. MS (ESI) m/z: calculated: 470.1; Observed: 471.0 ($M^{+}$+1).

Example 99

Synthesis of 1-(3-fluoro-4-(5-(1-phenylcyclopropyl) thiazolo[5,4-b]pyridin-2-yl)benzyl)-1H-pyrazole-3-carboxylic acid hydrochloride

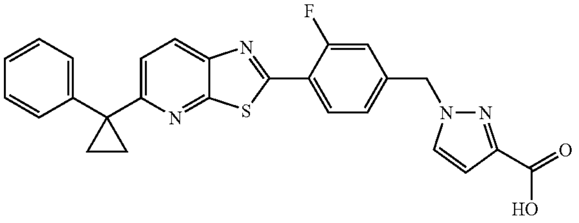

Step 1

In a sealable tube was dissolved ethyl 5H-pyrazole-3-carboxylate (0.137 g, 0.979 mmol) in ethyl alcohol (3 mL). To the solution was added tert-butoxide (0.0941 g, 0.979 mmol) followed by 2-(4-(bromomethyl)-2-fluorophenyl)-5-(1-phenylcyclopropyl)-thiazolo[5,4-b]pyridine (0.215 g, 0.489 mmol) and the reaction mixture was heated to 70° C. for 1 h. The crude reaction mixture containing an isomeric mixture was concentrated in vacuo and purified by silica gel chromatography to afford ethyl 1-(3-fluoro-4-(5-(1-phenyl-cyclopropyl)thiazolo[5,4-b]pyridin-2-yl)benzyl)-1H-pyrazole-3-carboxylate and ethyl 1-(3-fluoro-4-(5-(1-phenylcyclopropyl)thiazolo[5,4-b]pyridin-2-yl)benzyl)-1H-pyrazole-5-carboxylate. MS (ESI) m/z: calculated: 498.2; Observed: 499.0 ($M^{+}$+1).

Step 2

To a solution of ethyl 1-(3-fluoro-4-(5-(1-phenylcyclopropyl)thiazolo[5,4-b]pyridin-2-yl)benzyl)-1H-pyrazole-3-carboxylate (0.0993 g, 0.20 mmol) in THF (5 mL) was added a solution of lithium hydroxide (0.0095 mL, 1.00 mmol) in 1.0 mL of water. The reaction mixture was heated to 100° C. for 2 h. The crude reaction mixture was concentrated in vacuo. The residue was diluted with water and the pH was adjusted to 1 with 1N aq. HCl. The solid was collected by filtration, rinsed with water and $Et_2O$, and dried in vacuo at 50° C. for 2 h to afford 1-(3-fluoro-4-(5-(1-phenylcyclopropyl)-thiazolo [5,4-b]pyridin-2-yl)benzyl)-1H-pyrazole-3-carboxylic acid hydrochloride. MS (ESI) m/z: calculated: 470.1; Observed: 471.0 ($M^{+}$+1).

Example 100

Synthesis of 1-(3-fluoro-4-(5-(1-phenylcyclopropyl) thiazolo[5,4-b]pyridin-2-yl)benzyl)-1H-pyrazole-5-carboxylic acid hydrochloride

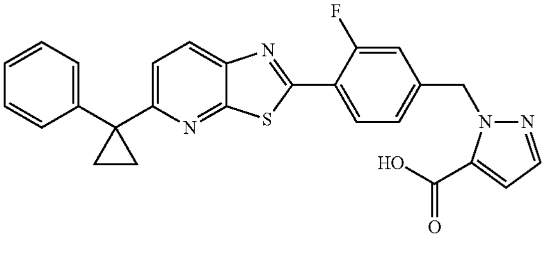

To a solution of ethyl 1-(3-fluoro-4-(5-(1-phenylcyclopropyl)thiazolo[5,4-b]pyridin-2-yl)benzyl)-1H-pyrazole-5-carboxylate (0.03561 g, 0.071 mmol) in THF (2 mL) was added a solution of lithium hydroxide (0.0034 mL, 0.36 mmol) in 1.0 mL of water. The reaction mixture was heated to 100° C. for 2 h. The crude reaction mixture was concentrate in vacuo. The residue was diluted with water and the pH was adjusted to 1 with 1N aq HCl. The solid was collected by filtration, rinsed with water and $Et_2O$, and dried in vacuo at 50° C. for 2 h to afford 1-(3-fluoro-4-(5-(1-phenylcyclopropyl)thiazolo [5,4-b]pyridin-2-yl)benzyl)-1H-pyrazole-5-carboxylic acid hydrochloride. MS (ESI) m/z: calculated: 470.1; Observed: 470.9 ($M^{+}$+1).

Example 101

Synthesis of 2-amino-2-(3-fluoro-4-(5-(1-phenylcyclopropyl)thiazolo[5,4-b]pyridin-2-yl)benzyl)propane-1,3-diol

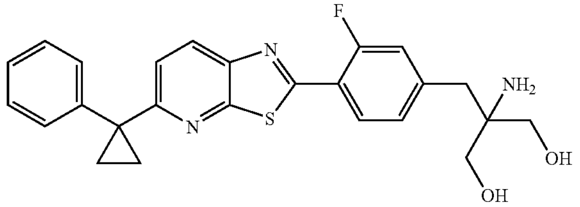

Step 1

In a sealable bottle, sodium tert-butoxide (0.120 g, 1.25 mmol) was added to a mixture of acetamidomalonic acid diethyl ester (0.272 g, 1.25 mmol) in THF (10.00 mL)/DMF (2.00 mL). The reaction mixture was heated to 80° C. for 20 min., cooled to ambient temperature, and a solution of 2-(4-(bromomethyl)-2-fluorophenyl)-5-(1-phenylcyclopropyl) thiazolo[5,4-b]pyridine (0.500 g, 1.14 mmol) in THF 4 mL was added slowly dropwise. The resulting mixture was heated to reflux (90° C.) for 1.5 h, and the color changed from orange to yellow. The reaction mixture was cooled, poured over ice water, and treated with EtOAc. The organic layer was washed with water, NaCl, dried over $MgSO_4$, filtered, and concentrated in vacuo. Purification by silica gel chromatography, 40 g column, 10-30% EtOAc/hexanes, followed by 30-50% (3% $Et_3N$ in EtOAc)/hexanes provided diethyl 2-acetamido-2-(3-fluoro-4-(5-(1-phenylcyclopropyl)thiazolo[5,4-b]pyridin-2-yl)benzyl)malonate. MS (ESI) m/z: calculated: 575.2; Observed: 576.1 ($M^+$+1).

Step 2

A solution of calcium chloride (0.159 g, 1.43 mmol) in 1.00 mL of water was added to a solution of diethyl 2-acetamido-2-((3-fluoro-4-(5-(1-phenylcyclopropyl)thiazolo[5,4-b]pyridin-2-yl)phenyl)methyl)malonate (0.330 g, 0.573 mmol) in THF (10.00 mL) and ethanol (10.00 mL). The reaction mixture was cooled to 0° C. in ice bath before the addition of sodium borohydride (0.108 g, 2.87 mmol); strong bubbled was observed and the solution became a yellow mixture. The reaction mixture was allowed to stir at ambient temperature for 2 h. DCM (5 mL) and additional sodium borohydride (0.108 g, 2.87 mmol) was added. After 18 h, the reaction mixture was poured over DCM/1 N HCl, and the organic layer was washed with 1 N HCl, dried over $MgSO_4$, filtered, and concentrated in vacuo. The residue was purified by silica gel chromatography, 40 g column, 0-15% MeOH/DCM to give N-(2-(3-fluoro-4-(5-(1-phenylcyclopropyl)thiazolo[5,4-b]pyridin-2-yl)benzyl)-1,3-dihydroxypropan-2-yl)acetamide. MS (ESI) m/z: calculated: 491.2; Observed: 492.1 ($M^+$+1).

Step 3

In a sealable tube a slurry of N-(3-(3-fluoro-4-(5-(1-phenylcyclopropyl)-thiazolo[5,4-b]pyridin-2-yl)phenyl)-1-hydroxy-2-(hydroxymethyl)propan-2-yl)acetamide (0.14 g, 0.28 mmol) in hydrochloric acid, 5 N (5.00 mL, 165 mmol) was heated to 120° C. The heterogeneous reaction mixture turned light green after 2 h of heating. The reaction mixture was cooled, filtered through a glass frit, and the solid was rinsed with water, EtOH, and $CHCl_3$. The EtOH and $CHCl_3$ filtrate was combined and concentrated, and this was combined with the isolated solid, and the material was purified by SFC (Sepapak 2 (250×21 mm, 5 micron) column using 50% methanol with 0.2% DEA as additive in supercritical $CO_2$ with a flow rate of 60 mL/min) to give 2-amino-2-(3-fluoro-4-(5-(1-phenylcyclopropyl)thiazolo[5,4-b]pyridin-2-yl)benzyl)propane-1,3-diol. MS (ESI) m/z: calculated: 449.2; Observed: 450.0 ($M^+$+1).

Example 102

Synthesis of (R)-2-amino-3-(3-fluoro-4-(5-(1-phenylcyclopropyl)thiazolo[5,4-b]pyridin-2-yl)phenyl) propanoic acid trifluoroacetic acid salt and (S)-2-amino-3-(3-fluoro-4-(5-(1-phenylcyclopropyl) thiazolo[5,4-b]pyridin-2-yl)phenyl)propanoic acid trifluoroacetic acid salt

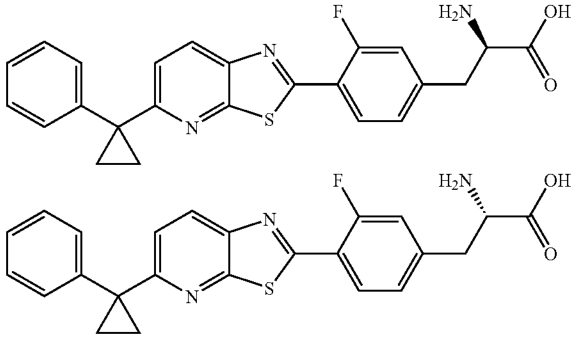

Step 1

In a sealable bottle, sodium tert-butoxide (0.0722 g, 0.751 mmol) was added to a mixture of diethyl 2-(tert-butoxycarbonyl)malonate (0.174 mL, 0.683 mmol) in THF (8.00 mL)/dmf (2.00 mL). The reaction mixture was heated to 80° C. for 20 min., and cooled to ambient temperature, at which point a solution of 2-(4-(bromomethyl)-2-fluorophenyl)-5-(1-phenylcyclopropyl)thiazolo[5,4-b]pyridine (0.300 g, 0.683 mmol) in THF 4 mL was added slowly dropwise. The resulting mixture was heated to reflux (90° C.) for 1.5 h. The reaction mixture was cooled, poured over ice water, and treated with EtOAc. The organic layer was washed with water, NaCl, dried over $MgSO_4$, filtered, and concentrated in vacuo. Purification by silica gel chromatography, 40 g column, 0-10% EtOAc/hexanes, followed by 30% (3% $Et_3N$ in EtOAc)/hexanes provided diethyl 2-(tert-butoxycarbonylamino)-2-(3-fluoro-4-(5-(1-phenylcyclopropyl)thiazolo[5,4-b]pyridin-2-yl)benzyl)malonate. MS (ESI) m/z: calculated: 633.2; Observed: 634.1 ($M^+$+1).

Step 2

In a sealable bottle 5 N HCl (3.00 mL, 0.322 mmol) was added to diethyl 2-(tert-butoxycarbonyl)-2-((3-fluoro-4-(5-(1-phenylcyclopropyl)thiazolo[5,4-b]pyridin-2-yl)phenyl) methyl)malonate (0.204 g, 0.322 mmol) in THF (3.00 mL). Solid was observed, and the reaction mixture was heated 90° C. for 18 h. The solvent was removed. To the oily residue was added water, and the resulting solid was, collected by filtration, washed with water, and dried in vacuo at 50° C. for 3 h to give (rac)-2-amino-3-(3-fluoro-4-(5-(1-phenylcyclopropyl)thiazolo[5,4-b]pyridin-2-yl)phenyl)propanoic acid hydrochloride salt. MS (ESI) m/z: calculated: 433.1; Observed: 434.0 ($M^+$+1).

Step 3

Triethylamine (0.0716 mL, 0.515 mmol) was added to a slurry of 2-amino-3-(3-fluoro-4-(5-(1-phenylcyclopropyl)thiazolo[5,4-b]pyridin-2-yl)phenyl)propanoic acid hydrochloride (0.110 g, 0.234 mmol) in THF (5.00 mL) and water (5.00 mL). The reaction mixture was cooled in ice bath and a solution of $Boc_2O$ (0.0868 g, 0.398 mmol) in THF (1 mL) was addded dropwise then the solution was stirred at ambient temperature for 18 h. The reaction mixture was diluted with water and EtOAc, pH was adjusterd to 5 with 1 N HCl, and the aq. layer was extracted with EtOAc; the combined organics were dried over $MgSO_4$, filtered, and concentrated in vacuo. The material was purified by chiral SFC (Column: Chiralpak AD-H (21×250 mm, 5 micron); A: Liquid $CO_2$; B: Isopropanol (0.2% DEA); Isocratic: 75:25 (A:B); Flow Rate: 70 mL/min; Outlet Pressure: 100 bar) to give (R)-2-(tert-butoxycarbonylamino)-3-(3-fluoro-4-(5-(1-phenylcyclopropyl)thiazolo[5,4-b]pyridin-2-yl)phenyl)propanoic acid and (S)-2-(tert-butoxycarbonylamino)-3-(3-fluoro-4-(5-(1-phenylcyclopropyl)thiazolo[5,4-b]pyridin-2-yl)phenyl)propanoic acid. MS (ESI) m/z: calculated: 533.2; Observed: 534.1 ($M^+$+1).

Step 4

Separately, the enantiomers of 2-(tert-butoxycarbonyl)-3-(3-fluoro-4-(5-(1-phenylcyclopropyl)thiazolo[5,4-b]pyridin-2-yl)phenyl)propanoic acid were processed according to the following procedure: To a solution of the 2-(tert-butoxycarbonyl)-3-(3-fluoro-4-(5-(1-phenylcyclopropyl)thiazolo[5,4-b]pyridin-2-yl)phenyl)propanoic acid (0.0503 g, 0.094 mmol) in DCM (1.0 mL, 15 mmol) was added trifluoroacetic acid (1.0 mL, 13 mmol), and the reaction mixture was stirred for 5 min at ambient temperature. The solvent was removed, the solid rinsed water and ether to give both (R)-2-amino-3-(3-fluoro-4-(5-(1-phenylcyclopropyl)thiazolo[5,4-b]pyridin-2-yl)phenyl)propanoic acid trifluoroacetic acid salt and (S)-2-amino-3-(3-fluoro-4-(5-(1-phenylcyclopropyl)thiazolo[5,4-b]pyridin-2-yl)-phenyl)propanoic acid trifluoroacetic acid salt. MS (ESI) m/z: calculated: 433.1; Observed: 434.0 ($M^+$+1).

Example 103

Synthesis of (R)-2-amino-4-(3-fluoro-4-(5-(1-phenylcyclopropyl)thiazolo[5,4-b]pyridin-2-yl)phenyl)butanoic acid trifluoroacetic acid salt and (S)-2-amino-4-(3-fluoro-4-(5-(1-phenylcyclopropyl)thiazolo[5,4-b]pyridin-2-yl)phenyl)butanoic acid trifluoroacetic acid salt

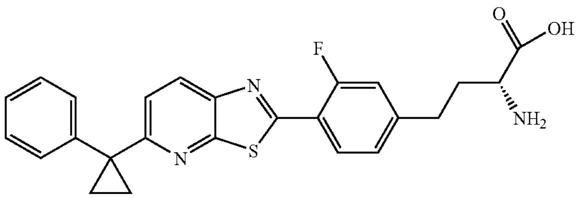

-continued

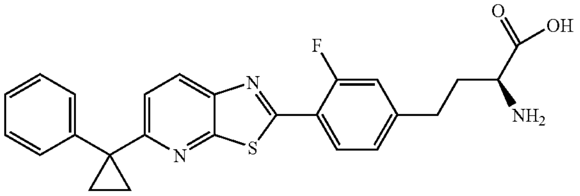

Step 1

In a sealable bottle, hydrochloric acid, 5N aq. (3.00 mL, 99 mmol) was added to diethyl 2-acetamido-2-(2-(3-fluoro-4-(5-(1-phenylcyclopropyl)thiazolo[5,4-b]pyridin-2-yl)phenyl)ethyl)malonate (0.279 g, 0.47 mmol). Solid was observed. The reaction mixture was heated to 120° C. for 1 h. 1 mL 5 N aq. HCl and 3 mL THF were added and heating continued at 120° C. for 2 hrs. The reaction mixture was cooled and the solvent was removed. To the oily residue was added water, solid was observed, collected by filtration, washed with water, and dried in vacuo to give (rac)-2-(tert-butoxycarbonylamino)-4-(3-fluoro-4-(5-(1-phenylcyclopropyl)thiazolo[5,4-b]pyridin-2-yl)phenyl)butanoic acid. MS (ESI) m/z: calculated: 447.1; Observed: 448.1 ($M^+$+1).

Step 2

Triethylamine (0.0967 mL, 0.695 mmol) was added to a slurry of (rac)-2-amino-4-(3-fluoro-4-(5-(1-phenylcyclopropyl)thiazolo[5,4-b]pyridin-2-yl)phenyl)butanoic acid hydrochloride (0.153 g, 0.316 mmol) in THF (5.00 mL, 61.7 mmol) and WATER (5.00 mL, 278 mmol). The reaction mixture was cooled in an ice bath, and a solution of $Boc_2O$ (0.117 g, 0.537 mmol) in THF 2 mL was added dropwise, and the solution was then stirred at ambient temperature for 18 h. The reaction mixture was diluted with water and EtOAc, pH was adjusted to 5 with 1 N aq. HCl, and the aqueous layer was extracted with EtOAc. The combined organics were dried over $MgSO_4$, filtered, and concentrated in vacuo, and the residue purified by chiral SFC (Column: Chiralpak AS-H (21×250 mm, 5 um); A: Liquid $CO_2$; B: Methanol; Isocratic: 70:30 (A:B); Flow Rate: 70 mL/min) to give separately (R)-2-(tert-butoxycarbonylamino)-4-(3-fluoro-4-(5-(1-phenylcyclopropyl)-thiazolo[5,4-b]pyridin-2-yl)phenyl)butanoic acid and (S)-2-(tert-butoxycarbonylamino)-4-(3-fluoro-4-(5-(1-phenylcyclopropyl)thiazolo[5,4-b]pyridin-2-yl)phenyl)butanoic acid. MS (ESI) m/z: calculated: 547.2; Observed: 548.1 ($M^+$+1).

Separately, the enantiomers of 2-(tert-butoxycarbonylamino)-4-(3-fluoro-4-(5-(1-phenylcyclopropyl)thiazolo[5,4-b]pyridin-2-yl)phenyl)butanoic acid were processed by the following procedure: 2-(tert-butoxycarbonyl)-4-(3-fluoro-4-(5-(1-phenylcyclopropyl)-thiazolo[5,4-b]pyridin-2-yl)phenyl)butanoic acid (0.047 g, 0.086 mmol) in DCM (2.0 mL) was added trifluoroacetic acid (1.0 mL, 13 mmol). After 5 min, the solvent was removed, the solid rinsed with water and diethyl ether to give both (R)-2-amino-4-(3-fluoro-4-(5-(1-phenylcyclopropyl)thiazolo[5,4-b]pyridin-2-yl)phenyl)butanoic acid trifluoroacetic acid salt and (S)-2-amino-4-(3-fluoro-4-(5-(1-phenylcyclopropyl)thiazolo[5,4-b]pyridin-2-yl)phenyl)butanoic acid trifluoroacetic acid salt. MS (ESI) m/z: calculated: 447.1; Observed: 448.1 ($M^+$+1).

Example 104

Synthesis of (R)-2-amino-4-(3-fluoro-4-(5-(1-phenylcyclopropyl)thiazolo[5,4-b]pyridin-2-yl)phenyl)-2-methylbutanoic acid and (S)-2-amino-4-(3-fluoro-4-(5-(1-phenylcyclopropyl)thiazolo[5,4-b]pyridin-2-yl)phenyl)-2-methylbutanoic acid

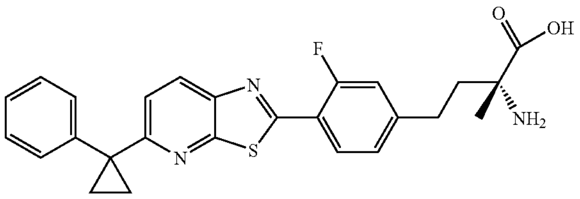

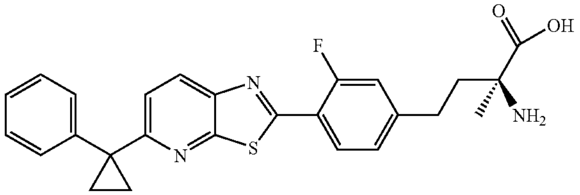

Step 1

In a sealable bottle under $N_2$ were combined fine cesium carbonate (0.399 g, 1.22 mmol) and ethyl 2-(diphenylmethyleneamino)propanoate (0.689 g, 2.45 mmol) in DMF (8 mL). The resulting slurry was allowed to stir for 1.5 h at ambient temperature. To the deep yellow reaction mixture was added 2-(2-fluoro-4-vinylphenyl)-5-(1-phenylcyclopropyl)-thiazolo[5,4-b]pyridine (0.380 g, 1.02 mmol) and the reaction mixture was heated to 40° C. After 18 h, the crude reaction mixture was concentrated in vacuo and purified by silica gel chromatography to afford material which was further purified by chiral SFC (Column: Chiralpak AD-H (21× 250 mm, 5 um); A: Liquid $CO_2$; B: Ethanol (0.2% IPA); Isocratic: 60:40 (A:B); Flow Rate: 70 mL/min; Outlet Pressure: 100 bar) to give both (R)-ethyl 2-(diphenylmethyleneamino)-4-(3-fluoro-4-(5-(1-phenylcyclopropyl)-thiazolo[5,4-b]pyridin-2-yl)phenyl)-2-methylbutanoateand (S)-ethyl 2-(diphenylmethyleneamino)-4-(3-fluoro-4-(5-(1-phenylcyclopropyl)thiazolo[5,4-b]pyridin-2-yl)phenyl)-2-methylbutanoate. MS (ESI) m/z: calculated: 653.3; Observed: 654.1 ($M^+$+1).

Separately, (R)-ethyl 2-(diphenylmethyleneamino)-4-(3-fluoro-4-(5-(1-phenyl-cyclopropyl)thiazolo[5,4-b]pyridin-2-yl)phenyl)-2-methylbutanoateand (S)-ethyl 2-(diphenylmethyleneamino)-4-(3-fluoro-4-(5-(1-phenylcyclopropyl) thiazolo[5,4-b]pyridin-2-yl)phenyl)-2-methylbutanoate were processed according to the following procedure: To a solution of ethyl 2-(diphenylmethyleneamino)-4-(3-fluoro-4-(5-(1-phenylcyclopropyl)-thiazolo[5,4-b]pyridin-2-yl) phenyl)-2-methylbutanoate (0.200 g, 0.307 mmol) in THF (2 mL) was added 1 N HCl. The reaction mixture was heated to 80° C. for 18 h. The reaction was judged complete by LCMS. The solvent was removed and the residue was diluted with water, the pH of the reaction mixture was adjusted to 1 with 1 N HCl. The solid observed was collected by filtration, and further purified by silica gel chromatography to afford, separately, (R)-2-amino-4-(3-fluoro-4-(5-(1-phenyl-cyclopropyl)thiazolo[5,4-b]pyridin-2-yl)phenyl)-2-methylbutanoic acid and (S)-2-amino-4-(3-fluoro-4-(5-(1-phenylcyclopropyl)thiazolo[5,4-b]pyridin-2-yl)phenyl)-2-methylbutanoic acid. MS (ESI) m/z: calculated: 461.2; Observed: 462.0 ($M^+$+1). $^1$H NMR (300 MHz, DMSO-$d_6$) δ ppm 8.55 (br. s., 3 H), 8.19-8.34 (m, 2 H), 7.23-7.51 (m, 7 H), 7.05 (d, J=8.6 Hz, 1 H), 2.82-3.00 (m, 1 H), 2.58-2.71 (m, 1 H), 2.08-2.20 (m, 2 H), 1.62-1.73 (m, 2 H), 1.52 (s, 3 H), 1.32-1.44 (m, 2 H)

Example 105

Synthesis of 2-(4-(1-azetidinylcarbonyl)-2-fluorophenyl)-5-(1-phenylcyclopropyl)-[1,3]thiazolo[5,4-b]pyridine

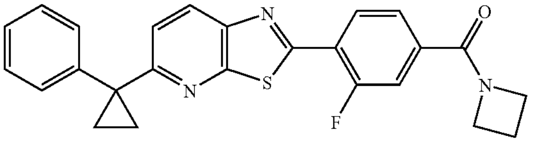

General procedure 1 for amide formation

To 3-fluoro-4-(5-(1-phenylcyclopropyl)thiazolo[5,4-b] pyridin-2-yl)benzoic acid (100 mg, 0.256 mmol) was added DMF (0.256 ml), N-ethyl-N-isopropylpropan-2-amine (98 μl, 0.563 mmol), HATU (117 mg, 0.307 mmol), and azetidine (21 μl, 0.307 mmol) before it was stirred at ambient temperature for 16 h. The reaction mixture was diluted with 100 mL of DCM, added to a separatory funnel, partitioned with water, washed 2 times with 50 mL of sodium bicarbonate (saturated, aqueous), separated, dried over sodium sulfate, and concentrated via rotovap to give the title compound after preparatory LC. MS (ESI) m/z: Calculated: 429.1; Observed: 430.1 ($M^+$+1).

Example 106

Synthesis of (3-fluoro-4-(5-(1-phenylcyclopropyl) thiazolo[5,4-b]pyridin-2-yl)phenyl)(morpholino) methanone

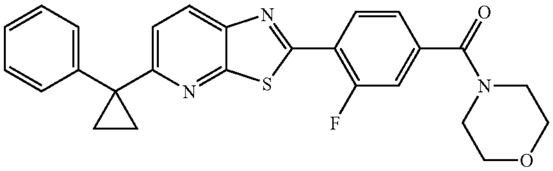

The title compound was synthesized using the described in Example 105 above using 3-fluoro-4-(5-(1-phenylcyclopropyl)thiazolo[5,4-b]pyridin-2-yl)benzoic acid (101 mg, 0.259 mmol) and morpholine. MS (ESI) m/z: Calculated: 459.1; Observed: 460.1 ($M^+$+1).

Example 107

Synthesis of R-2-(2-fluoro-4-(4-morpholinylcarbonyl)phenyl)-5-(1-phenyl-cyclopropyl)[1,3]thiazolo[5,4-b]pyridine

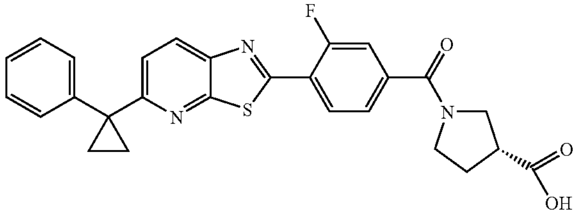

The title compound was synthesized using the procedure described in Example 105 above, with 3-fluoro-4-(5-(1-phenylcyclopropyl)thiazolo[5,4-b]pyridin-2-yl)benzoic acid (103 mg, 0.264 mmol) and (R)-pyrrolidine-3-carboxylic acid (36 mg, 0.317 mmol). MS (ESI) m/z: Calculated: 487.1; Observed: 488.1 ($M^{+}$+1).

Example 108

Synthesis of (3R)-1-((3-fluoro-4-(5-(1-phenylcyclopropyl)[1,3]thiazolo[5,4-b]pyridin-2-yl)phenyl)carbonyl)-3-piperidinecarboxylic acid

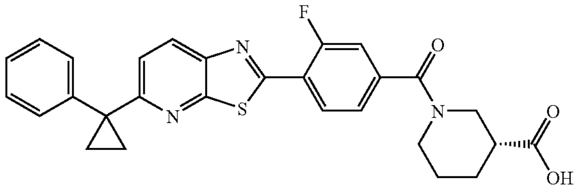

The title compound was synthesized using the procedure described in Example 105 above, with 3-fluoro-4-(5-(1-phenylcyclopropyl)thiazolo[5,4-b]pyridin-2-yl)benzoic acid (111 mg, 0.284 mmol) and (R)-piperidine-3-carboxylic acid (44 mg, 0.341 mmol). MS (ESI) m/z: Calculated: 501.2; Observed: 502.1 ($M^{+}$+1).

Example 109

Synthesis of 3-fluoro-N-(2-hydroxyethyl)-N-methyl-4-(5-(1-phenylcyclopropyl)-[1,3]thiazolo[5,4-b]pyridin-2-yl)benzamide

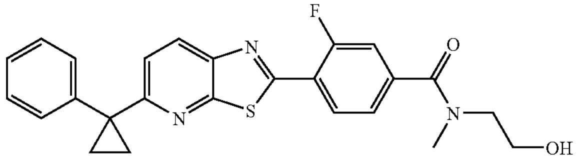

The title compound was synthesized using the procedure described in Example 105 above, with 3-fluoro-4-(5-(1-phenylcyclopropyl)thiazolo[5,4-b]pyridin-2-yl)benzoic acid (98 mg, 0.251 mmol) and 2-(methylamino)ethanol (24 µl, 0.301 mmol). MS (ESI) m/z: Calculated: 447.1; Observed: 448.1 ($M^{+}$+1).

Example 110

Synthesis of 3-fluoro-N-(2-methoxyethyl)-4-(5-(1-phenylcyclopropyl)[1,3]thiazolo[5,4-b]pyridin-2-yl)benzamide

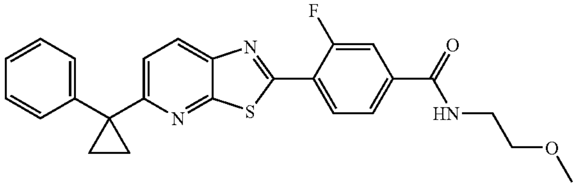

The title compound was synthesized using the procedure described in Example 105 above, with 3-fluoro-4-(5-(1-phenylcyclopropyl)thiazolo[5,4-b]pyridin-2-yl)benzoic acid (97 mg, 0.248 mmol) and 2-methoxyethylamine (26 µl, 0.298 mmol). MS (ESI) m/z: Calculated: 447.1; Observed: 448.1 ($M^{+}$+1).

Example 111

Synthesis of 3-fluoro-N-(2-hydroxyethyl)-4-(5-(1-phenylcyclopropyl)[1,3]thiazolo[5,4-b]pyridin-2-yl)benzamide

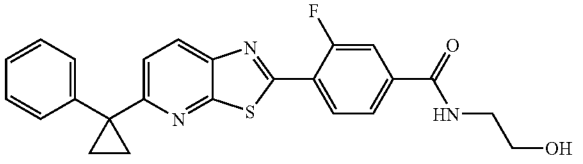

The title compound was synthesized using the procedure described in Example 105 above, with 3-fluoro-4-(5-(1-phenylcyclopropyl)thiazolo[5,4-b]pyridin-2-yl)benzoic acid (97 mg, 0.248 mmol) and ethanolamine (18 µl, 0.298 mmol). MS (ESI) m/z: Calculated: 433.1; Observed: 434.1 ($M^{+}$+1).

Example 112

Synthesis of 1-((3-fluoro-4-(5-(1-phenylcyclopropyl)[1,3]thiazolo[5,4-b]pyridin-2-yl)phenyl)carbonyl)-3-azetidinecarboxylic acid

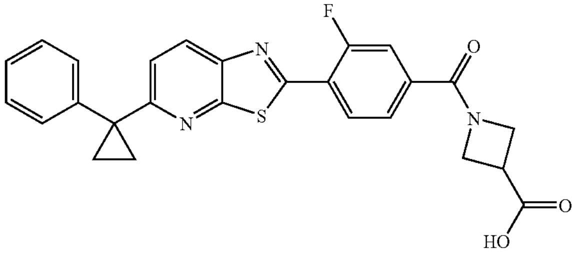

The title compound was synthesized using the procedure described in Example 105 above, with 3-fluoro-4-(5-(1-phenylcyclopropyl)thiazolo[5,4-b]pyridin-2-yl)benzoic acid (104 mg, 0.266 mmol) and azetidine-3-carboxylic acid (32 mg, 0.320 mmol). MS (ESI) m/z: Calculated: 473.1; Observed: 474.1 ($M^{+}$+1).

Example 113

Synthesis of N-cyclopropyl-3-fluoro-4-(5-(1-phenylcyclopropyl)[1,3]thiazolo[5,4-b]pyridin-2-yl)benzamide

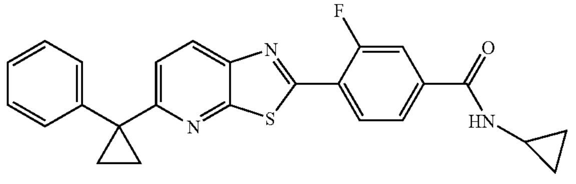

The title compound was synthesized using the procedure described in Example 105 above, with 3-fluoro-4-(5-(1-phenylcyclopropyl)thiazolo[5,4-b]pyridin-2-yl)benzoic acid (93 mg, 0.238 mmol) and cyclopropanamine (20 μl, 0.286 mmol). MS (ESI) m/z: Calculated: 429.1; Observed: 430.1 ($M^{+}$+1).

Example 114

Synthesis of 3-fluoro-N-(2-methoxyethyl)-N-methyl-4-(5-(1-phenylcyclopropyl)-[1,3]thiazolo[5,4-b]pyridin-2-yl)benzamide

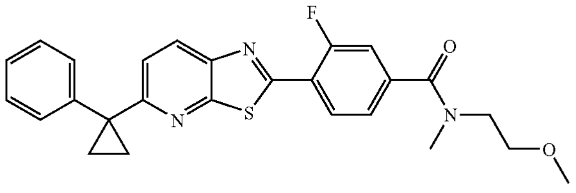

The title compound was synthesized using the procedure described in Example 105 above, with 3-fluoro-4-(5-(1-phenylcyclopropyl)thiazolo[5,4-b]pyridin-2-yl)benzoic acid (93 mg, 0.238 mmol) and N-(2-methoxyethyl)methylamine (31 μl, 0.286 mmol). MS (ESI) m/z: Calculated: 461.2; Observed: 462.1 ($M^{+}$+1).

Example 115

Synthesis of 3-(((3-fluoro-4-(5-(1-phenylcyclopropyl)[1,3]thiazolo[5,4-b]pyridin-2-yl)phenyl)carbonyl)amino)-3-methylbutanoic acid

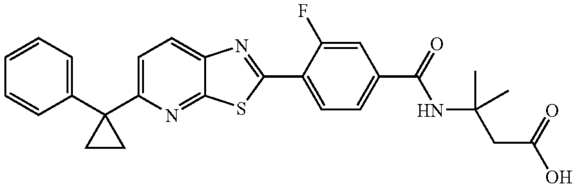

The title compound was synthesized using the procedure described in Example 105 above, with 3-fluoro-4-(5-(1-phenylcyclopropyl)thiazolo[5,4-b]pyridin-2-yl)benzoic acid (100 mg, 0.256 mmol) and 3-amino-3-methylbutanoic acid (36 mg, 0.307 mmol). MS (ESI) m/z: Calculated: 489.2; Observed: 490.1 ($M^{+}$+1).

Example 116

Synthesis of N-((3-fluoro-4-(5-(1-phenylcyclopropyl)[1,3]thiazolo[5,4-b]pyridin-2-yl)phenyl)carbonyl)-N-methyl-beta-alanine

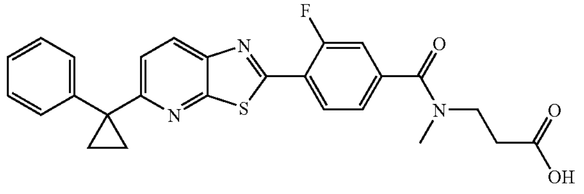

The title compound was synthesized using the procedure described in Example 105 above, with 3-fluoro-4-(5-(1-phenylcyclopropyl)thiazolo[5,4-b]pyridin-2-yl)benzoic acid (95 mg, 0.243 mmol) and 3-(methylamino)propanoic acid (75 mg, 0.730 mmol). MS (ESI) m/z: Calculated: 475.2; Observed: 476.1 ($M^{+}$+1).

Example 117

Synthesis of (rac)-3-(((3-fluoro-4-(5-(1-phenylcyclopropyl)[1,3]thiazolo[5,4-b]pyridin-2-yl)phenyl)carbonyl)amino)butanoic acid

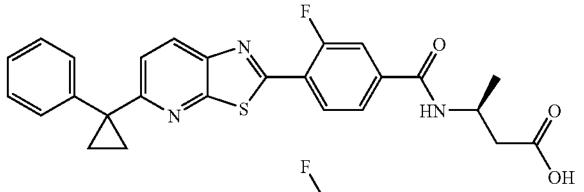

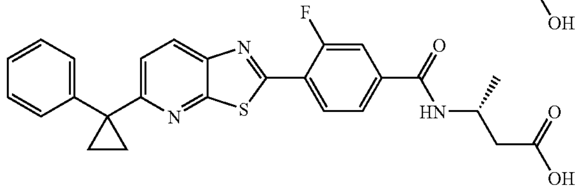

The title compound was synthesized using the procedure described in Example 105 above, with 3-fluoro-4-(5-(1-phenylcyclopropyl)thiazolo[5,4-b]pyridin-2-yl)benzoic acid (78 mg, 0.200 mmol) (rac)-3-aminobutyric acid (41 mg, 0.400 mmol). MS (ESI) m/z: Calculated: 475.1; Observed: 476.1 ($M^{+}$+1).

Example 118

Synthesis of 2,2,2-trifluoro-N-(3-fluoro-4-(5-(1-phenylcyclopropyl)[1,3]thiazolo[5,4-b]pyridin-2-yl)phenyl)acetamide

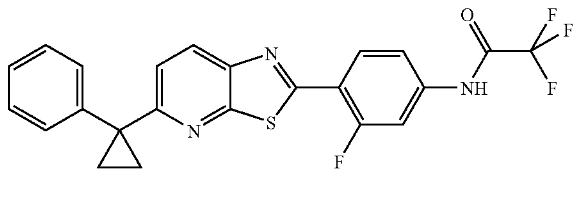

Step 1

3-Fluoro-4-(5-(1-phenylcyclopropyl)thiazolo[5,4-b]pyridin-2-yl)benzoic acid (105 mg, 269 μmol) was dissolved in thionyl chloride (5 mL) and was stirred at 65° C. for 1 h. The reaction mixture was concentrated before it was dissolved in DCM (3 mL); to this was added tetrabutylammonium bromide (8 mg, 27 μmol), water (269 μl, 269 μmol), and sodium azide (21.0 mg, 323 μmol) at 0° C. before it was stirred for 2 h. The reaction mixture was diluted with 75 mL of DCM, added to a separatory funnel, partitioned with water, washed 2 times with 50 mL of water, separated, dried over sodium sulfate, and concentrated via rotovap to give 3-fluoro-4-(5-(1-phenylcyclopropyl)thiazolo[5,4-b]pyridin-2-yl)benzoyl azide. MS (ESI) m/z: Calculated: 415.1; Observed: 416.0 ($M^{+}$+1).

Step 2

3-Fluoro-4-(5-(1-phenylcyclopropyl)thiazolo[5,4-b]pyridin-2-yl)benzoyl azide was dissolved in DCM (3 mL) before trifluoroacetic acid (41.4 μl, 538 μmol) was added at ambient T; the reaction mixture was stirred for 16 h at 80° C. to effect the rearrangement. The reaction mixture was diluted with 75 mL of DCM, added to a separatory funnel, partitioned with sodium bicarbonate (saturated, aqueous), washed 2 times with 50 mL of sodium bicarbonate (saturated, aqueous), separated, dried over sodium sulfate, and concentrated via rotovap to give 2,2,2-trifluoro-N-(3-fluoro-4-(5-(1-phenylcyclopropyl)[1,3]thiazolo[5,4-b]pyridin-2-yl)phenyl)acetamide as a yellow solid after flash chromatography. MS (ESI) m/z: Calculated: 457.1; Observed: 458.0 ($M^{+}$+1).

Example 119

Synthesis of 1-(3-fluoro-4-(5-(1-phenylcyclopropyl)[1,3]thiazolo[5,4-b]pyridin-2-yl)phenyl)-N-methylcyclopropanamine

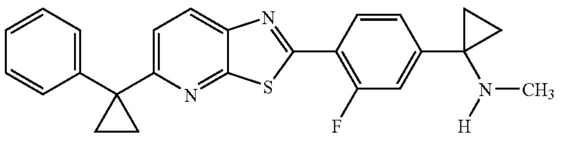

Step 1

A solution of 1-(3-fluoro-4-(5-(1-phenylcyclopropyl)thiazolo[5,4-b]pyridin-2-yl)phenyl)cyclopropanamine (0.108 g, 0.270 mmol) in methylene chloride (1.3 mL) was added di-tert-butyl dicarbonate (0.088 g, 0.4 mmol) and triethylamine (0.053 mL, 0.37 mmol) and heated at 50° C. for 6 h. The cooled reaction mixture was diluted with methylene chloride and washed with aqueous saturated sodium bicarbonate solution and brine. The organic layer was dried ($MgSO_4$), filtered, and concentrated in vacuo. Flash column chromatography with 10% to 20% ethyl acetate/hexanes afforded tert-butyl 1-(3-fluoro-4-(5-(1-phenyl-cyclopropyl)thiazolo[5,4-b]pyridin-2-yl)phenyl)cyclopropylcarbamate as a yellow amorphous solid. MS (ESI) m/z: Calculated: 501.6; Observed: 502.1 ($M^{+}$+1).

Step 2

A solution of tert-butyl 1-(3-fluoro-4-(5-(1-phenylcyclopropyl)thiazolo[5,4-b]pyridin-2-yl)phenyl)cyclopropylcarbamate (0.077 g, 0.15 mmol) in N,N-dimethylformamide (0.8 mL) under argon was cooled to 0° C. and added sodium hydride, 60% dispersion in mineral oil (0.009 g, 0.21 mmol). After stirring for 10 min, iodomethane (0.014 mL, 0.23 mmol) was added, and the reaction mixture was allowed to gradually warm to room temperature and stirred for 1 h. The reaction mixture was diluted with ethyl acetate and washed with water. The organic layer was dried ($MgSO_4$), filtered, and concentrated in vacuo. Flash column chromatography with 5% to 20% ethyl acetate/hexanes afforded tert-butyl (1-(3-fluoro-4-(5-(1-phenylcyclopropyl)[1,3]-thiazolo[5,4-b]pyridin-2-yl)phenyl)-cyclopropyl)methylcarbamate as a light yellow amorphous solid. MS (ESI) m/z: Calculated: 515.6; Observed: 516.2 ($M^{+}$+1).

Step 3

A solution of tert-butyl 1-(3-fluoro-4-(5-(1-phenylcyclopropyl)thiazolo[5,4-b]pyridin-2-yl)phenyl)cyclopropyl(methyl)carbamate (0.03 g, 0.058 mmol) in chloroform (0.5 mL) was added trifluoroacetic acid (0.5 mL, 6.5 mmol) and stirred at room temperature for 2 h. The reaction mixture was concentrated in vacuo, and the resulting crude product was purified via reverse phase preparative HPLC to afford '1-(3-fluoro-4-(5-(1-phenyl-cyclopropyl)[1,3]thiazolo[5,4-b]pyridin-2-yl)phenyl)-N-methylcyclopropanamine as a white amorphous solid. MS (ESI) m/z: Calculated: 415.5; Observed: 416.1 ($M^{+}$+1).

Example 120

Synthesis of 3-fluoro-N,N-dimethyl-4-(5-(1-phenylcyclopropyl)[1,3]thiazolo[5,4-b]pyridin-2-yl)aniline

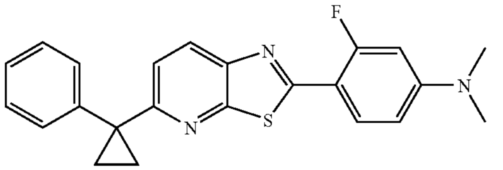

2,2,2-Trifluoro-N-(3-fluoro-4-(5-(1-phenylcyclopropyl)thiazolo[5,4-b]pyridin-2-yl)phenyl)acetamide (80 mg, 0.175 mmol) was dissolved in THF (1.7 mL) before methyl iodide (13 μl, 0.210 mmol) and lithium diisopropylamide (175 μl, 0.350 mmol) were added and stirred at 0° C. for 30 min. The reaction mixture was diluted with 75 mL of DCM, added to a separatory funnel, partitioned with sodium bicarbonate (saturated, aqueous), washed 2 times with 50 mL of water, separated, dried over sodium sulfate, and concentrated via rotovap to give the title compound after flash chromatography. MS (ESI) m/z: Calculated: 389.1; Observed: 390.1 ($M^{+}$+1).

Example 121

Synthesis of 3-fluoro-N-methyl-4-(5-(1-phenylcyclopropyl)[1,3]thiazolo[5,4-b]pyridin-2-yl)aniline

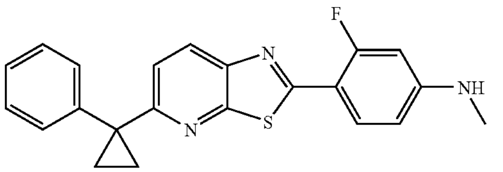

The title compound was obtained after separation via flash chromatography from 3-fluoro-N,N-dimethyl-4-(5-(1-phenylcyclopropyl) [1,3]thiazolo[5,4-b]pyridin-2-yl)aniline. MS (ESI) m/z: Calculated: 375; Observed: 376.1 ($M^{+}$+H).

Example 122

Synthesis of N-(3-fluoro-4-(5-(1-phenylcyclopropyl)[1,3]thiazolo[5,4-b]pyridin-2-yl)phenyl)-N-(methylsulfonyl)methanesulfonamide

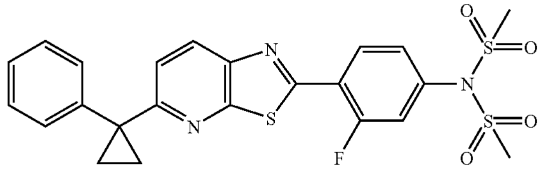

To 3-fluoro-4-(5-(1-phenylcyclopropyl)thiazolo[5,4-b]pyridin-2-yl)benzenamine (34 mg, 0.094 mmol) was added DCM (0.9 mL), triethylamine (26 μl, 0.188 mmol), and methanesulfonyl chloride (11 μl, 0.141 mmol) before it was stirred at ambient T for 1 h. The reaction mixture was diluted with 100 mL of DCM, added to a separatory funnel, partitioned with 5 N NaOH (aqueous), washed 3 times with 75 mL of 5 N NaOH (aqueous), separated, dried over sodium sulfate, and concentrated via rotovap to the title compound. MS (ESI) m/z: Calculated: 517.1; Observed: 518.0 ($M^+$+1).

Example 123

Synthesis of 4-((3-fluoro-4-(5-(1-phenylcyclopropyl)[1,3]thiazolo[5,4-b]pyridin-2-yl)phenyl)amino)-4-oxobutanoic acid

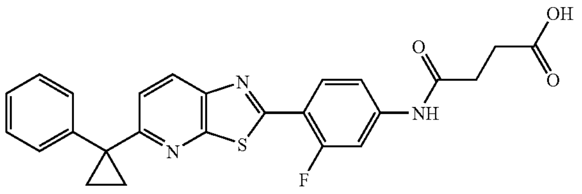

Step 1

3-Fluoro-4-(5-(1-phenylcyclopropyl)thiazolo[5,4-b]pyridin-2-yl)benzenamine (140 mg, 0.387 mmol) was dissolved in THF (3.9 mL) and N-ethyl-N-isopropylpropan-2-amine (270 μl, 1.55 mmol) before methyl 4-chloro-4-oxobutanoate (189 μl, 1.55 mmol) was added at ambient temperature and the reaction mixture was stirred at ambient temperature for 30 min. The reaction mixture was diluted with 100 mL of DCM, added to a separatory funnel, partitioned with water, washed 2 times with 50 mL of sodium bicarbonate (saturated, aqueous), separated, dried over sodium sulfate, and concentrated via rotovap to give methyl 4-(3-fluoro-4-(5-(1-phenylcyclopropyl)thiazolo[5,4-b]pyridin-2-yl)phenylamino)-4-oxobutanoate after flash chromatography. MS (ESI) m/z: Calculated: 475.1; Observed: 476.4 ($M^+$+1).

Step 2

To methyl 4-(3-fluoro-4-(5-(1-phenylcyclopropyl)thiazolo[5,4-b]pyridin-2-yl)-phenylamino)-4-oxobutanoate (123 mg, 0.259 mmol) was added THF/water (4:1) (2.587 m, 0.259 mmol) and lithium hydroxide hydrate (33 mg, 0.776 mmol) before it was stirred at ambient T for 30 min. The reaction mixture was concentrated, triturated with water, filtered, washed with water, and dried in a vacuum oven to give the title compound. MS (ESI) m/z: Calculated: 461.1; Observed: 462.0 ($M^+$+1).

Example 124

Synthesis of 3-((3-fluoro-4-(5-(1-phenylcyclopropyl)[1,3]thiazolo[5,4-b]pyridin-2-yl)phenyl)sulfamoyl)propanoic acid

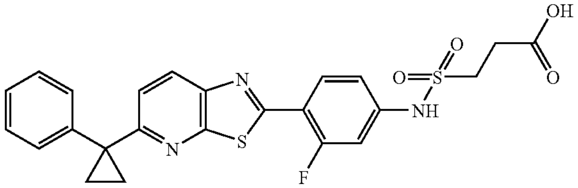

Step 1

To 3-fluoro-4-(5-(1-phenylcyclopropyl)thiazolo[5,4-b]pyridin-2-yl)benzenamine (50 mg, 0.138 mmol) was added DCM (1.4 mL), pyridine (0.112 ml), and methyl 3-(chlorosulfonyl)-propanoate (52 mg, 0.277 mmol) before it was stirred at ambient temperature for 3 h. The reaction mixture was diluted with 100 mL of DCM, added to a separatory funnel, partitioned with water, washed 2 times with 50 mL of water, separated, dried over sodium sulfate, and concentrated via rotovap to give methyl'3-((3-fluoro-4-(5-(1-phenylcyclopropyl)-[1,3]thiazolo[5,4-b]pyridin-2-yl)phenyl)sulfamoyl)propanoate after flash chromatography. MS (ESI) m/z: Calculated: 511.1; Observed: 512.0 ($M^+$+1).

Step 2

To methyl '3-((3-fluoro-4-(5-(1-phenylcyclopropyl)[1,3]thiazolo[5,4-b]pyridin-2-yl)phenyl)sulfamoyl)propanoate (35 mg, 0.068 mmol) was added THF/water (4:1) (0.684 ml) and lithium hydroxide hydrate (11 mg, 0.274 mmol) before it was stirred at ambient temperature for 3 h. The reaction mixture was concentrated to remove the THF, acidified with 5 N HCl, filtered, washed with water, and dried in a vacuum oven to give the title compound. MS (ESI) m/z: Calculated: 497.1; Observed: 498.0 ($M^+$+1).

Example 125

Synthesis of 1-(3-fluoro-4-(5-(1-phenylcyclopropyl)[1,3]thiazolo[5,4-b]pyridin-2-yl)phenyl)-2-pyrrolidinone

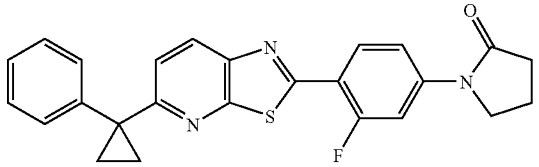

3-Fluoro-4-(5-(1-phenylcyclopropyl)thiazolo[5,4-b]pyridin-2-yl)benzenamine (110 mg, 0.304 mmol) was dissolved in ethyl 4-bromobutanoate (59 mg, 0.304 mmol) before it was placed in the microwave for 60 min at 140° C. The title compound was obtained after flash chromatography. MS (ESI) m/z: Calculated: 429.1; Observed: 430.1 ($M^+$+1).

Example 126

Synthesis of N-(3-fluoro-4-(5-(1-phenylcyclopropyl)[1,3]thiazolo[5,4-b]pyridin-2-yl)phenyl)-D-alpha-asparagine TFA salt

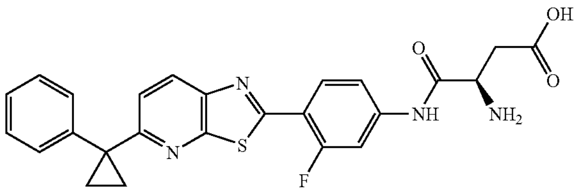

Step 1

To (R)-2-(tert-butoxycarbonyl)succinic acid (1.93 g, 8.28 mmol) was added ethyl acetate (8.3 mL) and N-((isopropylimino)methylene)propan-2-amine (2.59 mL, 16.6 mmol) before it was stirred at 60° C. for 2 h. The reaction mixture was diluted with 100 mL of diethyl ether, added to a separatory funnel, partitioned with sodium bicarbonate (saturated, aqueous), washed 2 times with 50 mL of sodium bicarbonate (saturated, aqueous), separated, dried over sodium sulfate, and concentrated via rotovap to give (R)-tert-butyl 2,5-dioxo-tetrahydrofuran-3-ylcarbamate. MS (ESI) m/z: Calculated: 215.1; Observed: 238.4 ($M^+$+Na).

Step 2

To 3-fluoro-4-(5-(1-phenylcyclopropyl)thiazolo[5,4-b]pyridin-2-yl)benzenamine (206 mg, 0.570 mmol) and (R)-tert-butyl 2,5-dioxo-tetrahydrofuran-3-ylcarbamate (123 mg, 0.570 mmol) was added benzene (5.7 mL) and acetic acid (163 µl, 2.85 mmol) before it was stirred at 80° C. for 1 h. The two regioisomers were separated via SFC (Column: Princeton Pyridine, Mobile Phase: 60:40 liquid $CO_2$/MeOH) to give (3R)-3-(tert-butoxycarbonylamino)-4-(3-fluoro-4-(5-(1-phenylcyclopropyl)thiazolo[5,4-b]pyridin-2-yl)phenylamino)-4-oxobutanoic acid and its regioisomer. MS (ESI) m/z: Calculated: 576.2; Observed: 577.1 ($M^+$+H).

Step 3

(3R)-3-(tert-Butoxycarbonylamino)-4-(3-fluoro-4-(5-(1-phenylcyclopropyl)thiazolo[5,4-b]pyridin-2-yl)phenylamino)-4-oxobutanoic acid (140 mg, 0.243 mmol) was dissolved in DCM (1 mL) before it was cooled to 0° C. and TFA (18 µl) was added; this was allowed to slowly warm to ambient T for 1 h before it was concentrated to give the title compound. MS (ESI) m/z: Calculated: 476.1; Observed: 477.1 ($M^+$+H).

Example 127

Synthesis of N-(3-fluoro-4-(5-(1-phenylcyclopropyl)[1,3]thiazolo[5,4-b]pyridin-2-yl)phenyl)-D-asparagine TFA salt

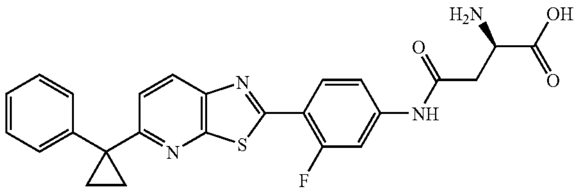

Step 1

(2R)-2-(tert-Butoxycarbonylamino)-4-(3-fluoro-4-(5-(1-phenylcyclopropyl)thiazolo[5,4-b]pyridin-2-yl)phenylamino)-4-oxobutanoic acid was obtained after SFC separation (Column: Princeton Pyridine, Mobile Phase: 60:40 liquid $CO_2$/MeOH) from (3R)-3-(tert-butoxycarbonylamino)-4-(3-fluoro-4-(5-(1-phenylcyclopropyl)thiazolo[5,4-b]pyridin-2-yl)phenylamino)-4-oxobutanoic acid. MS (ESI) m/z: Calculated: 576; Observed: 577.1 ($M^+$+H).

Step 2

(2R)-2-(tert-Butoxycarbonylamino)-4-(3-fluoro-4-(5-(1-phenylcyclopropyl)-thiazolo[5,4-b]pyridin-2-yl)phenylamino)-4-oxobutanoic acid (65 mg, 0.113 mmol) was added DCM (2 mL) before it was cooled to 0° C. and TFA (18 µl) was added; the reaction mixture was allowed to slowly warm to ambient temperature and stirred for 1 h before it was concentrated to give the title compound. MS (ESI) m/z: Calculated: 476; Observed: 477.1 ($M^+$+H).

Example 128

Synthesis of N-(3-fluoro-4-(5-(1-phenylcyclopropyl)[1,3]thiazolo[5,4-b]pyridin-2-yl)phenyl)-L-alpha-asparagine TFA salt

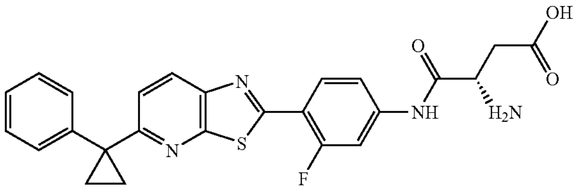

The title compound was prepared in a procedure similar to that of N-(3-fluoro-4-(5-(1-phenylcyclopropyl)[1,3]thiazolo[5,4-b]pyridin-2-yl)phenyl)-D-alpha-asparagine TFA salt above. MS (ESI) m/z: Calculated: 476.1; Observed: 477.0 ($M^+$+H).

Example 129

Synthesis of N-(3-fluoro-4-(5-(1-phenylcyclopropyl)[1,3]thiazolo[5,4-b]pyridin-2-yl)phenyl)-L-asparagine

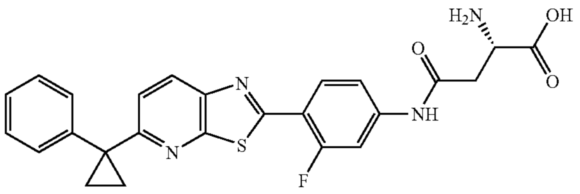

The title compound was prepared in a procedure similar to that of N-(3-fluoro-4-(5-(1-phenylcyclopropyl)[1,3]thiazolo[5,4-b]pyridin-2-yl)phenyl)-D-asparagine TFA salt above. MS (ESI) m/z: Calculated: 476.1; Observed: 477.1 ($M^+$+H).

Example 130

Synthesis of cis-3-((3-fluoro-4-(5-(1-phenylcyclopropyl)[1,3]thiazolo[5,4-b]pyridin-2-yl)phenyl)amino)cyclobutanecarboxylic acid

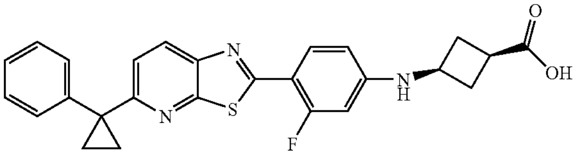

Step 1

To 3-fluoro-4-(5-(1-phenylcyclopropyl)thiazolo[5,4-b]pyridin-2-yl)benzenamine (183 mg, 0.506 mmol) and 3-oxocyclobutanecarboxylic acid (63.5 mg, 0.557 mmol) in DCM (2.5 mL) and triethylamine (212 μl, 1.519 mmol) was added titanium(IV) chloride in DCM (0.759 ml, 0.759 mmol) at ambient temperature. The reaction mixture was concentrated, suspended in water, filtered, washed with water, and dried in a vacuum oven to give 3-((3-fluoro-4-(5-(1-phenyl-cyclopropyl)[1,3]thiazolo[5,4-b]pyridin-2-yl)phenyl)amino)cyclobutanecarboxylic acid as yellow solid. MS (ESI) m/z: Calculated: 459.1; Observed: 460.4 ($M^+$+H).

Step 2

To 3-(3-fluoro-4-(5-(1-phenylcyclopropyl)thiazolo[5,4-b]pyridin-2-yl)-phenylamino)-cyclobutanecarboxylic acid (230 mg, 0.501 mmol) was added methanol (5.0 mL) and thionyl chloride (37 μl, 0.501 mmol) before it was stirred at ambient temperature for 30 min; the reaction mixture was concentrated, and the diastereomers were separated via SFC (Column: ChiralPak AS-H, Mobile Phase: liquid $CO_2$/20% MeOH with diethylamine; then Column: Princeton Pyridine, Mobile Phase: liquid $CO_2$/12% MeOH) to give methyl cis-3-((3-fluoro-4-(5-(1-phenyl-cyclopropyl)[1,3]thiazolo[5,4-b]pyridin-2-yl)phenyl)amino)-cyclobutanecarboxylate. MS (ESI) m/z: Calculated: 473.2; Observed: 474.1 ($M^+$+H).

Step 3

Methyl cis-3-((3-fluoro-4-(5-(1-phenylcyclopropyl)[1,3]thiazolo[5,4-b]pyridin-2-yl)phenyl)amino)cyclobutanecarboxylate (2.0 mg, 4.2 μmol) was dissolved in THF (42 μl) before 0.1 N sodium hydroxide (42 μl, 4.2 μmol) was added and stirred at ambient temperature for 16 h. The reaction mixture was acidified with 2 N HCl, diluted with THF, separated, dried over sodium sulfate, and was concentrated to give the title compound. MS (ESI) m/z: Calculated: 459.1; Observed: 460.0 ($M^+$+H).

Example 131

Synthesis of trans-3-((3-fluoro-4-(5-(1-phenylcyclopropyl)[1,3]thiazolo[5,4-b]pyridin-2-yl)phenyl)amino)cyclobutanecarboxylic acid

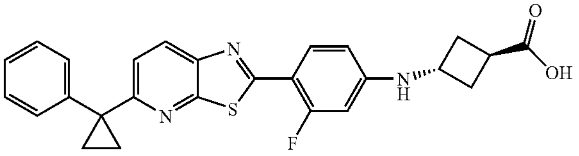

Step 1

Methyl trans-3-((3-fluoro-4-(5-(1-phenylcyclopropyl)[1,3]thiazolo[5,4-b]pyridin-2-yl)phenyl)amino)cyclobutanecarboxylate was obtained after SFC separation (Column: ChiralPak AS-H, Mobile Phase: liquid $CO_2$/20% MeOH with diethylamine; then Column: Princeton Pyridine, Mobile Phase: liquid $CO_2$/12% MeOH) from methyl cis-3-((3-fluoro-4-(5-(1-phenylcyclopropyl)-[1,3]thiazolo[5,4-b]pyridin-2-yl)phenyl)amino)cyclobutane-carboxylate. MS (ESI) m/z: Calculated: 473.2; Observed: 474.1 ($M^+$+H).

Step 2

Methyl trans-3-((3-fluoro-4-(5-(1-phenylcyclopropyl)[1,3]thiazolo[5,4-b]pyridin-2-yl)phenyl)amino)cyclobutanecarboxylate (2.0 mg, 4.2 μmol) was dissolved in THF (0.422 ml) before 0.1 N sodium hydroxide (169 μl, 17 μmol) was added and stirred for 16 h at ambient temperature. The reaction mixture was acidified with 2 N HCl, diluted with THF, separated, dried over sodium sulfate, and was concentrated to give the title compound. MS (ESI) m/z: Calculated: 459.1; Observed: 460.0 ($M^+$+H).

Example 132

Synthesis of (2S)-4-((3-fluoro-4-(5-(1-phenylcyclopropyl)[1,3]thiazolo[5,4-b]pyridin-2-yl)phenyl)amino)-2-hydroxy-4-oxobutanoic acid

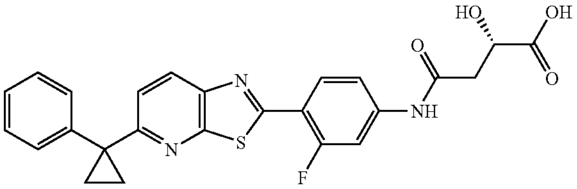

Step 1

To 3-fluoro-4-(5-(1-phenylcyclopropyl)thiazolo[5,4-b]pyridin-2-yl)benzenamine (70 mg, 0.194 mmol) and (S)-(−)-2-acetoxysuccinic anhydride (34 mg, 213 μmol) was added benzene (1.9 mL) and acetic acid (55 μl, 0.968 mmol) before it was stirred at 80° C. for 1 h. The reaction mixture was concentrated before the regioisomers were separated via SFC (Column: Chiralpak IC, Mobile Phase: liquid $CO_2$/40% MeOH) to give (2S)-2-acetoxy-4-(3-fluoro-4-(5-(1-phenylcyclopropyl)-thiazolo[5,4-b]pyridin-2-yl)phenylamino)-4-oxobutanoic acid. MS (ESI) m/z: Calculated: 519.1; Observed: 520.1 ($M^+$+H).

Step 2

(2S)-2-Acetoxy-4-(3-fluoro-4-(5-(1-phenylcyclopropyl)thiazolo[5,4-b]pyridin-2-yl)phenylamino)-4-oxobutanoic acid (7.0 mg, 13 μmol) was dissolved in THF (135 μl, 13 μmol) before 0.1 N sodium hydroxide (404 μl, 40 μmol) was added and stirred at ambient temperature for 24 h. The reaction mixture was concentrated to give (2S)-4-((3-fluoro-4-(5-(1-phenylcyclopropyl)[1,3]thiazolo[5,4-b]pyridin-2-yl)phenyl)amino)-2-hydroxy-4-oxobutanoic acid after preparative LC purification. MS (ESI) m/z: Calculated: 476.1; Observed: 477.7 ($M^+$+H).

Example 133

Synthesis of (3S)-4-(3-fluoro-4-(5-(1-phenylcyclopropyl)thiazolo[5,4-b]pyridin-2-yl)phenylamino)-3-hydroxy-4-oxobutanoic acid

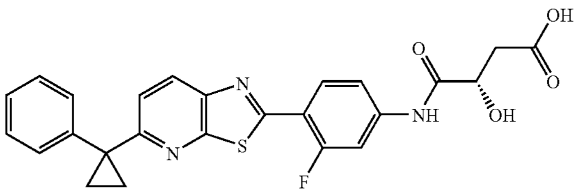

Step 1

(3S)-3-Acetoxy-4-(3-fluoro-4-(5-(1-phenylcyclopropyl)thiazolo[5,4-b]pyridin-2-yl)phenylamino)-4-oxobutanoic acid was obtained after SFC separation (Column: Chiralpak IC, Mobile Phase: liquid $CO_2$/40% MeOH) from (2S)-2-acetoxy-4-(3-fluoro-4-(5-(1-phenylcyclopropyl)thiazolo[5,4-b]pyridin-2-yl)phenylamino)-4-oxobutanoic acid in Example 132 above. MS (ESI) m/z: Calculated: 519.1; Observed: 520.1 ($M^+$+H).

Step 2

(3S)-3-Acetoxy-4-(3-fluoro-4-(5-(1-phenylcyclopropyl)thiazolo[5,4-b]pyridin-2-yl)phenylamino)-4-oxobutanoic acid (65 mg, 0.125 mmol) was dissolved in THF (1.3 mL) before 0.1 N sodium hydroxide (3.75 ml, 0.375 mmol) was added and stirred at ambient temperature for 24 h; the reaction had not gone to completion, so more NaOH was added and stirred for another 4 h. The reaction mixture was concentrated to remove the THF, acidified with 2 N HCl to crash out the product, filtered, washed with water, and dried in a vacuum oven to give the title compound. MS (ESI) m/z: Calculated: 477.1; Observed: 477.7 ($M^+$+H).

Example 134

Synthesis of (2R)-4-((3-fluoro-4-(5-(1-phenylcyclopropyl)[1,3]thiazolo[5,4-b]pyridin-2-yl)phenyl)amino)-2-hydroxy-4-oxobutanoic acid

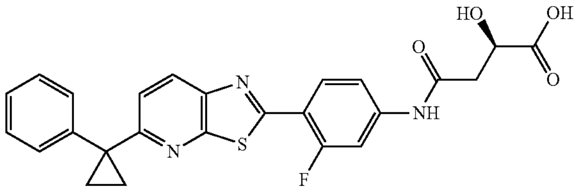

The title compound was prepared in a procedure similar to that of (2S)-4-((3-fluoro-4-(5-(1-phenylcyclopropyl)[1,3]thiazolo[5,4-b]pyridin-2-yl)phenyl)amino)-2-hydroxy-4-oxobutanoic acid above. MS (ESI) m/z: Calculated: 477.1; Observed: 478.0 ($M^+$+H).

Example 135

Synthesis of (3R)-4-((3-fluoro-4-(5-(1-phenylcyclopropyl)[1,3]thiazolo[5,4-b]pyridin-2-yl)phenyl)amino)-3-hydroxy-4-oxobutanoic acid

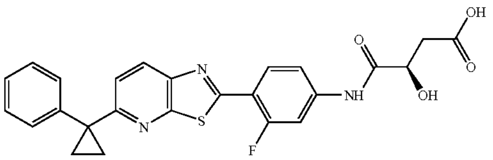

The title compound was prepared in a procedure similar to that of (3S)-4-((3-fluoro-4-(5-(1-phenylcyclopropyl)[1,3]thiazolo[5,4-b]pyridin-2-yl)phenyl)amino)-2-hydroxy-4-oxobutanoic acid above. MS (ESI) m/z: Calculated: 477.1; Observed: 478.0 ($M^+$+H).

Example 136

Synthesis of 2-(1H-indol-5-yl)-5-(1-phenylcyclopropyl)thiazolo[5,4-b]pyridine

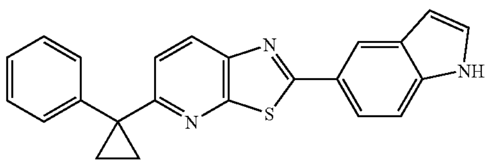

Step 1

A mixture of 3-amino-6-(1-phenylcyclopropyl)pyridine-2(1H)-thione (750 mg, 3.10 mmol), 1H-indole-5-carboxylic acid (499 mg, 3.10 mmol), 1H-benzo[d][1,2,3]triazol-1-ol hydrate (474 mg, 3.10 mmol), and N1-((ethylimino)methylene)-N3,N3-dimethylpropane-1,3-diamine hydrochloride (593 mg, 3.10 mmol) in DMF (3.1 mL) was stirred at ambient temperature for 16 h. The reaction mixture was diluted with 100 mL of EtOAc, added to a separatory funnel, partitioned with water, washed 2 times with 50 mL of water, separated, dried over sodium sulfate, and concentrated via rotovap to give N-(2-mercapto-6-(1-phenylcyclopropyl)pyridin-3-yl)-1H-indole-5-carboxamide. MS (ESI) m/z: Calculated: 385.1; Observed: 386.4 ($M^+$+H).

Step 2

To N-(2-mercapto-6-(1-phenylcyclopropyl)pyridin-3-yl)-1H-indole-5-carboxamide (360 mg, 0.934 mmol) was added toluene (9.3 mL) and camphor sulfonic acid (195 mg, 0.841 mmol) before it was heated to 100° C. for 16 h. The reaction mixture was diluted with 100 mL of DCM, added to a separatory funnel, partitioned with sodium bicarbonate (saturated, aqueous), washed 1 time with 50 mL of sodium bicarbonate (saturated, aqueous), separated, dried over sodium sulfate, and concentrated via rotovap to give the title compound after after flash chromatography. MS (ESI) m/z: Calculated: 367.1; Observed: 368.1 ($M^+$+H).

Example 137

Synthesis of 3-(5-(5-(1-phenylcyclopropyl)[1,3]thiazolo[5,4-b]pyridin-2-yl)-1H-indol-1-yl)propanoic acid

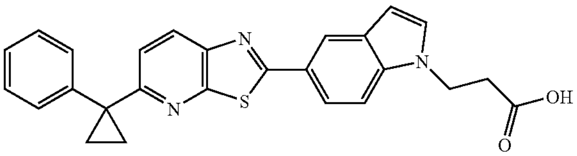

Step 1

To 2-(1H-indol-5-yl)-5-(1-phenylcyclopropyl)thiazolo[5,4-b]pyridine (90 mg, 0.245 mmol) was added acetonitrile (2.4 mL), ethylacrylate (80 μl, 735 μmol), and cesium carbonate (160 mg, 0.490 mmol) before it was stirred at ambient temp. for 3 h; the reaction mixture was quenched with 2 N HCl, concentrated, and was diluted with 75 mL of EtOAc, added to a separatory funnel, partitioned with water, washed 1 time with 50 mL of water, separated, dried over sodium sulfate, and concentrated via rotovap to give ethyl 3-(5-(5-(1-phenylcyclopropyl)[1,3]thiazolo[5,4-b]pyridin-2-yl)-1H-indol-1-yl)propanoate.

Step 2

Ethyl 3-(5-(5-(1-henylcyclopropyl)[1,3]thiazolo[5,4-b]pyridin-2-yl)-1H-indol-1-yl)propanoate was dissolved in aqueous THF (3 mL) before lithium hydroxide (18 mg, 0.735 mmol) was added and stirred at ambient temp. for 16 h. The reaction mixture was concentrated to remove THF, acidified with 2 N HCl, filtered, washed with water, and dried in a vacuum oven to give the title compound as an off white solid. MS (ESI) m/z: Calculated: 439.1; Observed: 439.8 ($M^{+}$+H).

Example 138

Synthesis of 4-(5-(5-(1-phenylcyclopropyl)[1,3]thiazolo[5,4-b]pyridin-2-yl)-1H-indol-1-yl)butanoic acid

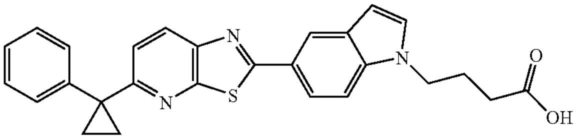

Step 1

2-(1H-Indol-5-yl)-5-(1-phenylcyclopropyl)thiazolo[5,4-b]pyridine (80 mg, 0.218 mmol) was dissolved in DMF (1.1 mL) before cesium carbonate (156 mg, 0.479 mmol) was added and stirred at ambient temperature for 1 h; to the reaction mixture was added methyl 4-bromobutanoate (43 mg, 239 μmol) before it was stirred for 20 h at 80° C. The reaction mixture was diluted with 100 mL of DCM, added to a separatory funnel, partitioned with water, washed 1 times with 50 mL of water, separated, dried over sodium sulfate, and concentrated via rotovap to give methyl 4-(5-(5-(1-phenylcyclopropyl)thiazolo[5,4-b]pyridin-2-yl)-1H-indol-1-yl)butanoate after flash chromatography. MS (ESI) m/z: Calculated: 467.2; Observed: 468.4 ($M^{+}$+H).

Step 2

Methyl 4-(5-(5-(1-phenylcyclopropyl)thiazolo[5,4-b]pyridin-2-yl)-1H-indol-1-yl)butanoate (63 mg, 0.135 mmol) was dissolved in THF (1.3 mL) before lithium hydroxide, monohydrate (11 mg, 0.269 mmol) was added and stirred at ambient temperature for 3 h. The reaction mixture was concentrated, acidified with 2 N HCl, filtered, washed with water, and dried in a vacuum oven to give the title compound. MS (ESI) m/z: Calculated: 453.2; Observed: 453.8 ($M^{+}$+H).

Example 139

Synthesis of (5-(5-(1-phenylcyclopropyl)[1,3]thiazolo[5,4-b]pyridin-2-yl)-1H-indol-1-yl)acetic acid

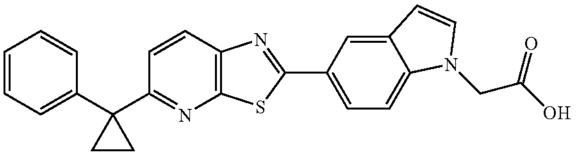

The title compound was prepared in a procedure similar to that of 4-(5-(5-(1-phenylcyclopropyl)[1,3]thiazolo[5,4-b]pyridin-2-yl)-1H-indol-1-yl)butanoic acid above. MS (ESI) m/z: Calculated: 425.1; Observed: 425.8 ($M^{+}$+H).

Example 140

Synthesis of 2-(1H-benzimidazol-5-yl)-5-(1-phenylcyclopropyl)[1,3]thiazolo[5,4-b]pyridine

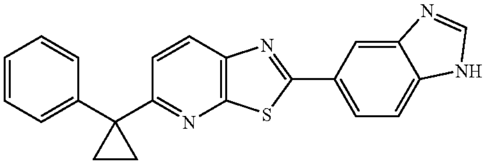

The title compound was prepared in a procedure similar to that of 2-(1H-indol-5-yl)-5-(1-phenylcyclopropyl)thiazolo[5,4-b]pyridine. MS (ESI) m/z: Calculated: 368.1; Observed: 369.1 ($M^{+}$+H).

Example 141

Synthesis of 3-(5-(5-(1-phenylcyclopropyl)[1,3]thiazolo[5,4-b]pyridin-2-yl)-1H-benzimidazol-1-yl)propanoic acid

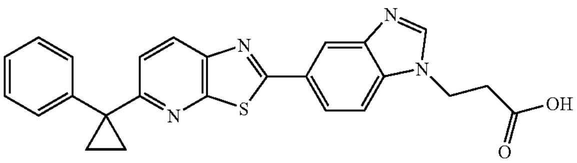

Step 1

To 2-(1H-benzo[d]imidazol-5-yl)-5-(1-phenylcyclopropyl)thiazolo[5,4-b]pyridine (100 mg, 0.271 mmol) was added acetonitrile (2.7 mL) before 7-methyl-1,5,7-triazabicyclo(4.4.0)dec-5-ene (1.949 μL, 0.014 mmol) and ethyl acrylate (36.2 μL, 0.326 mmol) were added and stirred at ambient temperature for 2 h to give a 2:1 mixture of regioisomers. Ethyl 3-(5-(5-(1-phenylcyclopropyl)thiazolo[5,4-b]pyridin-2-yl)-1H-benzo[d]imidazol-1-yl)propanoate was obtained after regioisomer separation via SFC (Column: ChiralPak AD-H; Mobile Phase: 50:50 liquid $CO_2$/isopropanol with 0.2% isopropylamine). MS (ESI) m/z: Calculated: 468.2; Observed: 469.2 ($M^+$+H).

Step 2

Ethyl 3-(6-(5-(1-phenylcyclopropyl)thiazolo[5,4-b]pyridin-2-yl)-1H-benzo[d]imidazol-1-yl)propanoate (27 mg, 0.058 mmol) was dissolved in pyridine (576 μL) before lithium iodide (30.8 mg, 0.230 mmol) was added and stirred at 100° C. for 36 h during which time more LiI (60 mg) was added. The reaction mixture was diluted with 75 mL of EtOAc, added to a separation funnel, partitioned with sodium bicarbonate (saturated, aqueous), washed 2 times with 50 mL of sodium bicarbonate (saturated, aqueous), and separated before the aqueous layer was acidified to pH 3 with 5 N HCl and extracted 2 times with 75 mL of EtOAc, dried over sodium sulfate, and concentrated via rotovap to give the title compound. MS (ESI) m/z: Calculated: 440.1; Observed: 440.8 ($M^+$+H).

Example 142

Synthesis of 3-(6-(5-(1-phenylcyclopropyl)[1,3]thiazolo[5,4-b]pyridin-2-yl)-1H-benzimidazol-1-yl)propanoic acid

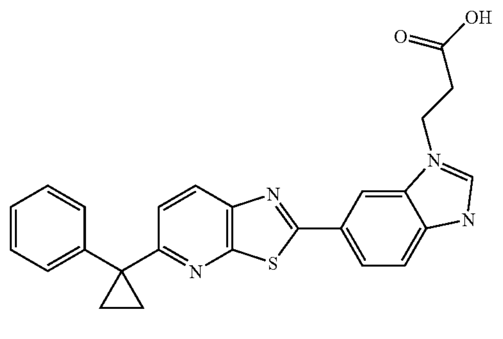

Step 1

Ethyl 3-(6-(5-(1-phenylcyclopropyl)thiazolo[5,4-b]pyridin-2-yl)-1H-benzo[d]imidazol-1-yl)propanoate was obtained after SFC separation (Column: ChiralPak AD-H; Mobile Phase: 50:50 liquid $CO_2$/isopropanol with 0.2% isopropylamine) from ethyl 3-(6-(5-(1-phenylcyclopropyl)thiazolo[5,4-b]pyridin-2-yl)-1H-benzo[d]imidazol-1-yl)propanoate. MS (ESI) m/z: Calculated: 468.2; Observed: 469.2 ($M^+$+H).

Step 2

The title compound was prepared in a procedure similar to that of 3-(5-(5-(1-phenyl-cyclopropyl) [1,3]thiazolo[5,4-b]pyridin-2-yl)-1H-benzimidazol-1-yl)propanoic acid above. MS (ESI) m/z: Calculated: 440.1; Observed: 440.8 ($M^+$+H).

Example 143

Synthesis of 3-(5-(5-(1-phenylcyclopropyl)[1,3]thiazolo[5,4-b]pyridin-2-yl)-1,3-dihydro-2H-isoindol-2-yl)propanoic acid

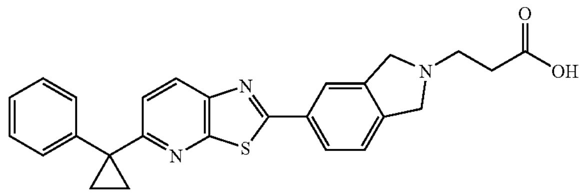

Step 1

To 3-amino-6-(1-phenylcyclopropyl)pyridine-2(1H)-thione (106 mg, 0.437 mmol) was added 2-(tert-butoxycarbonyl)isoindoline-5-carboxylic acid (115 mg, 0.437 mmol), 1H-benzo[d][1,2,3]triazol-1-ol hydrate (67.0 mg, 0.437 mmol), N1-((ethylimino)methylene)-N3,N3-dimethylpropane-1,3-diamine hydrochloride (84 mg, 0.437 mmol), and DMF (437 μL) before it was stirred at ambient T for 16 h. The reaction mixture was diluted with methanol before it was passed through a cartridge of cation exchange resinto give tert-butyl 5-(6-(1-phenylcyclopropyl)-2-thioxo-1,2-dihydropyridin-3-ylcarbamoyl)isoindoline-2-carboxylate after concentration. MS (ESI) m/z: Calculated: 487.2; Observed: 488.4 ($M^+$+H).

Step 2 tert-Butyl 5-(6-(1-phenylcyclopropyl)-2-thioxo-1,2-dihydropyridin-3-ylcarbamoyl)i-soindoline-2-carboxylate (213 mg, 0.437 mmol) was dissolved in toluene (4.4 mL) before camphor sulfonic acid (91 mg, 0.393 mmol) was added and stirred at 100° C. for 3 h. The reaction mixture was diluted with 75 mL of EtOAc, added to a separatory funnel, partitioned with sodium bicarbonate (saturated, aqueous), washed with sodium bicarbonate (saturated, aqueous), separated, dried over sodium sulfate, and concentrated via rotovap to give 2-(isoindolin-5-yl)-5-(1-phenylcyclopropyl)-thiazolo[5,4-b]pyridine after flash chromatography. MS (ESI) m/z: Calculated: 369.1; Observed: 370.4 ($M^+$+H).

Step 3

2-(Isoindolin-5-yl)-5-(1-phenylcyclopropyl)thiazolo[5,4-b]pyridine (75 mg, 0.203 mmol) was dissolved in methanol (2.0 mL) and DCM (1 mL) before ethyl acrylate (27.1 μL, 0.244 mmol) and 1-methyl-2,3,4,6,7,8-hexahydro-1H-pyrimido[1,2-a]pyrimidine (1.457 μL, 10.15 μmol) were added and stirred at ambient temperature for 16 h. Methyl 3-(5-(5-(1-phenylcyclopropyl)-thiazolo[5,4-b]pyridin-2-yl)isoindolin-2-yl)propanoate was obtained after purification via flash chromatography. MS (ESI) m/z: Calculated: 455.2; Observed: 456.4 ($M^+$+H).

Step 4

Methyl 3-(5-(5-(1-phenylcyclopropyl)thiazolo[5,4-b]pyridin-2-yl)isoindolin-2-yl)propanoate (42 mg, 0.092 mmol) was dissolved in THF (0.738 mL) and water (0.184 mL) before lithium hydroxide monohydrate (2.56 μL, 0.092 mmol) was added and stirred at ambient temperature for 2 h. The reaction mixture was concentrated, acidified with 1 N HCl, filtered, washed with water, and dried in a vacuum oven to give the title compound. MS (ESI) m/z: Calculated: 441.2; Observed: 442.2 ($M^+$+H).

Example 144

Synthesis of (5-(5-(1-phenylcyclopropyl)[1,3]thiazolo[5,4-b]pyridin-2-yl)-1,3-dihydro-2H-isoindol-2-yl)acetic acid

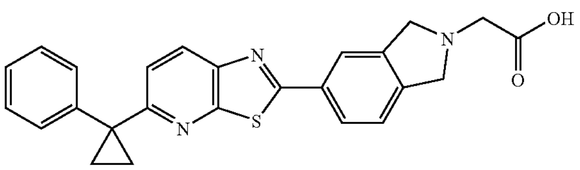

Step 1

2-(Isoindolin-5-yl)-5-(1-phenylcyclopropyl)thiazolo[5,4-b]pyridine (97 mg, 0.263 mmol) was dissolved in DCM (2.625 mL) and diisopropylethylamine (91 μL, 0.525 mmol) before methyl bromoacetate (48.5 μL, 0.525 mmol) was added and stirred at ambient temperature for 3 h. Methyl 2-(5-(5-(1-phenylcyclopropyl)thiazolo[5,4-b]pyridin-2-yl) isoindolin-2-yl)acetate was obtained after purification via flash chromatograpy. MS (ESI) m/z: Calculated: 441.2; Observed: 442.4 ($M^{+}$+H).

Step 2

Methyl 2-(5-(5-(1-phenylcyclopropyl)thiazolo[5,4-b]pyridin-2-yl)isoindolin-2-yl)acetate (17 mg, 0.039 mmol) was dissolved in THF (308 μL) and water (77 μL) before lithium hydroxide monohydrate (1 mg, 0.039 mmol) was added and stirred at 65° C. for 2 h. The reaction mixture was concentrated, acidified with 1 N HCl, and filtered. The solid was dissolved in DMSO and eluted through the frit to give the title compound after concentration. MS (ESI) m/z: Calculated: 427.1; Observed: 427.9 ($M^{+}$+H).

Example 145

Synthesis of N-(3-fluoro-4-(5-(1-phenylcyclopropyl)[1,3]thiazolo[5,4-b]pyridin-2-yl)-benzyl)glycine

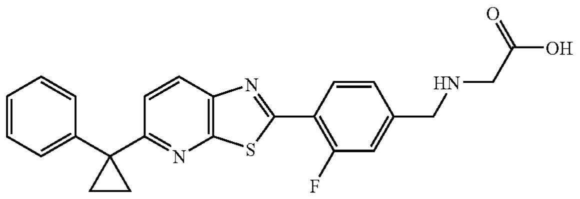

Glycine ethyl ester hydrochloride (224 mg, 1.602 mmol) was dissolved in MeOH (4.0 mL) and chloroform (4.0 mL) before diisopropylethylamine (279 μL, 1.602 mmol) was added and stirred at ambient temperature for 15 min. 3-Fluoro-4-(5-(1-phenylcyclopropyl)-thiazolo[5,4-b]pyridin-2-yl)benzaldehyde (300 mg, 0.801 mmol) and sodium triacetoxyhydroborate (340 mg, 1.602 mmol) were then added and stirred at ambient temperature for 24 h. The reaction mixture was diluted with 100 mL of EtOAc, added to a separatory funnel, partitioned with sodium bicarbonate (saturated, aqueous), washed 1 time with 50 mL of ammonium chloride (saturated, aqueous), separated, dried over sodium sulfate, and concentrated via rotovap to give ethyl 2-(3-fluoro-4-(5-(1-phenylcyclopropyl)thiazolo-[5,4-b]pyridin-2-yl)benzylamino)acetate after flash chromatography. MS (ESI) m/z: Calculated: 461.2; Observed: 461.9 ($M^{+}$+H).

Step 2

Ethyl 2-(3-fluoro-4-(5-(1-phenylcyclopropyl)thiazolo[5,4-b]pyridin-2-yl)-benzylamino)acetate (80 mg, 0.173 mmol) was dissolved in THF (1.4 mL) and water (347 μL) before lithium hydroxide monohydrate (21.82 mg, 0.520 mmol) was added and stirred at ambient temperature for 16 h. The reaction mixture was concentrated, acidified to pH 7 with 1 N HCl, filtered, and washed with water, DMSO, then water, and dried in a vacuum oven to give the title compound. MS (ESI) m/z: Calculated: 433.1; Observed: 433.8 ($M^{+}$+H).

Example 146

Synthesis of 2-(3-fluoro-4-(5-(1-phenylcyclopropyl)[1,3]thiazolo[5,4-b]pyridin-2-yl)phenyl)ethanamine

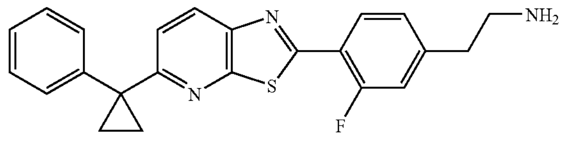

Step 1

To 3-fluoro-4-(5-(1-phenylcyclopropyl)thiazolo[5,4-b]pyridin-2-yl)benzaldehyde (1.42 g, 3.79 mmol) was added acetic acid (12.6 mL), nitromethane (1.44 mL, 26.5 mmol), and ammonium acetate (0.731 g, 9.48 mmol) before it was stirred at 100° C. for 4 h. The reaction mixture was cooled to ambient temperature. The product crashed out with water, and was filtered, washed with water, and dried in a vacuum oven to give 2-(2-fluoro-4-(2-nitrovinyl)phenyl)-5-(1-phenylcyclopropyl)thiazolo[5,4-b]pyridine. MS (ESI) m/z: Calculated: 417.1; Observed: 418.4 ($M^{+}$+H).

Step 2

To 2-(2-fluoro-4-(2-nitrovinyl)phenyl)-5-(1-phenylcyclopropyl)thiazolo[5,4-b]pyridine (0.788 g, 1.89 mmol) was added THF (9.44 mL), methanol (9.44 mL), water (9.44 mL), and acetic acid (9.44 mL) before zinc (0.987 g, 15.1 mmol) was added. The reaction mixture was heated to 65° C. for 18 h. The reaction mixture was concentrated, neutralized with aq $NaHCO_3$, and extracted with DCM. The organic layer was concentrated, filtered, washed with water, and dried in a vacuum oven to give the title compound after purification via preparatory LC. MS (ESI) m/z: Calculated: 389.1; Observed: 380.1 ($M^{+}$+H).

Example 147

Synthesis of 2-(3-fluoro-4-(5-(1-phenylcyclopropyl)[1,3]thiazolo[5,4-b]pyridin-2-yl)-phenyl)ethanol

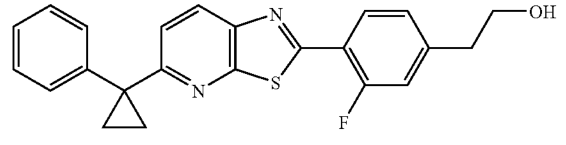

The title compound was obtained after flash chromatography separation from 2-(3-fluoro-4-(5-(1-phenylcyclopropyl)

[1,3]thiazolo[5,4-b]pyridin-2-yl)phenyl)ethanamine. MS (ESI) m/z: Calculated: 390.1; Observed: 391.1 ($M^+$+H).

Example 148

Synthesis of N-(2-(3-fluoro-4-(5-(1-phenylcyclopropyl)[1,3]thiazolo[5,4-b]pyridin-2-yl)-phenyl)ethyl) glycine

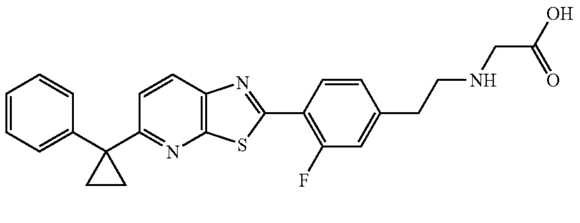

To 2-(3-fluoro-4-(5-(1-phenylcyclopropyl)thiazolo[5,4-b]pyridin-2-yl)phenyl)-ethanamine (83 mg, 0.213 mmol) was added glyoxylic acid monohydrate (39 mg, 0.426 mmol) and DCM (1 mL) before it was stirred for 5 h at ambient temperature. The reaction mixture was concentrated before adding concentrated hydrochloric acid (2.13 mL, 4.26 mmol) and heating to reflux for 16 h. The reaction mixture was diluted with 75 mL of DCM, added to a separatory funnel, partitioned with water, washed 1 time with 50 mL of water, separated, dried over sodium sulfate, and concentrated via rotovap to give the title compound after preparatory LC. MS (ESI) m/z: Calculated: 447.1; Observed: 448.1 ($M^+$+H).

Example 149

Synthesis of 2-(3-fluoro-4-(5-(1-phenylcyclopropyl)[1,3]thiazolo[5,4-b]pyridin-2-yl)phenyl)-N,N-dimethylethanamine

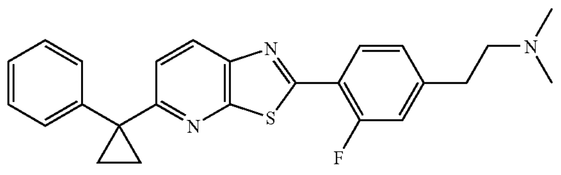

To 2-(3-fluoro-4-(5-(1-phenylcyclopropyl)thiazolo[5,4-b]pyridin-2-yl)phenyl)ethanamine (70 mg, 0.18 mmol) was added chloroform (9 mL), methanol (9 mL), and formaldehyde in water (15 mg, 0.18 mmol) at ambient temperature and was stirred for 1 h. Sodium triacetoxyborohydride (76 mg, 359 μmol) was added at ambient temperature before it was stirred for 1 h. The reaction mixture was quenched with water, diluted with 100 mL of DCM, added to a separatory funnel, partitioned with sodium bicarbonate (saturated, aqueous), washed 2 times with 50 mL of sodium bicarbonate (saturated, aqueous), separated, dried over sodium sulfate, and concentrated via rotovap to give the title compound after flash chromatography. MS (ESI) m/z: Calculated: 417.2; Observed: 418.1 ($M^+$+H).

Example 150

Synthesis of N-(2-(3-fluoro-4-(5-(1-phenylcyclopropyl)[1,3]thiazolo[5,4-b]pyridin-2-yl)phenyl)ethyl) acetamide

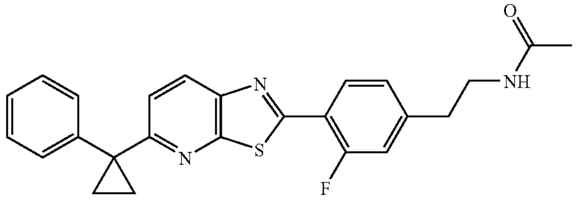

2-(3-Fluoro-4-(5-(1-phenylcyclopropyl)thiazolo[5,4-b]pyridin-2-yl)phenyl)-ethanamine (90 mg, 0.23 mmol) was dissolved in THF (2.3 mL) before acetyl chloride (33 μl, 0.462 mmol) was added and stirred at ambient temperature for 2 h. The reaction mixture was diluted with 100 mL of DCM, added to a separatory funnel, partitioned with sodium bicarbonate (saturated, aqueous), washed 2 times with 75 mL of sodium bicarbonate (saturated, aqueous), separated, dried over sodium sulfate, and concentrated via rotovap to give the title compound after purification via preparatory LC. MS (ESI) m/z: Calculated: 431.1; Observed: 432.1 ($M^+$+H).

Example 151

Synthesis of (2R,4R)-4-(3-fluoro-4-(5-(1-phenylcyclopropyl)thiazolo[5,4-b]pyridin$^{-2}$-yl)phenyl)pyrrolidine-2-carboxylic acid

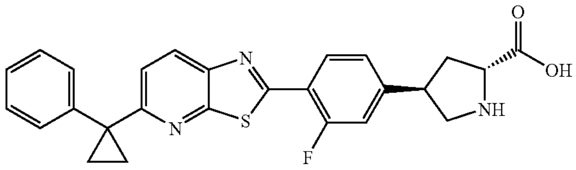

Step 1

(2S,4R)-1-tert-butyl 2-methyl 4-(3-fluoro-4-(5-(1-phenylcyclopropyl)thiazolo[5,4-b]pyridin-2-yl)phenyl)pyrrolidine-1,2-dicarboxylate (0.092 g, 0.16 mmol) in 2 mL DCM was treated with trifluoroacetic acid (0.25 ml, 3.2 mmol). After 4 h, the reaction was concentrated in vacuo and dried in vacuo.

Step 2

The resulting yellow oil was treated with 2 mL CHCL3 and triethylamine (0.11 ml, 0.80 mmol), sealed, and heated to 70° C. overnight. The reaction was partitioned between sat'd aq NaHCO3 and DCM. The organic was extracted 2×DCM. The combined organics were dried over sodium sulfate, filtered, and concentrated to give an orange solid. This material was treated with sodium tert-butoxide (0.031 g, 0.32 mmol) and 2 mL anhyd MeOH and allowed to stir overnight. The slurry was then sealed and heated to 60° C. for 3 h. Sodium hydroxide (0.32 ml, 0.32 mmol) was added and the reaction heated to 60° C. to complete hydrolysis. The reaction was cooled and the solvent was removed, and the solids treated with 0.64 mL 1N HCl and 2-3 mL 1M pH 6 phosphate buffer. After stirring 10 min, the mixture was filtered rinsing 1×1 mL water and 1×1 mL EtOH. The yellow solid was dried and purified by RPHPLC (Phenomenex Luna 5 um C8 (2), 150×21.2 mm, A=0.1% formic acid in water, B=0.1% formic acid in acetonitrile) to give (2R,4R)-4-(3-fluoro-4-(5-(1-phenylcyclopropyl)thiazolo[5,4-b]pyridin-2-yl)phenyl)pyrrolidine-2-carboxylic acid. MS (ESI) m/z: Calculated: 459.1; Observed: 460.1 ($M^+$+1).

BIOLOGICAL EXAMPLES

Example 1

In Vitro Assay

The activity of compounds of the invention was determined by a cell imaging-based assay measuring the degree of hS1P1 receptor internalization and a $Ca^{2+}$ mobilization assay measuring the level of S1P receptor activation. The receptor internalization assay was employed to determine the potency and efficacy of compounds on hS1P1 receptor, while $Ca^{2+}$ mobilization assay was used to determine selectivity among different S1P receptors and activity on S1P receptors from species such as rat, dog, and cyno. The hS1P1 receptor internalization assay was performed using a U2OS cell line expressing hS1P1-eGFP chimeric protein (Thermo Scientific, Soeborg, Denmark). Upon compound treatment, the hS1P1 receptor was internalized in cytoplasma and formed GFP-containing-endosomes. This event was detected by an automated microscope, ArrayScan (Thermo Scientific Cellomics, Pittsburg), and the degree of receptor internalization is quantitated by counting green fluorescent GFP-containing endosomes per cell. In this assay, hS1P1-eGFP expressing U2OS cells were starved in serum free media for two hours prior to compound treatment. Then compounds were incubated with the starved cells at 37° C. for one hour. Subsequently, compound-treated cells were fixed using 4% formaldehyde, and the nuclei were stained using Hoechst. Then the cells were imaged in ArrayScan. The potency and efficacy of the compounds were determined by plotting the number of green fluorescent GFP-containing endosomes per cell against corresponding compound concentration.

The $Ca^{2+}$ mobilization assay was performed using CHO cell lines co-expressing target S1P receptor and a chimeric $G_{q/i5}$ G-protein. Agonist, S1P and compounds, treatment of these cell lines activated PLC-β and IP3 pathway, and triggered release of $Ca^{2+}$ from intracellular storarage, such as ER. Since these cells were loaded with $Ca^{2+}$ sensitive fluorescent dye prior to compound treatment, when the intracellular $Ca^{2+}$ was elevated it bound to the $Ca^{2+}$ sensitive dye and made the dye emit fluorescence signal upon excitation. The level of receptor activiation was quantitated by measuring fluorescence intensity upon compound treatment. In this assay, the cells were starved in medium contain charcoal/dextran stripped serum for 16-20 hours. Compounds were added on cells loaded with $Ca^{2+}$ sensitive dye inside FLIPR (Molecular Devices, Sunnyvale, Calif.), and the fluorescence signal was measured simultaneously. CHO cells expressing only the chimeric $G_{q/i5}$ G-protein was tesed as the negative control. The potency and efficacy of the compounds were determined by plotting fluorescence intensity against corresponding compound concentration.

| Working Example No. | hS1P1 Receptor Internalization (bioimaging) EC50 IP (uM) | hS1P1 Receptor Internalization (biolimaging) Max (%) | Working Example No. | hS1P1 Receptor Internalization (bioimaging) EC50 IP (uM) | hS1P1 Receptor Internalization (biolimaging) Max (%) |
|---|---|---|---|---|---|
| 1 | 0.0025 | 98 | 44 | 0.0597 | 113 |
| 4 | 0.0012 | 121 | 45 | 0.0997 | 103 |
| 5 | 0.1297 | 90 | 46 | 0.0048 | 99 |
| 7 | 0.0326 | 108 | 47 | 0.0059 | 117 |
| 9 | 0.0286 | 144 | 51 | 0.0163 | 107 |
| 10 | 0.0420 | 97 | 51 | 0.0116 | 90 |
| 11 | 0.0008 | 96 | 52 | 1.1890 | 109 |
| 12 | 0.0020 | 101 | 54 | 0.0045 | 126 |
| 14 | 0.0206 | 66 | 57 | 0.0355 | 107 |
| 17 | 0.0210 | 148 | 60 | 0.7209 | 162 |
| 19 | 0.0014 | 121 | 61 | 2.4869 | 491 |
| 20 | 0.0312 | 160 | 62 | 3.7059 | 98 |
| 22 | 0.1918 | 157 | 67 | 0.0704 | 125 |
| 27 | 5.8799 | 81 | 72 | 0.0451 | 133 |
| 29 | 0.3343 | 91 | 79 | 0.0384 | 150 |
| 30 | 2.9093 | 79 | 80 | 0.5628 | 148 |
| 35 | 0.0187 | 90 | 82 | 0.0461 | 106 |
| 38 | 0.0037 | 111 | 85 | 1.2687 | 88 |
| 39 | 0.0212 | 83 | 91 | 0.0327 | 131 |
| 42 | 0.0102 | 119 | 96 | 0.0109 | 105 |
| 43 | 0.0003 | 122 | 98 | 0.0449 | 93 |
| 133 | 0.0022 | 133 | 105 | 3.3280 | 63 |
| 136 | 0.1911 | 101 | 109 | 2.3465 | 41 |
| 150 | 0.1843 | 155 | 113 | 0.7323 | 55 |
| 104 | 0.000162 | 113.85 | 118 | 0.2977 | 111 |
| 130 | 0.0116 | 89 | 121 | 0.7768 | 125 |
| 126 | 0.0006 | 100 | 124 | 0.9455 | 131 |

Example 2

Rat Lymphopenia Model . . . In Vivo Assay

Female Lewis rats (150-175 gms, 6-8 wks) were received from Charles River Laboratories and allowed to acclimatize for at least one week before being placed on study. Rats (n=4/group) were administered compound or vehicle (12.5% captisol in water orally (PO, 10 mL/kg) at time 0. At various time points following dosing (1, 4, 8, or 24 h), animals were sacrificed by $CO_2$ inhalation. Using a 20 G needle and 1 cc syringe, blood was collected by cardiac puncture. Approximately 500 uL of blood was placed in a microtainer tube containing EDTA (BD #365973), and the sample was mixed thoroughly. Differential cell counts were perfomed using an Advia 120 hematology system by Bayer.

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this invention | 200 |
| lactose spray dried | 148 |
| magnesium stearate | 2 |

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A compound of Formula (I):

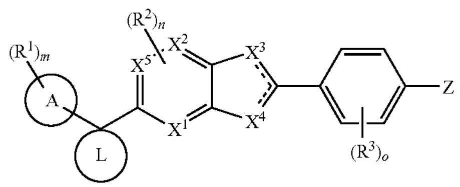

wherein:

m is 0, 1, 2 or 3;

n is 0, 1, 2 or 3;

o is 0, 1, 2 or 3;

A is a phenyl, heterocyclyl, three to six membered cycloalkyl, or a five or six membered heteroaryl ring;

L is a saturated 3, 4, 5, 6 or 7-member ring containing 0, 1 or 2 atoms selected from N, O and S and optionally containing a double bond, the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

$X^1$ is N or CH;

$X^2$ is N or CH;

$X^5$ is N or CH;

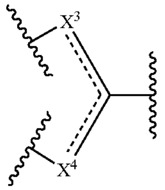

is selected from

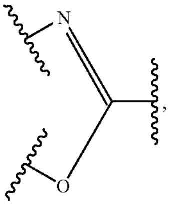,
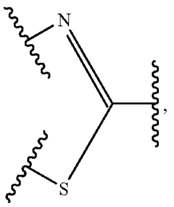,
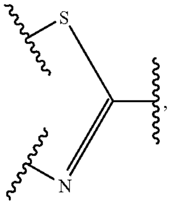,
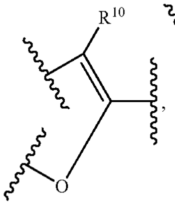,
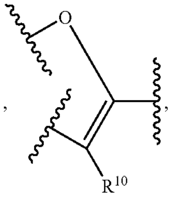,

-continued

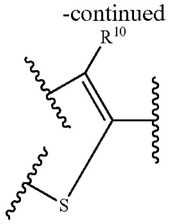

and

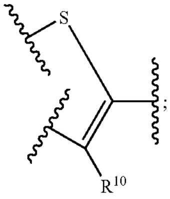

;

$R^1$ is selected from F, Cl, $C_{1-4}$alkyl, $C_{1-4}$haloalkyl, OH, —$OC_{1-4}$alkyl, and —$OC_{1-4}$haloalkyl;

$R^2$ is selected from F, Cl, $C_{1-4}$alkyl, $C_{1-4}$haloalkyl, OH, —$OC_{1-4}$alkyl, and —$OC_{1-4}$haloalkyl;

$R^3$ is selected from F, Cl, $C_{1-4}$alkyl, $C_{1-4}$haloalkyl, OH, —$OC_{1-4}$alkyl, amino, and —$OC_{1-4}$haloalkyl;

Z is:

(i) a cycloalkyl substituted with amino, monoalkylamino or dialkylamino group; a cycloalkylalkyl substituted with one or two carboxy groups; a monosubstituted amino, disubstituted amino, carboxyalkylamino, hydroxyalkyl, substituted hydroxyalkyl, hydroxyalkoxy, substituted hydroxyalkoxy, aminoalkyl, aminoalkoxy, carboxyalkyl, substituted carboxyalkyl, carboxyalkyloxy, substituted carboxyalkyloxy, carboxyalkoxyalkyl, substituted carboxyalkoxyalkyl, aminocarbonyl, acylamino, aminosulfonyl, sulfonylamino, heterocycloamino, heterocycloaminoalkyl, heterocycloaminocarbonyl, heterocycloaminooxy, or heteroaralkyl group;

(ii) a group of formula (b):

(b)

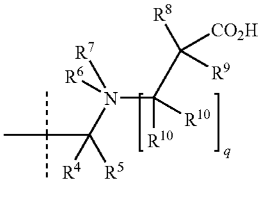

where:

q is 0, 1 or 2;

$R^4$ is selected from H, $C_{1-3}$haloalkyl, and $C_{1-6}$alkyl;

$R^5$ is selected from H, $C_{1-3}$haloalkyl, and $C_{1-4}$alkyl; or $R^4$ and $R^5$ together with the carbon atom to which they are attached form a 3, 4, 5, 6 or 7-member carbocyclic ring substituted by 0, 1 or 2 groups selected from F, Cl, $C_{1-4}$haloalkyl, OH, —$OC_{1-4}$alkyl, and —$OC_{1-4}$haloalkyl;

$R^6$ is a lone pair of electrons or O;

$R^7$ is H or $C_{1-6}$alkyl;

$R^8$ is selected from H, F, Cl, $C_{1-4}$alkyl, $C_{1-4}$haloalkyl, OH, —$OC_{1-4}$alkyl, and —$OC_{1-4}$haloalkyl; or $R^7$ and $R^8$, when taken together, form a group that is selected from —$(CR^{10}R^{10})$—, —$(CR^{10}R^{10})O$—, —$O(CR^{10}R^{10})$—, —$(CR^{10}R^{10})(CR^{10}R^{10})$—, and —$(CR^{10}R^{10})_3$—;

$R^9$ is selected from H, F, $C_{1-3}$haloalkyl, $C_{1-4}$alkyl, OH and $OC_{1-4}$alkyl; or $R^8$ and $R^9$ together with the carbon atom to which they are attached from cycloalkyl; and each $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; or (iii) when $R^3$ is on a carbon atom of the phenyl ring that is adjacent to the carbon of the phenyl ring that is bonded to Z, then $R^3$ and Z can combine to form —CH═CH—$NR^{11}$—, —$(CH_2)_2NR^{11}$—, —$CH_2NR^{11}CH_2$—, —$(CH_2)_2NR^{11}CH_2$—, —N═$CR^{11}$—NH—, or —N═CH—$NR^{11}$—, where $R^{11}$ is selected from hydrogen, hydroxyalkyl, aminoalkyl, carboxyalkyl, substituted hydroxyalkyl, substituted carboxyalkyl, or aminocarbonyl; or a pharmaceutically acceptable thereof; provided that when

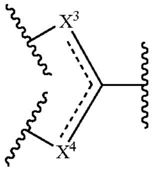

is selected from

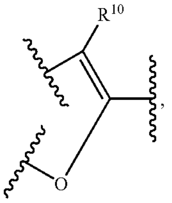

,

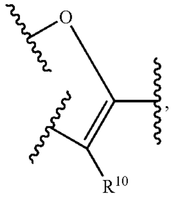

,

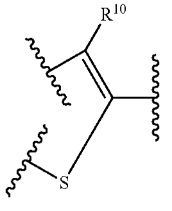

or

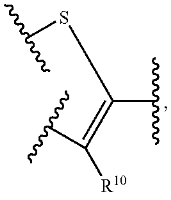

, then at least one of $X^1$, $X^2$ and $X^5$ is N.

2. The compound of claim 1 where the compound of Formula (I) has the Formula (Ia):

(Ia)

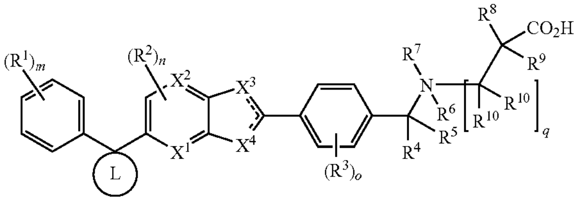

where:

$X^1$ is N or CH;

$X^2$ is N or CH;

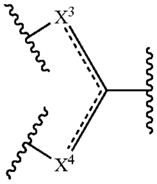

is selected from

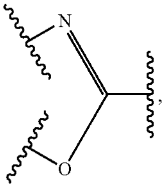,

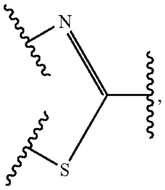,

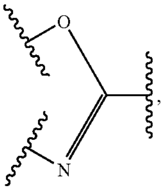,

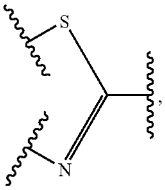,

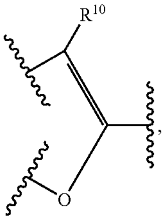,

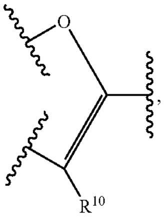,

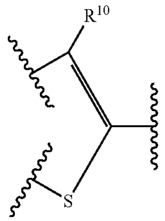

and

-continued

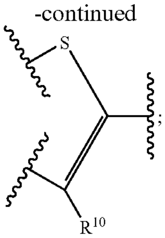;

L is a saturated 3, 4, 5, 6 or 7-member ring containing 0, 1 or 2 atoms selected from N, O and S, the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

m is 0, 1, 2 or 3;

n is 0, 1, 2 or 3;

o is 0, 1, 2 or 3;

q is 1 or 2;

$R^1$ is selected from F, Cl, $C_{1-4}$alkyl, $C_{l-4}$haloalkyl, OH, $OC_{1-4}$alkyl, and —$OC_{1-4}$haloalkyl;

$R^2$ is selected from F, Cl, $C_{1-4}$alkyl, $C_{1-4}$haloalkyl, OH, —$OC_{1-4}$alkyl, and —$OC_{1-4}$haloalkyl;

$R^3$ is selected from F, Cl, $C_{1-4}$alkyl, $C_{1-4}$haloalkyl, OH, —$OC_{1-4}$alkyl, and —$OC_{1-4}$haloalkyl;

$R^4$ is selected from H, $C_{1-3}$haloalkyl, and $C_{1-6}$alkyl;

$R^5$ is selected from H, $C_{1-3}$haloalkyl, and $C_{1-4}$alkyl; or $R^4$ and $R^5$ together with the carbon atom to which they are attached form a 3, 4, 5, 6 or 7-member carbocyclic ring substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl;

$R^6$ is a lone pair of electrons or O;

$R^7$ is H or $C_{1-6}$alkyl;

$R^8$ is selected from H, F, Cl, $C_{1-4}$alkyl, $C_{1-4}$haloalkyl, OH, $OC_{1-4}$alkyl, and $OC_{1-4}$haloalkyl; or $R^7$ and $R^8$, when taken together, form a group that is selected from —$(CR^{10}R^{10})$—, —$(CR^{10}R^{10})O$—, —$O(CR^{10}R^{10})$— and —$(CR^{10}R^{10})$—;

$R^9$ is selected from H, F, $C_{1-3}$haloalkyl, $C_{1-4}$alkyl, OH and $OC_{1-4}$alkyl; and $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; and $R^{10}$ is independently in each instance selected from H, F, Cl, $C_{1-4}$alkyl, $C_{1-4}$haloalkyl, OH, —$OC_{1-4}$alkyl, and —$OC_{1-4}$haloalkyl; or a pharmaceutically-acceptable salt thereof provided that when

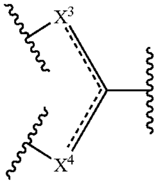

is selected from

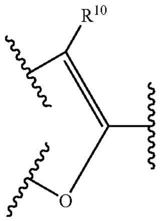 , 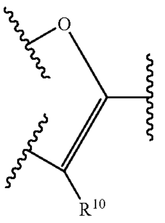 ,

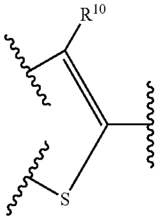 or 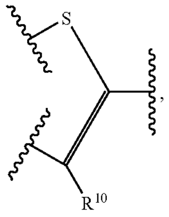 , then at least one of $X^1$, and $X^2$ is N.

3. The compound of claim 1 wherein

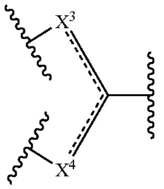 is 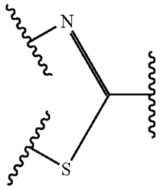 or

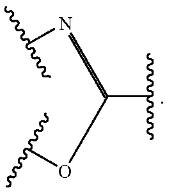 .

4. The compound of claim 1 wherein

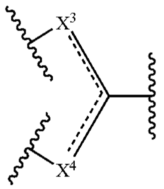 is 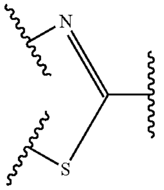 or

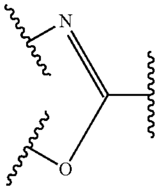

and L is a saturated 3, 4, 5, 6 or 7-member ring, the ring being substituted by 0, 1 or 2 groups selected from F, Cl, $C_{1-4}$alkyl, $C_{1-4}$haloalkyl, OH, —$OC_{1-4}$alkyl, and —OC $_{1-4}$haloalkyl.

5. The compound of claim 1 wherein

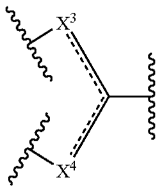 is 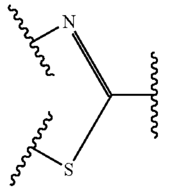 or

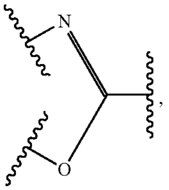 ,

L is a saturated 3, 4, 5, 6 or 7-member ring containing 1 or 2 atoms selected from N, O, or S and the ring being substituted by 0, 1 or 2 groups selected from F, Cl, $C_{1-4}$alkyl, $C_{1-4}$haloalkyl, OH, —$OC_{1-4}$alkyl, and —$OC_{1-4}$haloalkyl, n is 0, $X^1$ is N, and $X^2$ and $X^5$ are CH.

6. The compound of claim 4 where n is 0, L is cyclopropylene, cyclopentylene, or cyclohexylene, $X^1$ is N and $X^2$ and $X^5$ are CH.

7. The compound of claim 5 wherein $R^1$ is F, methyl, trifluoromethyl, methoxy, trifluroromethoxy, or hydroxyl.

8. The compound of claim 6 wherein A is five or six membered heteroaryl ring and $R^1$ is F, methyl, trifluoromethyl, methoxy, trifluroromethoxy, or hydroxyl.

9. The compound of claim 6 wherein A is phenyl and $R^1$ is F, methyl, trifluoromethyl, methoxy, trifluoromethoxy, or hydroxyl.

10. The compound of claim 6 wherein A is cycloalkyl and $R^1$ is F, methyl, trifluoromethyl, methoxy, trifluroromethoxy, or hydroxyl.

11. The compound of claim 8 where $R^3$ is F, Cl or $C_{1-4}$alkyl where alkyl is linear or branched and saturated.

12. The compound of claim 10 where $R^3$ is F, Cl or $C_{1-4}$alkyl where alkyl is linear or branched and saturated.

13. the compound of claim 9 where

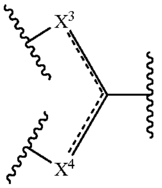 is 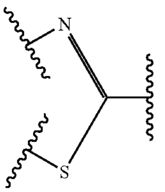 , m is 0 and o is 1 or 2.

14. The compound of claim 6 wherein Z is carboxyalkylamino, hydroxyalkyl, substituted hydroxyalkyl, hydroxyalkoxy, substituted hydroxyalkoxy, aminoalkyl, aminoalkoxy, carboxyalkyl, substituted carboxyalkyl, carboxyalkyloxy, substituted carboxyalkyloxy, carboxyalkoxyalkyl, substituted carboxyalkoxyalkyl, aminocarbonyl, or acylamino.

15. The compound of claim 6 wherein Z is a group of formula (b).

16. The compound of claim 9 wherein in group

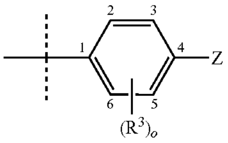

is 2-fluoro-4-(3-carboxyazetidin-1-ylmethyl)phenyl; 2-fluoro-4-(3-carboxy-3-hydroxyazetidin-1-ylmethyl)phenyl; 2-fluoro-4-(3-carboxy-3-fluoroazetidin-1-ylmethyl)phenyl; 2-fluoro-4-(3-carboxypyrrolidin-1-ylmethyl)phenyl; 2-fluoro-4-(R-3-carboxypyrrolidin-1-ylmethyl)phenyl; 2-fluoro-4-(carboxymethylNHCO-)phenyl; 2-fluoro-4-(2-carboxyethylNHCO-)phenyl; 2-fluoro-4-(3-carboxypropylNHCO-)phenyl; 2-fluoro-4-(S-3-carboxypyrrolidin-1-ylmethyl)phenyl; 2-fluoro-4-(2-carboxyethylNHCH$_2$-)phenyl; 2-fluoro-4-(1R,3S-3-carboxy-N-oxoazetidin-1-ylmethyl)phenyl; 2-fluoro-4-(1S,3R-3-carboxy-N-oxoazetidin-1-ylmethyl)phenyl; 2-fluoro-4-[R-1-(3-carboxyazetidin-1-yl)-ethyl)phenyl; 2-fluoro-4[S-1-(3-carboxyazetidin-1-yl)-ethyl)phenyl; 2-fluoro-4-(R-2-amino-2-carboxyethylCONH-)phenyl; 2-fluoro-4-(S-2-amino-2-carboxyethylCONH-)phenyl; 2-fluoro-4-(2-(carboxymethylaminoethyl)phenyl; 2-fluoro-4-[(2R,4R)-2-carboxypyrrolidin-4-yl]phenyl; 2-fluoro-4-(S-1-hydroxy-2-carboxyethylCONH-)phenyl; 2-fluoro-4-[(2S,4R)-2-carboxy-1-methylpyrrolidin-4-yl]phenyl; 2-fluoro-4-(S-3-amino-3-carboxybutyl)phenyl; 2-fluoro-4-(R-3-amino-3-carboxybutyl)phenyl; 2-fluoro-4-(3-amino-3-$CH_2OP(O)(OH)_2$-4-hydroxybutyl)phenyl; 2-fluoro-4-(S-2-carboxy-2-hydroxyethylCONH-)phenyl, 2-fluoro-4-(S-1-amino-2carboxyethylCONH-)phenyl, 2-fluoro-4-(R-1-amino-2-carboxyethylCONH-)phenyl, 2-fluoro-4-(R-2-hydroxy-2-carboxyethylCONH-)phenyl, 2-fluoro-4-(R-1-hydroxy-2-carboxyethylCONH-)phenyl, 2-fluoro-4-[(2S,4R)-2-carboxy-4-hydroxypyrrolidin-4-yl]phenyl, 2-fluoro-4-[(2S,4R)-2-carboxypyrrolidin-4-yl]phenyl; 1-(2-carboxyethyl-1,2,3,4-tetrahydroisoquinolin-6-yl; 2-fluoro-4-(4-carboxyimidazol-1-ylmethyl)phenyl; 2-fluoro-4-(cis-3-carboxycyclopropylamino]phenyl; 4-(2-carboxyethylamino)-phenyl; 2-fluoro-4-(3-hydroxyazetidin-1-ylmethyl)phenyl; 2-fluoro-4-(trans-3-carboxycyclopropylamino]-phenyl; 2-fluoro-4-(2-HOC(O)C(O)NH-ethyl)-phenyl; 2-fluoro-4-(3-carboxypropylamino)-phenyl; 2-fluoro-4-(3-carboxymethylazetidin-1-ylmethyl)phenyl; 2-fluoro-4-(2-carboxyethylamino)-phenyl; 2-fluoro-4-(4-carboxypyrazol-1-ylmethyl)-phenyl; 2-fluoro-4-[(2S,4R)-2-carboxypyrrolidin-4-yloxy]phenyl; 2-fluoro-4-(R-2-carboxyazetidin-1-ylmethyl)phenyl; 2-fluoro-4-(S-2-carboxyazetidin-1-ylmethyl)phenyl; 2-fluoro-4-(R-1-aminoethyl)phenyl; 2-fluoro-4-(3-carboxypropyl)phenyl; 1-(2-carboxyethyl)indol-5-yl; 3,5-dimethyl-4-(3R-glyceryloxy)phenyl; 2-fluoro-4-(R-2-carboxypyrrolidin-1-ylmethyl)-phenyl; 2-fluoro-4-(2-dimethylaminoethyl)-phenyl; 2-fluoro-4-(3-fluoroazetidin-1-ylmethyl)phenyl; 2-fluoro-4-(S-2-carboxypyrrolidin-1-ylmethyl)phenyl; 3-carboxypropylindol-5-yl; 3,5-dimethyl-4-(3S-glyceryloxy)phenyl; 2-fluoro-4-(1-methylaminocycloprop-1-yl)phenyl; 3,5-dimethyl-4-(azetidin-1-ylmethyl)phenyl; 2-fluoro-4-(2-amino-3-hydroxypropyl)phenyl; 2-fluoro-4-(2-amino-2-hydroxymethyl-3-hydroxypropyl)phenyl; 2-fluoro-4-(2-acetylaminoethyl)phenyl; indol-5-yl; 3,5-dimethyl-4-[(3-azetidin-1-ylpropyl)aminomethyl]-phenyl; 4-(hydroxymethyl)-3-methylphenyl; 2-fluoro-4-(2-hydroxyethyl)phenyl; 3,5-dimethyl-4-(hydroxymethyl)phenyl; 2-fluoro-4-(2-hydroxyethylNHCO-)-phenyl; 2-fluoro-4-(N,N-bis-methylsulfonylamino)phenyl; 2-fluoro-4-(2-oxopyrrolidin-1-yl)phenyl; 2-fluoro-4-(1-hydroxy-2,2,2-trifluoroethyl)phenyl; 3-methyl-4-(3-carboxyazetidin-1-ylmethyl)phenyl, 3,5-dimethyl-4-(3-carboxyazetidin-1-ylmethyl)phenyl, 2-methyl-4-(3-carboxyazetidin-1-ylmethyl)phenyl, 2-fluoro-4-(azetidin-1-ylmethyl)phenyl, 2-fluoro-4-(1-amino-1-methylethyl)phenyl, 2-fluoro-4-[1-(2-carboxyethylamino)-1-methylethyl-phenyl, 2-fluoro-4-[R-1-(3-carboxyazetidin-1-yl)propyl]phenyl, 2-fluoro-4-[S-1-(3-carboxyazetidin-1-yl)propyl]phenyl, 2-fluoro-4-(S-1-hydroxy-2,2,2-trifluoroethyl)-phenyl; 2-fluoro-4-(trifluoromethyl-CONH-)-phenyl; 2-fluoro-4-(2-hydroxymethyl-3-hydroxypropyl)phenyl; 2-fluoro-4-(2-methoxyethylNHCO-)phenyl; 4-hydroxymethyl-2-methylphenyl; 2-fluoro-4-(3,3-difluoroazetidin-1-ylmethyl)phenyl; 2-fluoro-4-(2-aminoethyl)phenyl; 2-fluoro-4-(3-carboxypyrazol-1-ylmethyl)phenyl; 4-hydroxymethylphenyl; 1,2,3,4-tetrahydroisoquinolin-6yl; 2-fluoro-4-(4-carboxycyclobutylmethyl)phenyl; 2-fluoro-4-(cyclopropylNHCO-)phenyl; 2-fluoro-4-(2-carboxyethylSO$_2$NH)phenyl; 2-fluoro-4-(5-carboxypyrazol-1-yl-methyl)phenyl; 2-fluoro-4-(cis)-3-carboxycyclobutylmethyl]phenyl; 2-fluoro-4-(R-1-hydroxy-2,2,2-trifluoroethyl)phenyl; 1-carboxymethylindol-5-yl; 2-fluoro-4-(2-hydroxyethylN($CH_3$)CO-)-phenyl; 2-fluoro-4-(trans)-3-carboxycyclobutylmethyl]phenyl; 2-fluoro-4-(2-methylsulfonylaminoethyl)-phenyl; 2-fluoro-4-(3,3-dicarboxycyclobutylmethyl)phenyl; 2-fluoro-4-(azetidin-1-ylcarbonyl)phenyl; 2-fluoro-4-(2-methoxyethylN($CH_3$)CO-)-phenyl; 2-fluoro-4-(morpholin-4-ylcarbonyl)phenyl; 2-fluoro-4-(1-amino-2,2,2-trifluoroethyl)phenyl; 2-fluoro-4-(R-3-amino-3-carboxypropyl-)-phenyl; 2-fluoro-4-(S-3-amino-3-carboxypropyl)-phenyl; 2-fluoro-4-hydroxymethylphenyl; 2-fluoro-4-(1R-(2-carboxyethylNH)ethyl)phenyl, 2-fluoro-4-(1S-(2-carboxyethylNH)ethyl)phenyl, 2-fluoro-4-(1-(2-carboxyethylNH)ethyl)-phenyl, 1S-(2-carboxyethylNH)ethyl, 2-fluoro-2-carboxyethylphenyl; 4-[(S)-1-aminoethyl]-2-fluorophenyl; 2-fluoro-4-(3-amino-3-hydroxymethyl-4-hydroxybutyl)phenyl; 2-fluoro-4-[(2S,4S)-2-hydroxymethylpyrrolidin-4-yl]-phenyl; 4-(3-carboxyazetidin-1-yl-methyl)phenyl; 2-fluoro-4-(S-$CH_2NHCH(CH_3)CO_2H$)-phenyl; 2-fluoro-4-(R-$CH_2NHCH(CH_3)CO_2H$)-phenyl; 2-fluoro-4-[(1-carboxycyclopropyl)-aminomethyl]-phenyl; 2-fluoro-4-(—$CH_2NHC(CH_3)_2CO_2H$))-phenyl; 2-(2-carboxyethyl)-3,4-dihydro-2-(1H)-isoquinolin-6-yl; 2-(carboxymethyl)-3,4-dihydro-2-(1H)-isoquinolin-6-yl; 2-fluoro-4-(carboxymethyloxymethyl)-phenyl; 2-fluoro-4-(1-hydroxyethyl)phenyl; 2-fluoro-4-(—$CH_2NHC(CH_3)_2$ $CH_2CO_2H$)-phenyl; 2-fluoro-4-(—$CH_2NHC(CH_2)_3CO_2H$)-phenyl; 2-fluoro-4-(—$CH_2NHCH(CH_3)CH_2CO_2H$)-phenyl; 2-fluoro-4-(—$CH(CH_3)NHCH(CH_3)CH_2CO_2H$)-phenyl; 2-fluoro-4-(S-$CH_2NHCH(CH_3)CH_2CO_2H$)-phenyl; 2-fluoro-4-(R-$CH_2NHCH(CH_3)CH_2CO_2H$)-phenyl; 2-fluoro-4-[(3S,1R)-$CH(CH_3)NHCH(CH_3)CH_2CO_2H$]-phenyl; 2-fluoro-4-[(3R,1S)-$CH(CH_3)NHCH(CH_3)CH_2CO_2H$]-phenyl; 2-fluoro-4-[$CH_2CH(NH_2)CO_2H$]-phenyl; 2-fluoro-4-[S-$CH_2CH(NH_2)CO_2H$]-phenyl; 2-fluoro-4-[R-$CH_2CH(NH_2)CO_2H$]-phenyl; 2-fluoro-4-[(S-$(CH_2)_2CH(NH_2)CO_2H$]-phenyl; 2-fluoro-4-(3R-carboxpyrrolidin-1-yl-carbonyl)phenyl; 2-fluoro-4-(3R-carboxypiperidin-1-ylcarbonyl)phenyl; 2-fluoro-4-(3-carboxyazetidin-1-ylcarbonyl)phenyl; 2-fluoro-4-(—$CONHC(CH_3)_2CH_2COOH$)-phenyl; 2-fluoro-4-[—$CON(CH_3)(CH_2)_2COOH$]-phenyl; 2-fluoro-4-(—$CONHCH(CH_3)CH_2COOH$)-phenyl; 2-fluoro-4-(—$NHCO(CH_2)_2COOH$)- phenyl; 2-fluoro-4-(—$CH_2NHCH_2COOH$)-phenyl; benzimidazol-5-yl; 2-(2-carboxyethyl)-1,3-dihydro-2-(1H)-isoindol-5-yl; 2-(carboxymethyl)-1,3-dihydro-2-(1H)-isoindol-5-yl; 1-(2-carboxyethyl)-benzimidazol-6-yl; 1-(2-carboxyethyl)-benzimidazol-5-yl; or 2-fluoro-4-(—$CONHCH(CH_3)$—$CH_2COOH$)-phenyl.

17. The compound of claim 9 where

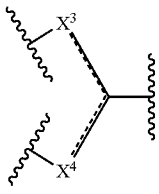

is

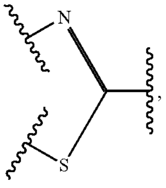

, m is 0 and wherein in group

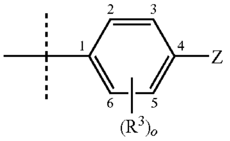

is 2-fluoro-4-(3-carboxyazetidin-1-ylmethyl)phenyl; 2-fluoro-4-(3-carboxy-3-hydroxyazetidin-1-ylmethyl)phenyl; 2-fluoro-4-(3-carboxy-3-fluoroazetidin-1-ylmethy)phenyl; 2-fluoro-4-(3-carboxypyrrolidin-1-ylmethyl)phenyl; 2-fluoro-4-(R-3-carboxypyrrolidin-1-ylmethyl)phenyl; 2-fluoro-4-(3-carboxypropylNHCO-)phenyl; 2-fluoro-4-(S-3-carboxypyrrolidin-1-ylmethyl)phenyl; 2-fluoro-4-(2-carboxyethylNH$CH_2$-)phenyl; 2-fluoro-4-(1R,3S-3-carboxy-N-oxoazetidin-1-ylmethyl)phenyl; 2-fluoro-4-(1S,3R-3-carboxy-N-oxoazetidin-1-ylmethyl)phenyl; 2-fluoro-4-[R-1-(3-carboxyazetidin-1-yl)-ethyl)phenyl; 2-fluoro-4-[S-1-(3-carboxyazetidin-1-yl)-ethyl)phenyl; 2-fluoro-4-(R-2-amino-2-carboxyethylCONH-)phenyl; 2-fluoro-4-(S-2-amino-2-carboxyethylCONH-)phenyl; 2-fluoro-4-(2-(carboxymethylaminoethyl)phenyl; 2-fluoro-4-[(2R,4R)-2-carboxypyrrolidin-4-yl]phenyl; 2-fluoro-4-(S-1-hydroxy-2-carboxyethylCONH-)phenyl; 2-fluoro-4-[(2S,4R)-2-carboxy-1-methylpyrrodin-4-yl]phenyl; 2-fluoro-4-(S-3-amino-3-carboxybutyl)phenyl; 2-fluoro-4-(R-3-amino-3-carboxybutyl)phenyl; 2-fluoro-4-(3-amino-3-$CH_2OP(O)(OH)_2$-4-hydroxybutyl)phenyl; 2-fluoro-4-(S-2-carboxy-2-hydroxyeth ylCONH-)phenyl, 2-fluoro-4-(S-1-amino-2-carboxyethylCONH-)phenyl, 2-fluoro-4-(R-1-amino-2-carboxyethylCONH-)phenyl, 2-fluoro-4-(R-2-hydroxy-2-carboxyethylCONH-)phenyl, 2-fluoro-4-(R-1-hydroxy-2-carboxyethylCONH-)phenyl, 2-fluoro-4-[(2S,4R)-2-carboxy-4-hydroxypyrrolidin-4-yl]phenyl, 2-fluoro-4-[(2S,4R)-2-carboxypyrrolin-4-yl]phenyl; 1-(2-carboxyethyl-1,2,3,4-tetrahydroisoquinolin-6-yl; 2-fluoro-4-(4-carboxyimidazol-1-ylmethyl)phenyl; 2-fluoro-4-(cis-3-carboxycyclopropylamino]-phenyl; 4-(2-carboxyethylamino)-phenyl; 2-fluoro-4-(3-hydroxyazetidin-1-ylmethyl)phenyl; 2-fluoro-4-(trans-3-carboxycyclopropylamino)-phenyl; 2-fluoro-4-(2-HOC(O)C(O)NH-ethyl)-phenyl; 2-fluoro-4-(3-carboxypropylamino)-phenyl; 2-fluoro-4-(3-carboxymethylazetidin-1-ylmethyl)phenyl; 2-fluoro-4-(2-carboxyethylamino)-phenyl; 2-fluoro-4-(4-carboxypyrazol-1-ylmethyl)-phenyl; 2-fluoro-4-[(2S,4R)-2-carboxypyrrolidin-4-yloxy]phenyl; 2-fluoro-4-(R-2-carboxyazetidin-1-ylmethyl)phenyl; 2-fluoro-4-(S-2-carboxyazetidin-1-ylmethyl)phenyl; 2-fluoro-4-(R-1-aminoethyl)phenyl; 2-fluoro-4-(3-carboxypropyl)phenyl; 1-(2-carboxyethyl)indol-5-yl; 3,5-dimethyl-4-(3R-glyceryloxy)phenyl; 2-fluoro-4-(R-2-carboxypyrrolidin-1-ylmethyl)-phenyl; 2-fluoro-4-(2-dimethylaminoethyl)-phenyl; 2-fluoro-4-(3-fluoroazetidin-1-ylmethyl)phenyl; 2-fluoro-4-(S-2-carboxypyrrolidin-1-ylmethyl)phenyl; 3-carboxypropylindol-5-yl; 3,5-dimethyl-4-(3S-glyceryloxy)phenyl; 2-fluoro-4-(1-methylaminocycloprop-1-yl)phenyl; 3,5-dimethyl-4-(azetidin-1-ylmethyl)phenyl; 2-fluoro-4-(2-amino-3-hydroxypropyl)phenyl; 2-fluoro-4-(2-amino-2-hydroxymethyl-3-hydroxypropyl)phenyl; 2-fluoro-4-(2-acetylaminoethyl)phenyl; indol-5-yl; 3,5-dimethyl-4-[(3-azetidin-1-ylpropyl)aminomethyl]-phenyl; 4-(hydroxymethyl)-3-methylphenyl; 2-fluoro-4-(2-hydroxyethyl)phenyl; 3,5-dimethyl-4-(hydroxymethyl)phenyl; 2-fluoro-4-(2-hydroxyethylNHCO-)-phenyl; 2-fluoro-4-(N,N-bis-methylsulfonylamino)phenyl; 2-fluoro-4-(2-oxopyrrolidin-1-yl)phenyl; 2-fluoro-4(1-hydroxy-2,2,2-trifluoroethyl)phenyl; 3-methyl-4-(3-carboxyazetidin-1-ylmethyl) phenyl, 3,5-dimethyl-4-(3-carboxyazetidin-1-ylmethyl) phenyl, 2-methyl-4-(3-carboxyazetidin-1-ylmethyl)phenyl, 2-fluoro-4-(azetidin-1-ylmethyl)phenyl, 2-fluoro-4-(1-amino-1-methylethyl)phenyl, 2-fluoro-4[1-(2-carboxyethylamino)-1-methylethyl]-phenyl, 2-fluoro-4[R-1-(3-carboxyazetidin-1-yl)propyl]phenyl, 2-fluoro-4-[S-1-(3-carboxyazetidin-1-yl)propyl]phenyl, 2-fluoro-4-(S-1-hydroxy-2,2,2-trifluoroethyl)-phenyl; 2-fluoro-4-(trifluoromethyl-CONH-)-phenyl; 2-fluoro-4-(2-hydroxymethyl-3-hydroxypropyl)phenyl; 2-fluoro-4-(2-methoxyethylNHCO-)phenyl; 4-hydroxymethyl-2-methylphenyl; 2-fluoro-4-(3,3-difluoroazetidin-1-ylmethyl) phenyl; 2-fluoro-4-(2-aminoethyl)phenyl; 2-fluoro-4-(3-Carboxypyrazol-1-ylmethyl)phenyl; 4-hydroxymethylphenyl; 1,2,3,4-tetrahydroisoquinolin-6-yl; 2-fluoro-4-(4-carboxycyclobutylmethyl)phenyl; 2-fluoro-4-(cyclopropylNHCO-)phenyl; 2-fluoro-4-(2-carboxyethyl$SO_2NH$)-phenyl; 2-fluoro-4-(5-carboxypyrazol-1-yl-methyl)phenyl; 2-fluoro-4-(cis)-3-carboxycyclobutylmethyl]phenyl; 2-fluoro-4-(R-1-hydroxy-2,2,2-trifluoroethyl)phenyl; 1-carboxymethylindol-5-yl; 2-fluoro-4-(2-hydroxyethylN($CH_3$)CO-)-phenyl; 2-fluoro-4-(trans)-3-carboxycyclobutylmethyl]phenyl; 2-fluoro-4-(2-methylsulfonylaminoethyl)phenyl; 2-fluoro-4-(3,3-dicarboxycyclobutylmethyl)phenyl; 2-fluoro-4-(azetidin-1-ylcarbonyl)phenyl; 2-fluoro-4-(2-methoxyethylN($CH_3$)CO-)-phenyl; 2-fluoro-4-(morpholin-4-ylcarbonyl)phenyl; 2-fluoro-4-(1-amino-2,2,2-trifluoroethyl)phenyl; 2-fluoro-4-(R-3-amino-3-carboxypropyl-)-phenyl; 2-fluoro-4-(S-3-amino-3-carboxypropy1)-phenyl; 2-fluoro-4-hydroxymethylphenyl; 2-fluoro-4-(1R-(2-carboxyethylNH)ethyl)phenyl, 2-fluoro-4-(1S-(2-carboxyethylNH)ethyl)phenyl, 2-fluoro-4-(1-(2-carboxyethylNH)ethyl)-phenyl, 1S-(2-carboxyethylNH)ethyl, 2-fluoro-2-carboxyethylphenyl; 4-[(S)-1-aminoethyl]-2-fluorophenyl; 2-fluoro-4-(3-amino-3-hydroxymethyl-4-hydroxybutyl)phenyl; 2-fluoro-4-[(2S,4S)-2-hydroxymethylpyrrolidin-4-yl]-phenyl; 4-(3-carboxyazetidin-1-yl-methyl)phenyl; 2-fluoro-4-(S-$CH_2NHCH(CH_3)CO_2H$)-phenyl; 2-fluoro-4-(R-$CH_2NHCH(CH_3)CO_2H$)-phenyl; 2-fluoro-4-[(1-carboxycyclopropyl)-aminomethyl]-phenyl; 2-fluoro-4-(—$CH_2NHC(CH_3)_2CO_2$1))-phenyl; 2-(2-carboxyethyl)-3,4-dihydro-2-(1H)-isoquinolin-6-yl; 2-(carboxymethyl)-3,4-dihydro-2-(1H)-isoquinolin-6-yl; 2-fluoro-4-(carboxymethyloxymethyl)-phenyl; 2-fluoro-4-(1-hydroxyethyl)phenyl; 2-fluoro-4-(—

$CH_2NHC(CH_3)_2CH_2CO_2H$)-phenyl; 2-fluoro-4-(—$CH_2NHC(CH_2)_3CO_2H$)-phenyl; 2-fluoro-4-(—$CH_2NHCH(CH_3)CH_2CO_2H$)-phenyl; 2-fluoro-4-(—$CH(CH_3)NHCH(CH_3)CH_2CO_2H$)-phenyl; 2-fluoro-4-(S-$CH_2NHCH(CH_3)CH_2CO_2H$)-phenyl; 2-fluoro-4-(R-$CH_2NHCH(CH_3)CH_2CO_2H$)-phenyl; 2-fluoro-4-[(3S,1R)-$CH(CH_3)NHCH(CH_3)CH_2CO_2H$]-phenyl; 2-fluoro-4-[(3R,1S)-$CH(CH_3)NHCH(CH_3)CH_2CO_2H$]-phenyl; 2-fluoro-4-[$CH_2CH(NH_2)CO_2H$]-phenyl; 2-fluoro-4-[S-$CH_2CH(NH_2)CO_2$]-phenyl; 2-fluoro-4-[R-$CH_2CH(NH_2)CO_2H$]-phenyl; 2-fluoro-4-[(S-$(CH_2)_2CH(NH_2)CO_2$]-phenyl; 2-fluoro-4-(3R-carboxypyrrolidin-1-yl-carbonyl)phenyl; 2-fluoro-4-(3R-carboxypiperidin-1-ylcarbonyl)phenyl; 2-fluoro-4-(3-carboxyazetidin-1-ylcarbonyl)phenyl; 2-fluoro-4-(—$CONHC(CH_3)_2CH_2COOH$)-phenyl; 2-fluoro-4-[—$CON(CH_3)(CH_2)_2COOH$]-phenyl; 2-fluoro-4-(—$CONHCH(CH_3)$-$CH_2COOH$)-phenyl; 2-fluoro-4-(—$NHCO(CH_2)_2COOH$)-phenyl; 2-fluoro-4-(—$CH_2NHCH_2COOH$)-phenyl; benzimidazol-5-yl; 2-(2-carboxyethyl)-1,3-dihydro-2-(1H)-isoindol-5-yl; 2-(carboxymethyl)-1,3-dihydro-2-(1H)-isoindol-5-yl; 1-(2-carboxyethyl)-benzimidazol-6-yl; 1-(2-carboxyethyl)-benzimidazol-5-yl; or 2-fluoro-4-(—$CONHCH(CH_3)$—$CH_2COOH$)-phenyl.

18. The compound of claim 9 wherein

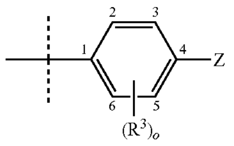

is 2-fluoro-4-(3-carboxyazetidin-1-ylmethyl)phenyl; 4-(3-carboxyazetidin-1-ylmethyl)phenyl, 3-methyl-4-(3-carboxyazetidin-1-ylmethyl)phenyl, 2-methyl-4-(3-carboxyazetidin-1-ylmethyl)phenyl, 2-amino-4-(3-carboxyazetidin-1-ylmethyl)phenyl, 2-fluoro-4-[R-1-(3-carboxyazetidin-1-yl)-ethyl)phenyl, 2-fluoro-4-]S-1-(3-carboxyazetidin-1-yl)-ethyl)phenyl, 2-fluoro-4-(R-3-carboxypyrrolidin-1-ylmethyl)phenyl, 2-fluoro-4-(S-3-carboxypyrrolidin-1-ylmethy)phenyl, 2-fluoro-4-(2-carboxyethylNHCH$_2$-)phenyl, 2-fluoro-4-[(2S,4R)-2-carboxy-1-methylpyrrolidin-4-yl]phenyl, 2-fluoro-4-[(2S,4R)-2-carboxypyrrolidin-4-yl]phenyl, 2-fluoro-4-(S-3-amino-3-carboxybutyl)-phenyl, 2-fluoro-4-(R-3-amino-3-carboxybutyl)-phenyl, 2-fluoro-4-[(S-$(CH_2)_2CH(NH_2)CO_2H$]phenyl, 2-fluoro-4-[(R-$(CH_2)_2CH(NH_2)$—$CO_2H$]-phenyl, 2-fluoro-4-[(1-carboxy)aminomethyl]-phenyl, 2-fluoro-4-(—NHCO—$(CH_2)_2COOH$)-phenyl, 2-fluoro-4-(S-2-carboxy-2-hydroxyethylCONH-)phenyl, or 2-fluoro-4-(S-1-amino-2-carboxyethylCONH-)phenyl.

19. A compound selected from:

1-((3-fluoro-4-(5(1-phenylcyclopropyl)thiazolo[5,4-b]pyridin-2-yl)phenyl)methyl)azetidine-3-carboxylic acid;

(R)-1-((3-fluoro-4-(5(1-phenylcyclopropypl)thiazolo[5,4-b]pyridine-2-yl)phenyl)methyl)pyrrolidine-3-carboxylic acid;

(S)-1-((3-fluoro-4-(5-(1-phenylcyclopropyl)thiazolo[5,4-b]pyridine-2-yl)phenyl)methyl)pyrrolidine-3-carboxylic acid;

1-((3-fluoro-4-(5-(1-phenylcyclopropyl)thiazolo[5,4-b]pyridine-2-yl)phenyl)methyl)-3-hydroxyazetidine-3-carboxylic acid;

3-fluoro-1-((3-fluoro-4-(5-(1-phenylcyclopropyl)thiazolo[5,4-b]pyridine-2-yl)phenyl)methyl)azetidine-3-carboxylic acid;

1-((3-fluoro-4-(5-(1-phenylcyclopent-3-enyl)thiazolo[5,4-b]pyridine-2-yl)phenyl)methyl)azetidine-3-carboxylic acid;

1-((3-fluoro-4-(5-(1-phenylcyclopentyl)thiazolo[5,4-b]pyridine-2-yl)phenyl)methyl)azetidine-3-carboxylic acid;

1-((3-fluoro-4-(5-(1-phenylcyclohexyl)thiazolo[5,4-b]pyridine-2-yl)phenyl)methyl)azetidine-3-carboxylic acid;

(1R,3S)-3-carboxy-1-(3-fluoro-4-(5-(1-phenylcyclopropyl)thiazolo[5,4-b]pyridin-2-yl)benzyl)azetidine 1-oxide;

(1S,3R)-3-carboxy-1-(3-fluoro-4-(5-(1-phenylcyclopropyl)thiazolo[5,4-b]pyridin-2-yl)benzyl)azetidine 1-oxide;

1-((3-fluoro-4-(5-(2-phenyloxetan-2-yl)thiazolo[5,4-b]pyridine-2-yl)phenyl)methyl)azetidine-3-carboxylic acid;

1-((3-fluoro-4-(6-(1-phenylcyclopropyl)benzo[d]thiazol-2-yl)phenyl)methyl)azetidine-3-carboxylic acid;

(R)-1-(3-fluoro-4-(5-(1-phenylcyclopropyl)thiazolo[5,4-b]pyridine-2-yl)phenyl)ethyl)azetidine-3-carboxylic acid;

(S)-1-(3-fluoro-4-(5-(1-phenylcyclopropyl)thiazolo[5,4-b]pyridine-2-yl)phenyl)ethyl)azetidine-3-carboxylic acid;

3-((3-fluoro-4-(5-(1-phenylcyclopropyl)thiazolo[5,4-b]pyridine-2-yl)phenyl)methylamino)propanoic acid;

(R)-3-(1-(3-fluoro-4-(5-(1-phenylcyclopropyl)thiazolo[5,4-b]pyridine-2-yl)phenyl)ethylamino)propanoic acid;

(S)-3-(1-(3-fluoro-4-(5-phenylcyclopropyl)thiazolo[5,4-b]pyridine-2-yl)-phenyl)ethylamino)propanoic acid;

3-(1-(3-fluoro-4-(5(1-phenylcyclopropyl)thiazolo[5,4-b]pyridine-2-yl)phenyl)ethylamino)propanoic acid;

3-(3-fluoro-4-(5-(1-phenylcyclopropyl)thiazolo[5,4-b]pyridine-2-yl)benzamido)propanoic acid;

2-(3-fluoro-4-(5-(1-phenylcyclopropyl)thiazolo[5,4-b]pyridine-2-yl)benzamido)acetic acid;

4-(3-fluoro-4-(5-(1-phenylcyclopropyl)thiazolo[5,4-b]pyridine-2-yl)benzamido)butanoic acid;

1-((2,6-dimethyl-4-(5-(1-phenylcyclopropyl)thiazolo[5,4-b]-pyridin-2-yl)phenyl-)-methyl)azetidine-3-carboxylic acid;

1-((2-methyl-4-(5-(1-phenylcyclopropyl)thiazolo[5,4-b]pyridine-2-yl)phenyl)methyl)-azetidine-3-carboxylic acid;

1-((3-methyl-4-(5-(1-phenylcyclopropyl)thiazolo[5,4-b]pyridine-2-yl)phenyl)methyl)azetidine-3-carboxylic acid;

1-(3-fluoro-4-(5-(1-phenylcyclopropyl)thiazolo[5,4-b]pyridine-2-yl)phenyl)cyclopropanamine;

3-(1-(3-fluoro-4-(5-(1-phenylcyclopropyl)thiazolo[5,4-b]pyridine-2-yl)phenyl)cyclopropylamino)propanoic acid;

2-(3-fluoro-4-(5-(1-phenylcyclopropyl)thiazolo[5,4-b]pyridine-2-yl)phenyl)propan-2-amine;

3-(2-(3-fluoro-4-(5(1-phenylcyclopropyl)thiazolo[5,4-b]pyridine-2-yl)phenyl)propan-2-ylamino)propanoic acid;

3-(3-fluoro-4-(5-1-phenylcyclopropyl)thiazolo[5,4-b]pyridine-2-yl)phenyl)propanoic acid;

(3-fluoro-4-(5-(1-phenylcyclopropyl)thiazolo[5,4-b]pyridine-2-yl)phenyl)methanol;

2-(3-fluoro-4-(5-(1-phenylcyclopropyl)thiazolo[5,4-b]pyridine-2-yl)benzyl)propane-1,3-diol;

3-(3-fluoro-4-(5-(1-phenylcyclopropyl)thiazolo[5,4-b]pyridine-2-yl)benzyl)cyclobutane-1,1-dicarboxylic acid;

(cis)-3-(3-fluoro-4-(5-(1-phenylcyclopropyl)thiazolo[5,4-b]pyridine-2-yl)benzyl)-cyclobutanecarboxylic acid;

(trans)-3-(3-fluoro-4-(5-(1-phenylcyclopropyl)thiazolo[5,4-b ]pyridine-2-yl)benzyl)-cyclobutanecarboxylic acid;

(R)-2,2,2-trifluoro-1-(3-fluoro-4-(5-(1-phenylcyclopropyl)-thiazolo[5,4-b]pyridine-2-yl)phenyl)ethanolol;

(S)-2,2,2-trifluoro-1-(3-fluoro-4-(5-(1-phenylcyclopropyl)thiazolo[5,4-b]pyridine-2-yl)phenyl)ethanol;

2(rac)-2,2,2-trifluoro-1-(3-fluoro-4-(5-(1-phenylcyclopropyl)thiazolo[5,4-b]pyridine-2-yl)phenyl)ethanamine;

1-(3-fluoro-4-(5(1-phenylcyclopropyl)thiazolo[5,4-b]pyridin-2-yl)benzyl)azetidin-3-ol;

2-(4-((3,3-difluoroazetidin-1yl)methyl)-2-fluorophenyl)-5-(1-phenylcydopropyl)-thiazolo[5,4-b]pyridine;

(R)-1-(1-(3-fluoro-4-(5(1-phenylcyclopropyl)thiazolo[5,4-b]pyridin-2-yl)phenyl)-propyl)azetidine-3-carboxylic acid;

(S)-1-(1-(3-fluoro-4-(5-(1-phenylcyclopropyl)thiazolo[5,4-b]pyridin-2-yl)phenyl)propyl)azetidine-3-carboxylic acid;

1-(3-fluoro-4-(5-(1-(2-fluorophenyl)cyclopropyl)thiazolo[5,4-b]pyridine-2-yl)benzyl)azetidine-3-carboxylic acid;

1-(3-fluoro-4-(5-(1-(4-hydroxyphenyl)cyclopropyl)thiazolo[5,4-b]pyridine-2-yl)benzyl)azetidine-3-carboxylic acid;

1-(3-fluoro-4-(5-(1-(4-fluorophenyl)cyclopropyl)thiazolo[5,4-b]pyridine-2-yl)benzyl)azetidine-3-carboxylic acid;

1-(3-fluoro-4-(5-(1-phenylcyclobutyl)thiazolo[5,4-b]pyridine-2-yl)benzyl)azetidine-3-carboxylic acid;

2-amino-2-(3-fluoro-4-(5-(1-phenylcyclopropyl)thiazolo[5,4-b]pyridin-2-yl)-phenethyl)-propane-1,3-diol;

(rac)-2-amino-4-(3-fluoro-4-(5-(1-phenylcyclopropyl)thiazolo[5,4-b]pyridine-2-yl)-phenyl)-2-(hydroxymethyl)butyl dihydrogen phosphate;

1-(3-fluoro-4-(6-(1-phenylcyclopropyl)thiazolo[4,5-c]pyridine-2-yl)benzyl)azetidine-3-carboxylic acid;

1-(3-amino-4-(5-(1-phenylcyclopropyl)thiazolo[5,4-b]pyridin-2-yl)benzyl)azetidine-3-carboxylic acid;

1-(4-(5-(1-cyclohexylcyclopropyl)thiazolo[5,4-b]pyridine-2-yl)-3-fluorobenzyl)azetidine-3-carboxylic acid;

1-(4-(5-(1-cyclopentylcyclopropyl)thiazolo[5,4-b]pyridin-2-yl)-3-fluorobenzyl)azetidine-3-carboxylic acid;

1-(4-(5-bi(cycloprop)ylthiazolo[5,4-b]pyridine-2-yl)-3-fluorobenzyl)-azetidine-3-carboxylic acid;

1-(4-(5-(1-(4,4-difluorocyclohexyl)cyclopropyl)thiazolo[5 ,4-b]pyridine-2-yl)-3-fluorobenzyl)azetidine-3-carboxylic acid;

(R)-1-(4-(5-(1-(3,3-difluorocyclopentyl)cyclopropyl)thiazolo[5,4-b]pyridine-2-yl)-3-fluorobenzyl)azetidine-3-carboxylic acid;

(S)-1-(4-(5-(1-(3,3-difluorocyclopentyl)cyclopropyl)thiazolo[5,4-b]pyridine-2-yl)-3-fluorobenzyl)azetidine-3-carboxylic acid;

1-(3-fluoro-4-(5-(1-(tetrahydro-2H-pyran-4-yl)cyclopropyl)thiazolo[5,4-b]pyridine-2-yl)benzyl)azetidine-3-carboxylic acid;

(2S,4R)-4-(3-fluoro-4-(5-(-phenylcyclopropyl)thiazolo[5,4-b]pyridine-2-yl)phenyl)-4-hydroxypyrrolidine-2-carboxylic acid;

(2S,4R)-4-(3-fluoro-4-(5-(1-phenylcyclopropyl)thiazolo[5,4]pyridine-2-yl)phenyl)-pyrrolidine-2-carboxylic acid;

(2S,4R)-4-(3-fluoro-4-(5-(1-phenylcyclopropyl)thiazolo[5,4-b]pyridine-2-yl)phenyl)-1-methylpyrrolidine-2-carboxylic acid;

((2S,4S)-4-(3-fluoro-4-(5-(1-phenylcyclopropyl)thiazolo[5,4-b]pyridine-2-yl)-phenyl)-pyrrolidin-2-yl)methanol;

((2-(3-fluoro-4-(5-(1-phenylcyclopropyl)[1,3]thiazolo[5,4-b]pyridin-2-yl)phenyl)ethyl)amino)(oxo)acetic acid;

2-(2-fluoro-4-((3-fluoroazetidin-1-yl)methyl)-phenyl)-5-(1-phenylcyclopropyl)-thiazolo[5,4-b]pyridine;

N-benzyl-2-(3-fluoro-4-(5-(1-phenylcyclopropyl)[1,3]thiazolo[5,4-b]pyridin-2-yl)-phenyl)ethanamine;

N-(2-(3-fluoro-4-(5-(1-phenylcyclopropyl)[1,3]thiazolo[5,4-b]pyridin-2-yl)phenyl)-ethyl)methanesulfonamide;

1-((3-fluoro-4-(6-(1-(pyridine-2-yl)cyclopropyl)benzo[d]thiazol-2-yl)phenyl)methyl)azetidine-3-carboxylic acid;

2-(4-(azetidin-1-ylmethyl)-3,5-dimethylphenyl)-5(1-phenyl-cyclopropyl)thiazolo[5,4-b]pyridine;

1-(4-(5(1-phenylcyclopropyl)thiazolo[5,4-b]pyridin-2-yl)benzyl)azetidine-3-carboxylic acid;

3-(3-fluoro-4-(5-(1-phenylcyclopropyl)thiazolo[5,4-b]pyridin-2-yl)-phenylamino)-propanoic acid;

4-(3-fluoro-4-(5-(1-phenylcyclopropyl)thiazolo[5,4-b]pyridin-2-yl)-phenylamino)-butanoic acid;

(R)-3-(2,6-dimethyl-4-(5(1-phenylcyclopropyl)thiazolo[5,4-b]pyridin-2-yl)phenoxy)propane-1 ,2-diol;

(S)-3-(2,6-dimethyl-4-(5(1-phenylcyclopropyl)thiazolo[5,4-b]pyridin-2-yl)phenoxy)propane-1 ,2-diol;

3-(4-(5-(1-phenylcyclopropyl)thiazolo[5,4-b]pyridin-2-yl)phenylamino)propanoic acid;

(S)-2-(3-fluoro-4-(5-(1-phenylcyclopropyl)thiazolo[5,4-b]pyridin-2-yl)benzylamino)propanoic acid;

(R)-2-(3-fluoro-4-(5-(1-phenylcyclopropyl)thiazolo[5,4-b]pyridin-2-yl)benzylamino)propanoic acid;

(2S,4R)-4-(4-(5-(1-phenylcyclopropyl)thiazolo[5,4-b]pyridin-2-yl)phenoxy)pyrrolidine-2-carboxylic acid;

1-(3-fluoro-4-(5-(1-phenylcyclopropyl)thiazolo[5,4-b]pyridin-2-yl)benzylamino)cyclopropanecarboxylic acid;

2-(3-fluoro-4-(5-(1-phenylcyclopropyl)thiazolo[5,4-b]pyridin-2-yl)benzylamino)-2-methylpropanoic acid;

(S)-1-(3-fluoro-4-(5-1-phenylcyclopropyl)thiazolo[5,4-b]pyridin-2-yl)benzyl)azetidine-2-carboxylic acid;

(R)-1-(3-fluoro-4-(5-(1-phenylcyclopropyl)thiazolo[5,4-b]pyridin-2-yl)-benzyl)-azetidine-2-carboxylic acid;

(S)-1-(3-fluoro-4-(5-(1-phenylcyclopropyl)thiazolo[5,4-b]pyridin-2-yl)-benzyl)-pyrrolidine-2-carboxylic acid;

(R)-1-(3-fluoro-4-(5-(1-phenylcyclopropyl)thiazolo[5,4-b]pyridin-2-yl)-benzyl)-pyrrolidine-2-carboxylic acid;

2-(1-(3-fluoro-4-(5-(1-phenylcyclopropyl)thiazolo[5,4-b]pyridin-2-yl)-benzyl)azetidin-3-yl)acetic acid;

5-(1-phenylcyclopropyl)-2-(1,2,3,4-tetrahydroisoquinolin-6-yl)thiazolo-[5,4-]-pyridine;

3-(6-(5-(1-phenylcyclopropyl)thiazolo[5,4-b]pyridin-2-yl)-3,4-dihydroisoquinolin-2(1H)-yl)propanoic acid;

2-(6-(5-(1-phenylcyclopropyl)thiazolo[5,4-b]pyridin-2-yl)-3,4-dihydroisoquinolin-2(1H)-yl)acetic acid;

1-(4-(5-(1-cyclobutylcyclopropyl)thiazolo[5,4-b]pyridin-2-yl)-3-fluorobenzyl)-azetidine-3-carboxylic acid;

1-(4-(5-(1-(3,3-difluorocyclobutyl)cyclopropyl)thiazolo[5,4-b]pyridin-2-yl)-3-fluorobenzyl)azetidine-3-carboxylic acid;

2-(3-fluoro-4-(5-(1-phenylcyclopropyl)thiazolo[5,4-b]pyridin-2-yl)benzyloxy)acetic acid;

2-(4-(1-azetidinylmethyl)-2-fluorophenyl)-5-(1-phenylcyclopropyl)-[1,3 ]thiazolo-[5,4-b]pyridine;

2-(4-(1-azetidinylmethyl)-2-fluorophenyl)-5-(1-phenylcyclopropyl)-[1,3 ]thiazolo-[5,4-b]pyridine;

4-(3-fluoro-4-(5-(1-phenylcyclopropyl)thiazolo[5,4-b]pyridin-2-yl)benzyl-amino)butanoic acid;

(rac)-3-(3-fluoro--4-(5-(1-phenylcyclopropyl)thiazolo[5,4-b]pyridin-2-yl)benzyl-amino)butanoic acid;

(S)-3-(3-fluoro-4-(5-(1-phenylcyclopropyl)thiazolo[5,4-b]pyridin-2-yl)benzyl-amino)butanoic acid;

(R)-3-(3-fluoro-4-(5-(1-phenylcyclopropyl)thiazolo[5,4-b]pyridin-2-yl)benzyl-amino)butanoic acid;

3-(1-(3-fluoro-4-(5-(1-phenylcyclopropyl)thiazolo[5,4-b]pyridin-2-yl)phenyl)-ethylamino)butanoic acid;

(S)-3-((R)-1-(3-fluoro-4-(5-(1-phenylcyclopropyl)thiazolo[5,4-b]pridin-2-yl)phenyl)ethylamino)butanoic acid;

(R)-3-((S)-1-(3-fluoro-4-(5-(1-phenylcyclopropyl)thiazolo[5,4-b]pyridin-2-yl)phenyl)ethylamino)butanoic acid;

(R)-3-((R)-1-(3-fluoro-4-(5-(1-phenylcyclopropyl)thiazolo[5,4-b]pyridin-2-yl)phenyl)ethylamino)butanoic acid;

(S)-3-((S)-1-(3-fluoro-4-(5-(1-phenylcyclopropyl)thiazolo[5,4-b]pyridin-2-yl)phenyl)ethylamino)butanoic acid;

(R)-1-(3-fluoro-4-(5-(1-phenylcyclopropyl)thiazolo[5,4-b-]pyridin-2-yl)phenyl)-ethanamine;

(S)-1-(3-fluoro-4-(5-(1-phenylcyclopropyl)thiazolo[5,4-b]pyridin-2-yl)phenyl)-ethanamine;

4-(3-fluoro-4-(5-(1-phenylcyclopropyl)thiazolo[5,4-b]pyridin-2-yl)phenyl)butanoic acid;

1-(3-fluoro-4-(5-(1-phenylcyclopropyl)thiazolo[5,4-b]pyridin-2-yl)benzyl)-1H-imidazole-4-carboxylic acid;

1-(3-fluoro-4-(5-(1-phenylcyclopropyl)thiazolo[5,4-b]pyridin-2-yl)benzyl)-1H-imidazole-5-carboxylic acid;

1-(3-fluoro-4-(5-(1-phenylcyclopropyl)thiazolo[5,4-b]pyridin-2-yl)benzyl)-1H-pyrazole-4-carboxylic acid;

1-(3-fluoro-4-(5-(1-phenylcyclopropyl)thiazolo[5,4-b]pyridin-2-yl)benzyl)-1H-pyrazole-3-carboxylic acid;

1-(3-fluoro-4-(5-(1-phenylcyclopropyl)thiazolo[5,4-b]pyridin-2-yl)benzyl)-1H-pyrazole-5-carboxylic acid;

(R)-2-amino-3-(3-fluoro-4-(5-(1-phenylcyclopropyl)thiazolo[5,4-b]pyridin-2-yl)phenyl)propanoic acid;

(S)-2-amino-3-(3-fluoro-4-(5-(1-phenylcyclopropyl)thiazolo[5,4-b]pyridin-2-yl)phenyl)propanoic acid;

(R)-2-amino-4-(3-fluoro-4-(5-(1-phenylcyclopropyl)thiazolo[5,4-b]pyridin-2-yl)phenyl)butanoic acid;

(S)-2-amino-4-(3-fluoro-4-(5-(1-phenylcyclopropyl)thiazolo[5,4-b]pyridin-2-yl)phenyl)butanoic acid;

(R)-2-amino-4-(3-fluoro-4-(5-(1-phenylcyclopropyl)thiazolo[5,4-b]pyridin-2-yl)phenyl)-2-methylbutanoic acid;

(S)-2-amino-4-(3-fluoro-4-(5-(1-phenylcyclopropyl)thiazolo[5,4-b]pyridin-2-yl)phenyl)-2-methylbutanoic acid;

2-(4-(1-azetidinylcarbonyl)-2-fluorophenyl)-5-(1-phenylcyclopropyl)-[1,3]thiazolo[5,4-b]pyridine;

(3-fluoro-4-(5-(1-phenylcyclopropyl)thiazolo[5,4-b]pyridin-2-yl)phenyl)(morpholino)methanone;

R-2-(2-fluoro-4-(4-morpholinylcarbonyl)phenyl)-5-(1-phenyl-cyclopropyl)-[1,3]thiazolo[5,4-b]pyridine;

(3R)-1-((3-fluoro-4-(5-(1-phenylcyclopropyl)[1,3]thiazolo[5,4-b]pyridin-2-yl)-phenyl)-carbonyl)-3-piperidinecarboxylic acid;

3-fluoro-N-(2-hydroxyethyl)-N-methyl-4-(5-(1-phenylcyclopropyl)-[1,3]thiazolo[5,4-b]pyridin-2-yl)benzamide;

3-fluoro-N-(2-methoxyethyl)-4-(5-(1-phenylcyclopropyl)[1,3]thiazolo[5,4-b]pyridin-2-yl)benzamide;

3-fluoro-N-(2-hydroxyethyl)-4-(5-(1-phenylcyclopropyl)[1,3]thiazolo[5,4-b]pyridin-2-yl)benzamide;

1-((3-fluoro-4-(5-(1-phenylcyclopropyl)[1,3]thiazolo[5,4-b]pyridin-2-yl)phenyl)carbonyl)-3-azetidinecarboxylic acid;

N-cyclopropyl-3-fluoro-4-(5-(1-phenylcyclopropyl)[1,3]thiazolo[5,4-b]pyridin-2-yl)benzamide;

3-fluoro-N-(2-methoxyethyl)-N-methyl-4-(5-(1-phenylcyclopropyl)-[1,3]thiazolo[5,4-b]pyridin-2-yl)benzamide;

3-(((3-fluoro-4-(5-(1-phenylcyclopropyl)[1,3]thiazolo[5,4-b]pyridin-2-yl)phenyl)carbonyl)amino)-3-methylbutanoic acid;

N-((3-fluoro-4-(5-(1-phenylcyclopropyl)[1,3]thiazolo[5,4-b]pyridin-2-yl)phenyl)carbonyl)-N-methyl-beta-alanine;

(rac)-3-(((3-fluoro-4-(5-(1-phenylcyclopropyl)[1,3]thiazolo[5,4-b]pyridin-2-yl)phenyl)carbonyl)amino)butanoic acid;

2,2,2-trifluoro-N-(3-fluoro-4-(5-(1-phenylcyclopropyl)[1,3]thiazolo[5,4-b]pyridin-2-yl)-phenyl)acetamide;

1-(3-fluoro-4-(5-(1-phenylcyclopropyl)[1,3]thiazolo[5,4-b]pyridin-2-yl)phenyl)-N-methylcyclopropanamine;

3-fluoro-N,N-dimethyl-4-(5-(1-phenylcyclopropyl)[1,3]thiazolo[5,4-b]pyridin-2-yl)-aniline;

3-fluoro-N-methyl-4-(5-(1-phenylcyclopropyl)[1,3]thiazolo[5,4-b]pyridin-2-yl)-aniline;

N-(3-fluoro-4-(5-(1-phenylcyclopropyl)[1,3]thiazolo[5,4-b]pyridin-2-yl)phenyl)-N-(methylsulfonyl)methanesulfonamide;

4-((3-fluoro-4-(5-(1-phenylcyclopropyl)[1,3]thiazolo[5,4-b]pyridin-2-yl)phenyl)amino)-4-oxobutanoic acid;

3-((3-fluoro-4-(5-(1-phenylcyclopropyl)[1,3]thiazolo[5,4-b]pyridin-2-yl)phenyl)sulfamoyl)propanoic acid;

1-(3-fluoro-4-(5-(1-phenylcyclopropyl)[1,3]thiazolo[5,4-b]pyridin-2-yl)phenyl)-2-pyrrolidinone;

N-(3-fluoro-4-(5-(1-phenylcyclopropyl)[1,3]thiazolo[5,4]pyridin-2-yl)phenyl)-D-alpha-asparagine;

N-(3-fluoro-4-(5-(1-phenylcyclopropyl)[1,3]thiazolo[5,4-b]pyridin-2-yl)phenyl)-D-asparagine;

N-(3-fluoro-4-(5-(1-phenylcyclopropyl)[1,3]thiazolo[5,4-b]pyridin-2-yl)phenyl)-L-alpha-asparagine;

N-(3-fluoro-4-(5-(1-phenylcyclopropyl)[1,3]thiazolo[5,4-b]pyridin-2-yl)phenyl)-L-asparagine;

cis-3-((3-fluoro-4-(5-(1-phenylcyclopropyl)[1,3]thiazolo[5,4-b]pyridin-2-yl)phenyl)amino)cyclobutanecarboxylic acid;

trans-3-((3-fluoro-4-(5-(1-phenylcyclopropyl)[1,3]thiazolo[5,4-b]pyridin-2-yl)phenyl)amino)cyclobutanecarboxylic acid;

(2S)-4-((3-fluoro-4-(5-(1-phenylcyclopropyl)[1,3]thiazolo[5,4-b]pyridin-2-yl)phenyl)amino)-2-hydroxy-4-oxobutanoic acid;

(3S)-4-(3-fluoro-4-(5-(1-phenylcyclopropyl)thiazolo[5,4-b]pyridin-2-yl)phenylamino)-3-hydroxy-4-oxobutanoic acid;

(2R)-4-((3-fluoro-4-(5-(1-phenylcyclopropyl)[1,3]thiazolo[5,4-b]pyridin-2-yl)phenyl)amino)-2-hydroxy-4-oxobutanoic acid;

(3R)-4-((3-fluoro-4-(5-(1-phenylcyclopropyl)[1,3]thiazolo[5,4-b]pyridin-2-yl)phenyl)amino)-3-hydroxy-4-oxobutanoic acid;

2-(1H-indol-5-yl)-5-(1-phenylcyclopropyl)thiazolo[5,4-b]pyridine;
3-(5-(5-(1-phenylcyclopropyl)[1,3]thiazolo[5,4-b]pyridin-2-yl)-1H-indol-1-yl)propanoic acid;
4-(5(5(1-phenylcyclopropyl)[1,3]thiazolo[5,4-b]pyridin-2-yl)-1H-indol-1-yl)-butanoic acid;
(5-(5-(1-phenylcyclopropyl)[1,3]thiazolo[5,4-b]pyridin-2-yl)-1H-indol-1-yl)acetic acid;
2-(1H-benzimidazol-5-yl)-5-(1-phenylcyclopropyl)[1,3]thiazolo[5,4-b]pyridine;
3-(5-(5-(1-phenylcyclopropyl)[1,3]thiazolo[5,4-b]pyridin-2-yl)-1H-benzimidazol-1-yl)propanoic acid;
3-(6-(5-(1-phenylcyclopropyl)[1,3]thiazolo[5,4-b]pyridin-2-yl)-1H-benzimidazol-1-yl)propanoic acid;
3-(5-(5-(1-phenylcyclopropyl)[1,3]thiazolo[5,4-b]pyridin-2-yl)-1,3-dihydro-2H-isoindol-2-yl)propanoic acid;
(5-(5-(1-phenylcyclopropyl)[1,3]thiazolo[5,4-b]pyridin-2-yl)-1,3-dihydro-2H-isoindol-2-yl)acetic acid;
N-(3-fluoro-4-(5-(1-phenylcyclopropyl)[1,3]thiazolo[5,4-b]pyridin-2-yl)benzyl)glycine;
2-(3-fluoro-4-(5-(1-phenylcyclopropyl)[1,3]thiazolo[5,4-b]pyridin-2-yl)phenyl)ethanamine;
2-(3-fluoro-4-(5-(1-phenylcyclopropyl)[1,3]thiazolo[5,4-b]pyridin-2-yl)phenyl)ethanol;
N-(2-(3-fluoro-4-(5-(1-phenylcyclopropyl)[1,3]thiazolo[5,4-b]pyridin-2-yl)phenyl)ethyl)glycine;
2-(3-fluoro-4-(5-(1-phenylcyclopropyl)[1,3]thiazolo[5,4-b]pyridin-2-yl)phenyl)-N,N-dimethylethanamine;
N-(2-(3-fluoro-4-(5-(1-phenylcyclopropyl)[1,3]thiazolo[5,4-b]pyridin-2-yl)phenyl)ethyl)acetamide; and
(2R,4R)-4-(3-fluoro-4-(5-(1-phenylcyclopropyl)thiazolo[5,4-b]pyridin-2-yl)phenyl)pyrrolidine-2-carboxylic acid;
2-amino-3-(3-fluoro-4-(5-(1-phenylcyclopropyl)thiazolo[5,4-b]pyridin-2-yl)phenyl)propan-1-ol;
N-(2,6-dimethyl-4-(5-(1-phenylcyclopropyl)thiazolo[5,4-b]pyridin-2-yl)benzyl)-3-(azetidin-1-yl)propan-1-amine;
(2-methyl-4-(5-(1-phenylcyclopropyl)thiazolo[5,4-b]pyridin-2-yl)phenyl)methanol;
(2,6-dimethyl-4-(5-(1-phenylcyclopropyl)thiazolo[5,4-b]pyridin-2-yl)phenyl)methanol;
(3-methyl-4-(5-(1-phenylcyclopropyl)thiazolo[5,4-b]pyridin-2-yl)phenyl)methanol;
(4-(5-(1-phenylcyclopropyl)thiazolo[5,4-b]pyridin-2-yl)phenyl)methanol;
1-(3-fluoro-4-(5-(1-phenylcyclopropyl)thiazolo[5,4-b]pyridin-2-yl)phenyl)ethanol;
2-amino-3-(3-fluoro-4-(5-(1-phenylcyclopropyl)thiazolo[5,4-b]pyridin-2-yl)phenyl)propanoic acid; or
a pharmaceutically acceptable salt thereof.

20. 1-((3-Fluoro-4-(5-(1-phenylcyclopropyl)thiazolo[5,4-b]pyridin-2-yl)phenyl)methyl)azetidine-3-carboxylic acid or a pharmaceutically acceptable salt thereof.

21. (R)-1-(1-(3-Fluoro-4-(5-(1-phenylcyclopropyl)thiazolo[5,4-b]pyridine-2-yl)phenyl)ethyl)azetidine-3-carboxylic acid or a pharmaceutically acceptable salt thereof.

22. (S)-2-Amino-4-(3-fluoro-4-(5-(1-phenylcyclopropyl)thiazolo[5,4-b]pyridin-2-yl)phenyl)-2-methylbutanoic acid or a pharmaceutically acceptable salt thereof.

23. A pharmaceutical composition comprising a compound of claim 1 and a pharmaceutically acceptable excipient.

24. A method for treating an S1P1 receptor mediated condition in a patient wherein the condition is selected from the group consisting of acute or chronic rejection of tissue grafts, systemic lupus erythematosus, multiple sclerosis, rheumatoid arthritis, inflammatory bowel diseases, atopic asthma, type I diabetes, acute respiratory distress syndrome, sepsis, ischemia-reperfusion injury, metastatic hepatocellular carcinoma, androgen-independent prostate cancer, multiple myeloma, bladder cancer, renal cancer, acute lymphoblastic leukemia, chronic lymphocytic leukemia, B-cell lymphoma, acute myeloid leukemia, mantle cell lymphoma, pancreatic cancer, breast cancer, Behcet's disease, glomerulonephritis, uveitis, psoriasis, myasthenia gravis, Hashimoto's thyroiditis, autoimmune hemolytic anemia, autoimmune thrombocytopenic purpura, hepatitis and Wegner's granuloma, said method comprising administering to the patient a therapeutically effective amount of a compound of claim 1.

25. The method of claim 24 wherein the disease is multiple sclerosis.

26. A pharmaceutical composition comprising a compound of claim 20 and a pharmaceutically acceptable excipient.

27. A pharmaceutical composition comprising a compound of claim 21 and a pharmaceutically acceptable excipient.

28. A pharmaceutical composition comprising a compound of claim 22 and a pharmaceutically acceptable excipient.

29. A method for treating an S1P1 receptor mediated condition in a patient wherein the condition is selected from the group consisting of acute or chronic rejection of tissue grafts, systemic lupus erythematosus, multiple sclerosis, rheumatoid arthritis, inflammatory bowel diseases, atopic asthma, type I diabetes, acute respiratory distress syndrome, sepsis, ischemia-reperfusion injury, metastatic hepatocellular carcinoma, androgen-independent prostate cancer, multiple myeloma, bladder cancer, renal cancer, acute lymphoblastic leukemia, chronic lymphocytic leukemia, B-cell lymphoma, acute myeloid leukemia, mantle cell lymphoma, pancreatic cancer, breast cancer, Behcet's disease, glomerulonephritis, uveitis, psoriasis, myasthenia gravis, Hashimoto's thyroiditis, autoimmune hemolytic anemia, autoimmune thrombocytopenic purpura, hepatitis and Wegner's granuloma, said method comprising administering to the patient a therapeutically effective amount of a compound of claim 19.

30. A method for treating an S1P1 receptor mediated condition in a patient wherein the condition is selected from the group consisting of acute or chronic rejection of tissue grafts, systemic lupus erythematosus, multiple sclerosis, rheumatoid arthritis, inflammatory bowel diseases, atopic asthma, type I diabetes, acute respiratory distress syndrome, sepsis, ischemia-reperfusion injury, metastatic hepatocellular carcinoma, androgen-independent prostate cancer, multiple myeloma, bladder cancer, renal cancer, acute lymphoblastic leukemia, chronic lymphocytic leukemia, B-cell lymphoma, acute myeloid leukemia, mantle cell lymphoma, pancreatic cancer, breast cancer, Behcet's disease, glomerulonephritis, uveitis, psoriasis, myasthenia gravis, Hashimoto's thyroiditis, autoimmune hemolytic anemia, autoimmune thrombocytopenic purpura, hepatitis and Wegner's granuloma, said method comprising administering to the patient a therapeutically effective amount of a compound of claim 20.

31. A method for treating an S1P1 receptor mediated condition in a patient wherein the condition is selected from the group consisting of acute or chronic rejection of tissue grafts, systemic lupus erythematosus, multiple sclerosis, rheumatoid arthritis, inflammatory bowel diseases, atopic asthma, type I diabetes, acute respiratory distress syndrome, sepsis, ischemia-reperfusion injury, metastatic hepatocellular carcinoma, androgen-independent prostate cancer, multiple myeloma, bladder cancer, renal cancer, acute lymphoblastic leukemia, chronic lymphocytic leukemia, B-cell lymphoma, acute myeloid leukemia, mantle cell lymphoma, pancreatic cancer, breast cancer, Behcet's disease, glomerulonephritis, uveitis, psoriasis, myasthenia gravis, Hashimoto's thyroiditis, autoimmune hemolytic anemia, autoimmune thrombocytopenic purpura, hepatitis and Wegner's granuloma, said method comprising administering to the patient a therapeutically effective amount of a compound of claim 21.

32. A method for treating an S1P1 receptor mediated condition in a patient wherein the condition is selected from the group consisting of acute or chronic rejection of tissue grafts, systemic lupus erythematosus, multiple sclerosis, rheumatoid arthritis, inflammatory bowel diseases, atopic asthma, type I diabetes, acute respiratory distress syndrome, sepsis, ischemia-reperfusion injury, metastatic hepatocellular carcinoma, androgen-independent prostate cancer, multiple myeloma, bladder cancer, renal cancer, acute lymphoblastic leukemia, chronic lymphocytic leukemia, B-cell lymphoma, acute myeloid leukemia, mantle cell lymphoma, pancreatic cancer, breast cancer, Behcet's disease, glomerulonephritis, uveitis, psoriasis, myasthenia gravis, Hashimoto's thyroiditis, autoimmune hemolytic anemia, autoimmune thrombocytopenic purpura, hepatitis and Wegner's granuloma, said method comprising administering to the patient a therapeutically effective amount of a compound of claim 22.

* * * * *

UNITED STATES PATENT AND TRADEMARK OFFICE

CERTIFICATE OF CORRECTION

PATENT NO. : 7,842,685 B2
APPLICATION NO. : 12/456687
DATED : November 30, 2010
INVENTOR(S) : Victor J. Cee et al.

It is certified that error appears in the above-identified patent and that said Letters Patent is hereby corrected as shown below:

Column 189, line 63, before "$C_{1-4}$haloalkyl" please insert --$C_{1-4}$alkyl,--.
Column 193, lines 29-31, after "is" please delete structure and insert -- 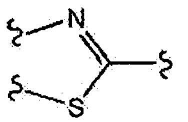 --.

Column 193, lines 37-39, after "or" please delete structure and insert

-- 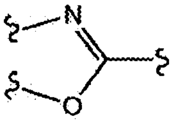 --.

Column 197, lines 11-13, after "where" please delete structure and insert

-- 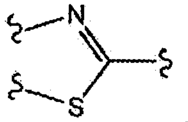 --.

Column 197, line 34, after the first instance of "2-fluoro-4-" please insert --(carboxymethylNHCO-)phenyl; 2-fluoro-4-(2-carboxyethylNHCO-)phenyl; 2-fluoro-4- --.
Column 197, line 46, "methylpyrrodin" should be --methylpyrrolidin--.
Column 197, line 56, "carboxypyrrolin" should be --carboxypyrrolidin--.
Column 198, line 64, "$CO_2$1))" should be --$CO_2H$))--.
Column 199, line 11, "$CO_2$]-phenyl" should be --$CO_2H$]-phenyl--.
Column 199, line 43, "ylmethy)phenyl" should be --ylmethyl)phenyl--.
Column 201, line 65, "fluoro-4-(5-(" should be --fluoro-4-5-1-(--.
Column 202, line 2, "[5,4]" should be --[5,4-b]--.
Column 202, line 22, "5(1-phenyl" should be --5-(1-phenyl--.
Column 202, line 23, "cyclopropyl)thiazolo" should be --cyclopropyl)-thiazolo--.
Column 202, line 24, "4-(5(1-phenylcyclopropyl" should be --4-(5-(1-phenylcyclopropyl--.
Column 202, line 30, "4-(5(1-phenylcyclopropyl" should be --4-(5-(1-phenylcyclopropyl--.
Column 202, line 41, "phenoxy)pyrrolidine" should be --phenoxy)-pyrrolidine--.

Signed and Sealed this
Sixteenth Day of August, 2011

David J. Kappos
*Director of the United States Patent and Trademark Office*

Column 202, line 43, “benzylamino)cyclopropanecarboxylic” should be --benzylamino)-cyclopropanecarboxylic--.
Column 202, line 46, “pyridin-2-yl)benzylamino)” should be --pyridin-2--yl)-benzylamino)--.
Column 202, line 58, “[5,4-]” should be --[5,4-b]--.
Column 203, line 9, “fluoro--4-(5” should be --fluoro--4-5--.
Column 203, line 18, “pridin” should be --pyridin--.
Column 203, line 52, “)phenyl” should be --)-phenyl--.
Column 203, line 54, “)phenyl” should be --)-phenyl--.
Column 203, line 57, “)phenyl” should be --)-phenyl--.
Column 204, line 9, “)phenyl” should be --)-phenyl--.
Column 204, line 14, “thiazolo[5,” should be --thiazolo-[5,-.
Column 204, line 17, “)phenyl” should be --)-phenyl--.
Column 204, line 20, “)phenyl” should be --)-phenyl--.
Column 204, line 23, “)phenyl” should be --)-phenyl--.
Column 204, line 37, “)phenyl” should be --)-phenyl--.
Column 204, line 39, “)phenyl” should be --)-phenyl--.
Column 204, line 43, “4]” should be --4-b]--.
Column 204, line 51, “)phenyl” should be --)-phenyl--.
Column 204, line 54, “)phenyl” should be --)-phenyl--.
Column 204, line 60, “)phenylamino” should be --)-phenylamino--.
Column 204, line 66, “)phenyl” should be --)-phenyl--.